(12) United States Patent
Ward et al.

(10) Patent No.: US 10,976,232 B2
(45) Date of Patent: Apr. 13, 2021

(54) METHODS AND DEVICES FOR MULTI-STEP CELL PURIFICATION AND CONCENTRATION

(71) Applicants: GPB SCIENTIFIC, INC., Richmond, VA (US); UNIVERSITY OF MARYLAND, BALTIMORE, Baltimore, MD (US); THE TRUSTEES OF PRINCETON UNIVERSITY, Princeton, NJ (US)

(72) Inventors: Anthony Ward, Rancho Santa Fe, CA (US); Khushroo Gandhi, Palo Alto, CA (US); Alison Skelley, Riverside, CA (US); Curt Civin, Baltimore, MD (US); James C. Sturm, Princeton, NJ (US); Lee Aurich, Oakland, CA (US); Michael Grisham, Richmond, VA (US); Joseph D'Silva, Princeton, NJ (US); Robert H. Austin, Princeton, NJ (US)

(73) Assignees: GPB Scientific, Inc., Richmond, VA (US); The Trustees of Princeton University, Princeton, NJ (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 15/595,548

(22) Filed: May 15, 2017

(65) Prior Publication Data

US 2017/0248508 A1 Aug. 31, 2017

Related U.S. Application Data

(63) Continuation-in-part of application No. PCT/US2016/048455, filed on Aug. 24, 2016.

(Continued)

(51) Int. Cl.
*G01N 15/00* (2006.01)
*G01N 15/10* (2006.01)
(Continued)

(52) U.S. Cl.
CPC .... *G01N 15/1056* (2013.01); *B01L 3/502715* (2013.01); *B01L 3/502746* (2013.01);
(Continued)

(58) Field of Classification Search
CPC .... B03C 1/02; B03C 1/30; B03C 1/32; B03C 2201/18; B03C 2201/22;
(Continued)

(56) References Cited

U.S. PATENT DOCUMENTS 4,756,427 A 7/1988 Göhde et al.
5,030,002 A 7/1991 North
(Continued)

FOREIGN PATENT DOCUMENTS

CA 1 248 873 1/1989
WO WO 2005/047529 5/2005
(Continued)

OTHER PUBLICATIONS

Agrawal, et al., "PDGF upregulates CLEC-2 to induce T regulatory cells," *Oncotarget* 6(30):28621-28632 (Sep. 2015).
(Continued)

*Primary Examiner* — Joseph C Rodriguez
(74) *Attorney, Agent, or Firm* — Law Office of Michael A. Sanzo, LLC

(57) ABSTRACT

Described herein are microfluidic devices and methods that can separate and concentrate particles in a sample.

13 Claims, 54 Drawing Sheets

Integrated Blood Preparation System with Downstream Analytical Modules

Related U.S. Application Data

(60) Provisional application No. 62/337,619, filed on May 17, 2016, provisional application No. 62/209,246, filed on Aug. 24, 2015, provisional application No. 62/233,915, filed on Sep. 28, 2015, provisional application No. 62/274,031, filed on Dec. 31, 2015, provisional application No. 62/324,293, filed on Apr. 18, 2016, provisional application No. 62/337,273, filed on May 16, 2016.

(51) Int. Cl.
| | |
|---|---|
| *B01L 3/00* | (2006.01) |
| *G01N 33/574* | (2006.01) |
| *G01N 33/50* | (2006.01) |
| *G01N 15/14* | (2006.01) |
| *G01N 33/68* | (2006.01) |

(52) U.S. Cl.
CPC ... *B01L 3/502753* (2013.01); *B01L 3/502761* (2013.01); *B01L 3/502776* (2013.01); *G01N 15/1404* (2013.01); *G01N 15/1459* (2013.01); *G01N 15/1484* (2013.01); *G01N 33/5091* (2013.01); *G01N 33/574* (2013.01); *G01N 33/6893* (2013.01); *B01L 2200/0652* (2013.01); *B01L 2300/0681* (2013.01); *B01L 2300/0867* (2013.01); *B01L 2400/043* (2013.01); *B01L 2400/082* (2013.01); *B01L 2400/086* (2013.01); *G01N 2015/008* (2013.01); *G01N 2015/0065* (2013.01); *G01N 2015/1006* (2013.01); *G01N 2015/1081* (2013.01); *G01N 2015/142* (2013.01); *G01N 2015/149* (2013.01)

(58) Field of Classification Search
CPC ... G01N 2015/0065; G01N 2015/0073; G01N 2015/008; G01N 2015/1081; G01N 15/1056; G01N 15/1404; G01N 15/1459; G01N 15/1484; G01N 33/574; G01N 33/5091; G01N 33/6893; B01L 3/502746; B01L 3/502753; B01L 3/502761; B01L 2400/0086; B01L 3/502715; B01L 3/502766

See application file for complete search history.

(56) References Cited

U.S. PATENT DOCUMENTS

| | | | |
|---|---|---|---|
| 5,240,856 A | 8/1993 | Goffe et al. | |
| 5,427,663 A | 6/1995 | Austin et al. | |
| 5,541,164 A | 7/1996 | Carson et al. | |
| 5,676,849 A | 10/1997 | Sammons et al. | |
| 5,707,799 A * | 1/1998 | Hansmann | B01L 3/502753 422/417 |
| 5,872,128 A | 2/1999 | Patel et al. | |
| 5,968,820 A | 10/1999 | Zborowski et al. | |
| 5,981,180 A | 11/1999 | Chandler et al. | |
| 6,241,894 B1 | 6/2001 | Briggs et al. | |
| 6,268,222 B1 | 7/2001 | Chandler et al. | |
| 6,514,295 B1 | 2/2003 | Chandler et al. | |
| 6,524,793 B1 | 2/2003 | Chandler et al. | |
| 6,528,165 B2 | 3/2003 | Chandler et al. | |
| 6,632,652 B1 | 10/2003 | Austin et al. | |
| 6,685,841 B2 | 2/2004 | Lopez et al. | |
| 6,881,315 B2 | 4/2005 | Iida et al. | |
| 6,881,317 B2 | 4/2005 | Huang et al. | |
| 6,913,697 B2 | 7/2005 | Lopez et al. | |
| 6,949,355 B2 | 9/2005 | Yamanishi et al. | |
| 7,150,812 B2 | 12/2006 | Huang et al. | |
| 7,318,902 B2 | 1/2008 | Oakey et al. | |
| 7,472,794 B2 | 1/2009 | Oakey et al. | |
| 7,682,838 B2 | 3/2010 | Wang et al. | |
| 7,735,652 B2 | 6/2010 | Inglis et al. | |
| 7,837,944 B2 * | 11/2010 | Auner | G01N 1/2202 422/503 |
| 7,846,393 B2 | 12/2010 | Tai et al. | |
| 7,863,012 B2 | 1/2011 | Rao et al. | |
| 7,977,095 B2 | 7/2011 | Bonyhadi et al. | |
| 7,988,840 B2 | 8/2011 | Huang et al. | |
| 7,993,821 B2 | 8/2011 | Chiu et al. | |
| 8,008,032 B2 | 8/2011 | Forsyth et al. | |
| 8,021,614 B2 | 9/2011 | Huang et al. | |
| 8,137,912 B2 | 3/2012 | Kapur et al. | |
| 8,168,389 B2 | 5/2012 | Shoemaker et al. | |
| 8,186,913 B2 | 5/2012 | Toner et al. | |
| 8,263,023 B2 | 9/2012 | Le Vot et al. | |
| 8,263,404 B2 | 9/2012 | Olken et al. | |
| 8,282,799 B2 | 10/2012 | Huang et al. | |
| 8,304,230 B2 * | 11/2012 | Toner | B01L 3/502746 435/288.5 |
| 8,329,422 B2 | 12/2012 | Rao et al. | |
| 8,354,075 B1 | 1/2013 | Tai et al. | |
| 8,579,117 B2 * | 11/2013 | Loutherback | G01N 27/44791 209/143 |
| 8,783,467 B2 | 7/2014 | Loutherback et al. | |
| 8,906,682 B2 | 12/2014 | June et al. | |
| 8,921,102 B2 | 12/2014 | Fuchs et al. | |
| 9,034,658 B2 | 5/2015 | Barber et al. | |
| 9,328,156 B2 | 5/2016 | June et al. | |
| 9,427,688 B2 * | 8/2016 | Reichenbach | B01D 43/00 |
| 9,435,728 B2 | 9/2016 | Tsukii et al. | |
| 9,610,582 B2 | 4/2017 | Kapur et al. | |
| 9,629,877 B2 | 4/2017 | Cooper et al. | |
| 9,878,327 B2 | 1/2018 | Smith et al. | |
| 9,895,694 B2 | 2/2018 | Kapur et al. | |
| 9,956,562 B2 | 5/2018 | Huang et al. | |
| 10,324,011 B2 | 6/2019 | D'Silva et al. | |
| 10,359,429 B2 | 7/2019 | Forsyth et al. | |
| 10,526,595 B2 | 1/2020 | Lee et al. | |
| 2001/0036624 A1 | 11/2001 | Sumita et al. | |
| 2002/0005982 A1 | 1/2002 | Spence et al. | |
| 2002/0090741 A1 | 7/2002 | Jurgensen et al. | |
| 2002/0110835 A1 | 8/2002 | Kumar et al. | |
| 2002/0115163 A1 | 8/2002 | Wang et al. | |
| 2002/0119482 A1 | 8/2002 | Nelson et al. | |
| 2002/0123078 A1 | 9/2002 | Seul et al. | |
| 2002/0164825 A1 | 11/2002 | Chen et al. | |
| 2003/0049563 A1 | 3/2003 | Iida et al. | |
| 2003/0096405 A1 | 5/2003 | Takayama et al. | |
| 2003/0113528 A1 | 6/2003 | Moya | |
| 2003/0119077 A1 | 6/2003 | Ts'o et al. | |
| 2003/0159999 A1 | 8/2003 | Oakey et al. | |
| 2003/0180762 A1 | 9/2003 | Tuma et al. | |
| 2004/0018116 A1 | 1/2004 | Desmond et al. | |
| 2004/0018611 A1 | 1/2004 | Ward et al. | |
| 2004/0019300 A1 | 1/2004 | Leonard et al. | |
| 2004/0033515 A1 | 2/2004 | Cao | |
| 2004/0043506 A1 | 3/2004 | Haussecker et al. | |
| 2004/0144651 A1 | 7/2004 | Huang et al. | |
| 2004/0166555 A1 | 8/2004 | Braff et al. | |
| 2004/0224402 A1 | 11/2004 | Bonyhadi et al. | |
| 2004/0229349 A1 | 11/2004 | Daridon | |
| 2004/0232074 A1 | 11/2004 | Peters et al. | |
| 2005/0061962 A1 | 3/2005 | Meuth et al. | |
| 2005/0164158 A1 | 7/2005 | Wang et al. | |
| 2005/0207940 A1 | 9/2005 | Butler et al. | |
| 2005/0266433 A1 | 12/2005 | Kapur et al. | |
| 2005/0272103 A1 | 12/2005 | Chen | |
| 2005/0282293 A1 | 12/2005 | Cosman et al. | |
| 2006/0035386 A1 | 2/2006 | Hattori et al. | |
| 2006/0121624 A1 | 6/2006 | Huang et al. | |
| 2006/0128006 A1 | 6/2006 | Gerhardt et al. | |
| 2006/0134599 A1 | 6/2006 | Toner et al. | |
| 2006/0160243 A1 | 7/2006 | Tang et al. | |
| 2006/0223178 A1 * | 10/2006 | Barber | B01L 3/502746 435/325 |
| 2006/0252087 A1 | 11/2006 | Tang et al. | |
| 2007/0026381 A1 | 2/2007 | Huang | |
| 2007/0026413 A1 | 2/2007 | Toner et al. | |
| 2007/0026414 A1 | 2/2007 | Fuchs et al. | |

(56) References Cited

U.S. PATENT DOCUMENTS

| | | | |
|---|---|---|---|
| 2007/0026415 A1 | 2/2007 | Fuchs et al. | |
| 2007/0026416 A1 | 2/2007 | Fuchs et al. | |
| 2007/0026418 A1 | 2/2007 | Fuchs et al. | |
| 2007/0026419 A1 | 2/2007 | Fuchs et al. | |
| 2007/0042339 A1 | 2/2007 | Toner et al. | |
| 2007/0059680 A1 | 3/2007 | Kapur et al. | |
| 2007/0059716 A1 | 3/2007 | Balis et al. | |
| 2007/0059718 A1 | 3/2007 | Kapur et al. | |
| 2007/0059719 A1 | 3/2007 | Kapur et al. | |
| 2007/0059774 A1 | 3/2007 | Kapur et al. | |
| 2007/0059781 A1 | 3/2007 | Kapur et al. | |
| 2007/0072290 A1 | 3/2007 | Hvichia et al. | |
| 2007/0160503 A1 | 7/2007 | Sethu et al. | |
| 2007/0172903 A1 | 7/2007 | Toner et al. | |
| 2007/0196820 A1 | 8/2007 | Kapur et al. | |
| 2007/0292401 A1 | 12/2007 | Harmon et al. | |
| 2008/0070792 A1 | 3/2008 | Stoughton et al. | |
| 2008/0090239 A1 | 4/2008 | Shoemaker et al. | |
| 2008/0113358 A1* | 5/2008 | Kapur | G01N 33/689 435/6.12 |
| 2008/0124721 A1 | 5/2008 | Fuchs et al. | |
| 2008/0248499 A1 | 10/2008 | Chiu et al. | |
| 2008/0314161 A1 | 12/2008 | Sparks et al. | |
| 2009/0136982 A1 | 5/2009 | Tang et al. | |
| 2010/0006479 A1* | 1/2010 | Reichenbach | B01D 43/00 209/132 |
| 2010/0055758 A1 | 3/2010 | Kapur et al. | |
| 2010/0059414 A1 | 3/2010 | Sturm et al. | |
| 2010/0066880 A1 | 3/2010 | Sato et al. | |
| 2010/0167337 A1 | 7/2010 | Tsingberg et al. | |
| 2010/0234674 A1 | 9/2010 | Wheeler et al. | |
| 2010/0291572 A1 | 11/2010 | Stoughton et al. | |
| 2010/0297733 A1 | 11/2010 | Lin et al. | |
| 2010/0301171 A1* | 12/2010 | Wood | B64C 23/04 244/200 |
| 2010/0326916 A1 | 12/2010 | Wrazel et al. | |
| 2011/0070642 A1 | 3/2011 | Cayre et al. | |
| 2011/0189650 A1 | 8/2011 | Ayliffe et al. | |
| 2011/0212440 A1 | 9/2011 | Viovy et al. | |
| 2011/0213288 A1 | 9/2011 | Choi et al. | |
| 2011/0306043 A1 | 12/2011 | Fuchs et al. | |
| 2012/0006728 A1 | 1/2012 | Huang et al. | |
| 2012/0015835 A1 | 1/2012 | Fuchs et al. | |
| 2012/0037544 A1 | 2/2012 | Lane et al. | |
| 2012/0063971 A1 | 3/2012 | Carlo et al. | |
| 2012/0078531 A1 | 3/2012 | Lo et al. | |
| 2012/0100521 A1 | 4/2012 | Soper et al. | |
| 2012/0100560 A1 | 4/2012 | Searson et al. | |
| 2012/0115755 A1 | 5/2012 | Oh et al. | |
| 2012/0178097 A1 | 7/2012 | Tai et al. | |
| 2012/0196273 A1 | 8/2012 | Huang et al. | |
| 2012/0258459 A1 | 10/2012 | Huang | |
| 2012/0258475 A1 | 10/2012 | Tang et al. | |
| 2012/0270209 A1 | 10/2012 | Shah et al. | |
| 2012/0295246 A1 | 11/2012 | Faustman et al. | |
| 2013/0079251 A1 | 3/2013 | Boles et al. | |
| 2013/0083315 A1 | 4/2013 | Lo et al. | |
| 2013/0143197 A1 | 6/2013 | Heyneker | |
| 2013/0189689 A1 | 7/2013 | Shoemaker et al. | |
| 2013/0209988 A1 | 8/2013 | Barber | |
| 2013/0260392 A1 | 10/2013 | Forsyth et al. | |
| 2013/0302796 A1 | 11/2013 | Fuchs | |
| 2013/0302797 A1 | 11/2013 | Kopf-Sill et al. | |
| 2013/0324418 A1 | 12/2013 | Fuchs et al. | |
| 2014/0030788 A1 | 1/2014 | Chen et al. | |
| 2014/0051064 A1 | 2/2014 | van den Engh | |
| 2014/0093867 A1 | 4/2014 | Burke et al. | |
| 2014/0154703 A1 | 6/2014 | Skelley et al. | |
| 2014/0234986 A1 | 8/2014 | Forsyth et al. | |
| 2014/0342375 A1 | 11/2014 | Grisham et al. | |
| 2015/0024482 A1 | 1/2015 | Frigault et al. | |
| 2015/0025243 A1 | 1/2015 | Mosher et al. | |
| 2015/0064153 A1 | 3/2015 | Civin et al. | |
| 2015/0268244 A1* | 9/2015 | Cho | G01N 15/1429 435/7.23 |
| 2015/0299317 A1 | 10/2015 | Orentas et al. | |
| 2015/0344956 A1 | 12/2015 | Kapur et al. | |
| 2016/0002737 A1 | 1/2016 | Fuchs et al. | |
| 2016/0047735 A1 | 2/2016 | Grisham et al. | |
| 2016/0081314 A1 | 3/2016 | Thurston et al. | |
| 2016/0139012 A1 | 5/2016 | D'Silva et al. | |
| 2016/0168539 A1 | 6/2016 | Civin et al. | |
| 2016/0244714 A1 | 8/2016 | Spuhler et al. | |
| 2016/0299126 A1* | 10/2016 | Koser | G01N 33/5008 |
| 2016/0339434 A1 | 11/2016 | Toner et al. | |
| 2016/0361360 A1 | 12/2016 | Chang et al. | |
| 2017/0023578 A1 | 1/2017 | Forsyth et al. | |
| 2017/0101680 A1 | 4/2017 | Kopf-Sill et al. | |
| 2017/0137515 A1 | 5/2017 | Chang et al. | |
| 2017/0166866 A1 | 6/2017 | Lliang et al. | |
| 2017/0209864 A1 | 7/2017 | Grisham et al. | |
| 2017/0224789 A1 | 8/2017 | Sonavaria et al. | |
| 2017/0248508 A1 | 8/2017 | Ward et al. | |
| 2017/0333900 A1 | 11/2017 | Grisham et al. | |
| 2018/0038876 A1 | 2/2018 | Arai | |
| 2018/0282811 A1 | 10/2018 | Koph-Sill et al. | |
| 2019/0071639 A1 | 3/2019 | Ward et al. | |
| 2019/0137369 A1 | 5/2019 | D'Silva et al. | |
| 2019/0366342 A1 | 12/2019 | Ward et al. | |
| 2020/0025656 A1 | 1/2020 | D'Silva et al. | |
| 2020/0025657 A1 | 1/2020 | D'Silva et al. | |
| 2020/0025669 A1 | 1/2020 | Ward et al. | |
| 2020/0056153 A1 | 2/2020 | Ward et al. | |

FOREIGN PATENT DOCUMENTS

| | | |
|---|---|---|
| WO | WO 2005/049168 | 6/2005 |
| WO | WO 2005/061075 | 7/2005 |
| WO | WO 2006/037561 | 4/2006 |
| WO | WO 2006/078470 | 7/2006 |
| WO | WO 2006/108087 | 10/2006 |
| WO | WO 2007/035498 | 3/2007 |
| WO | WO 2007/035585 | 3/2007 |
| WO | WO 2007/035586 | 3/2007 |
| WO | WO 2008/008515 | 1/2008 |
| WO | WO 2008/017871 | 2/2008 |
| WO | WO 2009/076560 | 6/2009 |
| WO | WO 2010/011934 | 1/2010 |
| WO | WO 2010/129441 | 11/2010 |
| WO | WO 2010/144745 | 12/2010 |
| WO | WO 2011/119962 | 9/2011 |
| WO | WO 2012/016136 | 2/2012 |
| WO | WO 2012/094642 A2 | 7/2012 |
| WO | WO 2013/049860 | 4/2013 |
| WO | WO 2014/004577 A1 | 1/2014 |
| WO | WO 2014/116183 | 7/2014 |
| WO | WO 2014/145075 | 9/2014 |
| WO | WO 2014/145152 A2 | 9/2014 |
| WO | WO 2015/058206 | 4/2015 |
| WO | WO 2015/084257 | 6/2015 |
| WO | WO 2015/162211 | 10/2015 |
| WO | WO 2015/164745 | 10/2015 |
| WO | WO 2016/073481 | 5/2016 |
| WO | WO 2017/035262 A1 | 3/2017 |
| WO | WO 2017/176764 | 10/2017 |
| WO | WO 2018/080997 | 5/2018 |
| WO | PCT/US2018/047426 | 8/2018 |
| WO | WO 2019/046052 | 3/2019 |
| WO | WO 2019/222049 | 11/2019 |
| WO | WO 2020/014538 | 1/2020 |

OTHER PUBLICATIONS

Campos-Gonzalez, et al., "Deterministic Lateral Displacement: The Next Generation Car T-Cell Processing?" *SLAS* 23(4): (Jan. 2018).

Chiche-Lapierre, et al., "Comparative analysis of Sepax S-100, COBE 2991, and Manual DMSO Removal Techniques From Cryopreserved Hematopoietic Stemm Cell Apheresis Product," *Cytotherapy* 18(6):S47 (2016).

Civin, et al., "Automated Leukocyte Processing by Microfluidic Deterministic Lateral Displacement," *Cytometry A* 89:1073-1083 (2016).

(56) References Cited

OTHER PUBLICATIONS

Couzin-Frankel, "Supply of Promising T-Cell Therapy is Strained," *Science* 356:1112 (Jun. 2017).
Disilva, J., "Throughout Microfluidic Capture of Rare Cells from Large Volumes of Blood," A Dissertation Presented to the Faculty of Princeton University in Candidacy for the Degree of Doctor of Philosophy, (May 2016).
Feng, et al., "Maximizing particle concentration in deterministic lateral displacement arrays," *Biomicrofluidics* 11:024121 (published online Apr. 2017).
Fousek, et al., "The Evolution of T-cell Therapies for Solid Malignancies," *Clinical Cancer Research* 21(5):3384-3392 (Aug. 2015).
Hokland, et al., "The Isopaque-Ficoll Method Re-evaluated: Selective Loss of Autologous Rosette-forming Lymphocytes During Isolation of Mononuclear Cells from Human Peripheral Blood," *Scand. J.Immunol.* 11(3):353-356 (Mar. 1980).
Johnson, et al., "Driving Gene-engineered T-cell Immunotherapy of Cancer," *Cell Res.* 27:38-58 (2017).
Koesdjojo, et al.,"DLD Microfluidic Purification and Characterization of Intact and Viable Circulating Tumor Cells in Peripheral Blood," *AACR Annual Meeting* Abstract #3956 (2016).
Kurihara, et al., "Imaging Brain Tumors by Targeting Peptide Radiopharmaceuticals through the Blood-Brain Barrier," *Cancer Research* 59(24):6159-6163 (Dec. 1999).
Li, et al., "Comparison of anti-CD3 and anti-CD28-coated beads with soluble anti-CD3 for expanding Human T-cells: Differing impact on CD8 T-cell phenotype and responsiveness to restimulation," *J. Transl. Med.* 8:104-118 (2010).
Levine, et al., "Global Manufacturing of CAR T-cell Therapy," *Mol. Therapy: Meth. Clin. Dev.* 4:92-101 (2017).
Mahnke, et al., "The who's who or T-cell differentiation: Human memory T-cell subsets," *Eur. J. Immunol.* 43:2797-2809 (2013).
Marktkamcham, et al., "The Effects of Anti-CD3/CD28 Coated Beads and IL-2 on Expanded T Cell for Immunotherapy," *Adv. Clin. Exp. Med.* 25:821-828 (2016).
National Cell Manufacturing Consortium. Achieving Large-Scale, Cost-Effective, Reproducible Manufacturing of High Quality Cells. A Technology Roadmap to 20205. (Feb. 2016).
Powell, et al., "Efficient clinical-scale enrichment of lymphocytes for use in adoptive immunotherapy using a modified counterflow centrifugal elutriation program," *Cytotherapy* 11(7):923-935 (2009).
Reddy, et al., "Isolation of Stem Cells from Human Umbilical Cord Blood," in Vemuri (eds) Stem Cells Assays. Methods in Molecular Biology vol. 407, Human Press, pp. 149-163 (2007).
Rhee, M., "Advanced Components of Microfluidic Systems for Bioanalytical Applications," A dissertation submitted in partial fulfillment of the requirements for the degree of Doctor of Philosophy in the University of Michigan, 2009.
Sadelain, et al., "Therapeutic T cell engineering," *Nature* 545:423-431 (May 2017).
Stroncek, et al., "Counter-flow elutriation of clinical peripherial blood mononuclear cell concentrates for the production of dendritic and T cell therapies," *J. Transl. Med.*12:241 (2014).
Trickett, et al., "T-cell Stimulation and Expansion Using Anti-CD3/CD28 Beads," *J/ Immunol. Meth* 275:251-255 (Apr. 2003).
Vonderheide, et al., "Engineering T cells for cancer: our synthetic future," *Immunol. Rev.* 257:7-13 (2014).
Wang, et al., "Clinical manufacturing of CAR T cells: a foundation of a promising therapy," *Mol. Ther. Oncolytics* 3:16015 (2016).
Zhang, et al., "Optimized DNA electroporation for primary human T cell engineering," *BMC Biotechnology* 18:4 (2018).
Zhu, et al., "Platelets Provoke Distinct Dynamics of Immune Response by Differentially Regulating $CD4^+$ T-cell Proliferation," *J. Throm. Haem.* 12:1156-1165 (2014).
U.S. Appl. No. 16/108,365, filed Aug. 22, 2018, Ward, et al.
U.S. Appl. No. 16/123,056, filed Sep. 6, 2018, D'Silva, et al.
U.S. Appl. No. 15/870,945, filed Jan. 13, 2018, Kopf-Sill, et al.
U.S. Appl. No. 60/414,258, filed Apr. 8, 2004 (posted by WIPO), Toner, et al.
International Search Report for PCT/US2016/048455, which the present CIP application claims priority to, completed Oct. 17, 2016.
Written Opinion for PCT/US2016/048455, completed Oct. 17, 2016.
Best, et al., "RNA-Seq of Tumor-Educated Platelets Enables Blood-Based Pan-Cancer, Multiclass, and Molecular Pathway Cancer Diagnostics," *Cancer Cell* 28:666-676 (Nov. 2015).
Deng, et al., "Manipulation magnetic microbeads in suspension using micromagnetic systems fabricated with soft lithography," *Applied Physics Letters* 78:1775 (Mar. 2001).
Harris, et al., "Single-Molecule DNA Sequencing of a Viral Genome," *Science* 320:106 (Apr. 2008).
Huang, et al., "Continuous Particle Separation Through Deterministic Lateral Displacement," *Science* 304:987-990 (May 2004).
Kanwar, et al., "Microfluidic device (ExoChip) for On-Chip isolation, quantification and characterization of circulating exosomes," *Lab Chip* 14(11):1891-1900 (Jun. 2014).
Lee, et al., "Exosomes and microvesicles: extracellular vesicles for genetic information transfer and gene therapy," *Human Molecular Genetics* 21(rev. issue 1):R125-R134 (Aug. 2012).
Margulies, et al., "Genome sequencing in microfabricated high-density picolitre reactors," *Nature* 437:376-380 (Sep. 2005).
Soni, et al., "Progress toward Ultrafast DNA Sequencing Using Solid State Nanopores," *Clin. Chem.* 53:1996-2001 (2007).
U.S. Appl. No. 14/774,260, filed Sep. 10, 2015, 2016/0139012 A1, May 19, 2016, D'Silva, et al.
U.S. Appl. No. 14/774,268, filed Sep. 10, 2015, 2016/0047735 A1, Feb. 18, 2016, Grisham, et al.
U.S. Appl. No. 14/941,957, filed Nov. 16, 2015, 2016/0168539 A1, Jun. 16, 2016, Civin, et al.
U.S. Appl. No. 14/995,894, filed Jan. 14, 2016, 2017/0023578 A1, Jan. 26, 2017, Forsyth, et al.
U.S. Appl. No. 15/204,693, filed Jul. 7, 2016, 2017/0101680 A1, Apr. 13, 2017, Kopf-Sill, et al.
U.S. Appl. No. 15/329,753, filed Jan. 27, 2017, 2017/0209864 A1, Jul. 27, 2017, Grisham, et al.
U.S. Appl. No. 15/478,405, filed Apr. 4, 2017, 2017/0333900 A1, Nov. 23, 2017, Grisham, et al.
Communication pursuant to Rules 161(2) and 162 EPC for European counterpart application EP 16840058.8, dated Apr. 19, 2018.
Response to Communication pursuant to Rules 161(2) and 162 EPC for European counterpart application EP 16840058.8 filed on Oct. 17, 2018.
Amended claims filed with Response to Communication pursuant to Rules 161(2) and 162 for European counterpart application EP 16840058.8 on Oct. 17, 2018.
Extended European Search Report for European counterpart application EP 16840058.8 dated Feb. 4, 2019.
Communication pursuant to Rules 70 and 70a for counterpart European application EP 16840058.4 dated Feb. 21, 2019.
Response to the Communication regarding Rules 70 and 70a and to the EP Search Opinion for counterpart European application EP 16840058.4 filed Aug. 21, 2019.
Amended claims filed with the Response to Rules 70 and 70a Communication and to the EP Search Opinion for counterpart European application EP 16840058.4, filed Aug. 21, 2019.
First Examination Report for counterpart European application EP 16840058.4 dated Dec. 13, 2019.
Lee, et al., "Continuous medium exchange and optically induced electroporation of cells in an integrated microfluidic system," *Microsystems and Nanoengineering* 1:1-9 (2015).
Morton, et al., "Crossing microfluidic streamlines to lyse, label and wash cells," *Lab Chip* 8:1448-1453 (2008).
Song, et al., "Automatic detecting and counting magnetic based-labeled target cells from a suspension in a microfluidic chip," *Electrophoresis* 40:897-905 (2019).
U.S. Appl. No. 16/343,754, filed Apr. 20, 2019, US-2019/0366342 A1, Dec. 5, 2019, Ward.
U.S. Appl. No. 16/587,022, filed Sep. 29, 2019, US-2020/0025656 A1, Jan. 23, 2020, D'Silva.
U.S. Appl. No. 16/587,057, filed Sep. 30, 2020, US-2020/0025669 A1, Jan. 23, 2020, Ward.

(56) References Cited

OTHER PUBLICATIONS

U.S. Appl. No. 16/588,137, filed Sep. 30, 2020, US-2020/0025657 A1, Jan. 23, 2020, D'Silva.
U.S. Appl. No. 16/662,033, filed Oct. 24, 2020, US-2020/0056153 A1, Feb. 20, 2020, Ward.
International Preliminary Report on Patentability for PCT/US2016/048455, which the present CIP application claims priority to, completed Oct. 17, 2016.
EPO communication Under Rules 161(2) and 162 for corresponding EP application 16840058.8 sent Apr. 19, 2018.
Al-Fundi, et al., "New design for the separation of microorganisms using microfluidic deterministic lateral displacement," *Robotics and Computer Integrated Manufacturing* 27(2):237-244 (2011).
Alix-Panabieres, et al., "Challenges in circulating tumour cell research," *Nature Reviews/Cancer* 14(9):623-631 ((Sep. 2014).
Basford, et al., "Umbilical cord blood processing using Prepacyte-CB increases haematopoietic progenitor cell availability over conventional Hetastarch separation," *Cell Prolif.* 42(6):751-761 (Dec. 2009).
Bowman, et al., "Inertia and scaling in deterministic lateral displacement," *Biomicrofluidics* 7(6) 64111:1-9 (Dec. 2013).
Böyum, "Separation of Leucocytes From Blood and Bone Marrow," *Scand. J. Clin. Lab. Invest. 21 Suppl.* 97:77-89 (1968).
Böyum, "Separation of White Blood Cells," *Nature* 204:793-794 (Nov. 1964).
Chen, et al., "Rare cell isolation and analysis in microfluidics," *Lab Chip* 14(4):626-645 (Feb. 2014).
Chou, et al., "Sorting by diffusion: An asymmetric obstacle course for continuous molecular separation," *PNAS* 96(24):13762-13765 (Nov. 1999).
Colase, et al., "Microfluidics and Coagulation Biology," *Annu. Rev. Biomed. Eng.* 15:283-303 (2013).
Collins, et al., "Particle separation using virtual deterministic lateral displacement (vDLD)," *Lab Chip* 14(9):1595-1603 (May 2014).
Davis, et al., "Deterministic hydrodynamics: Taking blood apart," *PNAS* 103(40):14779-14784 (Oct. 2006).
Davis, "Microfluidic Separation of Blood Components through Deterministic Lateral Displacement," Ph.D. Thesis, Princeton University, (Sep. 2008).
Devendra, et al., "Deterministic fractionation of binary suspensions moving past a line of microposts," *Microfluid Nanofluid* 17(3):519-526 (Apr. 2014).
D'Silva, et al., "Inhibition of Clot Formation in Deterministic Lateral Displacement Arrays for Processing Large Volumes of Blood for Rare Cell Capture," *Lab Chip* 15(10):2240-2247 (May 2015).
D'Silva, "Post Geometry Design for High-Throughput Harvesting of Nucleated Cells from Blood with Minimal Erythrocyte Contamination Using DLD Arrays," Chapter 4: 53-113, Ph.D. Dissertation, Princeton University ((May 2016).
Holmes, et al., "Separation of blood cells with differing deformability using deterministic lateral displacement," *Interface Focus* 4(6):20140011 (Dec. 2014).
Huang, et al., "A Microfluidics approach for the isolation of nucleated red blood cells (NRBCs) from the peripheral blood of a pregnant women," *Prenat. Diagn.* 28(10):892-899 (Oct. 2008).
Huang, et al., "Continuous Particle Separation Through Deterministic Lateral Displacement," *Science* 304(5673):987-990 (May 2004).
Huang, et al., "Role of Molecular Size in Ratchet Fractionation," *Physical Review Letters* 89(17):178301 (Oct. 2002).
iCELLATE cancer cell detection, "Cancer cell detection system for individualized cancer research and detection," available at: http://www.icellate.se (accessed Oct. 27, 2015).
Inglis, et al., "Critical particle size for fractionation by deterministic lateral displacement," *Lab Chip* 6(5):655-658 (May 2006).
Inglis, et al., "Determining blood cell size using microfluidic hydrodynamics," *J. Immunol. Methods* 329(1-2):151-156 ((Jan. 2008).
Inglis, et al., "Scaling deterministic lateral displacement arrays for high throughput and dilution-free enrichment of leukocytes," *J. Micromech. Microeng.* 21:054024 (2011).
Karabacak, et al., "Microfluidic, marker-free isolation of circulating tumor cells from blood samples," *Nature Protocols* 9(3):694-710 (Mar. 2014).
Krüger, et al., "Deformability-based red blood cell separation in deterministic lateral displacement devices—A simulation study," *Biomicrofluidics* 8(5):054114 (Oct. 2014).
Liu, et al., "Rapid isolation of cancer cells using microfluidic deterministic lateral displacement structure," *Biomicrofluidics* 7(1):11801 (Jan. 2013).
Liu, et al., "High throughput capture of circulating tumor cells using an integrated microfluidic system," *Biosensors and Bioelectronics* 47:113-119 (2013).
Long, et al., "Multi-directional sorting modes in deterministic lateral displacement devices," *Physical Review E* 78:046304 (2008).
Loutherback, et al., "Deterministic Microfluidic Ratchet," *Physical Review Letters* 102(4):045301 (Jan. 2009).
Loutherback, et al., "Deterministic separation of cancer cells from blood at 10mL/min," *API Advances* 2(4):42107 (Dec. 2012).
Loutherback, et al., "Improved performance of deterministic lateral displacement arrays with triangular posts," *Microfluid Nanofluid* 9:1143-1149 (2010).
Loutherback, "Microfluidic Devices for High Throughput Cell Sorting and Chemical Treatment," Dissertation, Princeton University, (Nov. 2011).
McGrath, et al., "Deterministic lateral displacement for particle separation: a review," *Lab Chip* 14(21):4139-4158 (Sep. 2014).
Nagrath, et al., "Isolation of rare circulating tumour cells in cancer patients by microchip technology," *Nature* 450(7173):1235-1239 (Dec. 2007).
Ranjan, et al., "DLD pillar shape design for efficient separation of spherical and non-spherical bioparticles," *Lab Chip* 12(21):4250-4262 (Sep. 2014).
Toner, et al., "Blood-on-a-Chip," *Annu. Rev. Biomed. Eng.* 7:77-103, C1-C3 (2005).
Yu, et al., "A Microfluidic Approach for Whole Blood Leucocytes Isolation for Leucocytes Immunophenotyping by Flow Cytometry," Congress Center Leipzig, Lepzig, Germany, Poster B228, (Jun. 2012).
Zeming, et al., "Asymmetrical Deterministic Lateral Displacement Gaps for Dual Functions of Enhanced Separation and Throughput of Red Blood Cells," *Sci. Rep* 6:22934 (Mar. 2016).
Zhang, et al., "Applications of Microfluidics in Stem Cell Biology," *Bionanoscience* 2(4):277-286 (Dec. 2012).
Zhang, et al., "Behavior of rigid and deformable particles in deterministic lateral displacement devices with different post shapes," *J. Chem. Phys.* 143(24):243145 (Dec. 2015).
Zheng, et al., "Deterministic lateral displacement MEMS device for continuous blood cell separation," Micro Electro Mechanical Systems, 2005. 18th IEEE International Conference.
Radisic, et al., "Micro- and nanotechnology in cell separation," *International Journal of Nanomedicine* 1(1):3-14 (2006).
Yi, et al., "Microfluidics technology for manipulation and analysis of biological cells," *Analytica Chimica Acta* 560:1-23 (2006).
APOCELL. ApoStream Technology. Available at http://www.apocell.com/ctc-technology-2/apostreamtm-technology. Last Accessed Jul. 16, 2018.
Response to Examination Report of Dec. 13, 2020 for counterpart European application EP 16840058, filed May 19, 2020.
Amended claims filed with Response to Examination Report of Dec. 13, 2020 for counterpart European application EP 16840058, filed May 19, 2020.
Office Action for copending U.S. Appl. No. 16/587,057, dated Sep. 9, 2020.
Inglis, David, "Microfluidic Devices for Cell Separation," A Dissertation presented to the faculty of Princeton University, Sep. 2007.
Examination Report for counterpart European application EP 16840058.8, dated Nov. 2, 2020., issued by European Patent Office.
Examination Report dated Dec. 7, 2020 for corresponding Australian application 2016331278.

(56) References Cited

OTHER PUBLICATIONS

Amendment & Response to Office Action for copending U.S. Appl. No. 16/587,057, filed Feb. 4, 2021.
Response to Examination Report of Nov. 2, 2020 (with amended claims attached) for counterpart European application 16840058.8, filed Feb. 18, 2021.
Response to Examination Report of Dec. 7, 2020 for corresponding Australian application 201631278, filed Feb. 26, 2021.

* cited by examiner

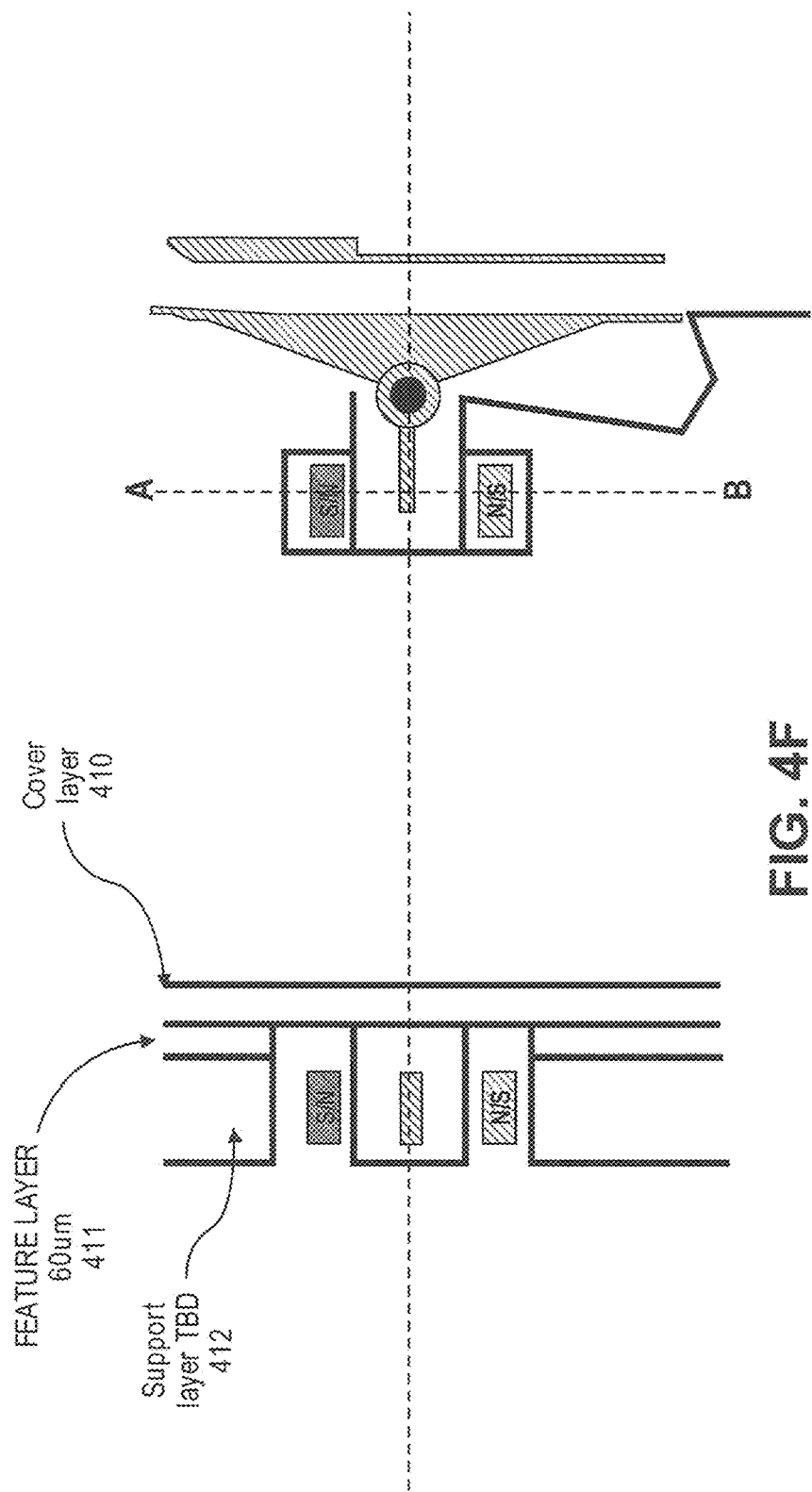

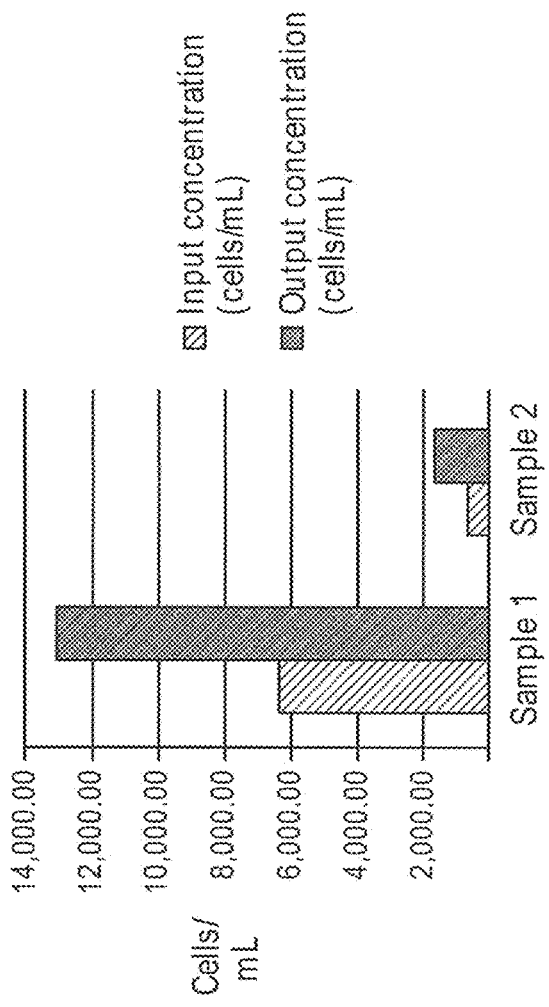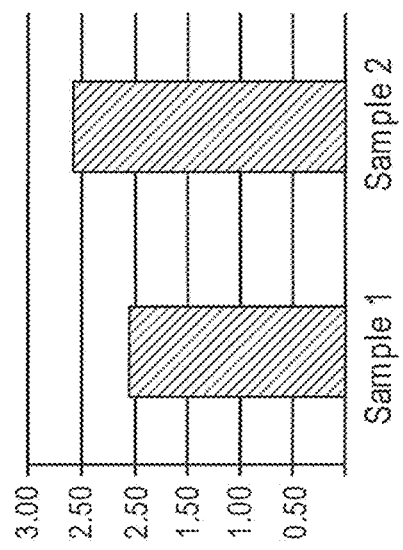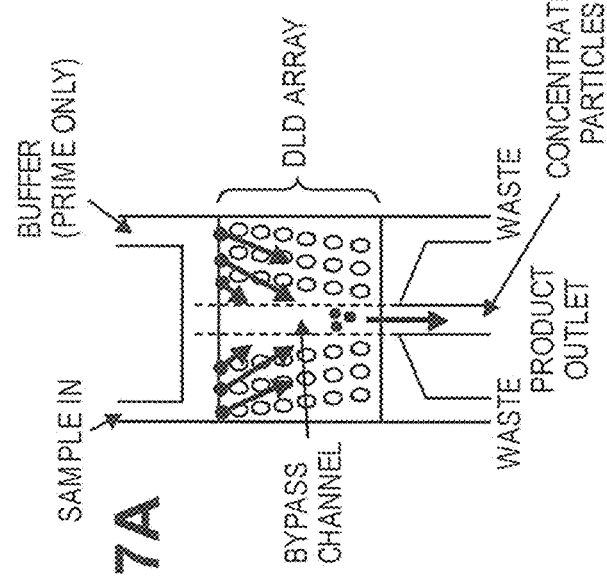

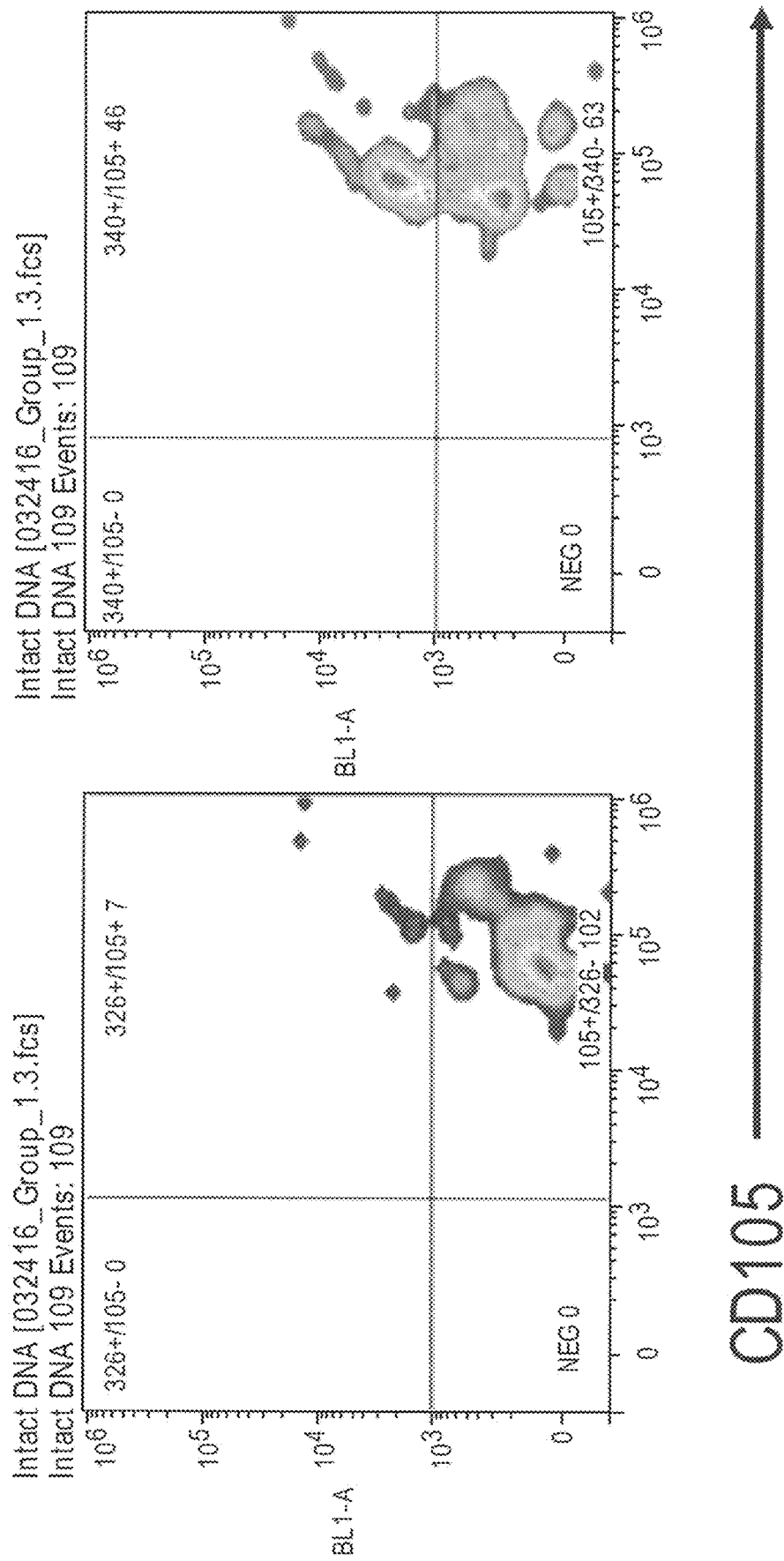

METHODS AND DEVICES FOR MULTI-STEP CELL PURIFICATION AND CONCENTRATION

CROSS-REFERENCE

The present application is a continuation-in-part of and claims priority to PCT/US2016/048455, filed on Aug. 24, 2016, which claims priority to U.S. Provisional Patent Application No. 62/274,031, filed on Dec. 31, 2015; U.S. Provisional Patent Application No. 62/209,246, filed on Aug. 24, 2015; U.S. Provisional Patent Application No. 62/233,915, filed on Sep. 28, 2015; U.S. Provisional Patent Application No. 62/324,293, filed on Apr. 18, 2016; and U.S. Provisional Patent Application No. 62/337,273, filed on May 16, 2016. The present application also claims priority to U.S. Provisional Patent Application No. 62/337,619, filed on May 17, 2016. All of these prior applications are hereby incorporated by reference in their entireties.

STATEMENT AS TO FEDERALLY SPONSORED RESEARCH

This invention was made with government support under Grant No. CA174121 awarded by the National Institutes of Health; National Cancer Institute and Grant No. HL110574 awarded by the National Institutes of Health; Heart, Lung, and Blood Institute. The government has certain rights in the invention.

BACKGROUND OF THE INVENTION

Isolation and enrichment of rare cells and particles from bodily fluids including blood, urine, saliva, mucous, semen, etc. can be used to understand the concentration, function, and genomic composition of the rare cells and particles and can provide information for diagnosing and treating diseases such as cancers. Given the low concentration of rare cells or particles within biological samples, some form of positive or negative selection or enrichment can be needed to detect and/or quantify rare cells or particles. An integrated, automated process that gently and uniformly processes cells and particles with virtually no cell loss is needed to achieve consistent reliable clinical information for diagnosing and treating disease.

SUMMARY OF THE INVENTION

Provided herein are systems and methods for isolating, separating, and/or enriching particles from a sample using multiple particle separation devices.

In one aspect, provided herein is a system comprising: (a) a first microfluidic channel configured to separate first particles of at least a critical size and second particles of less than the critical size based on sizes of the first particles and the second particles; and (b) a first magnet and a second magnet arranged adjacent to a first side of a second microfluidic channel, wherein the first magnet and second magnet are adjacent to each other, wherein a polarity of the first magnet is opposite a polarity of the second magnet, and wherein the first magnet is upstream of the second magnet in a flow direction of the second microfluidic channel.

In some cases, the first microfluidic channel and the second microfluidic channel are the same. In some cases, the first microfluidic channel and the second microfluidic channel are different. In some cases, the first microfluidic channel and the second microfluidic channel are in fluid communication. In some cases, the system further comprises a third magnet and a fourth magnet arranged adjacent to the second microfluidic channel on a second side of the second microfluidic channel opposite the first side, wherein a polarity of the third magnet is opposite a polarity of the fourth magnet, and wherein the third magnet is upstream of the fourth magnet in the flow direction of the second microfluidic channel. In some cases, the second microfluidic channel is formed in part by a tape or lid. In some cases, the first magnet and the second magnet each extend at least a width of the second microfluidic channel. In some cases, the system further comprises a first plurality of magnets arranged adjacent to the first side of the second microfluidic channel, wherein the first plurality of magnets extend at least a length of the second microfluidic channel. In some cases, the third magnet and the fourth magnet each extend at least a width of the second microfluidic channel. In some cases, the system further comprises a second plurality of magnets arranged adjacent to the second side of the second microfluidic channel, and wherein the second plurality of magnets extend at least a length of the second microfluidic channel. In some cases, the first magnet is aligned opposite to the third magnet, wherein the second magnet is aligned opposite to the fourth magnet, wherein the polarity of the first magnet is opposite the polarity of the third magnet, and wherein the polarity of the second magnet is opposite the polarity of the fourth magnet. In some cases, a configuration of the first magnet and the second magnet forms a Halbach array. In some cases, a configuration of the first plurality of magnets forms a Halbach array. In some cases, the system further comprises a third plurality of magnets stacked upon the first plurality of magnets. In some cases, the second plurality of magnets is configured such that a flow of the sample through the second microfluidic channel is perpendicular to each magnet of the first set of magnets. In some cases, the magnetic separator is configured to retain particles with magnetically susceptible labels and allow particles without magnetically susceptible labels to pass through. In some cases, a length of the second microfluidic channel is between about 10 millimeters and about 150 millimeters. In some cases, a width of the second microfluidic channel is constant along a length of the second microfluidic channel. In some cases, a width of the second microfluidic channel increases or decreases along at least a portion of a length of the second microfluidic channel. In some cases, the width of the second microfluidic channel increases, and wherein the increase in the width of the second microfluidic channel is a gradual increase or a step increase. In some cases, the width of the second microfluidic channel decreases, and wherein the decrease in the width of the second microfluidic channel is a gradual decrease or a step decrease. In some cases, the width of the second microfluidic channel at any point along the length of the second microfluidic channel is between about 200 µm and about 1600 µm. In some cases, wherein a depth of the second microfluidic channel increases or decreases proportionally with a width of the second microfluidic channel such that a flow rate of a sample through the second microfluidic channel is constant. In some cases, the depth of the second microfluidic channel increases, wherein the increase in the depth of the second microfluidic channel is a gradual increase or a step increase, or wherein the depth of the second microfluidic channel decreases, wherein the decrease in the depth of the second microfluidic channel is a gradual decrease or a step decrease. In some cases, a depth of the second microfluidic channel is constant along a length of the second microfluidic channel. In some cases, a depth of the second microfluidic channel increases or decreases along at least a portion of a length of the second microfluidic channel. In some cases, the depth of the second microfluidic channel at any point along a length of the second microfluidic channel is between about 100 µm and about 800 µm. In some cases, the system further comprises one or more support posts protruding from a base of the second microfluidic channel, wherein a height of each support post is equal to a height of the second microfluidic channel at a location of the support post along the second microfluidic channel, and wherein the one or more support posts contact a substrate, thereby preventing collapse of the substrate into the second microfluidic channel. In some cases, the one or more support posts are disposed along a center of the second microfluidic channel, and wherein the one or more support posts are evenly spaced along the center of the second microfluidic channel. In some cases, the system is capable of generating a magnetic field strength of at least 0.5 Tesla. In some cases, the strength of the magnetic field increases along a length of the second microfluidic channel.

In another aspect, disclosed herein is a method comprising passing a sample comprising first particles of at least a critical size and second particles less than the critical size through the system disclosed herein.

In some cases, the method further comprises contacting the sample with a chelating agent. In some cases, the sample comprises at least one white blood cell and at least one tumor cell, and wherein contacting the sample with a chelating agent prevents or reduces trogocytosis. In some cases, the sample comprises at least one white blood cell and at least one tumor cell, and wherein contacting the sample with the chelating agent prevents or reduces non-specific binding of the magnetically susceptible labels to the at least one white blood cell or the at least one tumor cell. In some cases, the first particles comprise at least one of white blood cells or tumor cells. In some cases, passing the first particles and the second particles comprises passing the sample through a deterministic lateral displacement (DLD) array. In some cases, the method further comprises passing a buffer into the system.

In another aspect, disclosed herein is a system for separating particles in a sample, the system comprising: (a) a first array of obstacles, wherein the first array of obstacles is configured to allow first particles of at least a first critical size to flow in a first direction and second particles of less than the first critical size to flow in a second direction different from the first direction, and wherein the first critical size is less than 3 µm; and (b) a magnetic separator configured to separate particles with magnetically susceptible labels from particles without magnetically susceptible labels, wherein the first array of obstacles is fluidically connected with the magnetic separator.

In some cases, the first critical size is no more than 1500 nm. In some cases, the second particles comprise one or more of micro-vesicles, bacteria, or protein aggregates. In some cases, the first critical size is no more than 200 nm. In some cases, the second particles comprise exosomes. In some cases, the first critical size is no more than 50 nm. In some cases, the second particles comprise nucleosomes. In some cases, the second particles comprise RNA or cell-free DNA. In some cases, the system further comprises a second array of obstacles, wherein the second array of obstacles is configured to allow third particles of at least a second critical size to flow in a third direction and fourth particles of less than the second critical size to flow in a fourth direction different from the third direction, wherein the second critical size is less than the first critical size, and wherein the second array of obstacles is fluidically connected with the first array of obstacles and the magnetic separator. In some cases, the second critical size is no more than 200 nm. In some cases, the fourth particles comprise exosomes. In some cases, the system further comprises a third array of obstacles, wherein the third array of obstacles is configured to allow fifth particles of at least a third critical size to flow in a fifth direction and sixth particles of less than the third critical size to flow in a sixth direction different from the fifth direction, wherein the third critical size is less than the second critical size, and wherein the third array of obstacles is fluidically connected with the first array of obstacles, the second array of obstacles, and the magnetic separator. In some cases, the third critical size is no more than 50 nm. In some cases, the sixth particles comprise nucleosomes. In some cases, the second particles comprise RNA or cell-free DNA. In some cases, the system further comprises a fourth array of obstacles, wherein the fourth array of obstacles is configured to allow seventh particles of at least a fourth critical size to flow in a seventh direction and eighth particles of less than the fourth critical size to flow in a eighth direction different from the seventh direction, wherein the fourth critical size is larger than the first critical size, and wherein the fourth array of obstacles is fluidically connected with the first array of obstacles. In some cases, the fourth critical size is no more than 5 µm. In some cases, the eighth particles comprise red blood cells. In some cases, the fourth critical size is no more than 20 µm. In some cases, the seventh particles comprise cell aggregates. In some cases, the system further comprises a filter, wherein the filter is configured to capture particles or particle aggregates larger than a pore size of the filter and allow particles or particle aggregates of no larger than the pore size to pass through, and wherein the filter is fluidically connected with the first array of obstacles. In some cases, the pore size is no more than 20 µm. In some cases, the system further comprises a particle sensor. In some cases, the particle sensor is fluidically connected with the first array of obstacles and the magnetic separator. In some cases, the particle sensor is a laser light scattering device, a fluorescence senor, or an impedance sensor. In some cases, the laser light scattering device is configured to generate a forward scattered beam and an orthogonal scattered beam, wherein the forward scattered beam and the orthogonal scattered beam are orthogonal to a flow stream containing the particles. In some cases, the laser light scattering device comprises a glass cuvette configured to scatter a laser beam generated by the laser light scattering device. In some cases, the laser light scattering device comprises molded layers configured to scatter a laser beam generated by the laser light scattering device. In some cases, the system further comprises a fluorescence-based particle separator configured to separate particles with fluorescent labels. In some cases, the fluorescence-based particle separator is fluidically connected with the first array of obstacles and the magnetic separator. In some cases, the fluorescence-based particle separator is a flow cytometer. In some cases, the magnetic separator is configured to retain particles with magnetically susceptible labels and allow particles without magnetically susceptible labels to pass through. In some cases, the magnetic separator is configured to separate particles with magnetically susceptible labels from particles without magnetically susceptible labels when the particles with magnetically susceptible labels and the particles without magnetically susceptible labels flow through the first array of obstacles. In some cases, the sample is in a solution comprising an anticoagulant. In some cases, the sample is in a solution comprising Kolliphor EL. In some cases, the magnetic separator is capable of generating a magnetic field of at least 0.5 Tesla. In some cases, the magnetic separator is configured to separate particles whose magnetic susceptibility is equal to or above a critical value from particles whose magnetic susceptibility is below the critical value. In some cases, the system further comprises a fluidic balancer, wherein the fluidic balancer is configured to maintain stability of a flow stream containing the particles. In some cases, the fluidic balancer is configured to generate a back flow of the flow stream containing the particles. In some cases, surfaces of two adjacent obstacles in a row of the array of obstacles define a gap, wherein the two adjacent obstacles defining the gap have a polygonal cross-section, and wherein a vertex of each of the two adjacent obstacles with the polygonal cross-section points toward each other in a direction substantially perpendicular to a flow direction of the sample through the array of obstacles.

In another aspect, disclosed herein is a method for separating particles in a sample, the method comprising: (a) providing a sample comprising first particles of at least a first critical size and second particles less than the first critical size; (b) passing the sample through a first array of obstacles, wherein the first array of obstacles allows the first particles to move in a first direction and the second particles to move in a second direction different from the first direction, and wherein the first critical size is less than 3 µm, thereby separating the first particles and the second particles; and (c) passing the sample through to a magnetic separator, wherein the magnetic separator is configured to separate particles with magnetically susceptible labels from particles without magnetically susceptible labels.

In some cases, the second particles comprise third particles and fourth particles, and the method further comprises labeling the third particles with magnetically susceptible labels. In some cases, surfaces of two adjacent obstacles in a row of the array of obstacles define a gap, wherein the two adjacent obstacles defining the gap have a polygonal cross-section, and wherein a vertex of each of the two adjacent obstacles with the polygonal cross-section points toward each other in a direction substantially perpendicular to a flow direction of the sample through the array of obstacles. the magnetic separator is fluidically connected with the array of obstacles, wherein i) the third particles and the fourth particles are subgroups of the first particles, or ii) the third particles and the fourth particles are subgroups of the second particles, and wherein the third particles comprise magnetically susceptible labels, and the fourth particles do not comprise magnetically susceptible labels, thereby separating the third particles and the fourth particles.

In another aspect, disclosed herein is a composition comprising two or more of: a nonsteroidal anti-inflammatory drug (NTHE), a dihydroxybenzoic acid (DHBA), a nucleoside, and a thienopyridine.

In some cases, the composition comprises the nucleoside, and the nucleoside is a ribonucleoside or a deoxyribonucleoside. In some cases, the composition comprises the nucleoside, and the nucleoside is selected from the group consisting of inosine, adenosine, and a derivative thereof. In some cases, the composition comprises the nucleoside, and the nucleoside is selected from the group consisting of cytidine, uridine, guanosine, thymidine, 5-methyl uridine, deoxyinosine, deoxyadenosine, deoxycytidine, deoxyuridine, deoxyguanosine, deoxythymidine, a derivative thereof, and a combination thereof. In some cases, the composition comprises the thienopyridine, and the thienopyridine is ticlopidine or a derivative thereof. In some cases, the composition comprises the thienopyridine, and the thienopyridine is selected from the group consisting of prasugrel, clopidogrel, and a derivative thereof. In some cases, the composition comprises the NTHE, and the NTHE is acetylsalicylic acid or a derivative thereof. In some cases, the NTHE is selected from the group consisting of choline, magnesium salicylates, choline salicylate, celecoxib, diclofenac potassium, diclofenac sodium, diclofenac sodium, misoprostol, diflunisal, etodolac, fenoprofen calcium, flurbiprofen, ibuprofen, indomethacin, ketoprofen, magnesium salicylate, meclofenamate sodium, mefenamic acid, meloxicam, nabumetone, naproxen, naproxen sodium, oxaprozin, piroxicam, rofecoxib, salsalate, sodium salicylate, sulindac, tolmetin sodium, valdecoxib, and a derivative thereof. In some cases, the composition comprises the DHBA, and the DHBA is protocatechuic acid or a derivative thereof. In some cases, the composition comprises the DHBA, and the DHBA is selected from the group consisting of 2-gentisic acid, hypogallic acid, Pyrocatechuic acid, α-Resorcylic acid, β-Resorcylic acid, γ-resorcylic acid, a derivative thereof, and a combination thereof. In some cases, the composition comprises a liquid composition, or a gel. In some cases, the composition comprises the liquid composition, and the liquid composition comprises about 4 millimolar of the nucleoside. In some cases, the composition comprises the liquid composition, wherein the liquid composition comprises from about 100 micromolar to about 200 micromolar of the thienopyridine. In some cases, the composition comprises the liquid composition, wherein the liquid composition comprises from about 0.5 micromolar to about 1 millimolar of the NTHE. In some cases, the composition comprises the liquid composition, wherein the liquid composition comprises between about 50 micromolar and 100 micromolar of the DHBA. In some cases, the composition further comprises a chelating agent. In some cases, the chelating agent is selected from the group consisting of ethylenediaminetetraacetic acid (EDTA) and Ethyleneglycoltetraacetic acid (EGTA). In some cases, the composition further comprises an excipient. In some cases, the excipient is selected from the group consisting of water, ethanol, phosphate buffered saline (PBS), dimethyl sulfoxide (DMSO), saline, Ringer's solution, dextrose, glucose, sucrose, dextran, mannose, mannitol, sorbitol, polyethylene glycol (PEG), phosphate, acetate, gelatin, polyacrylic acid, and vegetable oil.

In another aspect, disclosed herein is a method comprising: (a) obtaining a biological sample from a subject; and (b) contacting the biological sample with any composition disclosed herein.

In some cases, the contacting reduces or prevents platelet activation in the sample. In some cases, the platelet activation is induced by at least one of blood transport, transport through a deterministic lateral displacement (DLD) microfluidic device, temperature variation, or cancer-associated blood factors. In some cases, the biological sample comprises white blood cells, and contacting the biological sample with the chelating agent reduces trogocytosis in the biological sample. In some cases, the method further comprises contacting the sample with any composition disclosed herein.

In another aspect, disclosed herein is a system for enriching particles in a sample, the system comprising: (a) a first array of obstacles configured to allow first particles of at least a critical size to flow in a first direction to a first outlet and second particles of less than the critical size to flow in a second direction to a second outlet, wherein the critical size is less than 5 µm, and wherein the first particles comprise third particles with magnetically susceptible labels and fourth particles without magnetically susceptible labels;

(b) a magnetic separator fluidically connected to the first outlet, wherein the magnetic separator is configured to separate fourth particles from the third particles; and (c) a concentrator fluidically connected to the magnetic separator, wherein the concentrator is a microfluidic channel comprising an inlet, a second array of obstacles, a product outlet, and a waste outlet, wherein the second array of obstacles is configured to deflect the fourth particles so that the fourth particles flow through the product outlet in a solution at a higher concentration compared to in the sample.

In some cases, the sample is blood. In some cases, the third particles comprise particles with extrinsic magnetically susceptible labels, particles with intrinsic magnetically susceptible labels, or a combination thereof. In some cases, the third particles comprise particles with intrinsic magnetically susceptible labels. In some cases, the particles with intrinsic magnetically susceptible labels are red blood cells. In some cases, the third particles comprise particles with extrinsic magnetically susceptible labels. In some cases, the particles with extrinsic magnetically susceptible labels are white blood cells labeled with extrinsic magnetically susceptible labels. In some cases, the white blood cells are labeled with extrinsic magnetically susceptible labels through an antibody. In some cases, the antibody is an anti-CD45 antibody or an anti-CD66b antibody. In some cases, the fourth particles are rare cells. In some cases, the rare cells are circulating tumor cells. In some cases, the system further comprises a mixing module.

In another aspect, disclosed herein is a method for enriching particles in a sample, the method comprising: (a) mixing the sample with magnetically susceptible labels whereby first particles in the sample are labeled with the magnetically susceptible labels; (b) passing the sample through a first array of obstacles, wherein the first array of obstacles is configured to allow second particles of at least a critical size to flow in a first direction to a first outlet and third particles of less than the critical size to flow in a second direction to a second outlet, wherein the critical size is less than 3 µm, and wherein the second particles comprise (i) first particles labeled with magnetically susceptible labels from a), (ii) fourth particles without magnetically susceptible labels; (c) passing the second particles through a magnetic separator, thereby separating the first particles from the fourth particles; (d) concentrating the fourth particles with a concentrator, wherein the concentrator is a microfluidic channel comprising an inlet, a second array of obstacles, a product outlet, and a waste outlet, wherein the second array of obstacles is configured to deflect the fourth particles so that the fourth particles flow through the product outlet in a solution at a higher concentration compared to in the sample.

In another aspect, disclosed herein is a system for separating particles in a sample, the system comprising: a) a de-clump device; b) a first array of obstacles, wherein the first array of obstacles is configured to allow first particles of at least a first critical size to flow in a first direction and second particles of less than the first critical size to flow in a second direction different from the first direction, and wherein the first critical size is no greater than 5 µm; c) a second array of obstacles, wherein the second array of obstacles is configured to allow third particles of at least a second critical size to flow in a third direction and fourth particles of less than the second critical size to flow in a fourth direction different from the third direction, and wherein the second critical size is no greater than 1.5 µm; d) a magnetic separator configured to separate particles with magnetically susceptible labels; e) a particle dispenser, wherein the de-clump device, first array of obstacles, the second array of obstacles, the magnetic separator, and the particle dispenser are fluidically connected. In some cases, the de-clump device is a filter. In some cases, the filter is configured to capture particles or particle aggregates larger than a pore size of the filter and allow particles or particle aggregates of no larger than the pore size to pass through. In some cases, the pore size is no more than 20 µm. In some cases, the system further comprises a third array of obstacles, wherein the third array of obstacles is configured to allow fifth particles of at least a third critical size to flow in a fifth direction and sixth particles of less than the third critical size to flow in a sixth direction different from the third direction, wherein the third critical size is less than the second critical size, and wherein the third array of obstacles is fluidically connected with the second array of obstacles and the magnetic separator. In some cases, the third critical size is no more than 200 nm. In some cases, the fourth particles are exosomes. In some cases, the system further comprises a fourth array of obstacles, wherein the fourth array of obstacles is configured to allow seventh particles of at least a fourth critical size to flow in a seventh direction and eighth particles of less than the fourth critical size to flow in a eighth direction different from the seventh direction, wherein the fourth critical size is less than the third critical size, and wherein the fourth array of obstacles is fluidically connected with the third array of obstacles. In some cases, the fourth critical size is no more than 50 nm. In some cases, the seventh particles are nucleosomes. In some cases, the eighth particles are RNA or cell-free DNA. In some cases, the particle dispenser is a single cell dispenser. In some cases, the first particles comprise white blood cells and rare cells. In some cases, the second particles comprise red blood cells. In some cases, the sample is blood. In some cases, further comprising an analytical device In another aspect, disclosed herein is a system for separating particles in a sample, the system comprising: a) a first array of obstacles, wherein the first array of obstacles is configured to allow first particles of at least a first critical size to flow in a first direction and second particles of less than the first critical size to flow in a second direction different from the first direction, and wherein the first critical size is less than 3 µm; b) a magnetic separator configured to separate particles with magnetically susceptible labels from particles without magnetically susceptible labels, wherein the first array of obstacles is fluidically connected with the magnetic separator. In some cases, the first critical size is no more than 1500 nm. In some cases, the second particles comprise micro-vesicles, bacteria, and protein aggregates. In some cases, the first critical size is no more than 200 nm. In some cases, the second particles are exosomes. In some cases, the first critical size is no more than 50 nm. In some cases, the second particles are nucleosomes. In some cases, the second particles are RNA or cell-free DNA. In some cases, the system further comprises a second array of obstacles, wherein the second array of obstacles is configured to allow third particles of at least a second critical size to flow in a third direction and fourth particles of less than the second critical size to flow in a fourth direction different from the third direction, wherein the second critical size is less than the first critical size, and wherein the second array of obstacles is fluidically connected with the first array of obstacles and the magnetic separator. In some cases, the second critical size is no more than 200 nm. In some cases, the fourth particles are exosomes. In some cases, the system further comprises a third array of obstacles, wherein the third array of obstacles is configured to allow fifth particles of at least a third critical size to flow in a fifth direction and sixth particles of less than the third critical size to flow in a sixth direction different from the fifth direction, wherein the third critical size is less than the second critical size, and wherein the third array of obstacles is fluidically connected with the first array of obstacles, the second array of obstacles, and the magnetic separator. In some cases, the third critical size is no more than 50 nm. In some cases, the sixth particles are nucleosomes. In some cases, the second particles are RNA or cell-free DNA. In some cases, the system further comprises a fourth array of obstacles, wherein the fourth array of obstacles is configured to allow seventh particles of at least a fourth critical size to flow in a seventh direction and eighth particles of less than the fourth critical size to flow in a eighth direction different from the seventh direction, wherein the fourth critical size is larger than the first critical size, and wherein the fourth array of obstacles is fluidically connected with the first array of obstacles. In some cases, the fourth critical size is no more than 5 µm. In some cases, the eighth particles are red blood cells. In some cases, the fourth critical size is no more than 20 µm. In some cases, the seventh particles are cell aggregates. In some cases, further comprising a filter, wherein the filter is configured to capture particles or particle aggregates larger than a pore size of the filter and allow particles or particle aggregates of no larger than the pore size to pass through, and wherein the filter is fluidically connected with the first array of obstacles. In some cases, the pore size is no more than 20 µm. In some cases, the system further comprises a particle sensor. In some cases, the particle sensor is fluidically connected with the first array of obstacles and the magnetic separator. In some cases, the particle sensor is a laser light scattering device, a fluorescence senor, or an impedance sensor. In some cases, the laser light scattering device is configured to generate a forward scattered beam and an orthogonal scattered beam, wherein the forward scattered beam and the orthogonal scattered beam are orthogonal to a flow stream containing the particles. In some cases, the laser light scattering device comprises a glass cuvette configured to scatter a laser beam generated by the laser light scattering device. In some cases, the laser light scattering device comprises molded layers configured to scatter a laser beam generated by the laser light scattering device. In some cases, the system further comprises a fluorescence-based particle separator configured to separate particles with fluorescent labels. In some cases, the fluorescence-based particle separator is fluidically connected with the first array of obstacles and the magnetic separator. In some cases, the fluorescence-based particle separator is a flow cytometer. In some cases, the magnetic separator is configured to retain particles with magnetically susceptible labels and allow particles without magnetically susceptible labels to pass through. In some cases, the magnetic separator is configured to separate particles with magnetically susceptible labels from particles without magnetically susceptible labels when the particles with magnetically susceptible labels and the particles without magnetically susceptible labels flow through the first array of obstacles. In some cases, the sample is in a solution comprising an anticoagulant. In some cases, the sample is in a solution comprising Kolliphor EL. In some cases, the magnetic separator is capable of generating a magnetic field of at least 0.5 Tesla. In some cases, the magnetic separator is configured to separate particles whose magnetic susceptibility is equal to or above a critical value from particles whose magnetic susceptibility is below the critical value. In some cases, the system further comprises comprising a fluidic balancer, wherein the fluidic balancer is configured to maintain stability of a flow stream containing the particles. In some cases, the fluidic balancer is configured to generate a back flow of the flow stream containing the particles.

In another aspect, disclosed herein is a particle dispenser comprising: a) a fluidic duct configured to allow particles to flow into the fluid duct in a flow stream, and wherein the fluidic duct comprises a sensing zone; b) a sensor, wherein the sensor generates a signal when a particle of interest arrives in the sensing zone; c) a switch configured to receive the signal; d) a capture tube, wherein the capture tube is movable between a first position and a second position, wherein the capture tube is not fluidically connected with the fluidic duct at the first position, and is fluidically connected with the fluidic duct at the second position, wherein the capture tube remains at the first position unless is driven by the switch, wherein the switch drives the capture tube from the first position to the second position after receiving the signal; e) a pressure source configured to flush an air flow to the capture tube after the capture tube catches the particle of interest. In some cases, the particle of interest comprises a label. In some cases, the label is a fluorescent label or a magnetically susceptible label. In some cases, the signal is generated when the sensor detects the label. In some cases, the particle of interest causes impedance when passing the sensing zone, and the signal is generated when the sensor detects the impedance. In some cases, the particle dispenser is on a microfluidic device. In some cases, the capture tube is configured to catch the particle of interest with a plug of fluid from the flow stream. In some cases, the plug of fluid has a volume no more than 450 µL. In some cases, the capture tube is configured to move to the first position after the particle of interest passes into the capture tube. In some cases, the system further comprises a particle collector, wherein the dispenser is configured to dispense the particle of interest to the particle collector after passing into the capture tube. In some cases, the particle collector is a cell culture dish, a microscope slide, or a microliter plate. In some cases, the sensor is configured not to generate the signal when the capture tube is not at the first position. In some cases, the sensor is configured not to generate the signal when the particle of interest is in the capture tube.

In another aspect, disclosed herein is a system for separating particles in a sample, the system comprising: a) a first array of obstacles, wherein the first array of obstacles is configured to allow first particles of at least a first critical size to flow in a first direction and second particles of less than the first critical size to flow in a second direction different from the first direction, and wherein the first critical size is less than 3 µm; and b) a fluorescence-based particle separator configured to separate particles with first fluorescent labels from particles of second fluorescent labels or particles without fluorescent labels, wherein the first array of obstacles is fluidically connected with the fluorescence-based separator. In some cases, the fluorescence-based particle separator is a flow cytometer. In some cases, the system further comprises a particle dispenser. In some cases, the particle dispenser is fluidically connected with the fluorescence-based particle separator. In some cases, the particle dispenser is a single cell dispenser.

In another aspect, disclosed herein is a method for separating particles in a sample, the method comprising: a) providing a sample comprising first particles of at least a first critical size and second particles less than the first critical size; b) passing the sample through a first array of obstacles, wherein the first array of obstacles allows the first particles to move in a first direction and the second particles to move in a second direction different from the first direction, and wherein the first critical size is less than 3 µm, thereby separating the first particles and the second particles; c) passing third particles and fourth particles to a magnetic separator, wherein the magnetic separator is configured to separate particles with magnetically susceptible labels from particles without magnetically susceptible labels, wherein the magnetic separator is fluidically connected with the first array of obstacles, and wherein the third particles comprise magnetically susceptible labels, and the fourth particles do not comprise magnetically susceptible labels, thereby separating the third particles and the fourth particles, wherein i) the third particles and the fourth particles are subgroups of the first particles, ii) the third particles and the fourth particles are subgroups of the second particles, iii) the first particles and the second particles are subgroups of the third particles, or iv) the first particles and the second particles are subgroups of the fourth particles. In some cases, the second particles comprise red blood cells. In some cases, the third particles comprise red blood cells. In some cases, the first critical size is no more than 1500 nm. In some cases, the second particles are micro-vesicles or proteins. In some cases, the first critical size is no more than 200 nm. In some cases, the second particles are exosomes. In some cases, the first critical size is no more than 50 nm. In some cases, the second particles are nucleosomes. In some cases, the second particles are RNA or cell-free DNA. In some cases, the sample is blood. In some cases, the system further comprises passing the sample through a second array of obstacles, wherein the second array of obstacles is configured to allow fifth particles of at least a second critical size to flow in a third direction and sixth particles of less than the second critical size to flow in a fourth direction different from the third direction, wherein the second critical size is less than the first critical size, and wherein the second array of obstacles is fluidically connected with the first array of obstacles and the magnetic separator. In some cases, the sixth particles are a subgroup of the second particles, and wherein the third particles or the fourth particles are a subgroup of the sixth particles. In some cases, the second critical size is no more than 200 nm. In some cases, the second particles are exosomes. In some cases, the system further comprises passing the sample through a third array of obstacles, wherein the third array of obstacles is configured to allow seventh particles of at least a third critical size to flow in a fifth direction and eighth particles of less than the third critical size to flow in a sixth direction different from the fifth direction, the third critical size is less than the second critical size, and wherein the third array of obstacles is fluidically connected with the first array of obstacles, the second array of obstacles, and the magnetic separator. In some cases, the eighth particles are a subgroup of the sixth particles, and the third particles or the fourth particles are a subgroup of the sixth particles. In some cases, the third critical size is no more than 50 nm. In some cases, the second particles are nucleosomes. In some cases, the second particles are RNA or cell-free DNA. In some cases, the system further comprises, before step a), passing the sample through a fourth array of obstacles, wherein the fourth array of obstacles is configured to allow ninth particles of at least a fourth critical size to flow in a seventh direction and tenth particles of less than the fourth critical size to flow in a eighth direction different from the sixth direction, the fourth critical size is larger than the first critical size, and wherein the fourth array of obstacles is fluidically connected with the first array of obstacles. In some cases, the fourth critical size is no more than 5 µm. In some cases, the tenth particles are red blood cells. In some cases, the fourth critical size is no more than 20 µm. In some cases, the tenth particles are cell aggregates. In some cases, the method further comprises detecting one or more particles in the sample using a particle sensor. In some cases, the particle sensor is a later light scattering device, a fluorescence senor, or an impedance sensor. In some cases, the method further comprises separating particles in the sample using a fluorescence-based particle separator configured to separate particles with fluorescent labels. In some cases, the fluorescence-based particle separator is a flow cytometer. In some cases, the method further comprises capturing particles using a filter, wherein the filter is configured to capture particles or particle aggregates larger than a pore size of the filter and allow particles or particle aggregates equal or less than the pore size to pass through, and wherein the filter is fluidically connected with the first array of obstacles. In some cases, the pore size is no more than 20 µm. In some cases, the magnetic separator retains particles with magnetically susceptible labels from the sample when the sample flowing through the first array of obstacles. In some cases, the method further comprises detecting one or more particles in the sample using a particle sensor. In some cases, the particle sensor is a later light scattering device, a fluorescence senor, or an impedance sensor. In some cases, the magnetic separator is configured to retain particles with magnetically susceptible labels and allow particles without magnetically susceptible labels to pass through, thereby retaining the third particles in the magnetic separator and allowing the fourth particles to pass through the magnetic separator, wherein i) the third particles and the fourth particles are subgroups of the first particles, ii) the third particles and the fourth particles are subgroups of the second particles, or iii) the first particles and the second particles are subgroups of the fourth particles. In some cases, the magnetic separator is configured to separate particles with magnetically susceptible labels from particles without magnetically susceptible labels when the particles with magnetically susceptible labels and the particles without magnetically susceptible labels flowing through the first array of obstacles, wherein the magnetic separator separates third particles and fourth particles, and wherein the third particles comprise magnetically susceptible labels and the fourth particles do not comprise magnetically susceptible labels. In some cases, the third particles and the fourth particles are subgroups of the first particles. In some cases, the third particles and the fourth particles are subgroups of the second particles. In some cases, the first particles and the second particles are subgroups of the third particles. In some cases, the first particles and the second particles are subgroups of the fourth particles. In some cases, the sample is in a solution comprising an anticoagulant. In some cases, the sample is in a solution comprising Kolliphor EL. In some cases, the magnetic separator is capable of generating a magnetic field of at least 0.5 Tesla. In some cases, the sample is passed through the first array of obstacles at a flow rate of at least 240 µL/min.

In another aspect, disclosed herein is a method for separating particles in a sample, the method comprising: a) labeling one or more particles in a sample with labels, wherein each of the one or more labeled particles is labeled with a first label and a second label, wherein the first label and the second label are different, and wherein the sample comprises first particles of at least a first critical size and second particles less than the first critical size; b) passing the sample through a first array of obstacles, wherein the first array of obstacles allows the first particles to flow in a first direction and the second particles to flow in a second direction different from the first direction, thereby separating the first particles and the second particles; c) passing third particles and fourth particles into a magnetic separator, wherein the magnetic separator is configured to separate particles with magnetically susceptible labels from particles without magnetically susceptible labels, wherein the magnetic separator is fluidically connected with the first array of obstacles, and wherein the third particles comprise magnetically susceptible labels and the fourth particles do not comprise magnetically susceptible labels, thereby separating the third particles and the fourth particles, wherein i) the third particles and the fourth particles are subgroups of the first particles, ii) the third particles and the fourth particles are subgroups of the second particles, iii) the first particles and the second particles are subgroups of the third particles, or iv) the first particles and the second particles are subgroups of the fourth particles. In some cases, the first label and the second label recognize a marker on one of the labeled particles. In some cases, the first label is a fluorescent label and the second label is a magnetically susceptible label. In some cases, the first label recognizes a first marker and the second label recognizes a second marker, and wherein the first marker and the second marker are different. In some cases, the first label comprises a first antibody, and wherein the second label comprises a second antibody. In some cases, the one or more labeled particles are cells. In some cases, the one or more particles are cells and the marker is a cell surface protein. In some cases, the one or more particles are cells, and wherein the first marker is a first cell surface protein on the cells and the second marker is a second cell surface protein on the cells. In some cases, the first label and the second label are magnetically susceptible labels. In some cases, the first magnetically susceptible label and the second magnetically susceptible label have different magnetically susceptibilities. In some cases, the method further comprises passing the sample through a second array of obstacles, wherein the second array of obstacles is configured to allow fifth particles of at least a second critical size to flow in a third direction and sixth particles of less than the second critical size to flow in a fourth direction different from the third direction, wherein the second critical size is less than the first critical size, wherein the second array of obstacles is fluidically connected with the first array of obstacles and the magnetic separator. In some cases, the sixth particles are a subgroup of the second particles, and wherein the third particles or the fourth particles are a subgroup of the sixth particles.

In another aspect, disclosed herein is a method for dispensing a particle of interest, the method comprising: a) providing a sample comprising a particle of interest; b) passing the sample into a fluidic duct in a flow stream, wherein the fluidic duct comprises a sensing zone; c) detecting the particle of interest using a sensor, wherein the sensor generates a signal when the particle of interest arrives the sensing zone; d) moving a capture tube from a first position to a second position, wherein the capture tube is movable between the first position and the second position, wherein the capture tube is not fluidically connected with the fluidic duct at the first position and is fluidically connected with the fluidic duct at the second position, wherein the moving is driven by a switch configured to drive the capture tube from the first position to the second position after receiving the signal, and wherein the capture tube remains at the first position unless is driven by the switch, thereby catching the particle of interest from the fluidic duct into the capture tube; e) flushing an air flow to the capture tube after the particle of interest passes into the capture tube, and wherein the air flow flushed by a pressure source. In some cases, the particle of interest comprises a label. In some cases, the label is a fluorescent label or a magnetically susceptible label. In some cases, the signal is generated when the sensor detects the label. In some cases, the particle of interest causes impedance when passing the sensing zone, and the signal is generated when the sensor detects the impedance. In some cases, the particle dispenser is on a microfluidic chip. In some cases, the capture tube is configured to catch the particle of interest with a plug of fluid from the flow stream. In some cases, the plug of fluid has a volume no more than 450 µL. In some cases, the capture tube is configured to return to the first position after capturing the particle of interest. In some cases, the method further comprising collecting the particle of interest to a particle collector, wherein the particle of interest is dispensed to the particle collector after passing into the capture tube. In some cases, the particle collector is a cell culture dish, a microscope slide, or a microliter plate.

In another aspect, provided herein is a method for concentrating particles of at least a critical size in a sample, the method comprising: flowing the sample through a microfluidic channel comprising a first inlet, one or more arrays of obstacles, a product outlet, and a waste outlet, wherein the sample is flowed from the first inlet to the plurality of outlets, wherein the one or more arrays of obstacles is configured to deflect the particles of at least the critical size in a first direction so that the particles of at least the critical size flow through the product outlet in a solution, thereby concentrating the particles of at least the critical size by greater than 50 folds in the solution compared to in the sample. In some cases, the method further comprises flowing a buffer through the microfluidic channel, thereby filling the one or more arrays with the buffer. In some cases, the sample comprises particles of less than the critical size, and the one or more arrays deflect the particles of less than the critical size to a second direction so that the particles of less than the critical size flow through the waste outlet. In some cases, the microfluidic channel is filled with the buffer is flowing through the microfluidic channel. In some cases, the microfluidic channel comprises no more than one inlet, and the buffer is flowed in the first inlet. In some cases, the microfluidic device comprises a second inlet, and wherein the buffer is flowed into the microfluidic device through the second inlet. In some cases, the microfluidic channel comprises one array of obstacles. In some cases, the microfluidic channel comprises two arrays of obstacles. In some cases, the two arrays of obstacles are mirrored arrays. In some cases, the microfluidic channel further comprises a bypass channel connected to the product outlet. In some cases, the one or more arrays of obstacles is configured to deflect the particles of at least the critical size to the bypass channel connected to the product outlet. In some cases, the microfluidic channel comprises two arrays of obstacles, and the bypass channel is between the two arrays of obstacles. In some cases, concentration of the particles of at least the critical size in the solution is at least twice of concentration of the particles of at least the critical size in the sample. In some cases, the microfluidic channel comprises no more than one flow stream flowing through the microfluidic channel. In some cases, the method further comprises injecting an air plug through the microfluidic channel after the flowing the sample through the microfluidic channel. In some cases, the particles of at least the critical size are cells. In some cases, the cells are rare cells. In some cases, the rare cells are circulating tumor cells.

In another aspect, provided herein is a system for separating particles in a sample, the system comprising: a) an array of obstacles configured to allow first particles of at least a critical size to flow in a first direction to a first outlet and second particles of less than the critical size to flow in a second direction to a second outlet, wherein the critical size is less than 3 μm, and wherein the second particles comprise third particles labeled with magnetically susceptible labels and fourth particles without magnetically susceptible labels; b) a magnetic separator fluidically connected to the second outlet, wherein the magnetic separator is configured to separate the third particles from the fourth particles. In some case, the sample is blood. In some case, the first particles comprise red blood cells, white blood cells, rare cells or a combination thereof. In some case, the third particles are labeled with magnetically susceptible labels through an antibody or a polynucleotide. In some case, the third particles comprise exosomes, platelets, microvesicles, or a combination thereof. In some case, the third particles comprise exosomes. In some case, the exosomes are from tumor specific cells. In some case, the exosomes from tumor specific cells are labeled with magnetically susceptible labels through an anti-CD44 antibody. In some case, the exosomes are from T cells. In some case, the exosomes from T cells are labeled with magnetically susceptible labels through an anti-CD3 antibody. In some case, the exosomes are from B cells. In some case, the exosomes from B are labeled with magnetically susceptible labels through an anti-CD19 antibody. In some case, the exosomes are from stem cells. In some case, the exosomes from stem cells are labeled with magnetically susceptible labels through an anti-CD34 antibody. In some case, the exosomes are labeled with magnetically susceptible labels through an anti-CD63 antibody. In some case, the third particles comprise platelets. In some case, the platelets are labeled with magnetically susceptible labels through an anti-CD41 antibody. In some case, the fourth particles comprise nucleosomes, cell-free DNA, or a combination thereof. In some case, the fourth particles comprise cell-free DNA. In some case, the cell-free DNA is circulating tumor DNA. In some case, the system further comprises an analyzer of the cell-free DNA. In some case, the analyzer is a sequencer. In some case, the critical size is less than 1.5 μm.

In another aspect, provided herein is a system for enriching particles in a sample, the system comprising a) a first array of obstacles configured to allow first particles of at least a critical size to flow in a first direction to a first outlet and second particles of less than the critical size to flow in a second direction to a second outlet, wherein the critical size is less than 5 μm, and wherein the first particles comprise third particles with magnetically susceptible labels and fourth particles without magnetically susceptible labels; b) a magnetic separator fluidically connected to the first outlet, wherein the magnetic separator is configured to separate fourth particles from the third particles; c) a concentrator fluidically connected to the magnetic separator, wherein the concentrator is a microfluidic channel comprising an inlet, a second array of obstacles, a product outlet, and a waste outlet, wherein the second array of obstacles is configured to deflect the fourth particles so that the fourth particles flow through the product outlet in a solution at a higher concentration compared to in the sample. In some case, the sample is blood. In some case, the third particles comprise particles with extrinsic magnetically susceptible labels, particles with intrinsic magnetically susceptible labels, or a combination thereof. In some case, the third particles comprise particles with intrinsic magnetically susceptible labels. In some case, the particles with intrinsic magnetically susceptible labels are red blood cells. In some case, the third particles comprise particles with extrinsic magnetically susceptible labels. In some case, the particles with extrinsic magnetically susceptible labels are white blood cells labeled with extrinsic magnetically susceptible labels. In some case, the white blood cells are labeled with extrinsic magnetically susceptible labels through an antibody. In some case, the antibody is an anti-CD45 antibody or an anti-CD66b antibody. In some case, the fourth particles are rare cells. In some case, the rare cells are circulating tumor cells. In some case, the system further comprises a mixing module.

In another aspect, provided herein is a method for separating particles in a sample, the method comprising a) passing the sample through an array of obstacles configured to allow first particles of at least a critical size to flow in a first direction to a first outlet and second particles of less than the critical size to flow in a second direction to a second outlet, wherein the critical size is less than 3 μm, and wherein the second particles comprise third particles and fourth particles; b) labeling the third particles with magnetically susceptible labels; c) passing the second particles through a magnetic separator, thereby separating the third particles from the fourth particles. In some case, the sample is blood. In some case, the first particles comprise red blood cells, white blood cells, other blood cells or a combination thereof. In some case, the third particles are labeled with magnetically susceptible labels through an antibody or a polynucleotide. In some case, the third particles comprise exosomes, platelets, microvesicles, or a combination thereof. In some case, the third particles comprise exosomes. In some case, the third particles comprise exosomes, and the exosomes are from tumor specific cells. In some case, the exosome from tumor specific cells are labeled with magnetically susceptible labels through an anti-CD44 antibody. In some case, the third particles comprise exosomes, and the exosomes are from T cells. In some case, the exosome from tumor specific cells are labeled with magnetically susceptible labels through an anti-CD3 antibody. In some case, the third particles comprise exosomes, and the exosomes are from B cells. In some case, the exosome from tumor specific cells are labeled with magnetically susceptible labels through an anti-CD19 antibody. In some case, the third particles comprise exosomes, and the exosomes are from stem cells. In some case, the exosome from tumor specific cells are labeled with magnetically susceptible labels through an anti-CD34 antibody. In some case, the third particles comprise exosomes, and the exosomes are labeled with magnetically susceptible labels through an anti-CD63 antibody. In some case, the third particles comprise platelets. In some case, the platelets are labeled with magnetically susceptible labels through an anti-CD41 antibody. In some case, the fourth particles comprise nucleosomes, cell-free DNA, or a combination thereof. In some case, the fourth particles comprise cell-free DNA. In some case, the cell-free DNA is circulating tumor DNA. In some case, the method further comprises sequencing the cell-free DNA. In some case, the sequencing is next generation sequencing. In some case, the critical size of the first array of obstacle is less than 1.5 μm.

In another aspect, provide herein is a method for enriching particles in a sample, the method comprising a) mixing the sample with magnetically susceptible labels whereby first particles in the sample are labeled with the magnetically susceptible labels; b) passing the sample through a first array of obstacles, wherein the first array of obstacles is configured to allow second particles of at least a critical size to flow in a first direction to a first outlet and third particles of less than the critical size to flow in a second direction to a second outlet, wherein the critical size is less than 3 µm, and wherein the second particles comprise i) first particles labeled with magnetically susceptible labels from a), ii) fourth particles without magnetically susceptible labels; c) passing the second particles through a magnetic separator, thereby separating the first particles from the fourth particles; d) concentrating the fourth particles with a concentrator, wherein the concentrator is a microfluidic channel comprising an inlet, a second array of obstacles, a product outlet, and a waste outlet, wherein the second array of obstacles is configured to deflect the fourth particles so that the fourth particles flow through the product outlet in a solution at a higher concentration compared to in the sample. In some case, the sample is blood. In some case, the second particles further comprise particles with intrinsic magnetically susceptible labels. In some case, the particles with intrinsic magnetically susceptible labels are red blood cells. In some case, the first particles are white blood cells. In some case, the magnetically susceptible labels are bound to the white blood cells through an antibody. In some case, the antibody is anti-CD45 or anti-CD66b. In some case, the fourth particles are rare cells. In some case, the rare cells are circulating tumor cells.

In another aspect, provided herein is a system for separating particles in a sample, the system comprising: a) an array of obstacles configured to allow first particles of at least a critical size to flow in a first direction to a first outlet and second particles of less than the critical size to flow in a second direction to a second outlet, wherein the critical size is less than 3 µm, and wherein the second particles comprise third particles labeled with magnetically susceptible labels and fourth particles without magnetically susceptible labels; b) a magnetic separator fluidically connected to the second outlet, wherein the magnetic separator is configured to separate the third particles from the fourth particles. In some case, the sample is blood. In some case, the first particles comprise red blood cells, white blood cells, rare cells or a combination thereof. In some case, the third particles are labeled with magnetically susceptible labels through an antibody or a polynucleotide. In some case, the third particles comprise exosomes, platelets, microvesicles, or a combination thereof. In some case, the third particles comprise exosomes. In some case, the exosomes are from tumor specific cells. In some case, the exosomes from tumor specific cells are labeled with magnetically susceptible labels through an anti-CD44 antibody. In some case, the exosomes are from T cells. In some case, the exosomes from T cells are labeled with magnetically susceptible labels through an anti-CD3 antibody. In some case, the exosomes are from B cells. In some case, the exosomes from B are labeled with magnetically susceptible labels through an anti-CD19 antibody. In some case, the exosomes are from stem cells. In some case, the exosomes from stem cells are labeled with magnetically susceptible labels through an anti-CD34 antibody. In some case, the exosomes are labeled with magnetically susceptible labels through an anti-CD63 antibody. In some case, the third particles comprise platelets. In some case, the platelets are labeled with magnetically susceptible labels through an anti-CD41 antibody. In some case, the fourth particles comprise nucleosomes, cell-free DNA, or a combination thereof. In some case, the fourth particles comprise cell-free DNA. In some case, the cell-free DNA is circulating tumor DNA. In some case, the system further comprises an analyzer of the cell-free DNA. In some case, the analyzer is a sequencer. In some case, the critical size is less than 1.5 µm.

In another aspect, provided herein is a system for enriching particles in a sample, the system comprising a) a first array of obstacles configured to allow first particles of at least a critical size to flow in a first direction to a first outlet and second particles of less than the critical size to flow in a second direction to a second outlet, wherein the critical size is less than 5 µm, and wherein the first particles comprise third particles with magnetically susceptible labels and fourth particles without magnetically susceptible labels; b) a magnetic separator fluidically connected to the first outlet, wherein the magnetic separator is configured to separate fourth particles from the third particles; c) a concentrator fluidically connected to the magnetic separator, wherein the concentrator is a microfluidic channel comprising an inlet, a second array of obstacles, a product outlet, and a waste outlet, wherein the second array of obstacles is configured to deflect the fourth particles so that the fourth particles flow through the product outlet in a solution at a higher concentration compared to in the sample. In some case, the sample is blood. In some case, the third particles comprise particles with extrinsic magnetically susceptible labels, particles with intrinsic magnetically susceptible labels, or a combination thereof. In some case, the third particles comprise particles with intrinsic magnetically susceptible labels. In some case, the particles with intrinsic magnetically susceptible labels are red blood cells. In some case, the third particles comprise particles with extrinsic magnetically susceptible labels. In some case, the particles with extrinsic magnetically susceptible labels are white blood cells labeled with extrinsic magnetically susceptible labels. In some case, the white blood cells are labeled with extrinsic magnetically susceptible labels through an antibody. In some case, the antibody is an anti-CD45 antibody or an anti-CD66b antibody. In some case, the fourth particles are rare cells. In some case, the rare cells are circulating tumor cells. In some case, the system further comprises a mixing module.

In another aspect, provided herein is a method for separating particles in a sample, the method comprising a) passing the sample through an array of obstacles configured to allow first particles of at least a critical size to flow in a first direction to a first outlet and second particles of less than the critical size to flow in a second direction to a second outlet, wherein the critical size is less than 3 µm, and wherein the second particles comprise third particles and fourth particles; b) labeling the third particles with magnetically susceptible labels; c) passing the second particles through a magnetic separator, thereby separating the third particles from the fourth particles. In some case, the sample is blood. In some case, the first particles comprise red blood cells, white blood cells, other blood cells or a combination thereof. In some case, the third particles are labeled with magnetically susceptible labels through an antibody or a polynucleotide. In some case, the third particles comprise exosomes, platelets, microvesicles, or a combination thereof. In some case, the third particles comprise exosomes. In some case, the third particles comprise exosomes, and the exosomes are from tumor specific cells. In some case, the exosome from tumor specific cells are labeled with magnetically susceptible labels through an anti-CD44 antibody. In some case, the third particles comprise exosomes, and the exosomes are from T cells. In some case, the exosome from tumor specific cells are labeled with magnetically susceptible labels through an anti-CD3 antibody. In some case, the third particles comprise exosomes, and the exosomes are from B cells. In some case, the exosome from tumor specific cells are labeled with magnetically susceptible labels through an anti-CD19 antibody. In some case, the third particles comprise exosomes, and the exosomes are from stem cells. In some case, the exosome from tumor specific cells are labeled with magnetically susceptible labels through an anti-CD34 antibody. In some case, the third particles comprise exosomes, and the exosomes are labeled with magnetically susceptible labels through an anti-CD63 antibody. In some case, the third particles comprise platelets. In some case, the platelets are labeled with magnetically susceptible labels through an anti-CD41 antibody. In some case, the fourth particles comprise nucleosomes, cell-free DNA, or a combination thereof. In some case, the fourth particles comprise cell-free DNA. In some case, the cell-free DNA is circulating tumor DNA. In some case, the method further comprises sequencing the cell-free DNA. In some case, the sequencing is next generation sequencing. In some case, the critical size of the first array of obstacle is less than 1.5 µm.

In another aspect, provide herein is a method for enriching particles in a sample, the method comprising a) mixing the sample with magnetically susceptible labels whereby first particles in the sample are labeled with the magnetically susceptible labels; b) passing the sample through a first array of obstacles, wherein the first array of obstacles is configured to allow second particles of at least a critical size to flow in a first direction to a first outlet and third particles of less than the critical size to flow in a second direction to a second outlet, wherein the critical size is less than 3 µm, and wherein the second particles comprise i) first particles labeled with magnetically susceptible labels from a), ii) fourth particles without magnetically susceptible labels; c) passing the second particles through a magnetic separator, thereby separating the first particles from the fourth particles; d) concentrating the fourth particles with a concentrator, wherein the concentrator is a microfluidic channel comprising an inlet, a second array of obstacles, a product outlet, and a waste outlet, wherein the second array of obstacles is configured to deflect the fourth particles so that the fourth particles flow through the product outlet in a solution at a higher concentration compared to in the sample. In some case, the sample is blood. In some case, the second particles further comprise particles with intrinsic magnetically susceptible labels. In some case, the particles with intrinsic magnetically susceptible labels are red blood cells. In some case, the first particles are white blood cells. In some case, the magnetically susceptible labels are bound to the white blood cells through an antibody. In some case, the antibody is anti-CD45 or anti-CD66b. In some case, the fourth particles are rare cells. In some case, the rare cells are circulating tumor cells.

In another aspect, disclosed herein is a system for separating particles in a sample, the system comprising: (a) an array of obstacles configured to allow first particles of at least a critical size to flow in a first direction and second particles of less than the critical size to flow in a second direction different from the first direction, wherein: the critical size is less than 3 µm, surfaces of two adjacent obstacles in a row of the array of obstacles define a gap, the two adjacent obstacles defining the gap have a polygonal cross-section, wherein a vertex of each of the two adjacent obstacles with the polygonal cross-section points toward each other in a direction substantially perpendicular to a flow direction of the sample through the array of obstacles; and a magnetic separator configured to separate particles with magnetically susceptible labels from particles without magnetically susceptible labels, wherein the array of obstacles is fluidically connected with the magnetic separator.

In some cases, the two adjacent obstacles have a shape with substantial symmetry about an axis parallel to the flow direction of the sample. In some cases, a shape of the gap is substantially symmetrically relative to a plane parallel to the flow direction of the sample, wherein the plane is equidistant from the center of the cross-section of each of the two obstacles in the row. In some cases, the width of the plane is about ½ of the width of the gap, and greater than 50% of the flow of the sample occurs within the plane. In some cases, the polygonal cross-section is a quadrilateral cross-section. In some cases, the quadrilateral cross-section is a square cross-section. In some cases, the polygonal cross-section is a tear drop shaped cross-section. In some cases, the critical size is no more than 1500 nm. In some cases, the second particles comprise micro-vesicles, bacteria, and protein aggregates. In some cases, the critical size is no more than 200 nm. In some cases, the second particles comprise exosomes. In some cases, the critical size is no more than 50 nm. In some cases, the second particles comprise nucleosomes. In some cases, the second particles are RNA or cell-free DNA. In some cases, the system further comprises a filter, and the filter is configured to capture particles or particle aggregates larger than a pore size of the filter and allow particles or particle aggregates of no larger than the pore size to pass through, and the filter is fluidically connected with the array of obstacles. In some cases, the pore size is no more than 20 µm. In some cases, the system further comprises a particle sensor. In some cases, the particle sensor is fluidically connected with the first array of obstacles and the magnetic separator. In some cases, the particle sensor is a laser light scattering device, a fluorescence senor, or an impedance sensor. In some cases, the magnetic separator is configured to retain particles with magnetically susceptible labels and allow particles without magnetically susceptible labels to pass through. In some cases, the magnetic separator is configured to separate particles with magnetically susceptible labels from particles without magnetically susceptible labels when the particles with magnetically susceptible labels and the particles without magnetically susceptible labels flow through the first array of obstacles. In some cases, the magnetic separator is capable of generating a magnetic field of at least 0.5 Tesla. In some cases, the magnetic separator is configured to separate particles whose magnetic susceptibility is equal to or above a critical value from particles whose magnetic susceptibility is below the critical value. In some cases, further comprising a fluidic balancer, wherein the fluidic balancer is configured to maintain stability of a flow stream containing the particles. In some cases, the fluidic balancer is configured to generate a back flow of the flow stream containing the particles.

In another aspect, disclosed herein is a method for separating particles in a sample, the method comprising (a) providing a sample comprising first particles of at least a critical size and second particles less than the critical size; (b) passing the sample through an array of obstacles, wherein: the array of obstacles allows the first particles to move in a first direction and the second particles to move in a second direction different from the first direction, surfaces of two adjacent obstacles in a row of the array of obstacles define a gap, the two adjacent obstacles defining the gap have a polygonal cross-section, wherein a vertex of each of the two adjacent obstacles with the polygonal cross-section points toward each other in a direction substantially perpendicular to a flow direction of the sample through the array of obstacles, the critical size is less than 3 µm, thereby separating the first particles and the second particles; and passing third particles and fourth particles to a magnetic separator, wherein: the magnetic separator is configured to separate particles with magnetically susceptible labels from particles without magnetically susceptible labels, the magnetic separator is fluidically connected with the array of obstacles, and the third particles comprise magnetically susceptible labels, and the fourth particles do not comprise magnetically susceptible labels, thereby separating the third particles and the fourth particles, wherein i) the third particles and the fourth particles are subgroups of the first particles, or ii) the third particles and the fourth particles are subgroups of the second particles.

In some cases, the two adjacent obstacles have a cross-sectional shape with substantial symmetry about an axis parallel to the flow direction of the sample. In some cases, a shape of the gap is substantially symmetrically relative to a plane parallel to the flow direction of the sample, wherein the plane is equidistant from the center of the cross-section of each of the two obstacles in the row. In some cases, the width of the plane is about ½ of the width of the gap, and wherein greater than 50% of the flow of the sample occurs within the plane. In some cases, the polygonal cross-section is a quadrilateral cross-section. In some cases, the quadrilateral cross-section is a square cross-section. In some cases, the polygonal cross-section is a tear drop shaped cross-section. In some cases, the second particles comprise red blood cells. In some cases, the third particles comprise red blood cells. In some cases, the critical size is no more than 1500 nm. In some cases, the second particles comprise micro-vesicles or proteins. In some cases, the critical size is no more than 200 nm. In some cases, the second particles comprise exosomes. In some cases, the critical size is no more than 50 nm. In some cases, the second particles comprise nucleosomes. In some cases, the second particles are RNA or cell-free DNA. In some cases, the sample is blood. In some cases, the method further comprises detecting one or more particles in the sample using a particle sensor. In some cases, the particle sensor is a laser light scattering device, a fluorescence senor, or an impedance sensor. In some cases, the method further comprises capturing particles using a filter, wherein the filter is configured to capture particles or particle aggregates larger than a pore size of the filter and allow particles or particle aggregates equal or less than the pore size to pass through, and wherein the filter is fluidically connected with the first array of obstacles. In some cases, the pore size is no more than 20 µm. In some cases, the magnetic separator retains particles with magnetically susceptible labels from the sample when the sample flowing through the first array of obstacles. In some cases, the method further comprises detecting one or more particles in the sample using a particle sensor. In some cases, the particle sensor is a laser light scattering device, a fluorescence senor, or an impedance sensor. In some cases, the magnetic separator is configured to retain particles with magnetically susceptible labels and allow particles without magnetically susceptible labels to pass through, thereby retaining the third particles in the magnetic separator and allowing the fourth particles to pass through the magnetic separator. In some cases, the magnetic separator is configured to separate the third particles and the fourth particles when the third particles and the fourth particles flow through the array of obstacles. In some cases, the third particles and the fourth particles are subgroups of the first particles. In some cases, the third particles and the fourth particles are subgroups of the second particles. In some cases, the sample is in a solution comprising an anticoagulant. In some cases, the magnetic separator is capable of generating a magnetic field of at least 0.5 Tesla. In some cases, the sample is passed through the first array of obstacles at a flow rate of at least 240 µL/min

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A shows the relative directions of the forward scattered beam, sample flow stream, and orthogonal scattered beam of the light scattering device. FIG. 3B shows a flow intercept with a flow cell made of a glass cuvette. FIG. 3C shows a flow intercept with a flow cell made of molded layers. FIG. 3D shows flow cells with a Z sheath that allow better imaging of the particles and flow stream in the flow cell.

FIGS. 4A-4F show an exemplary particle dispenser. FIG. 4A shows a time point when a particle of interest arrives at a sensing zone of the particle dispenser. FIG. 4B shows a time point when the particle of interest has passed the sensing zone of the particle dispenser. FIG. 4C shows a time point when the particle of interest is captured by a capture tube. FIG. 4D shows a time point when the capture tube returns to its original position with the particle of interest. FIG. 4E shows a time point when an air flow is flushed into the capture tube. FIG. 4F shows an exemplary design of a switch driving the capture tube.

FIG. 6A demonstrates a schematic microfluidic channel with one inlet (a sample inlet) and one DLD array. FIG. 6B demonstrates a schematic microfluidic channel with two inlets (a sample inlet and a buffer inlet) and one DLD array. FIG. 6C demonstrates a schematic microfluidic channel with one inlet (a sample inlet) and two DLD arrays. FIG. 6D demonstrates a schematic microfluidic channel with three inlets (two sample inlets and a buffer inlet) and two DLD arrays. FIG. 6E depicts an exemplary 2-stage concentrator.

FIG. 7A is a schematic of the DLD device used in Example 8. FIG. 7B shows the input and output concentrations of sample 1 and sample 2 in Example 8. FIG. 7C shows the concentration factors for sample 1 and sample 2 in Example 8.

FIG. 10A shows labeling white blood cells with magnetic nanoparticles. FIG. 10B shows removing red blood cells by a DLD array. FIG. 10C shows removing magnetically labeled white blood cells by a magnetic chamber. FIG. 10D shows concentrating rare cells by another DLD array. FIG. 10E shows a physical layout of the system used for performing the method.

DETAILED DESCRIPTION OF THE INVENTION

I. Overview

Provided herein are devices and methods for concentrating particles in a sample. The methods can comprise flowing a sample through a deterministic lateral displacement (DLD) array of obstacles in a microfluidic channel. The DLD array can deflect particles of at least a critical size in the sample to a product outlet of the microfluidic channel. In the meantime, a portion of the sample that does not contain the particles can flow out of the microfluidic channel through one or more waste outlets. Thus, when collected in a solution flowed out of the microfluidic channel through the product outlet, the particles of at least the critical size can be concentrated in the solution. In some cases, the sample comprises particles of less than the critical size. The particles of less than the critical size can be deflected to a direction different from the particles of at least the critical size, e.g., to a waste outlet. In some cases, before a sample is flowed through a DLD array in the microfluidic channel, the microfluidic channel is filled with a buffer (e.g., by flowing the buffer through the microfluidic channel). For example, the buffer can comprise the same components as the sample except the particles to be concentrated.

Figure 6B:
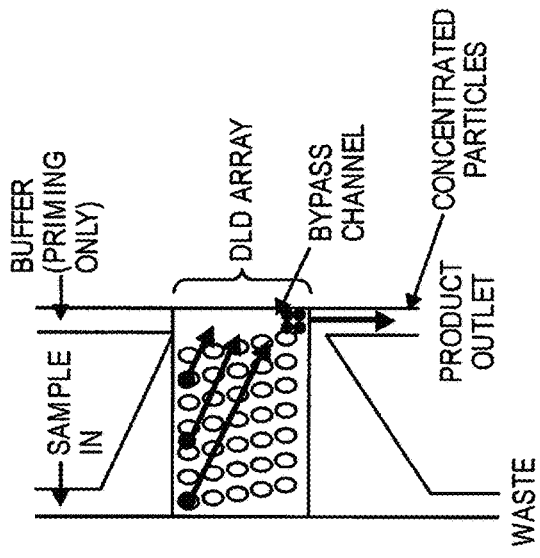
FIGS. 6A-6E are schematics of exemplary devices for concentrating particles.
Figure 6D:
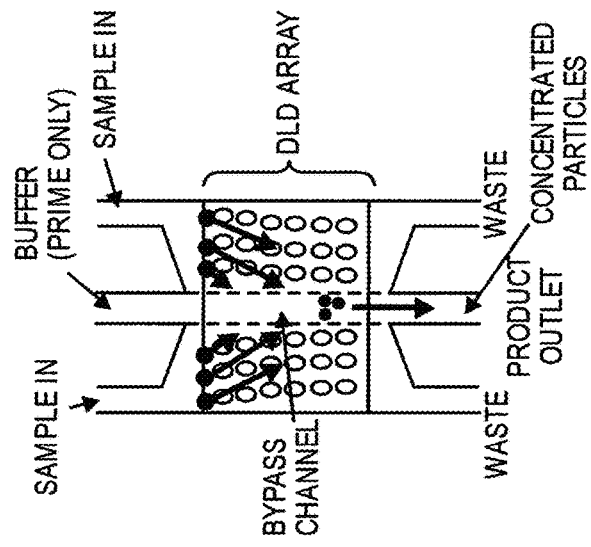
Figure 6A:
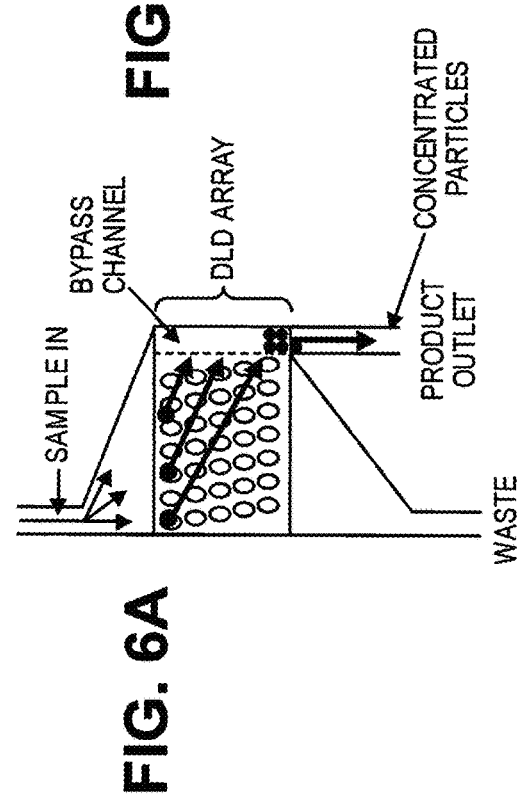
Figure 6C:
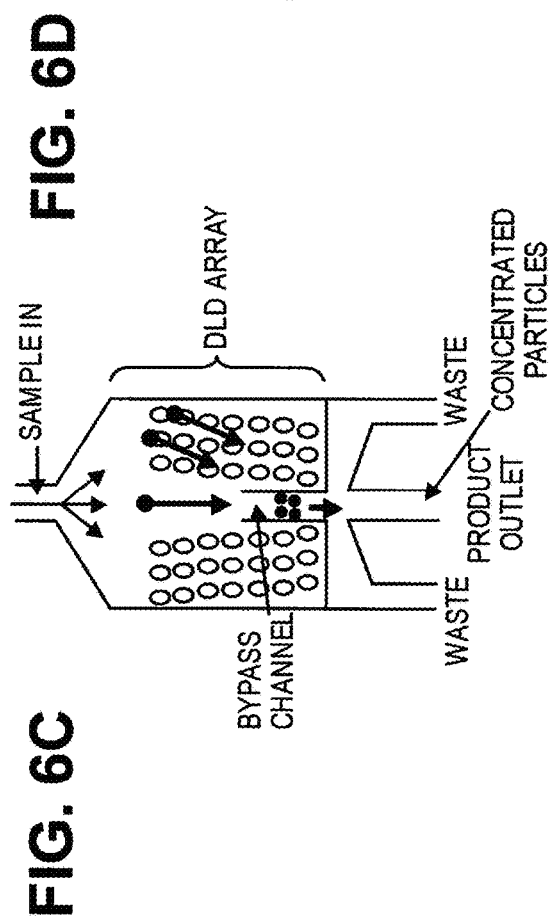

Schematic diagrams of exemplary devices and methods for concentrating particles in a sample are demonstrated in FIGS. 6A-6D. In FIG. 6A, a sample is loaded to a sample inlet of a microfluidic channel and flowed through a DLD array in the microfluidic channel. Particles of at least a critical size in the sample are deflected by the DLD array to a bypass channel connected to a product outlet. The particles flow out of the microfluidic channel in a solution through the product outlet, and a portion of the sample without the particles flows out of the microfluidic channel through a waste outlet. Thus, when flowing out of the microfluidic channel, the particles are concentrated in the solution. In FIG. 6B, a buffer is flowed through a microfluidic channel comprising a DLD array, so that the DLD array is filled with the buffer. A sample is then loaded to a sample inlet of a microfluidic channel and flowed through the DLD array. Particles of at least a critical size in the sample are deflected by the DLD array to a bypass channel connected to a product outlet. The particles flow out of the microfluidic channel in a solution through the product outlet, and a portion of the sample without the particles flows out of the microfluidic channel through a waste outlet. Thus, when flowing out of the microfluidic channel, the particles are concentrated in the solution. In FIG. 6C, a sample is loaded to a sample inlet of a microfluidic channel, and flowed through two DLD arrays in the microfluidic channel. Particles of at least a critical size in the sample are deflected by the DLD arrays to a bypass channel that is between the two DLD arrays and connected to a product outlet. The particles flow out of the microfluidic channel in a solution through the product outlet, and a portion of the sample without the particles flows out of the microfluidic channel through two waste outlets. Thus, when flowing out of the microfluidic channel, the particles are concentrated in the solution. In FIG. 6D, a buffer is flowed through a microfluidic channel comprising two DLD arrays, so that the DLD arrays are filled with the buffer. A sample is then loaded to the microfluidic channel through two sample inlets, and flowed through both DLD arrays. Particles of at least a critical size in the sample are deflected by the DLD arrays to a bypass channel that is between the arrays and connected to a product outlet. The particles flow out of the microfluidic channel in a solution through the product outlet, and a portion of the sample without the particles flows out of the microfluidic channel through two waste outlets. Thus, when flowing out of the microfluidic channel, the particles are concentrated in the solution.

Provide herein is an integrated system that allows the enrichment and isolation of particles in a sample (e.g., body fluid such as whole blood), and appropriate fractionation of the sample (e.g., body fluid such as whole blood). The particles can include intact large cells, platelets and microparticulates, sub-cellular vesicles containing proteins and/or nucleic acids, and plasma. The system can enable a comprehensive fractionation of whole blood for the purposes of a "liquid biopsy" to evaluate the relevant biological content in routine medical practice. The system can integrate the principles of deterministic lateral displacement (DLD), magnetic enrichment and flow cytometry to achieve a complete dissection of relevant components suitable for analytical characterization of all relevant categories of particles disclosed herein. The methods, devices, systems and kits can allow gentle and uniform processing a sample comprising cells, and obtaining highly purified and viable cells with high yield (e.g., no cell loss).

Provided herein are methods, devices, systems and kits for isolating and enriching particles (e.g., cells or subcellular components) from a sample (e.g., blood). The present disclosure allows efficient and effective separation of particles by integrating one or more of deterministic lateral displacement (DLD), magnetic properties-based separation, fluorescence-based separation, and other separation devices and methods. For example, methods, devices, and systems herein can comprise DLD arrays and magnetic separators. In some cases, the operation of the systems and devices herein (e.g., chip loading, flow rates, output collection) can be automated.

Figure 1:
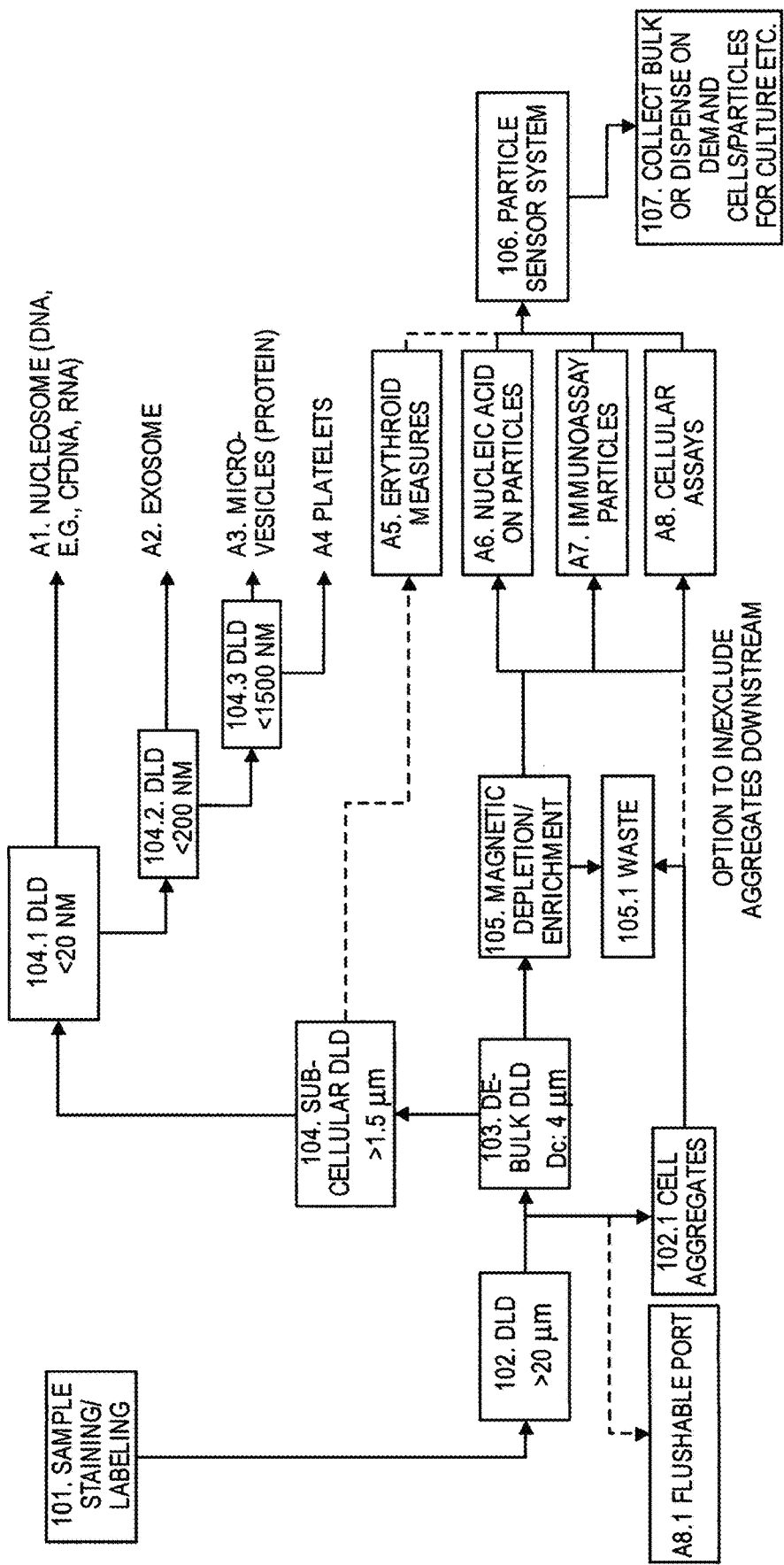
FIG. 1 shows an exemplary integrated system for separating particles from a blood sample using a combination of DLD arrays and a magnetic separator.

FIG. 1 demonstrates an exemplary system for separating and analyzing particles from a whole blood sample. One or more particles in the whole blood sample can be labeled before the sample enters the system (101). The labeled sample can then be passed through a first DLD array with a critical size of, e.g., 20 µm (102). The first DLD array can be a "de-clump" array, which removes aggregates of cells and other particles from the blood. The removed aggregates can be discarded, or collected for further analysis (102.1). The resulting sample can then be passed through a second DLD array with a critical size of no more than 5 µm, e.g., about 4 µm. In some cases, the second DLD array can comprise more than one zone of DLD obstacles with various critical sizes. A sample can flow through the zones. In some cases, the last zone the sample flows through can have a critical size of no more than 5 µm, e.g., about 4 µm. The second DLD array can be a "de-bulk DLD" array, which removes one or more types of particles that is abundant in the sample. In this case, the red blood cells and other smaller particles (e.g., subcellular particles) are separated from white blood cells and other cells larger than red blood cells (e.g., rare cells such as circulating tumor cells). The separated big cells can be labeled in step 101. In some cases, the white blood cells can be labeled with magnetic beads (e.g., through antibodies binding to white blood cell markers). In some cases, the rare cells (e.g., circulating tumor cells) can be labeled with magnetic beads, (e.g., through antibodies binding to rare cell markers). A magnetic bead can comprise a detectable tag, e.g., a fluorescent tag, for downstream detection and/or analysis. The white blood cells or rare cells labeled with magnetic beads can then be passed to a magnetic separator (105). In some cases, the magnetic separator can retain the cells with magnetic beads, and allow the other cells flow through. The retained cells can be released or flushed out of the magnetic separator to a collector for further analysis, or discarded to a waste collector (105.1). In another case, the magnetic separator can deflect the cells with magnetic beads from the flow of the other cells. The deflected cells with magnetic beads can be collected for further analysis, or discarded to a waste (105.1). Alternatively, the cells not labeled with magnetic beads can be collected for further analysis, or discarded to a waste (105.1). The collected cells from the magnetic separator can be further analyzed by Assays A6 (analyses of nucleic acids in the cells), A7 (immunoassay of the cells), and/or A8 (cellular assays). The red blood cells and other smaller particles separated from the second DLD array (102) can be passed to a third DLD array with a critical size of 1500 nm (104). The third DLD array can separate subcellular particles from the red blood cells. The red blood cells can be further analyzed by Assay A5. The subcellular particles separated by the third DLD array (104) can be further separated by a series DLD arrays with smaller critical sizes. In this case, the subcellular particles can be passed to a fourth DLD array with a critical size of 50 nm (104.1), which separates nucleosomes, RNA, and/or cell-free DNA from the sample. The resulting sample can be passed to a fifth DLD array with a critical size of 200 nm (104.2), which can separate exosomes and/or from larger particles. The resulting sample can be further passed to a sixth DLD array with a critical size of 1500 nm (104.3), which separates micro-vesicles and/or protein from the remaining particles in the sample. Any cells separated by the DLD arrays and magnetic separators can be detected and/or analyzed by a particle sensor system (106). The cells can then be sorted and/or collected for further processing, e.g., culturing (107).

In one aspect, provided herein is a system for separating particles, the system comprising one or more DLD arrays configured to separate particles smaller than the size of a cell, and a magnetic separator. The DLD arrays in the system can allow separation of subcellular components and biomolecules, such as DNA. DLD arrays of different critical sizes can be integrated in the system so that subcellular components and biomolecules of different sizes in a sample (e.g., blood) can be separated by passing a sample through the system. In some cases, the system for separating particles in a sample can comprise: a) a de-clump device; b) a first array of obstacles, wherein the first array of obstacles is configured to allow first particles of at least a first critical size to flow in a first direction and second particles of less than the first critical size to flow in a second direction different from the first direction, and wherein the first critical size is no greater than 5 µm; c) a second array of obstacles, wherein the second array of obstacles is configured to allow third particles of at least a second critical size to flow in a third direction and fourth particles of less than the second critical size to flow in a fourth direction different from the third direction, and wherein the second critical size is no greater than 1.5 µm; d) a magnetic separator configured to separate particles with magnetically susceptible labels; e) a particle dispenser, wherein the de-clump device, first array of obstacles, the second array of obstacles, the magnetic separator, and the particle dispenser are fluidically connected. The system can further comprise a third array of obstacles, wherein the third array of obstacles is configured to allow fifth particles of at least a third critical size to flow in a fifth direction and sixth particles of less than the third critical size to flow in a sixth direction different from the third direction, wherein the third critical size is less than the second critical size, and wherein the third array of obstacles is fluidically connected with the second array of obstacles and the magnetic separator. The third critical size can be no more than 200 nm. The system can further comprise a fourth array of obstacles, wherein the fourth array of obstacles is configured to allow seventh particles of at least a fourth critical size to flow in a seventh direction and eighth particles of less than the fourth critical size to flow in a eighth direction different from the seventh direction, wherein the fourth critical size is less than the third critical size, and wherein the fourth array of obstacles is fluidically connected with the third array of obstacles. The fourth critical size can be no more than 50 nm.

In some cases, the system for separating particles in a sample can comprise a) a first array of obstacles, wherein the first array of obstacles is configured to allow first particles of at least a first critical size to flow in a first direction and second particles of less than the first critical size to flow in a second direction different from the first direction, and wherein the first critical size is less than 3 µm; b) a magnetic separator configured to separate particles with magnetically susceptible labels from particles without magnetically susceptible labels, wherein the first array of obstacles is fluidically connected with the magnetic separator. In some cases, the system can comprise a DLD array of a no more than 1500 nm critical size, a DLD array of a 200 nm critical size, and a DLD array of a 50 nm critical size. Combination of the series of DLD arrays can allow separation of micro-vesicles, nucleosomes and exosomes.

In another aspect, the system can comprise a combination of one or more DLD arrays with a particle separator other than a magnetic separator. In some cases, the system for separating particles in a sample can comprise: a) a first array of obstacles, wherein the first array of obstacles is configured to allow first particles of at least a first critical size to flow in a first direction and second particles of less than the first critical size to flow in a second direction different from the first direction, and wherein the first critical size is less than 3 µm; b) a fluorescence-based particle separator configured to separate particles with first fluorescent labels from particles of second fluorescent labels or particles without fluorescent labels, wherein the first array of obstacles is fluidically connected with the fluorescence-based separator. In some cases, such system can further comprise a particle dispenser disclosed herein.

In another aspect, the system for separating particles can comprise a particle dispenser. The dispenser can be a single particle dispenser that allows dispensing a single particle enriched by the system to a specified location for downstream analysis. The specified location can be a microscope slide or a cell culture dish or similar receiver. The dispenser can dispense the single particle with a defined volume of solution. For example, the dispenser can dispense the single particle in a solution of a small volume, thereby concentrating the single particle on the specified location.

In some cases, the particle dispenser can comprise: a) a fluidic duct configured to allow particles to flow into the fluid duct in a flow stream, and wherein the fluidic duct comprises a sensing zone; b) a sensor, wherein the sensor generates a signal when a particle of interest arrives in the sensing zone; c) a switch configured to receive the signal; d) a capture tube, wherein the capture tube is movable between a first position and a second position, wherein the capture tube is not fluidically connected with the fluidic duct at the first position, and is fluidically connected with the fluidic duct at the second position, wherein the capture tube remains at the first position unless is driven by the switch, wherein the switch drives the capture tube from the first position to the second position after receiving the signal; and e) a pressure source configured to flush an air flow to the capture tube after the capture tube catches the particle of interest.

In another aspect, provided herein are methods for separating particles using any of the devices or systems herein. In some aspect, such a method can comprise: a) providing a sample comprising first particles of at least a first critical size and second particles less than the first critical size; b) passing the sample through a first array of obstacles, wherein the first array of obstacles allows the first particles to move in a first direction and the second particles to move in a second direction different from the first direction, and wherein the first critical size is less than 3 µm, thereby separating the first particles and the second particles; and c) passing third particles and fourth particles to a magnetic separator, wherein the magnetic separator is configured to separate particles with magnetically susceptible labels from particles without magnetically susceptible labels, wherein the magnetic separator is fluidically connected with the first array of obstacles, and wherein the third particles comprise magnetically susceptible labels, and the fourth particles do not comprise magnetically susceptible labels, thereby separating the third particles and the fourth particles, wherein i) the third particles and the fourth particles are subgroups of the first particles, ii) the third particles and the fourth particles are subgroups of the second particles, iii) the first particles and the second particles are subgroups of the third particles, or iv) the first particles and the second particles are subgroups of the fourth particles.

In another aspect, methods for separating particles herein can include labeling the particles. A particle can be labeled with one label. A particle can be labeled with two or more different labels. A particle can be labeled with two or more labels of the same types. For example, a particle can be labeled with two or more fluorescent labels. A particle can be labeled with two or more labels of different types. For example, a particle can be labeled with a fluorescent label and a magnetically susceptible label. In some cases, a label can comprise different tags, e.g., a fluorescent tag and a magnetic tag. In some cases, the labels can bind to different markers on the particle. Labeling a particle with multiple labels can allow the particle to be enriched by multiple means, thereby achieving a high purity. In some cases, the labeled particle can be separated by one or more DLD array and a magnetic separator. In some cases, the method can comprise: a) labeling one or more particles in a sample with labels, wherein each of the one or more labeled particles is labeled with a first label and a second label, wherein the first label and the second label are different, and wherein the sample comprises first particles of at least a first critical size and second particles less than the first critical size; b) passing the sample through a first array of obstacles, wherein the first array of obstacles allows the first particles to flow in a first direction and the second particles to flow in a second direction different from the first direction, thereby separating the first particles and the second particles; c) passing third particles and fourth particles into a magnetic separator, wherein the magnetic separator is configured to separate particles with magnetically susceptible labels from particles without magnetically susceptible labels, wherein the magnetic separator is fluidically connected with the first array of obstacles, and wherein the third particles comprise magnetically susceptible labels and the fourth particles do not comprise magnetically susceptible labels, thereby separating the third particles and the fourth particles, wherein i) the third particles and the fourth particles are subgroups of the first particles, ii) the third particles and the fourth particles are subgroups of the second particles, iii) the first particles and the second particles are subgroups of the third particles, or iv) the first particles and the second particles are subgroups of the fourth particles.

In another aspect, provided herein is a method for dispensing a single particle of interest using any particle dispenser provided herein. In some cases, the method can comprise: a) providing a sample comprising a particle of interest; b) passing the sample into a fluidic duct in a flow stream, wherein the fluidic duct comprises a sensing zone; c) detecting the particle of interest using a sensor, wherein the sensor generates a signal when the particle of interest arrives the sensing zone; d) moving a capture tube from a first position to a second position, wherein the capture tube is movable between the first position and the second position, wherein the capture tube is not fluidically connected with the fluidic duct at the first position and is fluidically connected with the fluidic duct at the second position, wherein the moving is driven by a switch configured to drive the capture tube from the first position to the second position after receiving the signal, and wherein the capture tube remains at the first position unless is driven by the switch, thereby catching the particle of interest from the fluidic duct into the capture tube; and e) flushing an air flow to the capture tube after the particle of interest passes into the capture tube, and wherein the air flow flushed by a pressure source.

In another aspect, the systems herein can further comprise other components for particle separation, detection and/or analysis. In some cases, a system can comprise one or more particle separators other than DLD arrays or magnetic separators. For example, a system can comprise a fluorescence-based particle separator, such as a flow cytometer (e.g., a fluorescence-activated cell sorter). In some cases, a system can also comprise one or more particle sensors. The particle sensors can detect and analyze the particles separated from a sample. For example, the particle sensors can comprise a laser light scattering device.

In another aspect, also provided herein are kits for separating particles from a sample. In some cases, the kits can be used to isolate specific cells and/or subcellular components from a sample, e.g., a blood. The kits can comprise any systems and/or devices provided herein. In some cases, the kits can comprise one or more buffers and reagents for processing the particles, e.g., washing buffers, labeling reagents, etc. In some cases, the kits can also comprise instructions for using the systems and/or devices herein.

In another aspect, provided herein is a system that uses three independent or orthogonal approaches in a prescribed sequence to enrich and deposit very rare particles and soluble analytes of interest from a sample using a combination of DLD, magnetic properties and spectral emission profile to enrich and specifically deposit particles as rare as 1 particle in 1 billion in the sample without the need for harsh chemical agents or density centrifugation techniques. In some cases, the system can use DLD, followed by magnetic depletion of non-target particles, and then spectral profiling to identify and enumerate particles of interest prior to deposition. In some cases, the system can use DLD, followed by magnetic enrichment of target particles, and then spectral profiling to identify and enumerate cells or particles of interest prior to deposition. In some cases, the system can use DLD to remove clumps of particles with specific cut off criteria to enrich for the following populations of interest: i) clusters of circulating tumor cells; ii) aggregates of cells from aged samples; iii) aggregates of cells from body fluids that are not digestible with preparatory mechanisms. In some cases, the system can use DLD in the de-bulking zone with specific cut off criteria above the critical size to enrich any cell larger than a normal erythrocyte and/or any synthetic particle above about 4 µm in size. In some cases, the system can use DLD in the initial fractionation zone with specific cut off criteria above the critical size to enrich discrete fractions of particles below about 5 µm, e.g., 4 µm size that include separation of: fraction 1: 1.0-4.0 µm Platelets and apoptotic bodies; fraction 2: 0.1-1.0 nm, containing micro-vesicles, bacteria, and similar sized protein aggregates; fraction 3: 0.02 µm-0.1 um, containing nano-vesicles including viruses, and nucleic acid containing nucleosomes; and, fraction 4: Sub 0.02 µm—complex freely available analytes of interest including short 6-7 base microRNA species. In some cases, the system can use magnetic separation devices to remove particles above a certain magnetic susceptibility criteria. In some cases, the particle to be separated can have at least 100 labels (e.g., antigen molecules) on the particle. For example, the particle to be separated can have about 10000 labels (e.g., antigen molecules). In some cases, the system can use a particle sensor using impedance and/or spectral signatures to generate and deliver an actuation signal and deliver an impetus to physically displace a particle of interest to another location in a X-Y-Z space. In some cases, the X-Y-Z space can be defined relative to a point away from the point of interrogation at a time t delayed that is proportional to the distance travelled by a particle following interrogation and identification. In some case, the impetus can be an opto-acoustic pulse in a fluid path, a mechanically driven pressure wave in the same medium at an angle to effect displacement to a different discrete trajectory and ejection, or a pressure source using a different medium at an angle to effect displacement to a different discrete trajectory. In some cases, the medium can be the same fluid as the sample. In some cases, the medium can be a different fluid than the sample. In some cases, the medium is a common or inert gas. In some cases, the system can use one or more specific labels to achieve separation conditions. For example, on the basis of one or more magnetically susceptible labels and one or more direct spectral labels, a desired population of particles can be enriched from particles passing through the system with targeted specific identification by the labels. For example, the group of non-labeled particles is selectively enriched. In some cases, use of the spectral labels to specifically eliminate non-desired particles (e.g., particles not magnetically labelled) can be a secondary clean up approach. For example, such secondary clean up approach can allow purifying a single cell in a sample comprising more than 1 million (e.g., a billion) particles. In some cases, the system can use specific labels to achieve separation conditions such that on the basis of one or more magnetically susceptible labels and no direct spectral labels the particle of interest passes through the system with no target specific identification resulting in enrichment for a desired particle population. For example, particles without labels or with negative labels (e.g., labels not recognized by the system) are selectively enriched. In some cases, the system can use single specific labels to achieve separation conditions. For example, on the basis of one or more specific magnetically susceptible labels and one or more direct spectral labels, a desired population of particles can be enriched when the particles of interest passes through the system with only scattered light information. In some cases, particles with confirmed and/or identified light scatter information can be positively depleted. In some cases, the system can use signal specific labels to achieve separation conditions such that on the basis of one or more specific magnetically susceptible labels and no direct spectral labels, the particles of interest pass through the system with only scattered light information results in enrichment for a desired population of particles. For example, particles without any spectral and light scatter confirmation/identification can be positively depleted.

In another aspect, the system can further comprise a fluid path monitor. In some cases, the fluid path monitor can be used to maintain appropriate pressure in the fluid separation channel.

In some cases, the methods, systems, devices and kits can be used to enrich cancer cells (e.g., from solid tumors or hematological malignancies). In some cases, the methods, systems, devices and kits can be used for depleting normal leukocytes, e.g., using CD45, nuclear dye, and/or light scatter properties. In some cases, the methods, systems, devices and kits can be used for enriching cells of hematological malignancies with known phenotypes. In some cases, the methods, systems, devices and kits can be used for enriching bacteria, e.g., for early enrichment of bacteria for improved management of sepsis. The enriched bacteria can be further detected, analyzed and/or cultured.

In another aspect, the methods, systems, devices and kits can be used for enriching particles (e.g., cells) that have sizes greater than the critical sizes of a de-clump DLD array and a de-bulk DLD array, wherein, optionally the particles have or do not have certain light scatter characteristics and/or spectral labels. In some cases, the methods, systems, devices and kits can be used for enriching rare particles (e.g., rare cells) that have sizes greater than the critical sizes of a de-clump DLD array and a de-bulk DLD array, wherein, optionally the rare particles have or do not have certain light scatter characteristics and/or spectral labels. For example, the rare particles can be rare cells at a frequency of <0.001% of leukocytes. In some cases, the rare particles can be rare cells at frequency of above 0.001% of leukocytes. Reagents and methods for identifying, capturing, and separating particles with labels (e.g., fluorescent labels) can be those described in Canadian Patent No. CA 1248873 and U.S. Pat. Nos. 5,981,180, 6,268,222, 6,514,295, 6,524,793, 6,528,165, which are incorporated herein by reference in their entireties.

In another aspect, the methods, systems, devices and kits can be used to recover an enriched preparation of intentionally introduced synthetic nano- and micro-particles suitable for particle-based nucleic acid detection assays and/or immunoassays. The nano- and micro-particles can be recovered and quantitated.

In another aspect, disclosed herein is an integrated blood preparation system capable of partitioning blood components into logical compartments from a hematological and oncological perspective. Multiple discrete blood fractions can be generated by preparing the blood (and/or particles) with an appropriate mix of diluent, tagged reagents (e.g., labels) that are specific to a certain analyte, and then passing the blood (and/or particle mixture) through a filter, and then a defined sequence of microfluidic elements that include pre-sizing mixing and a series of DLD arrays that are strategically sequenced. This sequence of DLDs can confer the ability to separate subcellular fractions that contain either RNA/DNA or proteins, the ability to de-bulk erythrocytes, and can leave a stream of normal leukocyte and any cells that may be physically larger than normal leukocytes, but smaller than the filter.

These leukocyte cell fractions, labelled as desired with a magnetically tagged reagent, can then be used to separate the population of interest in either a positive or negative selection approach. Following this, as a function of device design—or ability to switch configurations—a discrete stream of known leukocytes, or as in the case of CTC, non-leukocytes, can be interrogated by an on microfluidic chips based detection, such as fluorescence or impedance. Once an event that has suitable properties is detected, a pressure pulse can be generated to sort and dispense a small volume of liquid off the microfluidic device into a suitable collection device, e.g., a tube, slide, plate, or plate containing culture media. Further the collection device can logically be in a format for downstream analytical, functional and other characterization streams. Such logical applications for cells include evaluation of genetic material, functional ability of the cell to proliferate in the presence or absence of potential therapeutic agents, or the ability to secrete specific biological materials capable of messaging other parts of the body. Such materials include RNA (e.g., miRNA), DNA (e.g., genomic DNA), proteins in small vesicles or simply as free floating in the circulation.

II. Systems and Devices

Systems for separating particles from a sample provided herein can comprise a combination of two or more devices for separating particles based on different types of characteristics of the particles. In some cases, systems herein can comprise a device configured to separate particle based on their sizes (e.g., hydrodynamic sizes). In some cases, the device can be a microfluidic device, e.g., a microfluidic device comprising one or more deterministic lateral displacement (DLD) arrays. The systems can further comprise one or more devices configured to separate particles based on the particles' characteristics other than size, such as magnetic susceptibilities, fluorescence, affinity to a capture moiety, etc. In some cases, the system can further comprise a magnetic separator configured to separate particles with magnetic susceptible labels from particles without magnetic susceptible labels. In some cases, the system can further comprise a magnetic separator configured to separate particles with different magnetic susceptibilities, e.g., particles comprising labels with different magnetic susceptibilities. In some cases, the system can comprise devices for separating particles based on the fluorescence properties of the particles. For example, the system can comprise a flow cytometer, e.g., a fluorescence-activated cell sorter (FACS). In some cases, the multiple devices can be fluidically connected with each other. The systems can also comprise one or more analytical devices, such as particle sensors and particle counters.

The systems herein can use three different approaches in a serial process to physically separate particles in a sample, such as whole blood or other body fluid. The first approach can use one or more DLD arrays to physically separate particles (e.g., cells) above certain critical sizes from the sample. In the example of blood, a first "de-clump" DLD can be designed to remove from the analysis any clinically irrelevant aggregates of cells, e.g., cell aggregates that are the result of sample being old (e.g., more than 24 hours old), or improperly collected. Further, this de-clump DLD can also be used to capture clinically relevant aggregates of cells, such as clumps of rare cells. The clumps of rare cells can comprise clumps of tumor cells, such as clumps of circulating tumor cells (CTCs) (e.g., CTC clusters).

The de-aggregated sample can be then passed through a "de-bulking" DLD designed to separate particles (e.g., cells) of interest greater than a second critical size to the next separation approach. All particles, vesicles and other body fluid components below the second critical size can be passed through a series of "n" discrete "fractionation" DLD arrays each with critical size designed for the enrichment and separation of macro-particles, micro-particles, nanoparticles and small fragments of molecules such as nucleic acids (including micro RNA), respectively, for further analysis. The number of discrete "fractionation" DLD arrays for size resolution can be infinite. All particles above the second critical size in the de-bulking DLD array can be passed through a magnetic field for either negative depletion or positive enrichment, where the particles can be separated using magnetic properties, resulting in two discrete products, magnetic and non-magnetic, that can be further separated on the basis of a spectral signal actuated physical dispense mechanism, which comprises the third separation mechanism. In addition to intrinsic particle properties, either magnetic or spectral specific tagging or identification agents, combined with either a magnetic moiety and/or a spectral reporter can be used to achieve a high throughput multi-parametric sort mechanism to define, either by positive or negative characteristic association, and process sizes of particles that can have been intrinsic to the body fluid or intentionally added to the complex mixture prior to separation.

Particles can be intentionally added to a sample prior to separation, where these particles possess size characteristics in excess of the critical size of the "de-bulking" DLD. In some cases, the particles can possess intrinsic or conferred magnetic and/or identifiable spectral properties. These uniquely identifiable particles can create an addressable suspension array for capturing potential analytes in suspension in the sample. Such analytics include analysis and quantitation of specific proteins and/or nucleic acids using specific affinity binding agents. In addition to direct assessment of analytes using affinity reagents, the systems can capture reaction-specific reporter products that have been specifically generated in a liquid phase reaction in the sample prior to any physical separation.

The system can comprise a particle sensor configured to detect a signature to elicit an actuation signal. An actuation signal can be from a magnetically labeled cell via a change in impedance, or by a light scatter, morphological, colorimetric, or fluorescent spectral signature in the case of an imaged or spectrally unique signature, or combination thereof. The particle sensor can be tuned to generate an actuation signal (e.g., using Boolean logic) from a range of potential inputs, impedance, light scatter, and/or one or more types of fluorescence signals. The number of types of fluorescence signals can be infinite and can be generated from the waveform of a spectral profile, such as in the case of a spectral analyzer, or as in the case of a flow cytometer which collects "bins" of light within specific wavelength ranges or in color detection using bright field imaging or a combination thereof. All measureable emitted energy measurements are potentially signal inducing, including direct, fluorescent, anisotropic, polarized and quenching/non quenching light management constructs.

Once an actuation signal is generated, the signal can be used to initiate a cell deposition sequence that induces a change in the fluid path such that cells can be deposited off the device, e.g., analogous to FACS based cell sorting but instead uses, e.g., a piezo driven pressure pulse to deflect a plug of fluid from the microfluidic device at a precise time after the initial dispense signal is received and processed, thus allowing for specific cell deposition at a defined time later. The time can be calculated based on the linear travel time to the intercept of the pulse within, referenced hereafter as the sort window.

A. Deterministic Lateral Displacement (DLD) Devices

The systems herein can comprise a microfluidic device allowing deterministic lateral displacement of particles in a sample flowing through the device, based on the sizes of the particles. In some cases, the device can comprise one or more arrays of obstacles (e.g., DLD arrays). The obstacles can be tilted at a small angle of a few degrees from the direction of the sample flow. Particles of at least a critical size can be deflected to a first direction and particles of less than the critical size can flow in a second direction that can be different from the first direction. In some cases, the particles of at least the critical size can be deflected to a direction along the titled array axis. Exemplary devices for separating particles based on size (e.g., DLD devices) are described, e.g., in Huang et al. *Science* 304, 987-990 (2004), U.S. Pat. Nos. 7,150,812, 7,318,902, 7,472,794, 7,735,652, 7,988,840, 8,021,614, 8,263,023, 8,282,799, 8,304,230, 8,579,117, 8,921,102, U.S. Patent Application Nos. 20070196820, 20060223178, 20040144651, PCT Publication Nos. WO2012094642, WO 2014145152, and U.S. Application No. 60/414,258, which are incorporated herein by reference in their entireties. In some cases, the operating conditions (e.g. chip loading, flow rates, output collection) can be automated.

Figure 2:
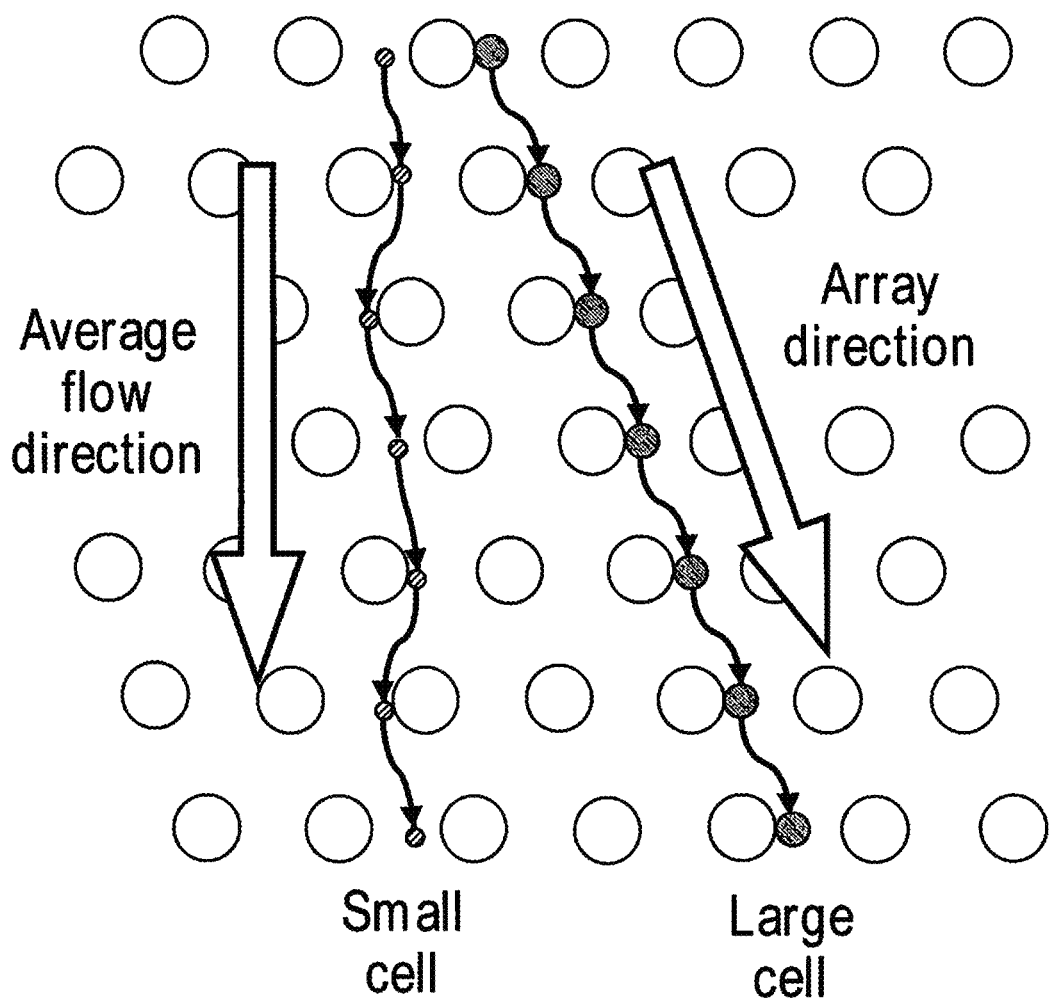
FIG. 2 shows an exemplary deterministic lateral displacement array.

An exemplary DLD array is shown in FIG. 2. The DLD array comprises a plurality of obstacles. A sample comprising small cells and large cells can be passed through the DLD array. The small cells are smaller than the critical size of the DLD array, and flow in the average flow direction. The large cells are larger than the critical size, and deflected to flow along with the array direction. Thus, the small cells and large cells are separated by the DLD array.

The DLD device can comprise a body defining a microfluidic flow channel for containing fluid flow. One or more arrays of obstacles can be disposed within the flow channel, such that fluid flowing through the channel flows around the obstacles. The obstacles can extend across the flow channel. The obstacles can be fixed to, integral with, or abutting the surface of the flow channel at each end of the obstacle.

A DLD device can have different configurations for separating particles in a sample. In some cases, the sample can be introduced to a flow-through chamber containing obstacles aligned in rows. Each row can be shifted relative to the row before. The gap between the obstacles and the tilt of the array (e.g., degree of shift) can direct particles (e.g., cells) above a certain critical size to follow the tilt of the array. These particles (e.g., cells) can be deflected at an angle towards either a side wall, or, in the case of a mirrored array, to the central bypass channel. The array can contain different zones, each zone comprising obstacles of different sizes and/or geometries. These zones can be continuous. In some cases, these zones can be designed to create different critical diameters. As the sample flows through the array, a first zone can remove large cells, and successive zones can remove smaller cells. In some cases, the process of removing the larger cells can prevent or reduce the clogging of the particles (e.g., cells) of the downstream portion of the array with smaller gaps and smaller critical size. In some cases, the process can prevent or reduce the damage of particles (e.g., cells) by being forced through smaller gap sizes. The particles (e.g., cells) of different sizes can be all combined in the side or central bypass channel. The particles (e.g., cells) can also be removed sequentially and kept separate for a size fractionation.

a. Critical Size

A critical size can refer to a parameter describing the size limit of particles that are able to follow the laminar flow of fluid nearest one side of a gap through which the particles are travelling when flow of that fluid diverges from the majority of fluid flow through the gap. Particles larger than the critical size can be deflected from the flow path of the fluid nearest that side of the gap into the flow path of the majority of the fluid flowing through the gap. In a DLD device, such a particle can be displaced by the distance of (the size of one obstacle+the size of the gap between obstacles) upon passing through the gap and encountering the downstream column of obstacles, while particles having sizes lower than the critical size will not necessarily be so displaced. When a profile of fluid flow through a gap is symmetrical about the plane that bisects the gap in the direction of bulk fluid flow, the critical size can be identical for both sides of the gap. In some cases, when the profile is asymmetrical, the critical sizes of the two sides of the gap can differ. When assessing a non-spherical particle, its size can be considered to be the spherical exclusion volume swept out by rotation of the particle about a center of gravity in a fluid, at least for particles moving rapidly in solution. The size characteristics of non-spherical particles can be determined empirically using a variety of known methods, and such determinations can be used in selecting or designing appropriate obstacle arrays for use as described herein. Calculation, measurement, and estimation of exclusion volumes for particles of all sorts can be used.

When a sample comprising first particles of at least a critical size and second particles smaller than the critical size flow through a DLD array, an array of obstacles in the DLD device (e.g., a DLD array) can deflect the first particles to a first direction and allow second particles to flow in a second direction different from the first direction, thus separating the first particles from the second particles. The critical size of the DLD arrays herein can be about, or no more than 0.05 nm, 1 nm, 5 nm, 10 nm, 15 nm, 20 nm, 25 nm, 30 nm, 35 nm, 40 nm, 50 nm, 55 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1500 nm, 1700 nm, 1800 nm, 1900 nm, 2000 nm, 3000 nm, 4000 nm, 5000 nm, 6000 nm, 7000 nm, 8000 nm, 9000 nm, 10 µm, 20 µm, 30 µm, 40 µm, 50 µm, 60 µm, 70 µm, 80 µm, 90 µm, or 100 µm. In some cases, the critical size can be about, or greater than 1 µm, 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, or 100 µm.

The DLD arrays can be configured to have critical sizes that allows for separating particles in a body fluid, e.g., blood. In some cases, DLD arrays can be used to separate cell aggregates from other particles in the body fluid. For example, the DLD arrays can have a critical size of at least 20 µm. In some cases, the cell aggregates can be platelet aggregates. In some cases, the cell aggregates can be clusters of rare cells, e.g., clusters of circulating tumor cells. In some cases, the cell aggregates can be clumps of cells from aged samples. In some cases, the cell aggregates can be clumps of cells from body fluids that are not digestible with preparatory mechanisms. The cell aggregates can comprise two or more cells. For example, the cell aggregates can comprise about, or at least 2, 3, 4, 5, 10, 20, 30, 40, 50, 60, 70, 80, 90, 100, 150, 200, 300, 400, or 500 cells. In some cases, the cell aggregates can be clumps of rare cells. For example, the cell aggregates can be clumps of tumor cells such as clumps of circulating tumor cells (e.g., circulating tumor cells clusters) comprising about, or at least 2, 3, 4, 5, 10, 20, 30, 40, 50, 60, 70, 80, 90, 100 200, 300, 400, or 500 circulating tumor cells. In some cases, the number of cells in a clump of tumor cells can be 2, 3, 4, 5, 10, 20, 30, 40, 50, 60, 70, 80, 90, 100, 200, 300, 400, 500, or any number in between. In some cases, the cell aggregates separated by the DLD device can be directed to flow into a collector for further analysis. In some cases, the cell aggregates can be directed to a collector and discarded. In some cases, the cell aggregates can be directed to the collector bypassing other components of the system. In some cases, DLD arrays for removing particle aggregates can be referred to as de-clump DLD arrays.

The DLD arrays can be configured to have a critical size for separating cells and subcellular particles in a body fluid. In some cases, the DLD arrays can have a critical size for separating blood cells from subcellular particles in blood. The critical size of the DLD arrays can be from about 1 µm and about 10 µm, about 1.5 µm and about 8 µm, about 1.5 µm and about 7 µm, about 1.5 µm and about 6 µm, about 1.5 µm and about 5 µm, or about 1.5 µm and 4 about µm. The term "about" and its grammatical equivalents in relation to a reference numerical value can include a range of values plus or minus 10% from that value. For example, the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value.

In some cases, the critical size of such DLD arrays can be about 1 µm, 2 µm, 3 µm, 4 µm, 5 µm, 6 µm, 7 µm, 8 µm, 9 µm, 10 µm, or any number in between. In some cases, the critical size of such DLD arrays can be no more than 5 µm, e.g., about 4 µm. In another case, the critical size of such DLD arrays can be 4 µm. In some cases, different types of the blood cells separated from the DLD arrays can be further separated. For example, the red blood cells can be depleted by another DLD array or a magnetic separator. In another example, white blood cells and other circulating rare cells, such as tumor cells and stem cells can be separated from red blood cells by such DLD arrays. In some cases, such DLD arrays can be referred to as de-bulk DLD arrays. This type of DLD can remove cells to specifically minimize the number of DLD processes that the cells are subjected to. The cells removed by this type of DLD arrays can include immune cells, and any abnormal cells that might be present in the blood sample. This type of DLD arrays can also remove any assay-specific particles (e.g., magnetic beads) that might have been added in the sample. For example, the assay-specific particles can be labels with beads such as magnetic beads, 5.6 µm spectrally indexed beads (e.g., from Luminex, BD-CBA), light scatter indexed particles, latex, hydrogels (e.g., from Firefly Bio). The DLD arrays can also be used for effective "washing/removal of unreacted background" of labeling applied in labeling module. The washing and/or labeling can be performed by configuring the DLD arrays in a "car wash" device as described in PCT Application No. WO 20140145152, which is incorporated herein by reference in its entirety.

A "car wash" device can comprise a plurality of inlets and a plurality of outlets with one or more DLD arrays (e.g., with tilted obstacles array) disposed there between. The plurality of inlets can be configured to flow a plurality of flow streams toward the plurality of outlets, wherein the plurality of flow streams each comprises a separate fluid. A "car wash" device can comprise a channel with two or more inlet. One of the inlets can be configured to allow a sample comprising particles to flow in; the other inlets can allow reagents for processing the particles to flow in. In some cases, a "car wash device" can comprise about, or at least 2, 3, 4, 5, 6, 7, 8, 9, 10, 11, 12, 13, 14, 15, 16, 17, 18, 19, 20 or more inlets. In some cases, a "car wash device" can comprise about, or at least 2, 3, 4, 5, 6, 7, 8, 9, 10, 11, 12, 13, 14, 15, 16, 17, 18, 19, 20 or more outlets. The inlets can be configured to flow the same number of separate flow streams in laminar, flow streams across a tilted post array toward the outlets (e.g., 2 outlets), a product outlet, and a waste outlet. In some cases, a "car wash" device can comprise multiple product outlets. For examples, particles with different sizes can flow to different product outlets. A first flow stream comprises a sample comprising particles and the other flow streams comprise reagents for processing the particles. In some cases, a "car wash" device can comprise 6 inlets configured to flow six separate flow streams in laminar, flow streams across a tilted post array toward 2 outlets, a product outlet, and a waste outlet. A first flow stream can comprise a sample comprising particles, a second stream can comprise a buffer, a third stream can comprise a fix and permeabilization stream, a fourth stream can comprise a buffer, a fifth stream can comprise an intracellular label stream, and a sixth stream can comprise a buffer. In some cases, a multi-stream device as described herein can comprise a plurality of parallel flow streams flowing from an input portion of the device to an output portion of the device, wherein at least 4 of the flow streams comprise a reagent. The at least 4 flow streams comprising a reagent can comprise the same and/or different reagent. In some cases, each of the flow streams comprising a reagent can be bounded by two parallel flow streams, each of which carries a buffer. The buffer can be a wash buffer. A "car wash" device can be configured to deflect particles from the sample stream through one or more flow streams comprising reagents. In some cases, a "car wash" device can be configured to deflect particles (e.g., leukocytes in a sample comprising leukocytes and RBCs, e.g., blood) of at least a critical size from the sample stream through the subsequent five parallel flow streams in series (e.g., sample→buffer-→fix/permeabilize→buffer→intracellular Label→buffer). The buffer streams can serve to wash reagents adsorbed non-specifically (e.g., weakly) to the particles (e.g., cells) and unbound reagents from the preceding adjacent flow stream from the environment of the particles deflected through the streams. The buffer stream can remove or substantially remove non-specifically bound and unbound reagent from a particle as well as from the stream comprising the particles. In some cases, a waste outlet can have a width that is greater than the width of the product outlet. The waste outlet can comprises reagents (e.g., surface labeling Mabs, fix/perm reagents, and intracellular binding agents comprising a label as well as undesired particles, e.g., RBCs, below the critical size of the tilted post array).

The DLD arrays herein can be configured as a component of a "car wash" device. In some cases, the "car wash" device can be configured to label and wash the particles in a sample. At mean time, the particles in the sample are separated by the DLD arrays based on their sizes. One or more of the labeling, particle separation, reagent addition, particle-reagent incubation, and washing steps can be performed one or more times. The particles can be labeled with any labels herein. In some cases, at least one of the particles can be labeled with one label. In some cases, at least one of the particles can be labeled with more than one label. The labeled particles can be further analyzed. In some cases, the labeled particles can be subject to pathogen detection, specifically inserted particle detection, and/or cellular assays. In some cases, the labeled particles can be isolated and/or analyzed, e.g., for any downstream applications disclosed herein.

In some cases, particles in a sample can be labeled with a first labeling reagent, and then the first labeling reagent can be washed and removed. One or more steps of the labeling, washing and removing of the first labeling reagent can be performed using a first DLD array. In some cases, the labeled particles can be further labeled with a second labeling reagent, and then the second labeling reagent can be washed and removed. One or more steps of the labeling, washing and removing of the first labeling reagent can be performed using a second DLD array. The first and/or second DLD array can be upstream of a magnetic separator, e.g., the particles are labeled with the first and/or second labeling reagents before passing into a magnetic separator.

The DLD arrays can be configured to have a critical size for separating different types of subcellular particles in a body fluid, e.g., blood. In some cases, the DLD arrays can be used to separate platelets and/or apoptotic bodies from other smaller particles. The critical size of such DLD arrays can be from about 1 µm and about 4 µm, about 1 µm and about 5 µm, about 1 µm and about 6 µm, about 1 µm and about 7 µm, or about 1 µm and about 8 µm. In some cases, the critical size of such DLD arrays can be about 0.5 µm, 1 µm, 1.5 µm, 2 µm, 2.5 µm, 3 µm, 3.5 µm, 4 µm, 4.5 µm, 5 µm, 5.5 µm, 6 µm, 6.5 µm, 7 µm, 7.5 µm, 8 µm, or any number in between. In some cases, the critical size of such DLD can be about 1.5 µm. In another case, the critical size of such DLD can be about 1.0 µm.

The DLD arrays can be used to separate micro-vesicles, bacteria, protein aggregates, and/or proteins from smaller particles. The critical size of the DLD arrays separating micro-vesicles, bacteria, protein aggregates, and/or proteins can be from about 100 nm to about 1000 nm, about 100 nm to about 1100 nm, about 100 nm to about 1200 nm, about 100 nm to about 1300 nm, about 100 nm to about 1400 nm, or about 100 nm to about 1500 nm. In some cases, the critical size of such DLD arrays can be about 50 nm, 100 nm, 110 nm, 120 nm, 130 nm, 140 nm, 150 nm, 160 nm, 170 nm, 180 nm, 190 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, or any number in between. In some cases, the critical size of such DLD arrays can be about 1000 nm. In another case, the critical size of such DLD arrays can be about 1500 nm.

In some cases, the DLD arrays can be used to separate nano-vesicles including viruses, nucleic acid containing exosomes, nucleosome, and/or DNA from smaller particles, such as complex freely available particles, including RNA (e.g., miRNA (e.g., short 6-7 base miRNA), cell-free RNA) and DNA (e.g., cell-free DNA such as circulating tumor DNA). The critical size of such DLD arrays can be from about 20 nm to about 100 nm, about 20 nm to about 150 nm, about 20 nm to about 200 nm, about 20 nm to about 250 nm, about 50 nm to about 100 nm, about 50 nm to about 150 nm, about 50 nm to about 200 nm, or about 50 nm to about 250 nm. In some cases, the critical size of such DLD arrays can be about 20 nm, 25 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180, nm 190 nm, 200 nm, 210 nm, 220 nm, 230 nm, 240 nm, 250 nm, or any number in between. In some cases, the critical size of such DLD arrays can be 50 nm. In another case, the critical size of such DLD arrays can be 30 nm.

b. Obstacles of DLD Arrays

The obstacles of the DLD arrays can be organized into rows and columns (use of the terms rows and columns does not mean or imply that the rows and columns are required to be perpendicular to one another). Obstacles that are aligned in a direction transverse to fluid flow in the flow channel can be referred to as obstacles in a column. Obstacles adjacent to one another in a column can define a gap through which fluid flows. Obstacles in adjacent columns can be offset from one another by a degree characterized by a tilt angle, designated ε (epsilon). Thus, for several columns adjacent to one another (e.g., several columns of obstacles that are passed consecutively by fluid flow in a single direction generally transverse to the columns), corresponding obstacles in the columns can be offset from one another such that the corresponding obstacles form a row of obstacles that extends at the angle ε relative to the direction of fluid flow past the columns. The tilt angle can be selected and the columns can be spaced apart from each other such that 1/ε (when ε can be expressed in radians) can be an integer, and the columns of obstacles repeat periodically. The maximum operable value of ε can be ⅓ radian. The value of ε can be preferably ⅕ radian or less, and a value of 1/10 radian has been found to be suitable in various embodiments of the arrays described herein. The obstacles in a single column can also be offset from one another by the same or a different tilt angle. By way of example, the rows and columns can be arranged at an angle of 90 degrees with respect to one another, with both the rows and the columns tilted, relative to the direction of bulk fluid flow through the flow channel, at the same angle of ε.

The cross-sectional shape of the obstacles of the DLD arrays can be a circle, triangle, square, rectangle, pentagon, hexagon, heptagon, octagon, nonagon, decagon, hendecagon, dodecagon, hexadecagon, icosagon, or star. In some cases, a triangle can be an acute triangle, equilateral triangle, isosceles triangle, obtuse triangle, rational triangle, right triangle (30-60-90 triangle, isosceles right triangle, Kepler triangle), or scalene triangle. In some cases, the cross-sectional shape of a post or obstacle can be a quadrilateral, e.g., a diamond (or a rotated square, where a vertex of the rotated square points in the direction of the flow of the sample), cyclic quadrilateral, square, kite, parallelogram, rhombus, Lozeng, rhomboid, rectangle, tangential quadrilateral, trapezoid, trapezium, or isososceles trapezoid. In some cases, the cross-sectional shape of a post or obstacle can be a crescent, ellipse, lune, oval, Reuleauz polygon, Reuleaux triangle, lens, vesica piscis, salinon, semicircle, tomoe, magatama, triquetra, asteroid, deltoid super ellipse, or tomahawk. In some cases, a cross-sectional shape with a point has a sharpened point. In some cases, a cross-sectional shape with a point has a rounded point. In some cases, a cross-sectional shape with more than one point has all rounded points, all sharpened points or at least one rounded point and at least one sharpened point. In some cases, an obstacle can have a cylindrical shape. In some cases, the obstacles can be the same, e.g., having the same shape and size. In some cases, the obstacles can have different shapes and/or sizes. Arrays comprising obstacles with different shapes and/or sizes can have different critical sizes.

Figure 14A:
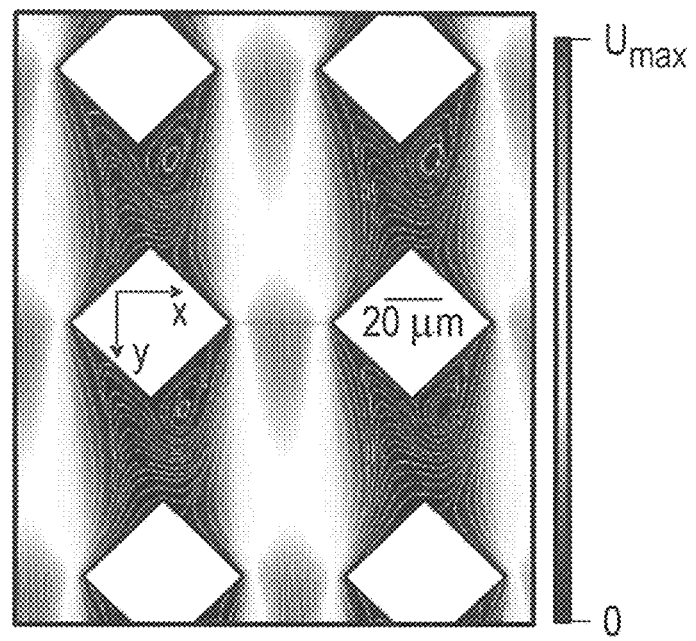
FIG. 14A shows surface plot of fluid velocity in a DLD array with 60 μm diamond posts, 40 μm gaps, and 1/20 tilt at Re of 20.
Figure 14B:
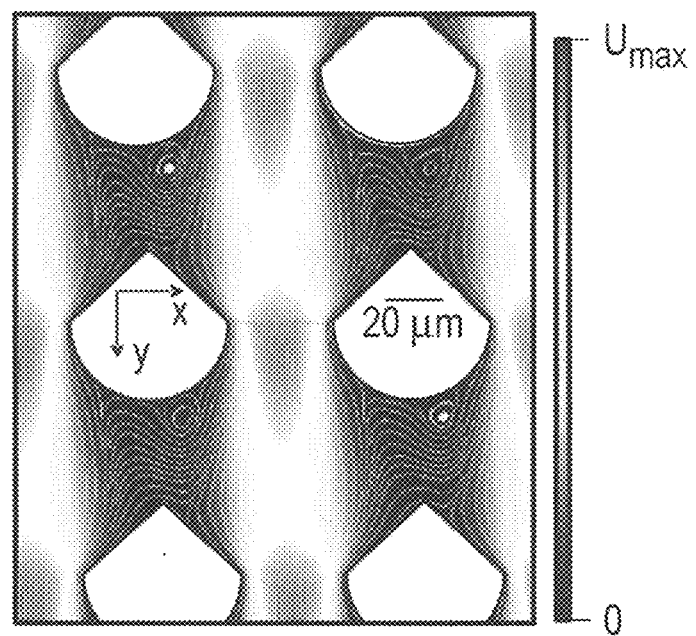
FIG. 14B shows surface plot of fluid velocity in a DLD array with 60 μm teardrop posts, 40 μm gaps, and 1/20 tilt at Re of 20.
Figure 14C:
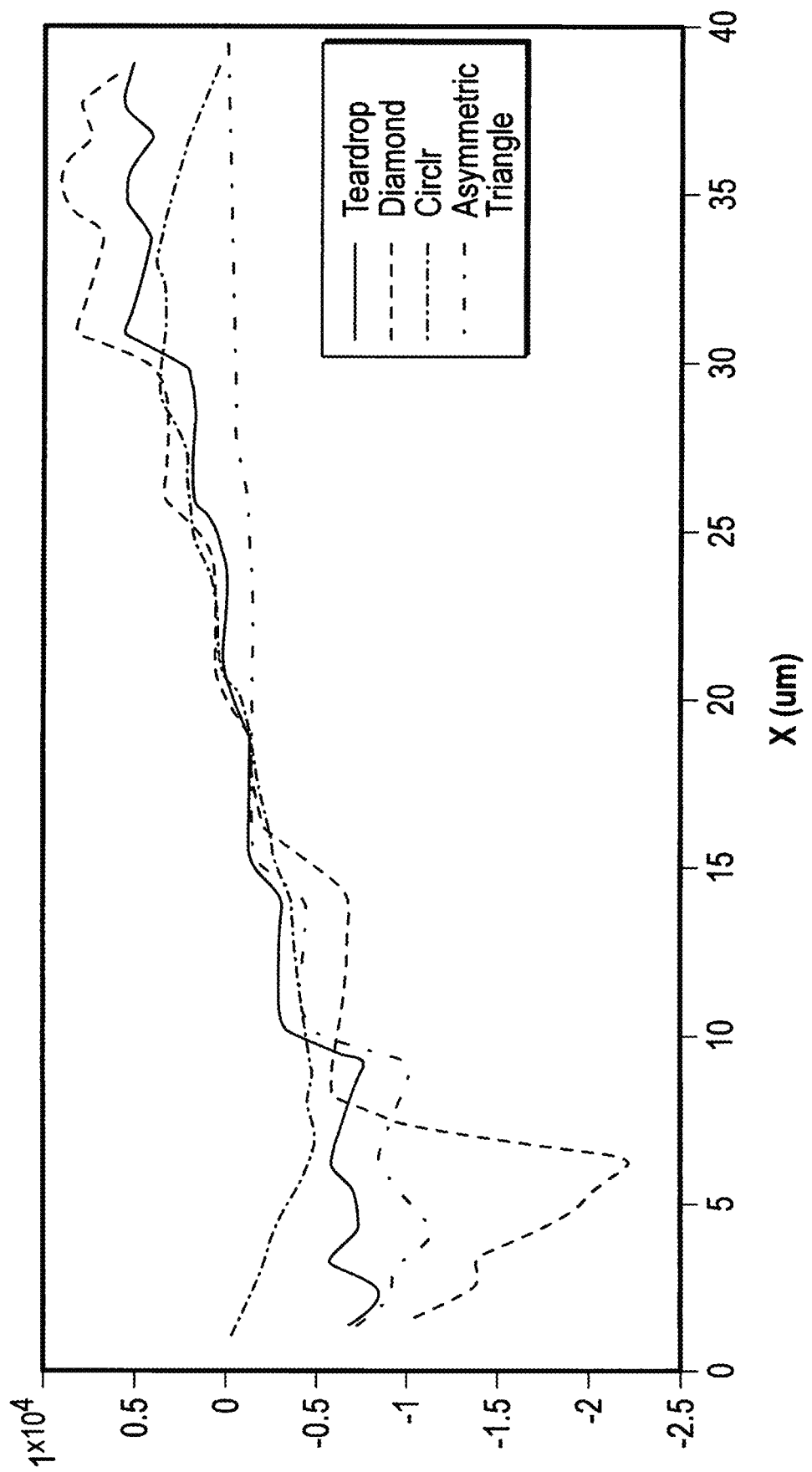
FIG. 14C shows centripetal acceleration of the fluid in the gap for teardrop posts, diamond posts, circular posts, and asymmetric triangular posts at Re of 20.

In some cases, the shape of obstacles can be custom designed, e.g. for optimizing the flow rate in the arrays. Such custom designed shapes include airfoil shape or tear drop shape. A tear drop shape can be one demonstrated in FIG. 14C. For example, a tear drop shape can be a combination of a triangle and a partial circle (e.g., semi-circle) as shown in FIG. 14C. In some cases, a tear drop shape is symmetrical. Alternatively, a tear drop shape can be asymmetrical. The shape of obstacles can be designed to achieve high throughput of separation and/or processing particles. In some cases, the obstacles can all be in the same shape and configuration. In some cases, the obstacles can have different shapes and/or sizes. The obstacles with different shapes and/or sizes can have different critical sizes.

The obstacles of the DLD arrays can have shapes so that the surfaces (upstream of, downstream of, or bridging the gap, relative to the direction of bulk fluid flow) of two obstacles defining a gap are asymmetrically oriented about the plane that extends through the center of the gap and that can be parallel to the direction of bulk fluid flow through the channel. In these cases, the portions of the two obstacles can cause asymmetric fluid flow through the gap. The result can be that the velocity profile of fluid flow through the gap can be asymmetrically oriented about the plane. As a result, the critical size for particles passing through the gap adjacent to one of the obstacles can be different than the critical size for particles passing through the gap adjacent to the other of the obstacles. In some cases, the obstacles of the DLD arrays can have shapes so that the surfaces (upstream of, downstream of, or bridging the gap, relative to the direction of bulk fluid flow) of two obstacles defining a gap are symmetrically oriented about the plane that extends through the center of the gap and that can be parallel to the direction of bulk fluid flow through the channel. In these cases, the portions of the two obstacles can cause symmetric fluid flow through the gap. The result can be that the velocity profile of fluid flow through the gap can be symmetrically oriented about the plane.

In some cases, methods taking advantage of obstacles with optimized cross-sectional shapes can be used to isolate a first type of particles in a sample comprising the first types of particles and a second type of particles, thereby purifying the first type of particles from the sample.

The cross-sectional shape can be made to reduce shear rate of the flow, thus reducing shear-induced compression and/or damage of the particles (e.g., cells) flowing through the array of obstacles. In some cases, the gap between the obstacles is symmetrical, and the two obstacles forming the gap have vertices that point at one another across the gap. The cross-sectional shape of the obstacle can be any shape that has a vertex in the gap that yields a symmetrical gap, e.g., quadrilateral (e.g., diamond), hexagon, octagon, decagon, etc. For example, the surfaces of two adjacent obstacles in a row of an array of obstacles can define a gap. The two adjacent obstacles defining a gap can have a polygonal cross-section, and a vertex of each of the two adjacent obstacles with the polygonal cross-section can point toward each other in a direction substantially perpendicular to a direction of average flow of the sample flowing through the array of obstacles.

When separating first particles of at least a critical size (e.g., white blood cells) from second particles smaller than the critical size (e.g., red blood cells), the obstacles can have cross-sectional shape that is made to reduce the displacement of the second particles to the product comprising the first particles. To this end, the cross-sectional shape can be made to have symmetry about an axis parallel to the flow direction (e.g., average flow direction) of the sample. In some cases, the surfaces of two adjacent obstacles in a row of the array of obstacles define a gap, whose shape is substantially symmetrical relative to a plane parallel to the flow direction of the sample. The plane can be equidistant from the center of the cross-section of each of the two obstacles in the row. In some cases, the cross-sectional shape of the two adjacent obstacles can be made so that a great fraction of the sample flow is close to the center of the gap defined by the two obstacles. For example, if the width of the plane equals to ½ of the width of the gap, there can be at least 30%, 40%, 50%, 60%, 70%, 80%, 90%, or 95% of the flow of the sample occurs within the plane. In some cases, the cross-section of the obstacles is in a diamond shape. In some cases, the cross-section of the obstacles is in a tear drop shape or a modified tear drop shape (with a vertex pointing into the gap). "Modified" refers to the fact that the edge of the tear drop is not smooth but has an abrupt point.

A device can be made from any of the materials from which micro- and nano-scale fluid handling devices are typically fabricated, including silicon, glasses, plastics, and hybrid materials. The flow channel can be constructed using two or more pieces which, when assembled, form a closed cavity (preferably one having orifices for adding or withdrawing fluids) having the obstacles disposed within it. The obstacles can be fabricated on one or more pieces that are assembled to form the flow channel, or they can be fabricated in the form of an insert that can be sandwiched between two or more pieces that define the boundaries of the flow channel. Materials and methods for fabricating such devices are known in the art.

Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) can be used to fabricate silicon-based devices with small gaps, small obstacles and large aspect ratios (ratio of obstacle height to lateral dimension). Thermoforming (embossing, injection molding) of plastic devices may also be used. Additional methods include photolithography (e.g., stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) may be employed. In some cases, the devices can be fabricated by 3D printing. Methods for 3D printing include stereolithography, fused deposition modeling (FDM), electron beam free-from fabrication (EBF), direct metal laser sintering (DMLS), Electron Beam Melting (EBM), Selective Laser Melting (SLM), Selective Heat Sintering (SHS), Selective Laser Sintering (SLS), Plaster-based 3D Printing (PP), Laminated Object Manufacturing (LOM), Stereolithography (SLA) and Digital Light Processing (DLP).

The system can comprise one or more DLD arrays for separating particles. In some cases, the system can comprise about 1, 2, 3, 4, 5, 6, 7, 8, 9, 10, 11, 12, 13, 14, 15, 16, 17, 18, 19, 20, or more arrays of obstacles. In some cases, two or more the arrays of obstacles in the system can be fluidically connected with each other. In some cases, the arrays of obstacles can be fluidically connected with other components in the system. For example, one or more of the obstacles in the system can be fluidically connected with a magnetic separator. In some cases, all of the arrays of obstacles are disposed in the flow channel in the system.

An array of obstacles can comprise one or more zones. A zone can be an area on a device with the same or similar sized post (obstacles) and gaps. In some cases, an array of obstacles in a device can comprises 1, 2, 3, 4, 5, 6, 7, 8, 9, or 10 zones. In some cases, a channel in a device comprises at least 1, 2, 3, 4, 5, 6, 7, 8, 9, or 10 zones. In some cases, an array of obstacles can comprise more than one zone of obstacles, at least two zone comprising obstacles of different sizes and/or geometries.

The system can comprise multiple DLD arrays for separating particles based on different sizes. In some cases, the DLD arrays have different critical sizes from each other. When a sample passes through the system, particles of different sizes can be separated by the multiple DLD arrays. In some cases, the system can comprise a first array of obstacle, wherein the first array of obstacles can be configured to allow first particles of at least a first critical size to flow in a first direction and second particles of less than the first critical size to flow in a second direction different from the first direction. The system can further comprise a second array of obstacles, wherein the second array of obstacles can be configured to allow third particles of at least a second critical size to flow in a third direction and fourth particles of less than the second critical size to flow in a fourth direction, wherein the second critical size can be less than the first critical size. In some cases, the system can further comprise a third array of obstacles, wherein the third array of obstacles can be configured to allow fifth particles of at least a third critical size to flow in a fifth direction and sixth particles of less than the third critical size to flow in a sixth direction, and wherein the third critical size can be less than the second critical size. In some cases, the system can further comprise a fourth array of obstacles, wherein the fourth array of obstacles can be configured to allow seventh particles of at least a fourth critical size to flow in a seventh direction and eighth particles of less than the fourth critical size to flow in a eighth direction, and wherein the fourth critical size can be less than the third critical size. In some cases, the system can further comprise a fifth array of obstacles, wherein the fifth array of obstacles can be configured to allow ninth particles of at least a fifth critical size to flow in a ninth direction and tenth particles of less than the fifth critical size to flow in a tenth direction, and wherein the fifth critical size can be less than the fourth critical size. In some cases, the system can further comprise a sixth array of obstacles, wherein the sixth array of obstacles can be configured to allow eleventh particles of at least a sixth critical size to flow in a eleventh direction and twelfth particles of less than the sixth critical size to flow in a twelfth direction, and wherein the sixth critical size can be less than the fifth critical size. In some cases, the system can further comprise an $n^{th}$ array of obstacles, wherein the $n^{th}$ array of obstacles can be configured to allow at least two subgroups of the particles from the $(n-1)^{th}$ array to flow in different directions, wherein the critical size of the $n^{th}$ array can be smaller than the $(n-1)^{th}$ array. In some cases, the system can comprise 2, 3, 4, 5, 6, 7, 8, 9, 10, 11, 12, 13, 14, 15, 16, 17, 18, 19, 20 or more arrays of obstacles with different critical sizes to separate particles of different sizes. In some cases, two or more the arrays of obstacles in the system can be fluidically connected with each other. In some cases, the arrays of obstacles can be fluidically connected with other components in the system. For example, one or more of the obstacles in the system can be fluidically connected with a magnetic separator. In some cases, all of the arrays of obstacles are disposed in the flow channel in the system.

In some cases, particles larger than a critical size deflected by a DLD array can be directed to bypass the downstream DLD arrays. Bypassing the particles can avoid clogging in the downstream DLD arrays. In some cases, bypassing the particles can allow the particles to be collected (e.g., for further processing or analysis) or discarded. In some cases, the particles can be bypassed by one or more bypass channels that remove output from an array. Although described here in terms of removing particles above the critical size of a DLD array, the bypass channel can also be used to remove output from any portion of the array.

The system can comprise only one DLD array for separating particles. In some cases, the array has a maximum pass-through size that can be several times larger than the cut-off size, e.g., when separating white blood cells from red blood cells. This result can be achieved using a combination of a large gap size d and a small bifurcation ratio ε. In some cases, the ε can be at most ½, e.g., at most ⅓, 1/10, 1/30, 1/100, 1/300, or 1/1000. In such cases, the obstacle shape can affect the flow profile in the gap; however, the obstacles can be compressed in the flow direction, in order to make the array short.

In some cases a DLD array can have a tilt angle ε (with respect to the direction of fluid flow) of at least ⅓, ¼, ⅕, ⅙, 1/7, ⅛, 1/9, 1/10, 1/11, 1/12, 1/13, 1/14, 1/15, 1/16, 1/17, 1/18, 1/19, 1/20, 1/21, 1/22, 1/23, 1/24, 1/25, 1/26, 1/27, 1/28, 1/29, 1/30, 1/31, 1/32, 1/33, 1/34, 1/35, 1/36, 1/37, 1/38, 1/39, 1/40, 1/41, 1/42, 1/43, 1/44, 1/45, 1/46, 1/47, 1/48, 1/49, 1/50, 1/51, 1/52, 1/53, 1/54, 1/55, 1/56, 1/57, 1/58, 1/59, 1/60, 1/61, 1/62, 1/63, 1/64, 1/65, 1/66, 1/67, 1/68, 1/69, 1/70, 1/71, 1/72, 1/73, 1/74, 1/75, 1/76, 1/77, 1/78, 1/79, 1/80, 1/81, 1/82, 1/83, 1/84, 1/85, 1/86, 1/87, 1/88, 1/89, 1/90, 1/91, 1/92, 1/93, 1/94, 1/95, 1/96, 1/97, 1/98, 1/99, 1/100, 1/110, 1/120, 1/130, 1/140, 1/150, 1/160, 1/170, 1/180, 1/190, 1/200, 1/300, 1/400, 1/500, 1/600, 1/700, 1/800, 1/900, 1/1000, 1/2000, 1/3000, 1/4000, 1/5000, 1/6000, 1/7000, 1/8000, 1/9000, or 1/10,000 radian.

c. Multiplexed Deterministic Arrays

Deterministic separation can be achieved using multiplexed deterministic arrays. Putting multiple arrays on one device can increase sample-processing throughput, and can allow for parallel processing of multiple samples or portions of the sample for different fractions or manipulations. In some cases, the multiplex device can include two devices attached in series, e.g., a cascade. For example, the output from the major flux of one device can be coupled to the input of a second device. Alternatively, the output from the minor flux of one device can be coupled to the input of the second device. In some cases, DLD arrays herein can comprise multiplexed deterministic arrays described in U.S. Pat. No. 8,585,971, which is incorporated herein by reference in its entirety.

i. Duplexing

Two arrays can be disposed side-by-side, e.g., as mirror images. In such an arrangement, the critical sizes of the two arrays can be the same or different. Moreover, the arrays can be arranged so that the major flux flows to the boundary of the two arrays, to the edge of each array, or a combination thereof. Such a multiplexed array can also contain a central region disposed between the arrays, e.g., to collect particles above the critical size or to alter the sample, e.g., through buffer exchange, reaction, or labeling.

ii. Multiplexing on a Device

In addition to forming a duplex, two or more arrays that have separated inputs can be disposed on the same device. Such an arrangement could be employed for multiple samples, or the plurality of arrays can be connected to the same inlet for parallel processing of the same sample. In parallel processing of the same sample, the outlets can or cannot be fluidically connected. For example, when the plurality of arrays has the same critical size, the outlets can be connected for high throughput samples processing. In another example, the arrays cannot all have the same critical size or the particles in the arrays cannot all be treated in the same manner, and the outlets cannot be fluidically connected. In some cases, multiplexing can also be achieved by placing a plurality of duplex arrays on a single device. A plurality of arrays, duplex or single, can be placed in any possible three-dimensional relationship to one another.

In some cases, the system or device (e.g., one or more DLD arrays) can be integrated into a blood collection system (e.g., a blood collection tube), and subsequently processed by centrifugation into sub-compartments. In some cases, the system or device can be positively or negatively pressure driven for vacuum-based blood collection tube technology.

d. Microfluidic Channels for Concentrating Particles

Provided herein also include microfluidic channels for concentrating particles. A microfluidic channel for concentrating particles can be any DLD device disclosed in the application. A microfluidic channel for concentrating particles can comprise one or more DLD arrays that deflect particles (e.g., particles of at least a critical size) in a solution flowing out of the microfluidic channel through a product outlet. A portion of the sample (e.g., a portion that does not contain the particles) can flow out of the microfluidic channel through one or more waste outlets. Thus, the deflected particles (e.g., particles of at least a critical size) can be concentrated in the solution.

A microfluidic channel for concentrating particles in a sample can comprise at least 1, 2, 3, 4, 5, 6, 7, 8, 9, or 10 inlets. An inlet used for flowing a sample into the microfluidic channel can be referred to as a "sample inlet". An inlet used for flowing a buffer into the microfluidic channel can be referred to as a "buffer inlet". A microfluidic channel for concentrating particles can comprise no more than one inlet. In some cases, the inlet is a sample inlet. In some cases, the inlet is both a sample inlet and a buffer inlet. For example, a buffer can be flowed in the microfluidic channel through the inlet. Then a sample can be flowed in the microfluidic channel through the same inlet. A microfluidic channel for concentrating particles can comprise more than one inlet. In such microfluidic channel, one or more of the inlets can be sample inlets. In some cases, a microfluidic channel for concentrating particles can comprise two inlets. For example, one of the two inlets can be a sample inlet, and the other inlet can be a buffer inlet. In some cases, both inlets are sample inlets. In some cases, a microfluidic channel for concentrating particles can comprise three inlets. For example, two of the inlets can be sample inlets, and the third inlet can be a buffer inlet.

A microfluidic channel for concentrating particles in a sample can comprise at least 1, 2, 3, 4, 5, 6, 7, 8, 9, or 10 outlets. An outlet through which the concentrated particles flow out of the microfluidic channel can be referred to as a "product outlet". An outlet through which a solution not containing concentrated particles flow out of the microfluidic channel can be referred to as a "waste outlet". A microfluidic channel for concentrating particles can comprise two or more outlets. In some cases, one or more, but not all, of the outlets are product outlets. In some cases, a microfluidic channel for concentrating particles can comprise two outlets. For example, one of the two inlets can be a product outlet, and the other outlet can be a waste outlet. In some cases, a microfluidic channel for concentrating particles can comprise three outlets. For example, two of the outlets can be product outlets, and the third one can be a waste outlet.

A microfluidic channel for concentrating particles can comprise at least 1, 2, 3, 4, 5, 6, 7, 8, 9, 10, 11, 12, 13, 14, 15, 16, 17, 18, 19, or 20 DLD arrays disclosed in the application. In some cases, a microfluidic channel for concentrating particles comprises one DLD array. A In some cases, a microfluidic channel for concentrating particles comprises two DLD arrays. In some cases, a microfluidic channel for concentrating particles comprises two mirrored DLD arrays.

A microfluidic channel for concentrating particles can comprise at least 1, 2, 3, 4, 5, 6, 7, 8, 9, 10, 11, 12, 13, 14, 15, 16, 17, 18, 19, 20 bypass channels. Particles flowing through the microfluidic channel can be deflected by a DLD array in the microfluidic channel to a bypass channel. The bypass channel can be connected to an outlet (e.g., a product outlet). In some cases, a bypass channel can be between a DLD array and a boundary of the microfluidic channel. In some cases, a bypass channel can be between two DLD arrays in the microfluidic channel.

A microfluidic channel for concentrating particles can be used in combination with any other devices and/or systems disclosed herein. For example, a microfluidic channel for concentrating particles can be connected (e.g., fluidically connected) with one or more devices for separating particles disclosed herein, e.g., DLD devices and magnetic separators. In some cases, a microfluidic channel for concentrating particles is connected (e.g., fluidically connected) with a DLD device for separating particles. In some cases, a microfluidic channel for concentrating particles is connected (e.g., fluidically connected) with a magnetic separator. In some cases, a microfluidic channel for concentrating particles is connected (e.g., fluidically connected) with a DLD device for separating particles and a magnetic separator, e.g., between the DLD device and the magnetic separator, or after a DLD device and a magnetic separator (e.g., DLD array—magnetic separator—concentrator (e.g., second DLD array).

A concentrating device can be single-stage, e.g., comprises a DLD array. In other cases, a concentrating device can be multiple-stage. For example, a concentrating device can be a 2-stage concentrator, in which the first stage comprises a DLD array and the second stage comprises a DLD array. For a multiple-stage concentrating device, each stage can concentrate a sample for the same or different folds.

Figure 6E:
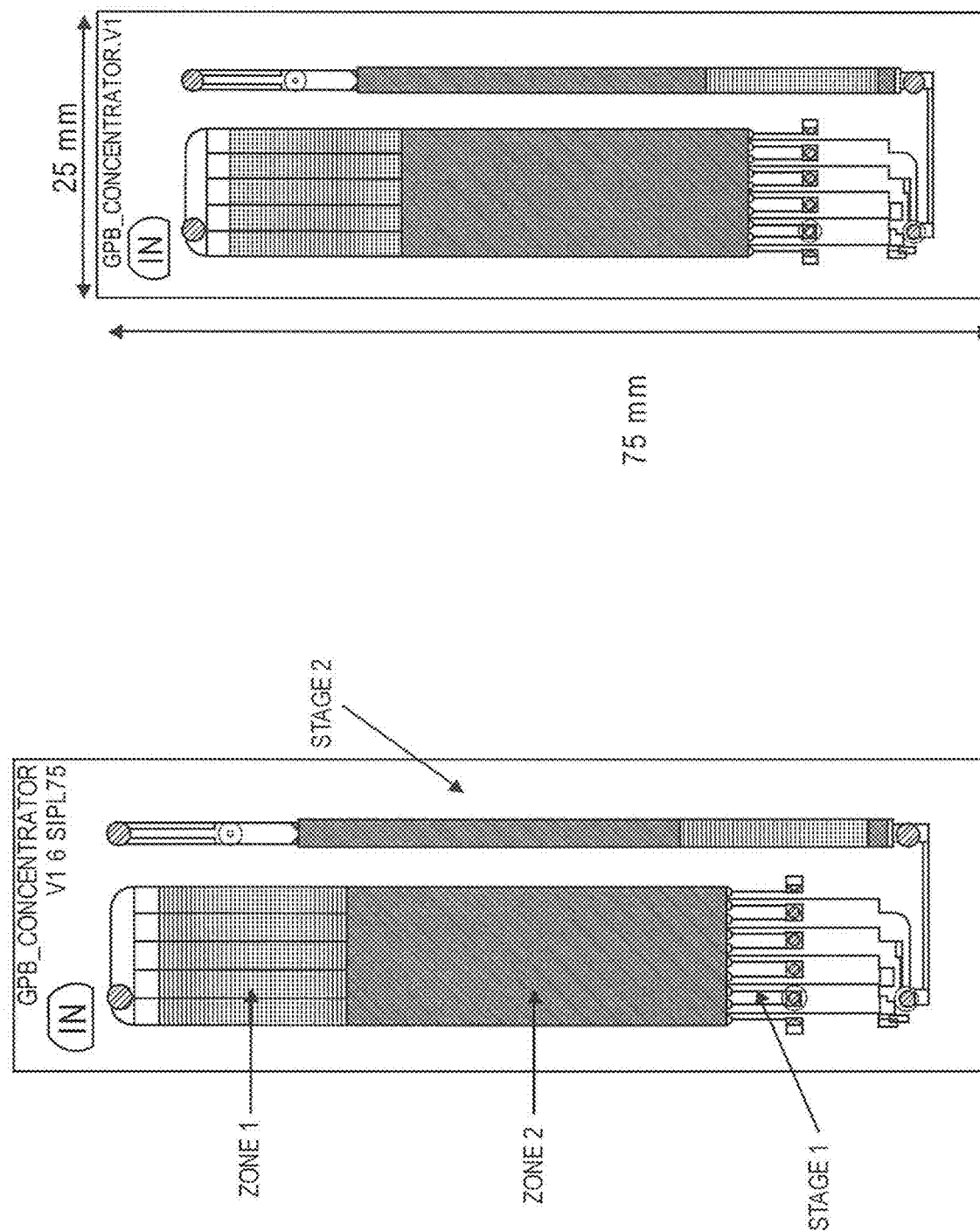

FIG. 6E shows an exemplary 2-stage concentrating device that can concentrate particles about 10× concentration per stage. In the first stage, the device comprises one inlet that feeds the entire width of a DLD array. The DLD array can bump particles towards the central bypass channel. The first stage further comprises 2 outlets: one for concentrated products, and the other for waste (e.g., buffer and anything below critical diameter). In some cases, the concentrator can comprise a single channel. Alternatively, the concentrator can comprise multiple channels in parallel to increase throughput. The DLD array can have a single zone or multiple zones. The obstacles in the DLD array can be in any shape disclosed herein.

Following passage through a concentrator (e.g., a second DLD array), particles (e.g., cells) can be concentrated about, or at least 2, 3, 4, 5, 6, 7, 8, 9, 10, 15, 20, 50, 100, 250, 500, 750, 1000, or 5000-fold. In some cases, a concentrator can comprise two or more (e.g., 3, 4, 5, 6, 7, 8, 9, 10, 20, 25, 50 or more) stages (e.g., different DLD arrays), and each stage can concentrate particles about, or at least, 2, 3, 4, 5, 6, 7, 8, 9, 10, 15, 20, 50, 100, 250, 500, 750, 1000, or 5000-fold. In some cases, different stages of a concentrator can concentrate particles to different levels (e.g., one stage concentrates 10×, a second stage concentrates 5×). In some cases, different stages of a concentrator can concentrate particles at the same level (e.g., each stage concentrates 10×). A first stage of a concentrator can provide a higher level of concentration of particles than a second stage or a lower level of concentration of particles than a second stage of the concentrator.

B. Filters

In some cases, the retained particles can be discarded. In some cases, the retained particles can be further analyzed. For example, the retained particles can be examined on the filter. In another example, the retained particles can be flushed out of the filter for further analysis. The filter can be used to separate large particles or particle aggregates from a sample. In some cases, a filter can be used to separate cell aggregates disclosed herein. The filter can be configured to capture particles or particle aggregates larger than a pore size of the filter and allow particles or particle aggregates of no larger than the pore size to pass through. In some cases, the sample can pass through the filter before flowing into any DLD arrays. In some cases, particles deflected by a DLD array can be passed through a filter to remove and/or collect a subgroup of particles larger than a certain size. In some cases, a filter can be configured to monitor flow stream of a sample to provide a feedback mechanism. The feedback mechanism can be optical, electrical, or any means known in the art.

The pore size of a filter herein can be at least 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, or 30 μm. In some cases, the pore size can be no more than 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, or 30 μm. In some cases, the pore size of a filter can be no more than 20 μm.

C. Magnetic Separators

The systems provided herein can comprise a magnetic separator, (e.g., a device separating particles based on their magnetic susceptibilities). In some case, the magnetic separator can be configured to separate particles with magnetically susceptible labels from particles without magnetically susceptible labels. In some cases, the magnetic separator can configured to separate particles whose magnetic susceptibility is equal to or above a critical value from particles whose magnetic susceptibility is below the critical value. The ability of the magnetic separator to separate particles based on their magnetic susceptibilities can be balanced by the flow rate at which the sample passing the magnetic separator. In some cases, the magnetic separator can be combined with one or more DLD arrays herein for separating different types of particles. For example, the magnetic separator can be fluidically connected with one or more DLD arrays herein. In some cases, the magnetic separator can be downstream of a DLD array (e.g., particles separated by the DLD arrays are further separated by the magnetic separator). In some cases, the magnetic separator can be upstream of a DLD array (e.g., particles separated by the magnetic separator are further separated by the DLD arrays). A magnetic separator can be upstream and downstream of a DLD array. In some cases, the magnetic separator can comprise a channel. A sample can flow through the channel and particles in the sample can be retained in the channel or deflected to a wall of the channel.

The magnetic separator can be used to for selecting particles in a sample. In some cases, the magnetic separator can be used to positively select particles in a sample. For example, one or more desired particles can be attracted to a magnetic field in the magnetic separator, thus being separated from other particles in the sample. In some cases, the magnetic separator can be used to negatively select particles in a sample. For example, one or more non-desired particles can be attracted to a magnetic field in the magnetic separator, thus being separated from other particles in the sample. In either case, the population of particles containing the desired particle can be collected for analysis or further processing.

Selection of particles by the magnetic separator can be achieved in different ways. In some cases, the magnetic separator can select a population of particles in a sample by retaining the particles in the separator by magnetic force. For example, the particles can be retained on one or more magnetic surfaces or one or more arrays of magnetic obstacles. The non-selected particles in the sample can be allowed to pass through the magnetic separator. In some cases, the retained particles can be released from the magnetic separator. For example, the retained particles can be released by increasing the overall flow rate of the fluid flowing through the device, decreasing the magnetic field, or through some combination of the two. In some cases, the magnetic separator can retain a first group of particles and deflect a second group of particles, thereby separating the first and second groups of particles from other particles in the sample. For example, the first group of particle can be retained on the wall of the magnetic separator. The first group of particles can be magnetic susceptible (e.g., comprising magnetic susceptible labels, or having intrinsic magnetic susceptibility). The magnetic separator can be configured to have a magnetic force holding the first group of particles on the wall. The magnetic force holding the first group of particles can be stronger than the perpendicular flow force on the first group of particles. The second group of particles can also feel a magnetic force, but cannot be held on the wall. This may be due to less magnetic susceptibility, stronger perpendicular flow force, greater weight, greater flow resistance (e.g., due to sizes and/or shapes) of the second group of particles compared to the first group of particles. The second group of particles can be deflected (e.g., pulled toward the wall) to a direction different from the sample flow stream, but can still flow through the magnetic separator.

The magnetic separator can select a population of particles in a sample by directing the particle to flow in a direction different from the flow of the non-selected particles in the sample. For example, the selected particles can be attracted to the magnetic force generated by the magnetic separator and deflected from the flow of the non-selected particles that are not magnetic susceptible. In some cases, the magnetic separator and one or more DLD arrays can be used to separate particles simultaneously. For example, the magnetic separator can generate a magnetic field across the DLD arrays. Particles flowing through the DLD arrays can be deflected by both the DLD arrays and the magnetic force. In any of the cases above, the selected particles can be collected for further analysis and/or processing. In some cases, the particles with magnetically susceptible labels can be directed to a stream flow a DLD array. The particles can be directed from both sides of the flow stream. In some cases, the flow stream can be in or close to the middle of the DLD array. In some cases, the flow stream can be between two DLD arrays (e.g., two mirrored DLD arrays), wherein particles with magnetically susceptible labels can be directed from one or both of the DLD arrays to the flow stream. In some cases, the magnetic field can be configured to be symmetric about an axis along the length of the DLD device (e.g., a channel of the DLD device). The labeled particles (e.g., by magnetically susceptible labels) can migrate (e.g., directed by a magnetic field) towards or away from the axis.

The magnetic separation can occur as a 2-stage capture and release. The particles with magnetically susceptible labels can be attracted to a magnetic region in a magnetic separator and immobilized while the other particles flow through. In some cases, the separation can be a negative selection. The particles with magnetically susceptible labels can be left in the magnetic separator, or flushed out and collected. In some cases, the separation can be a positive selection. The particles with magnetically susceptible labels can be collected after the entire sample is processed by removing the magnetic field, and then collecting the eluent in a separate container. In some cases, the magnetic region can have a magnetic field gradient that immobilizes the particles with magnetically susceptible labels against a side wall. In some cases, the magnetic region can be metallic elements fabricated in or near the channel that create an induced local magnetic field in the presence of an external magnetic field. In some cases, the magnetic region can also be an array of microposts (e.g., made from plastic) embedded with magnetic particles. These microposts can induce local magnetic fields that attract the particles with magnetically susceptible labels and free magnetically susceptible labels as they flow through the array. Once the external magnetic field is removed the microposts may no longer attract the particles with magnetically susceptible labels, which can then be eluted form the device.

The magnetic separator can be any device that can generate a magnetic field. In some cases, the magnetic separator can be a chamber with one or more magnetic surfaces. In some cases, a magnetic-activated cell sorting (MACS) column can be used to effect selection of magnetically susceptible particles. If the particles are magnetically susceptible, it can be attracted to the MACS column under a magnetic field, thereby permitting enrichment of the desired particles relative to other constituents of the sample. In some cases, the magnetic separator can contain one or more magnetic obstacles. Magnetic susceptible particles in a sample can bind to the obstacles, thus being retained in the magnetic separator.

Figure 19A:
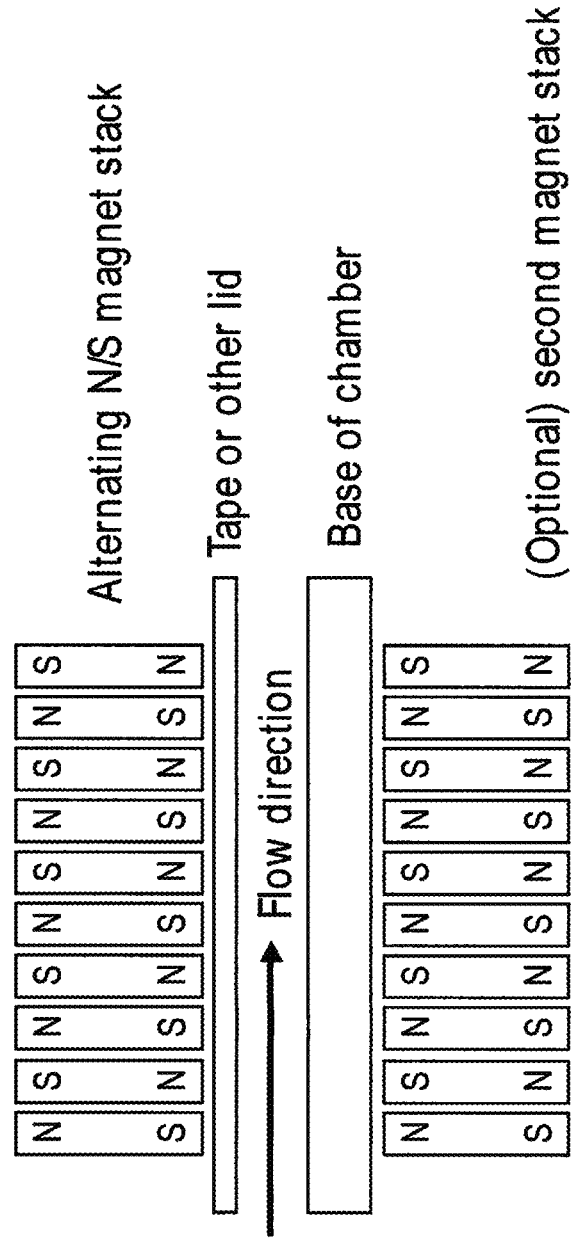
FIGS. 19A and 19B illustrate embodiments of arrangement of magnets relative to a microfluidic channel.
Figure 19B:
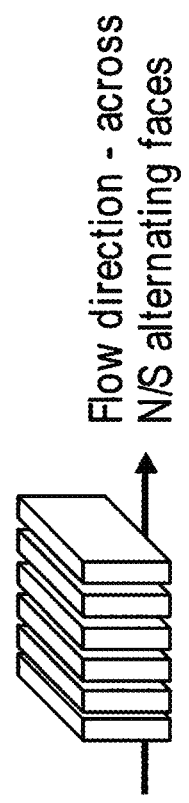

The magnetic separator herein can comprise a source of a magnetic field. In some cases, the source of the magnetic field can include hard magnets, soft magnets, electromagnets, superconductor magnets, or a combination thereof. In some cases, a spatially non-uniform permanent magnet or electromagnet can be used to create organized and in some cases periodic arrays of magnetic particles within an otherwise untextured microfluidic channel, e.g., as described in Deng et al. Applied Physics Letters, 78, 1775 (2001), which is incorporated herein by reference in its entirety. In some cases, a non-uniform magnetic field may not a regular periodicity. An electromagnet can be used to create a non-uniform magnetic field in a device. The non-uniform field can create regions of higher and lower magnetic field strength, which, in turn, can attract magnetic particles in a periodic arrangement within the device. Other external magnetic fields can be used to create magnetic regions to which magnetic particles attach. A hard magnetic material can also be used in the fabrication of the device, thereby obviating the need for electromagnets or external magnetic fields. In some cases, the systems can comprise a plurality of channels having magnetic regions, e.g., to increase volumetric throughput. In some cases, these channels may be stacked vertically. In some cases, a magnetic separator can comprise a stack of magnets. For example, the magnets can be arranged with poles alternating and/or stacked side by side. This configuration can create magnetic field gradient. The strength of the gradient can be controlled by the adjusting the number of magnets, the magnetic force of the magnets, and/or the alignment of the magnets. FIG. 19A illustrates arrangements of magnets relative to a microfluidic channel in a magnetic separator. FIG. 19A illustrates a plurality of magnets arranged above a microfluidic channel (e.g., above a tape or other lid), where the plurality of magnets have alternating polarities, wherein the polarities alternate in a flow direction of the microfluidic channel. A second plurality of magnets can be arranged below the microfluidic channel, where the second plurality of magnets have alternating polarities, and wherein the polarities alternate in a flow direction of the microfluidic channel. FIG. 19B illustrates a plurality of magnets arranged with alternating polarities in flow direction. The microfluidic channel can be offset between magnetic stacks. When there are stacks one both sides of the microfluidic channel, the channel can sit closer to one stack than another. As shown in FIG. 19A, the "tape side" of the channel can sit much closer to one magnet stack than the other side of the channel. FIG. 19A is an example of an offset channel. The tape can be thinner than the channel base. In other cases, the thickness of the tape can be equal or greater than the channel base. The net migration of magnetic particles can be towards the closer magnetic stack, in this case towards the lid. In some cases, the microfluidic channel may not be offset between the magnetic stacks. For example, the distance between the microfluidic channel and one stack can be substantially the same as the distance between the microfluidic channel and the other stack. A stack of magnets can include about, or at least 1, 2, 3, 4, 5, 6, 7, 8, 9, 10, 11, 12, 13, 14, 15, 16, 17, 18, 19, 20, 25, 30, 40, 50, 75, or 100 magnets. A type of magnet in one stack can be different than a type of magnet in a second stack. A type of magnet in one stack can be the same as a type of magnet in a second stack. A stack can comprise more than one type of magnet. A magnet can be permanent magnet and can comprise neodymium iron boron (NdFeB), samarium cobalt (SmCo), alnico, or ceramic or ferrite magnets.

The distance between the microfluidic channel (e.g., side of a channel) and a stack of magnets can be about, or at least 1 μm, 10 μm, 20 μm, 30 μm, 40 μm, 50 μm, 60 μm, 70 μm, 80 μm, 90 μm, 100 μm, 200 μm, 400 μm, 600 μm, 800 μm, 1000 μm, 1200 μm, 1500 μm, 2000 μm, 3000 μm, or 5000 μm. In some cases, the distance between the microfluidic channel (e.g., side of a microfluidic channel) and a stack of magnets can be from about 1 μm to about 10 mm, e.g., from about 50 μm to 5 mm, 80 μm to 2 mm, or 100 μm to 1.5 mm. In the cases where the distance between the microfluidic channel (e.g., side of a microfluidic channel) and a first stack on one side is greater than the distance between the microfluidic channel and a second stack on the other side (e.g., the microfluidic channel is offset), the distance between the microfluidic channel and the first stack can be at least 1 μm, 10 μm, 20 μm, 30 μm, 40 μm, 50 μm, 60 μm, 70 μm, 80 μm, 90 μm, 100 μm, 200 μm, 400 μm, 600 μm, 800 μm, 1000 μm, 1200 μm, 1500 μm, 2000 μm, 3000 μm, or 5000 μm, and the distance between the microfluidic channel and the second stack can be at least 1 μm, 10 μm, 20 μm, 30 μm, 40 μm, 50 μm, 60 μm, 70 μm, 80 μm, 90 μm, 100 μm, 200 μm, 400 μm, 600 μm, 800 μm, 1000 μm, 1200 μm, 1500 μm, 2000 μm, 3000 μm, or 5000 μm. In some cases, the distance between the microfluidic channel and the first stack can be from about 1 μm to about 500 μm, and the distance between the microfluidic channel and the second stack can be from about 500 μm to about 5 mm. In some cases, the distance between the microfluidic channel and the first stack can be from about 1 μm to about 1 mm, and the distance between the microfluidic channel and the second stack can be from about 1 mm to about 10 mm. For example, the distance between the microfluidic channel and the first stack can be about 100 μm, and the distance between the microfluidic channel and the second stack can be about 1.5 mm.

A microfluidic channel can be covered by one, two (e.g., on two sides of the microfluidic channel), or more stacks of magnets. The stacks can cover at least 20%, 30%, 40%, 50%, 60%, 70%, 80%, 90%, or 100% of the length of the microfluidic channel. In some cases, the one or two stacks can cover the entire length of the microfluidic channel.

In some cases, a magnetic separator comprises obstacles, e.g., a DLD array with obstacles that are magnetic. In some cases, such obstacles deflect magnetically labeled particles flowing in a microfluidic channel. In certain cases, obstacles can attract magnetically labeled particles flowing in a microfluidic channel.

Accumulation of magnetic particles can occur on a lid (e.g., tape-side) surface. A magnet can cover the full-width of a microfluidic channel, and an alternating stack can cover the full length of the microfluidic channel. Magnet height can be increased or decreased; if magnet height is increased, field strength can increase. To create an area with lots of field gradients, magnets that are narrow in width can be used. In some cases, in the N/S direction, if the magnet height is increased, the pull strength and force of the magnet is also increased. The result can still be a stack with the same number of nodes, but the magnitude of force pulling the particles is higher in those nodes. Any magnet combinations that result in a strong pull force on the magnetically-labeled particles can be used here. For example, a Halbach array can be used. In some cases, there can be one chamber before DLD concentrator, second "cleanup" chamber after DLD concentrator to take advantage of slower linear flowrate after removing excess fluid in concentration module. One exemplary configuration of the system can be, from upstream to downstream, (1) DLD separator, (2) magnetics, (3) DLD Concentrator, and (4) magnetic separator. In some cases, after the sample goes through the concentrator, the volume can be significantly smaller, so a linear flowrate across the magnet can be significantly reduced, allowing more residence time for the magnetic separation to take place.

In another example, the magnets can be arranged such that they form a Halbach array, a special arrangement of magnets that augments the magnetic field on one side of the array while cancelling the field to near zero on the other side. This can achieved by having a spatially rotating pattern of magnetization. In some embodiments, a magnetic separator can comprise two sets or arrays of magnets. In some embodiments, a magnetic separator can comprise an array of magnets along opposite sides of a microfluidic channel. In some embodiments, a magnet on one side of a channel may be aligned with a magnet on the opposite side of the channel, and the two magnets may have opposite polarities. In some embodiments, one or more arrays of magnets may be configured such that the flow of a sample through a microfluidic channel is perpendicular to the magnetic field generated by the one or more arrays of magnets. In another embodiment, one or more arrays of magnets may be configured such that the flow of a sample through a microfluidic channel is parallel to the magnetic field generated by the one or more arrays of magnets. Magnets can be arranged in single or double stacks one or more sides of a microfluidic channel, e.g., a microfluidic channel with a single depth and single width, a microfluidic channel with two or more depths and/or widths (e.g., staircase), a microfluidic channel with a gradual increase or decrease in depth and/or width in a flow direction.

In some embodiments, a magnetic separator can comprise ferromagnetic structures (e.g., magnetic field generating structures, or MFGs) for altering the magnetic field gradient generated by one or more magnets. In some aspects, ferrormagnetic structures can shape the external magnetic field in order to create locally high magnetic field gradients to assist in capturing flowing magnetic particles. In some embodiments, ferromagnetic structures can be used to increase or decrease the distance over which a magnet can capture a magnetically susceptible label. Ferromagnetic structures can be positioned anywhere on the magnetic separator. In some embodiments, the ferromagnetic structure can be positioned within the channel. In some embodiments, the ferromagnetic structure can be positioned outside of the channel. Non-limiting examples of materials that can be used to fabricate a ferromagnetic structure include iron, cobalt, nickel, gadolinium, dysprosium, chromium dioxide, and compounds according to the chemical structures MnAs, MnBi, EuO, and Y3Fe5O12. Any number of ferromagnetic structures can be used to alter the magnetic field generated by the one or more magnets. In some embodiments, the ferromagnetic structures can extend the entire length of the channel. In some embodiments, the ferromagnetic structures can extend a portion of the entire length of the channel. In some embodiments, the ferromagnetic structures can be positioned on both sides of the channel. In some embodiments, the ferromagnetic structures can be positioned on only one side of the channel.

The magnetic separator can comprise a magnetic region for generating a magnetic field. The magnetic region can be fabricated with either hard or soft magnetic materials, such as iron, steel, nickel, cobalt, rare earth materials, neodymium-iron-boron, ferrous-chromium-cobalt, nickel-ferrous, cobalt-platinum, and strontium ferrite. In some cases, the magnetic region can be fabricated directly out of magnetic materials, or the magnetic materials can be applied to another material. In some cases, the magnetic region can be made of hard magnetic materials. The magnetic region comprising hard magnetic materials can generate a magnetic field without other actuation. In some cases, the magnetic region can be made of soft magnetic materials. The magnetic region made of soft magnetic materials can enable release and downstream processing of bound particles simply by demagnetizing the material. Depending on the magnetic material, the application process can include cathodic sputtering, sintering, electrolytic deposition, or thin-film coating of composites of polymer binder-magnetic powder. In some cases, the magnetic region can comprise a thin film coating of micromachined obstacles (e.g., silicon posts) by spin casting with a polymer composite, such as polyimide-strontium ferrite (the polyimide serves as the binder, and the strontium ferrite as the magnetic filler). After coating, the polymer magnetic coating can be cured to achieve stable mechanical properties. After curing, the magnetic separator can be exposed to an external induction field, which governs the preferred direction of permanent magnetism in the magnetic separator. The magnetic flux density and intrinsic coercivity of the magnetic fields from the obstacles can be controlled by the % volume of the magnetic filler.

The magnetic separator can generate a magnetic field. In some cases, the magnetic field strength generated by the magnetic separator can be between about 0.01 and about 10 Tesla. In some cases, the magnetic field strength can be at least 0.01 Tesla, 0.05 Tesla, 0.1 Tesla, 0.2 Tesla, 0.3 Tesla, 0.4 Tesla, 0.5 Tesla, 0.6 Tesla, 0.7 Tesla, 0.8 Tesla, 0.9 Tesla, 1 Tesla, 2 Tesla, 3 Tesla, 4 Tesla, 5 Tesla, 6 Tesla, 7 Tesla, 8 Tesla, 9 Tesla, or 10 Tesla. In a particular case, the magnetic field strength can be at least 0.5 Tesla. In some cases, the magnetic separator can generate a field gradient of about 100 Tesla/m to about 1,000,000 Tesla/m. For example, the field gradient can be at least 10 Tesla/m, $10^2$ Tesla/m, $10^3$ Tesla/m, $10^4$ Tesla/m, $10^5$ Tesla/m, or $10^6$ Tesla/m.

The magnetic field can be adjusted to influence supra and paramagnetic particles with magnetic mass susceptibility, e.g., ranging from 0.1-200×10 m$^3$/kg. The paramagnetic particles of use can be classified based on size: particulates (1-5 µm in the size of a cell diameter); colloidal (on the order of 100 nm); and molecular (on the order of 2-10 nm). The fundamental force acting on a paramagnetic entity can be:

$$F_b = \frac{1}{2\mu_o} \Delta \chi V_G \nabla B^2$$

where $F_b$ can be the magnetic force acting on the paramagnetic entity of volume $V_b$, $\Delta_\chi$ can be the difference in magnetic susceptibility between the magnetic particle, $\chi_b$, and the surrounding medium, $\chi_f$, to can be the magnetic permeability of free space, B can be the external magnetic field, and $\nabla$ can be the gradient operator. The magnetic field can be controlled and regulated to enable attraction and retention of a wide spectrum of particulate, colloidal, and molecular paramagnetic entities.

The magnetic separator can be used to separate rare cells (e.g., circulating tumor cells) from white blood cells using magnetic beads and applying magnetic fields to isolate the labeled cells (e.g., cells with magnetic susceptible labels) as well as free magnetic beads from the unlabeled cells. In some cases, the white blood cells can be labeled with magnetic beads using one or more types of antibodies. In some cases, the white blood cells can be labeled with different types of magnetic beads, e.g., magnetic beads with different sizes, shapes, and/or magnetic susceptibilities. Such separation can be a negative selection of the rare cells (e.g., circulating tumor cells). The magnetic separator can pull the white blood cells from the rare cells, and leave the unmodified rare cells for downstream analysis. In some cases, the rare cells (e.g., circulating tumor cells) can be labeled with magnetic beads using one or more antibodies. Such separation can be a positive selection of the rare cells. The magnetic separation can pull the rare cells (e.g., circulating tumor cells) from the white blood cells background.

The magnetic separation can exist in different types. In some cases, the magnetic separation can exist as a static magnetic separation. For example, the particles of interest can be labeled with magnetically susceptible labels, and then a container containing the sample comprising the particles of interest can be exposed to a magnetic field gradient that attracts and retain all the magnetically labeled particles and free magnetically susceptible labels to the side of the container. The bulk sample containing un-labeled cells can then be removed from the container (e.g., using a pipet or other means). The separation can be either a positive selection or negative selection. In some cases, the magnetic separation can exist as a flow-through module in which the sample containing labeled and unlabeled particles is flowed past a region with a magnetic field gradient. In some cases, a sample can be passed through multiple magnetic fields (e.g., in the same magnetic separator or multiple magnetic separators). The multiple magnetic fields can have different magnetic field gradients. In some cases, a sample can be passed through multiple magnetic field gradients, e.g., a series of magnetic field gradients with increased or decreased magnetic field strengths. In some cases, a sample can be passed through a magnetic field gradient whose strength is continuous ramping. In some cases, a sample can be passed through any combination of magnetic fields disclosed herein. Particles labeled with magnetically susceptible labels and free magnetically susceptible labels can be pulled from the sample into a flow stream and then retained in the magnetic separator (e.g., at the wall) or exit the magnetic separator (e.g., to a waste collector). In some cases, the particles can exit the magnetic separator in a separate channel. This separation can be either a positive selection or negative selection. In some cases, micro-patterns of magnetic material can also be used (e.g., in a continuous flow fashion) to displace cells labeled with magnetically susceptible labels (e.g., magnetic or paramagnetic beads) from the direction of fluid flow. For example, cells can be separated with devices described in Applied Physics Letters, Vol. 85, pp. 593-595 (2004), which is incorporated herein by reference in its entirety. In some cases, the magnetic separation can also occur simultaneously with a DLD separation. A magnetic field gradient can be applied across the DLD device. Labeled particles that are large enough to be deflected by the DLD array can feel instead a stronger magnetic force directing them away from the DLD deflection angle. The particles can remain in the sample with other particles that are below the critical size and can exit in a waste stream. The strength of magnetic field can depend on the tilt of the DLD array. DLD arrays with a larger tilt (e.g., greater shift of obstacles in each subsequent row) can involve a lower magnetic force (e.g., the magnetically-labeled particles can move less distance to be directed off the major flux and back into the minor flux).

Figure 18A:
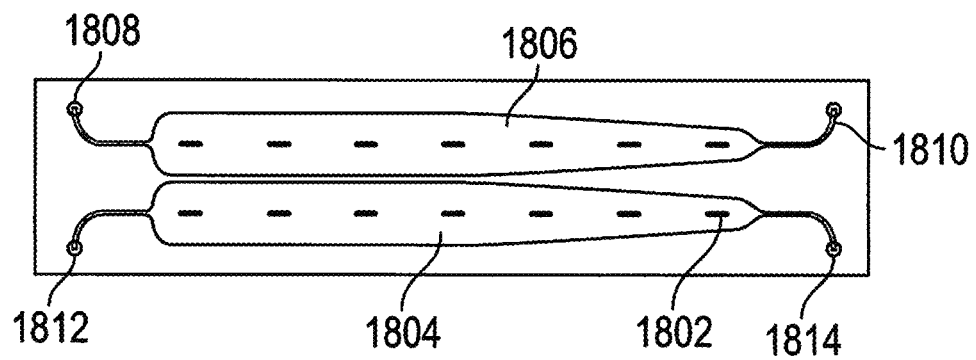
FIGS. 18A and 18B illustrate embodiments of microfluidic channel designs in a magnetic separator.
Figure 18B:
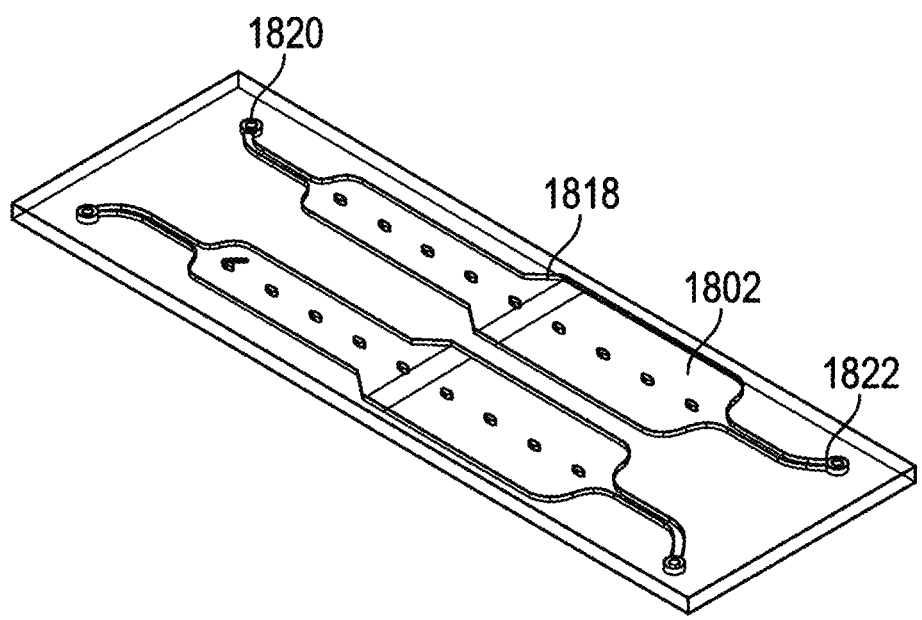

In some embodiments, the magnetic separator can comprise one or more microfluidic channels, e.g., about 1 to about 20 microfluidic channels, e.g., 1, 2, 3, 4, 5, 6, 7, 8, 9, 10, 11, 12, 13, 14, 15, 16, 17, 18, 19, or 20 microfluidic channels. Examples of microfluidic channels are illustrated in FIGS. 18A and 18B. The dimensions of the microfluidic channel can vary in length, width and/or depth. In some embodiments, the length of a microfluidic channel can be from about 10 millimeters to about 150 millimeters, or about 1 to about 1500 mm. In some embodiments, the length of a microfluidic channel can be less than about 10 millimeters. In some embodiments, the length of the microfluidic channel can be greater than about 150 millimeters. In some embodiments, the length of the microfluidic channel can be about 10 millimeters, about 20 millimeters, about 30 millimeters, about 40 millimeters, about 50 millimeters, about 60 millimeters, about 70 millimeters, about 80 millimeters, about 90 millimeters, about 100 millimeters, about 110 millimeters, about 120 millimeters, about 130 millimeters, about 140 millimeters, or about 150 millimeters. For example, a magnetic separator can comprise a microfluidic channel having a length of 100 millimeters. In some embodiments, the width of the microfluidic channel can be constant along the length of the microfluidic channel (see e.g., FIG. 18A (1804). For example, a magnetic separator can comprise a microfluidic channel having a length of 120 millimeters and a width of 250 microns.

In some embodiments, the depth of the microfluidic channel can be from about 100 microns to about 800 microns, or about 10 microns to about 8000 microns. In some embodiments, the depth of the microfluidic channel can be less than about 100 microns. In some embodiments, the depth of the microfluidic channel may be greater than about 800 microns. In some embodiments, the depth of the channel can be about 25 microns, about 50 microns, about 75 microns, about 100 microns, about 125 microns, about 150 microns, about 175 microns, about 200 microns, about 225 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, about 1000 microns, about 1050 microns, about 1100 microns, about 1150 microns, about 1200 microns, about 1250 microns, about 1300 microns, about 1350 microns, about 1400 microns, about 1450 microns, about 1500 microns, about 1550 microns, about 1600 microns, about 1650 microns, about 1700 microns, about 1750 microns, about 1800 microns, about 1850 microns, about 1900 microns, about 1950 microns, or about 2000 microns. In some embodiments, the depth of the microfluidic channel can increase along at least a portion of the microfluidic channel. In some embodiments, the depth of the microfluidic channel can decrease along at least a portion of the microfluidic channel. In some embodiments, the increase in the depth of the microfluidic channel can be a gradual increase (e.g., a taper) or a step increase (see e.g., FIG. 18B, microfluidic channel 1818)). In some embodiments, the decrease in the depth of the microfluidic channel can be a gradual decrease (e.g., a taper) or a step decrease. In some embodiments, the depth of the microfluidic channel does not decrease along the length of the microfluidic channel. In one example, a magnetic separator can comprise a microfluidic channel having a depth of 100 microns for the first half of the microfluidic channel, and increase to a depth of 250 microns for the second half of the channel. In a second example, a magnetic separator can comprise a microfluidic channel having a depth at the beginning of the microfluidic channel of about 700 microns that gradually tapers to a depth of 350 microns at the end of the microfluidic channel. A microfluidic channel can have multiple depths (e.g., 2, 3, 4, 5, 6, 7, 8, 9, or 10 depths). The depths can change, e.g., to maintain a cross-sectional area to keep linear flow rate the same, or keep same width to force linear flow rate to increase as chamber gets shallower.

In some embodiments, the width of the microfluidic channel can be from about 200 microns to about 1600 microns, or about 20 microns to about 16,000 microns. In some embodiments, the width of the microfluidic channel can be less than about 200 microns. In some embodiments, the width of the microfluidic channel can be greater than about 1600 microns. In some embodiments, the width of the microfluidic channel can be about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, about 1000 microns, about 1050 microns, about 1100 microns, about 1150 microns, about 1200 microns, about 1250 microns, about 1300 microns, about 1350 microns, about 1400 microns, about 1450 microns, about 1500 microns, about 1550 microns, about 1600 microns, about 1650 microns, about 1700 microns, about 1750 microns, about 1800 microns, about 1850 microns, about 1900 microns, about 1950 microns, about 2000 microns, about 2100 microns, about 2200 microns, about 2300 microns, about 2400 microns, or about 2500 microns. In some embodiments, the width of the microfluidic channel can increase along at least a portion of the microfluidic channel. In some embodiments, the width of the microfluidic channel can decrease along at least a portion of the microfluidic channel. In some embodiments, the increase in the width of the microfluidic channel can be a gradual increase (e.g., a taper) or a step increase (see e.g., FIG. 18B (microfluidic channel 1818 with inlet 1820 and outlet 1822)). In some embodiments, the decrease in the width of the microfluidic channel can be a gradual decrease (e.g., a taper) (see e.g., FIG. 18A (microfluidic channel 1806 with inlet 1808 and outlet 1810)) or a step decrease. In some embodiments, the width of the channel does not change over the length the microfluidic channel (see e.g., FIG. 18A (microfluidic channel 1804 with inlet 1812 and outlet 1814)). For example, a magnetic separator can comprise a microfluidic channel having a width of 250 microns for the first half of the microfluidic channel, and increase to a width of 1250 microns for the second half of the channel. In another example, a magnetic separator can comprise a microfluidic channel having a width at the beginning of the microfluidic channel of about 1300 microns that gradually tapers to a width of 200 microns at the end of the microfluidic channel.

Shear stress can induce platelet activation, and any changes in the dimensions of the microfluidic channel can affect the flow (e.g., the flow rate, the flow profile, the flow turbulence) of a fluid through the channel, thereby affecting the shear stress applied to a particle within the fluid. Flow rate can generally refer to the volume of fluid which passes per unit time, and be defined by the dot product:

$$Q = v \cdot A,$$

wherein 'Q' is the flow rate, 'v' is the flow velocity, and 'A' is the cross sectional vector area. At any point along the length of the channel, the depth of the microfluidic channel can increase or decrease proportionally with the width of the microfluidic channel such that the flow rate (e.g., volumetric flow rate) of a fluid through the channel is maintained (e.g., constant).

In some aspects, a magnetic separator can comprise a microfluidic channel, and the microfluidic channel can comprise one or more posts disposed along the center of the channel. In general, a magnetic separator can comprise one or more microfluidic channels, and the channel can be formed at least in part by a lid. Any material can be used to form the lid (e.g., tape). The one or more posts disposed along the center of the channel can be useful for preventing the lid from collapsing in on the channel. For example, a magnetic separator can comprise a first substrate comprising a channel, a second substrate (e.g., a lid or tape) sealably coupled to the first substrate, thereby forming a microfluidic channel through which a sample can flow, and 10 posts evenly spaced along the length of the microfluidic channel to prevent collapse of the second substrate into the channel. A magnetic separator can comprise any number of posts. In some embodiments, a magnetic separator can comprise 1 post. In some embodiments, the magnetic separator can comprise about 2 posts, about 5 posts, about 10 posts, about 15 posts, about 20 posts, about 25 posts, about 50 posts, about 75 posts, or about 100 posts. In some embodiments, the magnetic separator can comprise greater than about 100 posts. FIGS. 18A and 18B illustrate posts (1802) in a microfluidic channel (1804) and (1818) of a magnetic separator.

The system can comprise one or more magnetic separators. In some cases, the system can comprise more than one magnetic separator. In some cases, the system can comprise a first magnetic separator upstream of a DLD array, and a second magnetic separator downstream of the same or a different DLD array. For example, the magnetic field of the first magnetic separator and the magnetic field of the second magnetic separator can have different strengths, which can allow separation of particles with different magnetic susceptibilities.

D. Other Particle Separators

The systems herein can further comprise one or more particle separators other than DLD arrays or magnetic separators. The other particle separators can be used in combination with the DLD arrays and magnetic separators provided herein. In some cases, the system can comprise a fluorescence-based particle separator. For example, the fluorescence-based particle separator can be a fluorescence-based flow cytometer. In some cases, the fluorescence-based particle separator can be fluidically connected with one or more other components in the system. For example, the fluorescence-based particle separator can be fluidically connected with one or more DLD arrays. In another example, the fluorescence-based particle separator can be fluidically connected with a magnetic separator. In another example, the fluorescence-based particle separator can be fluidically connected with one or more DLD arrays and a magnetic separator. In some cases, the systems can comprise a cell sorter. The cell sorter can be used to further separate and/or analyze cells separated by the DLD arrays and/or magnetic separator from other subcellular particles. In some cases, the cell sorter can be a single cell sorting device, e.g., and can be a Raft array (e.g., the Cellcraft™ system (Cell Microsystems), and a DEPArray™ (lab-on-a-chip technology platform). In some cases, systems can comprise a light scattering-based particle separator.

The system can comprise a flow cytometer. Manipulation of cells in devices in a flow cytometer can be accomplished using hydrodynamic forces. A suspension of particles (e.g., cells) can be injected into the center of a flowing sheath fluid. In some cases, forces of the surrounding sheath fluid confine the sample stream to a narrow core that can carry cells through a path of a laser that can excite associated fluorophores and create a scatter pattern. In some cases, particles (e.g., cells) analyzed by flow cytometry can be labeled. In some cases, particles (e.g., cells) that are analyzed by flow cytometry are labeled using a "car wash" device as described in PCT Application No. WO 20140145152, which is incorporated herein by reference in its entirety. In some cases, a particle analyzed by a flow cytometer can be labeled with a quantum dot, and a fluorescent label. In some cases, a flow cytometry can comprise one or more cytometric bead arrays.

The system can comprise a fluorescence-activated cell sorter (FACS). In some cases, a sample can be subject to flow cytometry, e.g., FACS, before the sample can be applied to device for treatment and/or purification described herein. In some cases, a flow cytometer can be in fluid communication with a device for treatment and/or purification described herein; in some cases, a flow cytometer can be fluidly connected upstream of a device for treatment and/or purification; in some cases, a flow cytometer can be fluidly connected downstream of a device for treatment and/or purification described herein. In some cases, a flow cytometer can be fluidly connected upstream and downstream of a device for treatment and/or purification described herein.

FACS can be used to sort a heterogeneous mixture of particles, e.g., cells, into two or more containers. FACS can be based on the light scattering and fluorescent characteristics of each type of cell. A suspension of particles (e.g., cells) can be entrained in a flowing stream of liquid. There can be separation between particles in the liquid. The stream of particles (e.g., cells) can be broken into droplets (e.g., by a vibrating mechanism). In some cases, only one particle (e.g., cell) can be in each droplet. In some cases, before the stream breaks into droplets, the liquid passes through a fluorescence measuring station. The fluorescence characteristics can be measured. A charge can be given to each droplet based on the fluorescence measurement, and the charged droplets can pass through an electrostatic deflection system that can divert droplets to containers based on charge.

The systems herein can comprise an acoustic focusing flow cytometer (e.g., Attune® Acoustic Focusing Flow Cytometer; Life Technologies™). In some cases, an acoustic focusing can be used on a sample before the sample can be applied to a device comprising an array of ordered obstacles. Acoustic focusing cytometry can use ultrasonic waves (e.g., over 2 MHz) rather than hydrodynamic forces to position cells in a focused line along a central axis of a capillary. (see e.g., www.lifetechnologies.com/us/en/home/life-science/cell-analysis/flow-cytometry/flow-cytometers/attune-acoustic-focusing-flow-cytometer/acoustic-focusing-technology-overview.htm). Acoustic focusing can be independent of sample input rate. Acoustic focusing can enable cells to be tightly focused at a point of laser interrogation. Acoustic focusing can occur without high velocity or high volumetric sheath fluid. In some cases, volumetric syringe pumps can enable absolute cell counting without beads. In some cases, acoustic resonance can be driven by a piezoelectric device.

Acoustic focusing can make use of an optical cell for sample interrogation, one or more lasers, and electronics for collecting fluorescence and/or scatter information. In some cases, acoustic focusing makes use of a pump, e.g., a syringe pump. In some cases, a frequency used in acoustic focusing can be about 0.1, 0.2, 0.3, 0.4, 0.5, 0.6, 0.7, 0.8, 0.09, 1, 1.5, 2, 2.5, 3, 3.5, 4, 4.5, 5, 5.5, or 6 MHz. In some cases, a flow rate in an acoustic focusing cytometer can be at least 10, 25, 50, 100, 200, 500, 1000, 2000, or 5000 µL/min.

E. Analytical Devices

The systems can comprise one or more analytical devices for analyzing particles separated by the systems. Examples of analytical devices include affinity columns, cell counters, particle sorters, e.g., fluorescent activated cell sorters, capillary electrophoresis, microscopes, spectrophotometers, sample storage devices, and sample preparation devices, sequencing machines (e.g., next-generation sequencing machine, e.g., from Illumina), mass spectrometers, HPLC, gas chromatograph, atomic absorption spectrometers, fluorescence detectors, radioactivity counters, scintillation counters, spectrophotometers, cell counters, and coagulometers. In some cases, some devices for separating particles herein can also be used as analytical devices. For example, a device separating particles based on the characteristics of the particles can be used as a detector of the characteristics. In some cases, an analytical device can be a flow cytometer. The flow cytometer can sort cells based the labels on the cells, thus analyzing the percentage of one or more types of cells in a sample.

F. Particle Sensors

The systems herein can further comprise one or more particle sensors. In some cases, the particle sensors can be used to detect labeled particles downstream of the DLD arrays or the magnetic separator. In some cases, the particle sensors can be used to focus particles for interrogation at a location (e.g., a defined location). In some cases, the particles can be focused on a defined location by generation of sheath flow, planar and encompassing laminar core streams in the system herein. In some cases, the particles sensors can detect the particles by generating and/or measuring laser light scatter, fluorescence of the particles (e.g., by a fluorescence emitter), impedance caused by the particles, charges of the particles, multiple light sources, multiparameter emission, or any combination thereof. For example, the particle sensor can be a laser light scattering device, a fluorescence senor, or an impedance sensor. In some cases, the particle sensors can be configured to detect, record, and/or convert individual particle associated reporter signals. The particle sensors can also be configured to associate impedance and colorimetric measurements in a coherent data stream, thus generating a signal when certain conditions are met. For example, the conditions can be a series conditions defined by the user of the system. In some cases, the particle sensor can be fluidically connected with one or more other components of the system. For example, the particle sensor can be fluidically connected with one or more DLD arrays. In another example, the particle sensor can be fluidically connected with a magnetic separator. In another example, the particle sensor can be fluidically connected with one or more DLD arrays and a magnetic separator.

Examples of sensors include image sensors, light sensors, temperature sensors, pH sensors, optical sensors, ion sensors, colorimetric sensors, a sensor able to detect the concentration of a substance, or the like, e.g., as discussed herein. Image sensors can include charge coupled devices (CCD) (e.g., CCD chips) and other suitable sensors to obtain an electronic image of particles. Light sensors can include photodiodes, avalanche photodiodes, and phototransistors configured to detect one or more of light emitted by, transmissivity of light shone through, and reflectivity of light from the particles. Light sensors can also include photomultipliers, diode arrays, cameras, microscopes, and complementary metal-oxide semiconductors. Temperature sensors can include thermocouples and thermometers. Pressure sensors can include barometers and stress or strain gauges.

The particle sensor can comprise a light source. Examples of light source include ultraviolet light source (e.g., light sources that produce light below about 400 nm), light emitting diodes that emit light (e.g., blue light emitting diodes, green light emitting diodes, organic light-emitting diodes, polymer light-emitting diodes, solid-state lighting, LED lamp, and AMOLED), and lasers (e.g., Ruby laser, Gas laser, Semiconductor laser, Chemical laser, Dye laser, Metal-vapor laser, Solid-state laser, Ion laser, Quantum well laser, Free-electron laser, and Gas dynamic laser). In some cases the light can detect scattered and/or emitted light of specific frequency, polarity, and anisotropy (e.g., multiple excitations, full spectrum emission, phases, time and plane).

In some cases, the particle sensor can comprise a computer module. The computer module can be used to detect and interpret light signatures, e.g., to create an actuation event. For example, the actuation event can be used to activate a particle dispenser disclosed herein.

The particle sensor can be coupled with a "car wash" device as described in PCT Application No. WO 20140145152, which is incorporated herein by reference in its entirety. In some cases, particles flowed into a "car wash" device can be deflected to flow across a plurality of parallel flow streams, each of which comprises a reagent for processing the particles. In some cases, the particles can be processed by the "car wash" device and conferred the ability to be separated by the particle dispenser herein. For example, the particles can be labeled (e.g., with a surface label or intracellular label) by the "car wash" device, and become detectable by a sensor of the particle dispenser. When such labeled particles pass through the particle separator, one or more particles of interest can be separated and/or dispensed by the particle dispenser. The "car wash" device can be used to label the particles with any label disclosed herein. For example, the "car wash" device can label the particles with magnetic susceptible labels, fluorescent labels, radioactive labels, electric charge, or any combination thereof. In some cases, the "car wash" device can be coupled with the particle dispenser herein. For example, the sensor of the particle dispenser can be configured to detect one or more particles of interest flowing in one of the flow streams in the "car wash" device. When a particle of interest is detected by the sensor, it can be captured into the capture tube of the particle dispenser from the flow stream of the "car wash" device.

Laser Scattering Devices

The particles sensors can include a laser scattering device. The particle sensors can include any laser scattering device known in the art, e.g., laser scattering device used in flow cytometers. In some cases, the laser scattering device can be used on a microfluidic device. In some cases, the laser scattering device can be used off a microfluidic device.

Figure 3A:
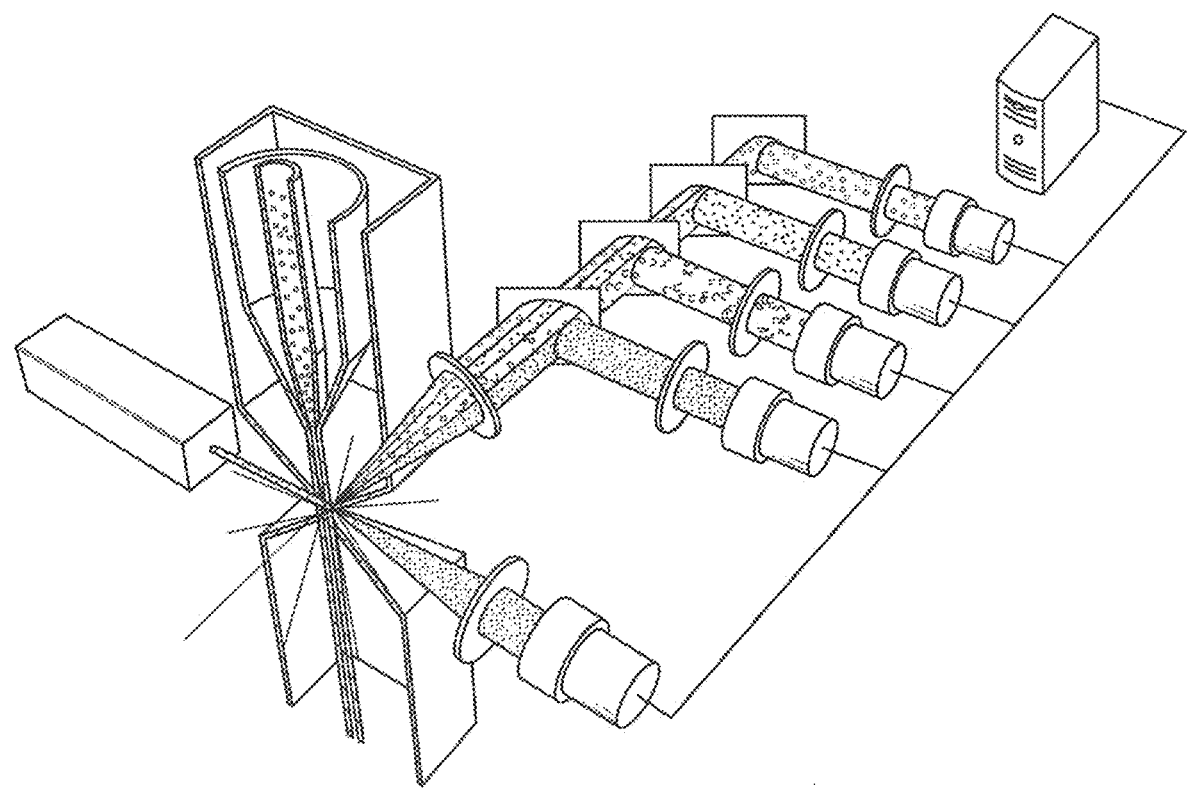
FIGS. 3A-3D show the design of a light scattering device.

In some cases, the laser scattering device can be configured to enable forward light scatter and orthogonal light scatter. In some cases, the laser scattering device can comprise a laser emitter, and a light collector, for detecting particles in a flow stream. In some cases, the laser light scattering device can be configured to generate a forward scattered beam and an orthogonal scattered beam, wherein the forwarded scattered beam, the orthogonal scattered beam (e.g., beams to be collected by a light collector (e.g., an objective), and the fluid stream containing the particles are orthogonal to each other. (FIG. 3A) To measure all parameters in a planer microfluidic device herein, at least one light path option may need to be given up to light collection. In other cases, an alternative approach can be used, e.g., a waveguide built in the microfluidic device. With the laser scattering device herein, signals (e.g., fluorescence) from the particles can be collected back in an objective (e.g., a microscopic objective). Information about diameter of the particles can also be gathered. In some cases, cell granularity can also be measured.

Figure 3B:
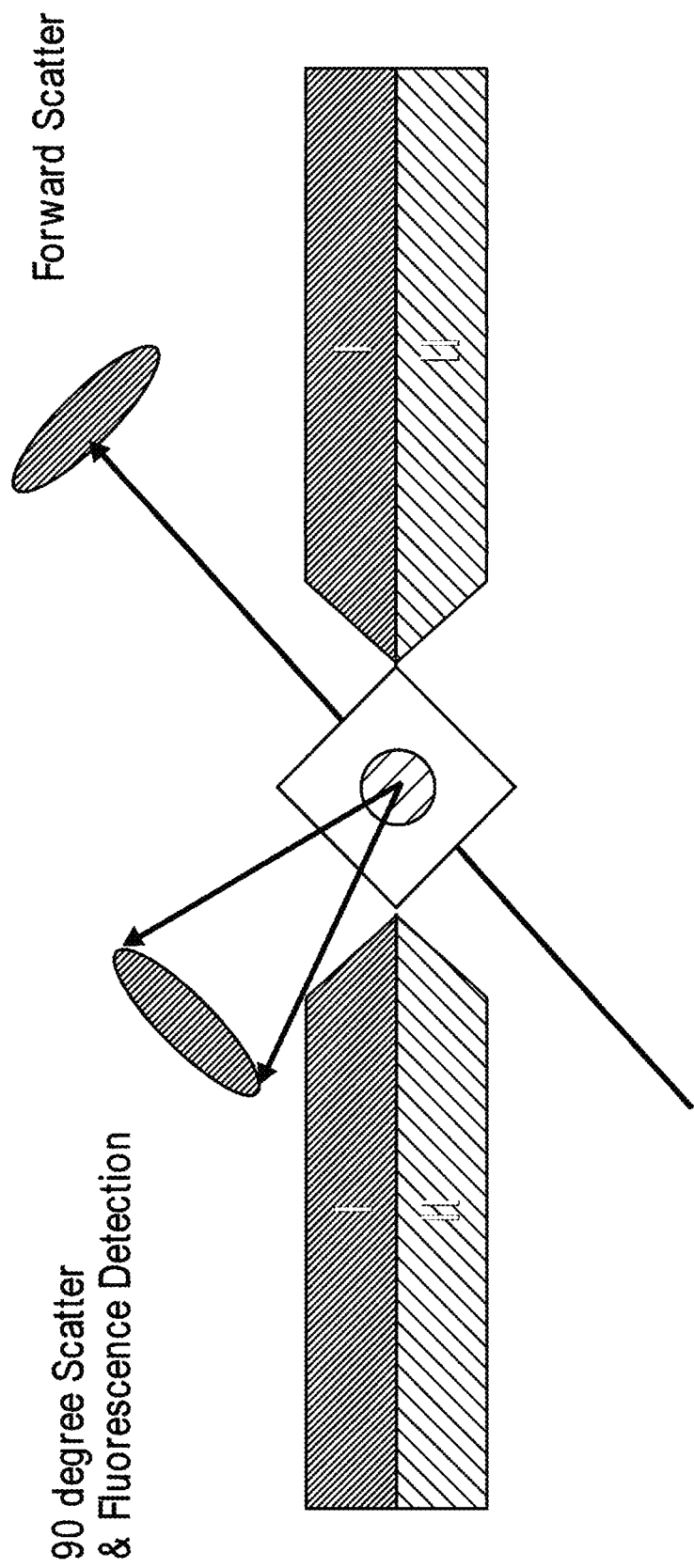
Figure 3C:
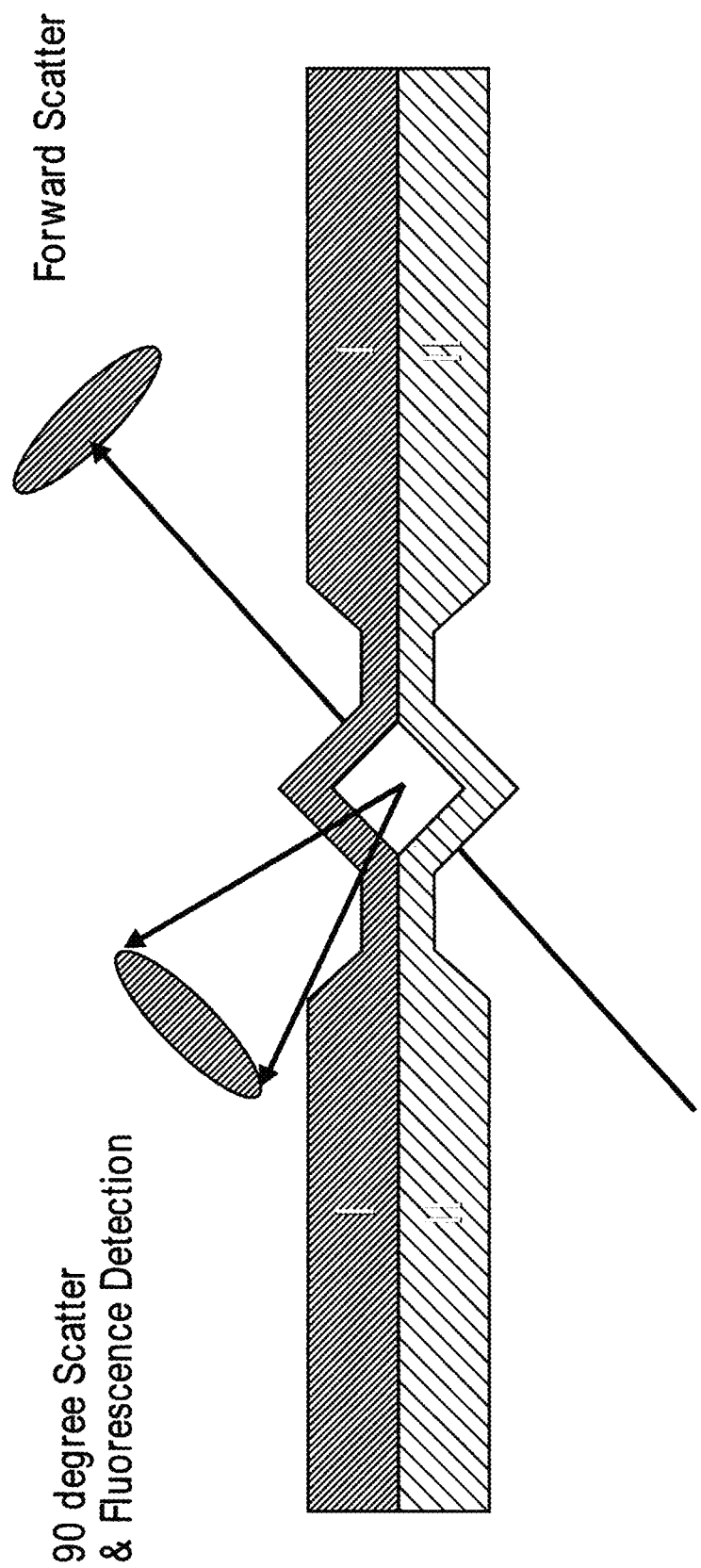
Figure 3D:
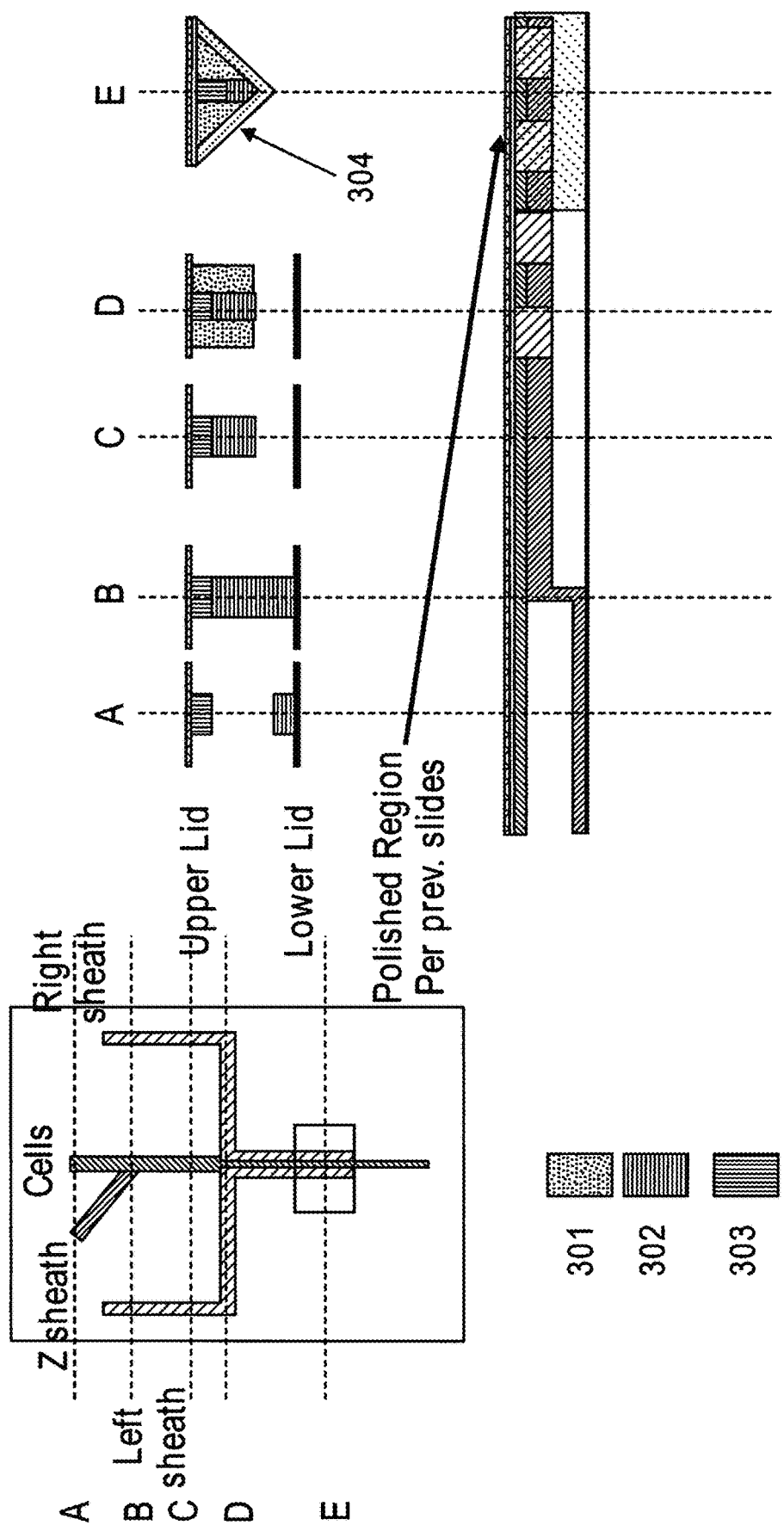

A flow intercept with a flow cell can be included in the particle separation. Such device can be a planar device. The flow stream containing the particles can flow through the flow cell. The flow cell can be configured to allow laser scattered by the particles in the flow stream. In some cases, the flow intercept can be a glass cuvette (FIG. 3B). In some cases, the laser light scattering device comprises a glass cuvette configured to scatter a laser beam generated by the laser light scattering device. For example, the glass cuvette can be the flow intercept. In some cases, the flow intercept can be molded in the particle separation device (FIG. 3C). The internal geometry of the flow cell can be angular (e.g., quadrilateral) or circular. In some cases, the laser light scattering device comprises a flow cell molded in layers configured to scatter a laser beam generated by the laser light scattering device. For example, the flow cell molded in layers can be the flow intercept. In some cases, the flow intercept can have a surface with an angle relative to surface of the particle separating device. For example, the angle can be between 0° and 90°. In some cases, the angle can be 45°. In some cases, the flow intercept can comprise a Z sheath that controls the depth of the flow cell. Configuration of the depth of a flow cell in certain range can allow better imaging of the flow stream and/or particles inside the flow cell. As shown in FIGS. 3D, A, B, C, D and E are different cross sectional views of flow cell designs. 301 indicates the left or right sheath of the flow cell. 302 indicates the Z sheath. 303 indicates particles in the stream. 304 indicates the lower surface of a flow cell. In some cases, the configuration of a flow cell can be triangular, as shown in E. The E design can be used to manufacture the intercept molded layer as shown in FIG. 3C. The E design can represent a schematic to align fluid flow a planar device aligned with delivering the light scatter characteristics in the angled dual layer flow cell. In some cases, both the top and bottom layers can have thin membranes to close the delivery from a 2-piece molded part. The Z sheath can be the sheath that controls the balance of the particles (e.g., cells) in the z direction. Without the Z sheath, the left and right sheaths can make the flow cell have a depth that can cause difficulties in imaging the particles and flow stream in the flow cell. In some cases, the E design can allow the particles and/or the flow stream in the flow cell to be imaged. In some case, the scattered beams obtained from the design can comprise a forward scattered beam and a 90° scattered beam. In some case, the scattered beams obtained from the design can comprise a forward scattered beam and a scattered beam that is not 90° relative to the forward scattered beam. In some cases, one or more the designs (e.g., the E design) can improve the sensitivity of the imaging and/or light scattering. For example, the sensitivity can be improved by focusing the light (e.g., laser) more effectively compared with a design that does not comprise a Z sheath.

G. Particle Dispensers

The systems herein can comprise a particle dispenser that deposit particles separated from the system to a location (e.g., a defined location). The particle dispenser can comprise a sensor for detecting the presence of a particle of interest flowing through a region, and a capture module that can be activated after the detection of the particle of interest. When activated, the capture module can capture the particle of interest and deposit it to a location (e.g., a defined location).

The particle dispenser herein can comprise a sensor for detecting the presence of a particle of interest, a capture module for catching the particle of interest, and/or a dispensing module that dispense the particle of interest to a location (e.g., a defined location). In some cases, the sensor and capture module can be configured as described in U.S. Pat. Nos. 4,756,427 and 5,030,002, which are incorporated herein by reference in their entirety. The dispensing module can comprise a pressure source that flushes an air flow for ejecting the captured particles of interest. In some cases, the pressure source can be configured to create and dispense sufficient fluid so as to cause a disturbance and an ejection of a plug of fluid (e.g., a plug of fluid containing one or more particles of interest) to a location, e.g., a collection device.

The particle dispenser can comprise one or more of the following components: a fluidic duct configured to allow particles to flow into the fluid duct in a flow stream, and wherein the fluidic duct comprises a sensing zone; a sensor, wherein the sensor generates a signal when a particle of interest passes the sensing zone; a switch configured to receive the signal; a capture tube, wherein the capture tube can be movable between a first position and a second position, wherein the capture tube can be not fluidically connected with the fluidic duct at the first position, and can be fluidically connected with the fluidic duct at the second position, wherein the capture tube remains at the first position unless driven by the switch, wherein the switch drives the capture tube from the first position to the second position after receiving the signal to catch the particle of interest from the fluidic duct; a pressure source configured to flush an air flow to the capture tube after the capture tube catches the particle of interest.

Figure 4A:
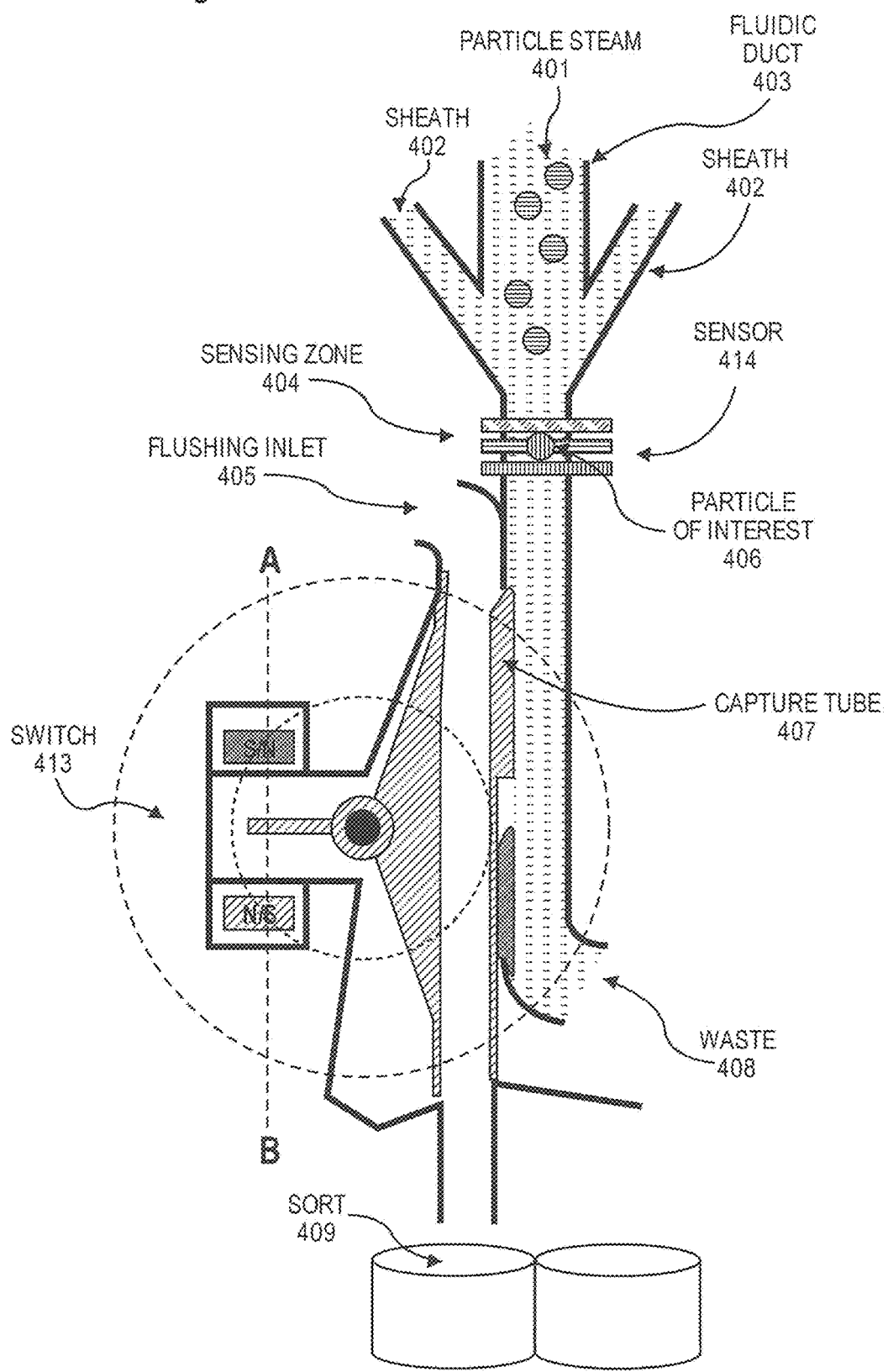
Figure 4B:
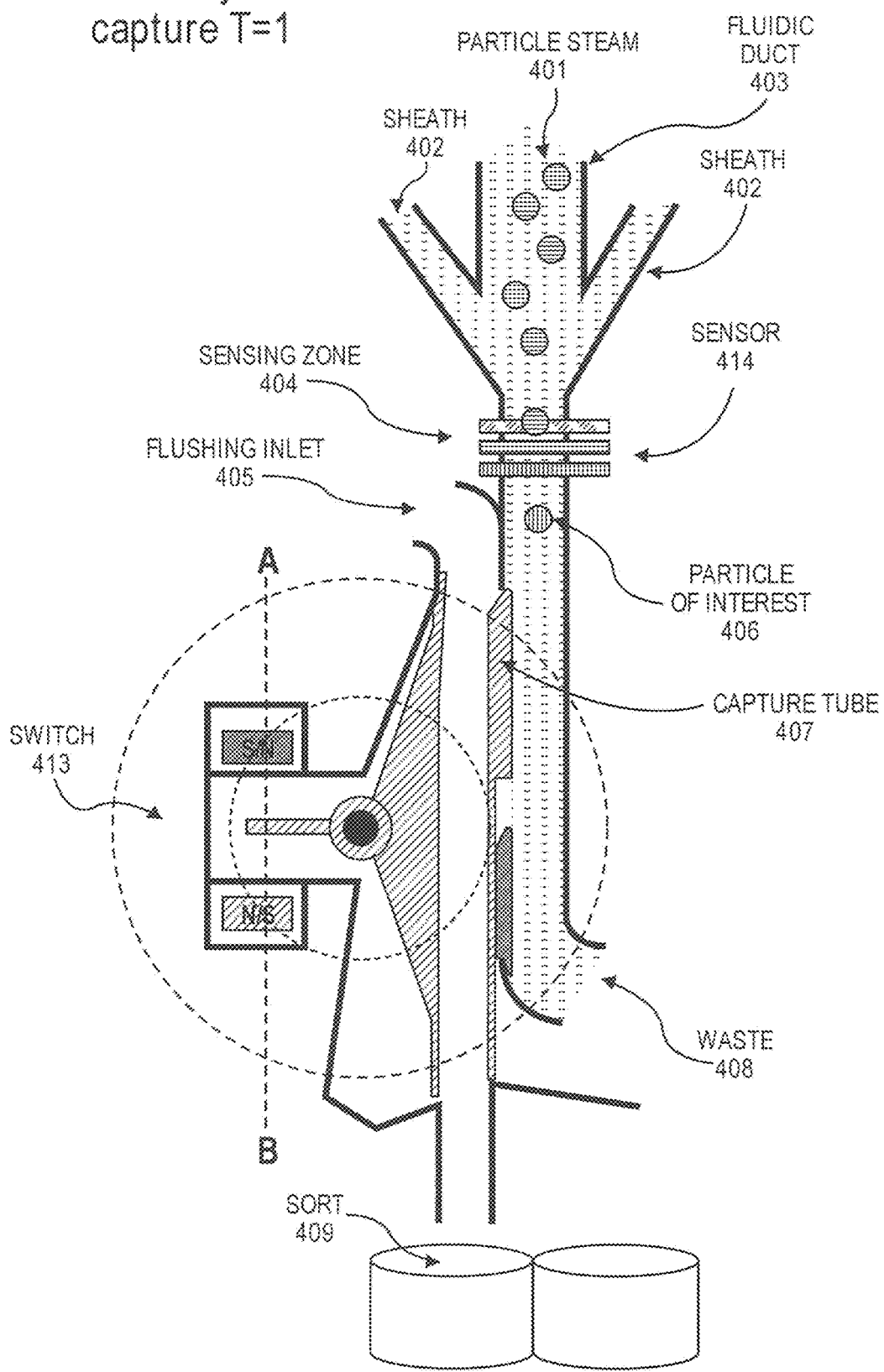
Figure 4C:
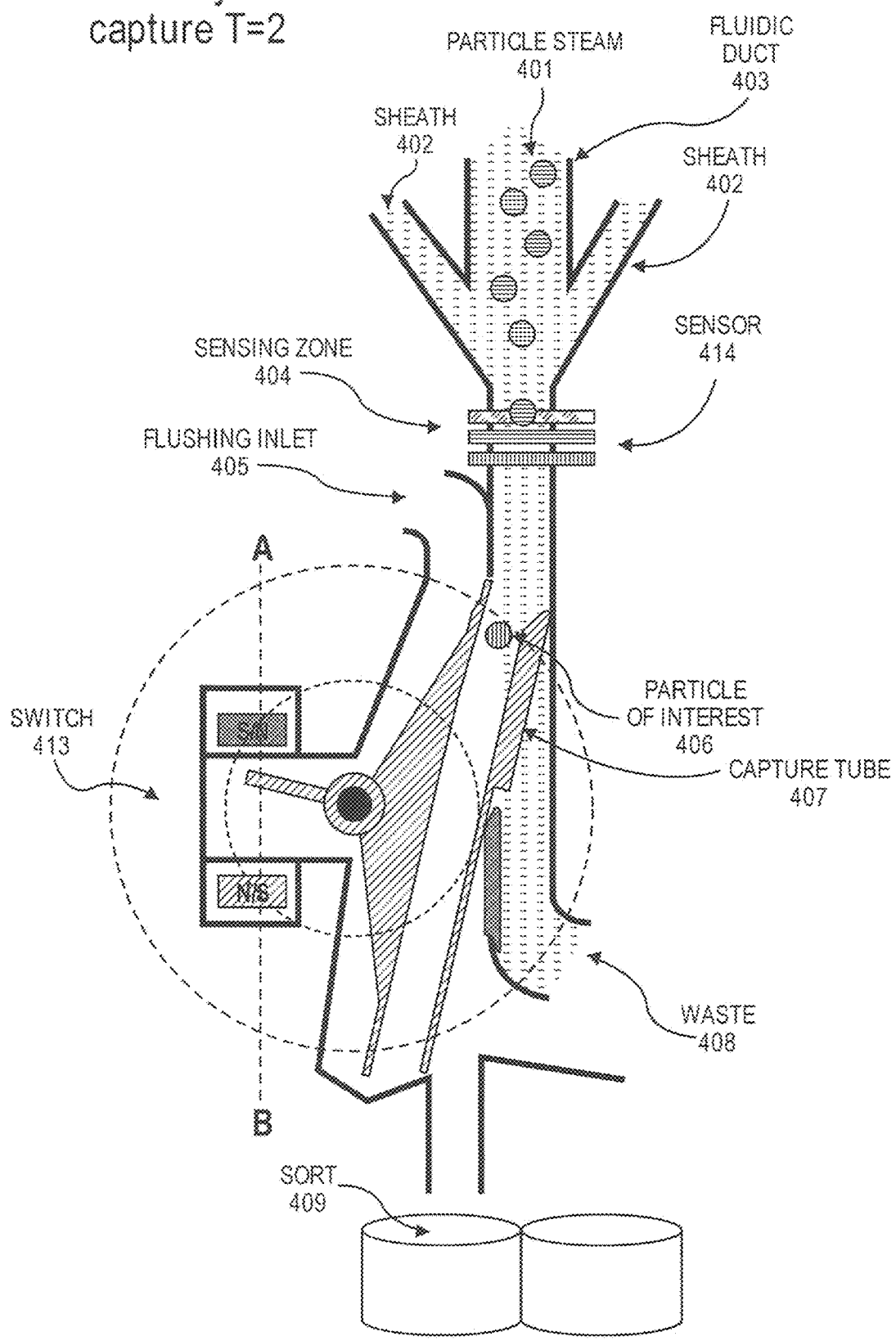

An exemplary particle dispenser is shown in FIGS. 4A-4F. The particle dispenser comprises a fluidic duct (403). A sample comprising a particle of interest (406) flows into the fluidic duct (403) of the particle dispenser. In some cases, the sample can be loaded directly to the fluidic duct (403). In another case, the sample can flow from a particle separation system herein to the fluidic duct (403), which is fluidically connected to the particle separation system. The sensor (414) can sense the passing of the particle of interest (406) through the sensing zone (404) and generate a signal. The switch (414) can regulate the position of the capture tube (407) in response to the signal. The capture tube (407) can move to a position fluidically connected with the particle stream (401) and catch the particle of interest (406), as shown in FIG. 4C. The particle of interest (406) is the dispensed to a location (409), e.g., for sorting. Other particles are directed to a waste (408) along with the fluidic duct (403). The particle dispenser also comprises a flushing inlet (405), which can flush an air flow to the capture tube after a particle of interest is captured. The air pressure can facilitate the dispensing of the particle of interest, e.g., with a small volume of solution.

The particle dispenser can include any particle sensors herein for detecting the presence of a particle of interest. In some cases, the particle dispenser can use measurement of impedance across two points to detect the presence of the cell. In some cases, the particle dispenser can use optical means (e.g., detector of laser-induced fluorescence) to detect the presence of the particle of interest. In some cases, the particle sensor can use non-fluorescent light properties such as light scatter and/or absorbance (e.g., light absorption by heme groups in cells, non-fluorescent lipid staining for cells (e.g., adipocytes)). The particle of interest can be labeled to be detectable by the particle dispenser. In some cases, the particle of interest can be a cell. The cell can comprise any label disclosed herein. In some cases, the cell can comprise one or more fluorescent molecules. For example, the cell can comprise one or more genes expressing fluorescent proteins. Such genes can include DNA or RNA binding moiety-reporter DNA constructs. In another example, the cell can comprise one or more genetically inserted reporter DNA constructs. In another example, one or more genes in the cell can be deleted, wherein the deletion result in fluorescent property change of the cell. In some cases, the sensor can be configured to detect one or more types of labels. For example, the sensor can be configured to detect one or more types of fluorescent labels. In some cases, the sensor can be configured to detect at least 1, 2, 3, 4, 5, 6, 7, 8, 9, 10 types of fluorescent labels.

The particle sensor can comprise a capture module for catching the particle of interest after its presence can be detected. In some cases, the particle sensor can comprise a capture tube. The capture tube can be activated by the signal generated when a particle of interest can be detected by the sensor. The activated capture tube can catch the particle of interest to location (e.g., a defined location).

The particle sensor can be configured to direct the particle of interest from a flow stream into a capture tube. In some cases, the particle of interest can be pushed into the capture tube with a plug of fluid (e.g., a plug of fluid from the flow stream). For example, the plug of fluid can be sufficiently large to cause deflection of the particle of interest within the flow stream position to move to an alternate fluid stream.

The volume of the plug of fluid containing the particle of interest can be related to (e.g., proportional to the flow rate of the flow stream containing the particle of interest, the diameter of catch tube, and/or the time the capture tube in fluidically connection with the flow stream. The volume of the plug of fluid can be no more than 5, 10, 50, 100, 150, 200, 250, 300, 350, 400, 450, 500, 550, 600, 700, 800, 900, or 1000 μL. In some cases, the plug of fluid can be no more than 450 μL. In some cases, the plug of fluid can be at least 450 μL.

The capture tube can be made in a way that prevents or reduces leakage of solution caught into the capture tube. In some cases, the capture tube can be coated with hydrophobic materials. The hydrophobic coating can prevent or reduce the leakage of solution (e.g., around the hinge apparatus). In some cases, the capture tube can be charged. For example, a charge plate can be placed at the end of the capture tube. The charging of the capture tube can promote clean transfer of fluid (e.g., plugs of fluid containing particles of interest). In some cases, the capture tube can comprise a leakage collector at a part of the tube where the leaked solution would flow to, e.g., at the bottom of the tube. The leakage collector can be outside of the capture tube or over the exit port of the capture tube. In some cases, the leakage collector can be configure to self-aspirate the leakage, e.g., as a function of vacuum.

The particle sensor can be configured to direct a particle of interest using an air bubble. The air bubble can be generated by a pressure source. The pressure source can be fluidically connected with the flow stream containing the particle of interest. In some cases, the air bubble can direct a particle of interest from a flow stream to a capture tube. In some cases, the air bubble can be used to direct a particle of interest from a first flow stream to a second flow stream. In some cases, the air bubble can be used to direct a particle of interest from a first flow stream to a capture tube a cross one or more flow streams.

The particle dispenser can catch a plurality of particles of interest into a channel for dispensing. The particles of interest can line up (e.g., in single file) in the channel. The particles can be in a solution. The volume of the solution can be small, e.g., less than 100 pt. In some cases, the particles in the channel can be in a solution of less than 0.01 μL, 0.1 μL, 1 μL, 5 μL, 10 μL, 20 μL, 30 μL, 40 μL, 50 μL, 60 μL, 70 μL, 80 μL, 90 μL, or 100 μL. The particles can be pass into a dispense module of the particle dispenser. In some cases, the dispense module comprise a particle sensor. In some cases, the dispense module comprise no particle sensor. The particle dispenser can be configured to dispense the particles of interest to a location (e.g., a defined location). For example, the particle dispenser can be configured to dispense the plurality of particles of interest one by one on to a surface, such as a microscope slide or a microarray slide. In some cases, the particles can remain in the channel for further processing and/or analysis. In some cases, the particles can be directed to a device from the channel for further processing and/or analysis. For example, the particles can be directed to a "car wash" device for further processing. Examples of "car wash" devices are described in PCT Patent WO2014014515, which is incorporated herein by reference in its entirety. In some cases, the analytical device can count the number of the particles and record images of the particles (e.g., images of individual particles). In some cases, such analytical device can count the number of the particles and record images of the particles at the same time.

The particle dispenser can be configured to be a blind dispense of a purified sample stream. In some cases, the sample can flow into a dispense module that ejects drops of the sample solution. The ejected drops may or may not contain particles. These drops can be dispensed to a location, e.g., a slide or a multi-well plate. In some cases, the drops can be dispensed without further interrogation. In some cases, the drops containing particles can be identified by a droplet or non-droplet sorting mechanism.

The particle dispenser herein can be configured to dispense any number of particles of interest. In some cases, the particle dispenser can be configured to dispense one particle, e.g., a single cell dispenser. In some cases, the particle dispenser can dispense a single particle, e.g. a single cell, with an ejection. In some cases, the particle can dispense a plurality of particles, e.g., with an ejection.

The switch can comprise a magnetic driver. The magnetic driver can be configured to control the position of the capture tube in response to the signal generated by the sensor. The switch can comprise a planar space with voids. The switch can also comprise a lock/key system for controlling the position of the capture tube.

The particle dispenser can dispense one or more particle of interest to a location. In some cases, the location can be a random location. In some cases, the location can be a defined location, e.g., a known location. In some cases, the location can be a particle collector. In some cases, the particle collector can include a slide (e.g., a microscope slide, or a microarray slide), a cell culture dish, a cell culture well, a microtube, a test tube, and a microliter plate. In some cases, the container can be on stage allowing for 1-dimentional, 2-dimensional, or 3-dimensional moving of the container.

The particle dispenser can be configured to use on a microfluidic device or off a microfluidic device disclosed herein. In some cases, the particle dispenser can be used on a microfluidic device, e.g., to achieve enhanced sorting rate. The particle dispenser can comprise a fluidic duct connected with one or more channels from a microfluidic device herein. The particles processed by the microfluidic device can be dispensed by the particle dispenser to a defined location for further processing and/or analysis. When used off a microfluidic device, the particle dispenser can be treated for sterilization. Such treatments can include use of bleach, ethanol, and/or other sterilization chemicals and approaches. In some cases, the sterilization treatment can be integrated as part of the assembly process of the particle dispenser.

The particle dispenser can be used with a cell sorter. In some cases, the particle dispenser can be used to dispense the sorted cells to a defined location herein. The cell sorters can include flow cytometers, e.g., FACS and MACS, and piezo-driven cell sorters. The particle dispenser can also be used with cell sorters known in the art, including those described in U.S. Patent Application Nos. US20120078531, US20130083315, US20100066880, US20020005354, and US20140051064, which are incorporated herein by reference in their entireties.

The particle dispenser can be placed downstream of any device for separating particles herein. In some cases, the particle dispenser can be downstream of one or more DLD arrays. In some cases, the particle dispenser can be downstream of a magnetic separator. In some cases, the particle dispenser can be downstream of any other particle separators or analytical devices herein.

The systems herein can comprise a fluidic balancer to maintain the stability of flow streams containing particles (e.g., by reducing or preventing the wave of the flow streams) in the systems. The component can be configured to generate a back flow stream of the flow stream of the particles in system. In some cases, the back flow stream can have a fluidic resistance that is similar or the same as the fluidic resistance of the flow stream containing the particles. In some cases, the fluidic balancer can be included in a particle dispenser herein.

In some cases, when the capture tube is capturing or dispensing a first particle of interest, a second particle of interest can arrive to the sensing zone. In these cases, the particle dispenser can be configured to abort the signal generated in response to the second particle of interest, so the capturing and/or dispensing of the first particle of interest can be completed. In some cases, the sensor can be configured not to generate any signal when the capture tube is not at the first position, e.g., at the second positon or moving between the first position and the second position. In some cases, the sensor can be configured not to generate any signal when a particle of interest is in the capture tube.

The particle dispenser can be a multi-parameter fluorescently triggered cell dispensing system. The particle dispenser can be downstream of a DLD array. In some cases the dispenser can be downstream of a DLD array and upstream or downstream of a magnetic separator (immunomagnetic cell separator). The particle dispenser can be used isolate one or more particles (e.g., cells). For example, the particle dispenser can detect the label of a particle of interest, capture and dispense it to a location, thereby isolating the particle of interest from other particles in a sample. In some cases, the particle dispenser can comprise a sensor configured to detect more than one labels. Such particle dispenser can be used to isolate multiple particles by detecting their labels and dispense these particles to different locations, thereby isolating these particles from other particles and separate them from each other. Such particle separator can allow for particle separation without intermediary losses between platform technologies by combining size separation, fluorescence separation and/or Boolean logic separation. The particle dispenser can allow separation of particle without the need of cell lysis and/or high pressure in the separation process. In some cases, the particle dispenser, combined with other components in the system herein, can isolate CTC at the concentration of 0.1/mL blood, or 1 CTC in 1 billion cells in a sample. In some cases, the particle dispenser, combined with other components in the system herein, can isolate non-CTC cells at the concentration of less than 10/mL in whole blood.

H. Temperature Control

The systems herein can comprise a temperature controller. The temperature control can be used to regulate the activity of particles (e.g., cell activities) in the system, and/or for processing particles (e.g., cell lysis) for subsequent analysis. In some cases, a temperature control can comprise a heater element. A heater element can comprise a metal heating element, a ceramic heating element, a composite heating element, or combinations thereof. In some cases, a heater element can comprise a nichrome element (e.g., a nichrome wire, a nichrome ribbon or a nichrome strip), a resistance wire element, an etched foil element, radiative heating element (e.g., a heating lamp), a molybdenum disilicide element, a positive temperature coefficient (PTC) ceramic element, a tubular heating element, a screen-printed metal-ceramic element, or combinations thereof. In some cases, a temperature control apparatus can comprise a laser. The laser can be gas laser, chemical laser, dye laser, metal-vapor laser, solid-state laser, semiconductor laser, free electron laser, gas dynamic laser, Raman laser, nickel-like Samarium laser, or any type of laser known in the art. In some cases, the temperature control can comprise a cooling element. The cooling element can comprise channels with air or fluid flowing inside. In some cases, the cooling element can be coupled with the heating element, under the control of a temperature sensor. In some cases, the cooling element can cool the sample and the buffer to about 4° C. before, during, or after analysis, separation and/or processing. In some cases, the temperature control can set the sample to different temperatures at different steps performed by the system herein. For example, the temperature control can cool the sample to about 4° C. before separation, and warm the sample to about 37° C. to facilitate a reaction (e.g., enzyme digestion, or labeling). In some cases, the temperature control can create temperature cycling in the system. For example, the temperature control can be used to create thermocycles for performing PCR with the sample. In some cases, the temperature control can sense and control the sample temperature before, during, and/or after any of the steps performed by the system herein, including the sample labeling, mixing with reagents, de-bulking, de-clump, DLD separation, magnetic separation, fluorescent separation, other separation, particle analysis, particle dispensing, and any particle processing steps. The temperature control can allow reducing biological activity associated with phagocytosis, ensuring consistent labeling and other reactions and performance, reducing diffusion of active species during DLD and/or magnetic separations, slowing immune cell reaction and/or response to immunotherapies that might alter the stability of the patient same over time, ensuring that rare cells (e.g., CTCs) are set to a controlled culture environment as soon as possible following isolation, and/or processing including cell lysis for downstream analytical genomics.

In some cases, the temperature control can comprise a temperature sensor. The temperature senor can be configured to detect the temperature of one or more devices and/or elements of system, and/or any sample in the systems. In some cases, the temperature control can be integrated with another device in the system. For example, in the case where the system comprises a microfluidic DLD device, the microfluidic device can comprise a temperature control, which can detect and regulate the temperature of the sample in the microfluidic device.

The system can comprise a humidity control. The humidity control can reduce or prevent evaporation of a solution in the system. A humidity control can be a humidifier, such as an evaporative humidifier, a natural humidifier, a vaporizer, an impeller humidifier, an ultrasonic humidifier, a forced-air humidifier, or combinations thereof. In some cases, the humidity control can be regulated by the temperature control disclosed herein. For example, the humidity control can be turned on or tuned up when the temperature of the sample reaches a certain temperature. In another example, the humidity control can be turned on or tuned up when the temperature control will regulate the sample to a certain temperature. In some cases, the humidity control and/or temperature control can be coupled with another device in the system. For example, the humidity control and/or temperature can be coupled with a particle dispenser (e.g., a single cell dispenser) disclosed herein. The temperature control and/or humidity control can reduce or prevent the evaporation of the solution containing the dispensed single particle (e.g., single cell).

III. Samples

The methods, devices, systems, and/or kits described herein can separate particles from a sample. Samples can include all complex mixtures of particles or body fluids including, peripheral blood, bone marrow, bronchial and alveolar lavages, urine and gastric and pleural effusions. In some cases, samples can be mammalian, non-mammalian in origin, or mixed in with mammalian in the case of infectious agents such as prions, virus, bacteria, parasites, in a mammalian host. In some cases, samples can also include body fluid from cancer patients where normal disease processes shed circulating tumor cells, which can be enriched for in the de-bulking DLD array, or similarly for particles below the critical dimension can be enriched for tumor specific nucleic acids contained in micro- and/or nano-vesicles and free floating. In some cases, apoptotic bodies, micro-vesicles, nucleosomes, exosomes and free floating nucleic acids, such as miRNA can be captured in the below critical dimension pathway from the de-bulking DLD. Samples can be diluted to run more effectively through the system.

A. Types of Samples

A sample can be a biological sample. In some cases, a biological sample can be a body fluid. In some cases, the sample can be a blood sample. The blood sample can be, e.g., peripheral blood, maternal blood, G-CSF mobilized adult peripheral blood, or cord blood. Cord blood can be, e.g., umbilical cord blood, or placental cord blood. A biological sample can include serum, plasma, sweat, tears, ear flow, sputum, synovial fluid, lymph, bone marrow suspension, urine, saliva, semen, vaginal flow or secretion, cerebrospinal fluid, feces, cervical lavage, sebum, semen, prostatic fluid, Cowper's fluid, pre-ejaculatory fluid, female ejaculate, brain fluid (e.g., cerebrospinal fluid), ascites, milk (e.g., breast milk), cerumen, secretions of the respiratory, intestinal or genitourinary tract, broncheoalveolar lavage fluid, amniotic fluid, aqueous humor, and water samples). A sample can be fluids into which cells have been introduced (for example, culture media and liquefied tissue samples). A sample can be a lysate. A biological sample can be cyst fluid, pleural fluid, peritoneal fluid, pericardial fluid, lymph, chyme, chyle, bile, interstitial fluid, menses, pus, sebum, mucosal secretion, stool water, pancreatic juice, lavage fluid from sinus cavities, bronchopulmonary aspirate, or blastocyl cavity fluid. A biological sample can be a tissue sample or biopsy.

A sample can be from a subject. In some cases, the sample can be from an animal, e.g., human, mouse, rat, cat, dog, cow, chicken, donkey, rabbit, chimpanzee, gorilla, orangutan, horse, guinea pig, pig, or rhesus monkey. In some cases, the sample can be from a plant, or fungus. In some cases, the sample can comprise a plant or a fungus.

In some cases, a sample can comprise a buffer. The buffer can be free or substantially free of a reagent. In some cases, the methods, devices, systems, and/or kits described herein can be used for buffer/medium exchange. In some cases, the sample can be a cell culture sample.

In some cases, a sample can be from a body of water. A body of water can be, e.g., from a creek, pond, river, ocean, lake, sea, puddle, stream canal, wetland, marsh, reservoir, harbor, bay, artificial lake, barachois, basin, bayou, beck, bight, billabong, boil, brook, burn, channel, cove, draw, estuary, firth, fjord, glacier, gulf, inlet, kettle, kill, lagoon, loch, mangrove swamp, Mediterranean sea, mere, mill pond, moat, oxbow lake, phytotelma, pool (swimming pool, reflecting pool), pothole, rapid, roadstead, run, salt marsh, sea loch, sea lough, source, spring, strait, stream, subglacial, lake, swamp, tarn, tide pool, vernal pool, wash, or wetland.

In some cases, a sample can be an industrial sample. In some cases, a sample with yeast can be a beer production sample. In some cases, a sample can be from a bioterror attack. In some cases, a sample from a bioterror attack comprises a virus, e.g., smallpox virus or influenza virus. In some cases, a sample from a bioterror attack comprises anthrax. In some cases, a sample from a bioterror attack comprises more than one type of infective agent.

In some cases, a sample can be from a hospital or other medical health care facility. In some cases, a sample can be from a wastewater treatment facility. In some cases, a sample can be from an algal biofuel production facility. In some cases, a sample can be from a brewery. In some cases, a sample can be from a public water system. In some cases, a sample can be from a sewage system. In some cases, particles related to water borne disease can be detected in a sample. In some cases, such sample can be any water comprising disease-causing microorganisms and/or chemical compounds. For example, the methods, systems, devices and/or kits herein can be used to detect whether the sample comprises particles related to a water borne disease. Examples of water borne diseases include amoebiasis, cryptosporidiosis, cyclosporiasis, giardiasis, microsporidiosis, schistosomiasis, dracunculiasis, taeniasis, fasciolopsiasis, hymenolepiasis, echinococcosis, coenurosis, enterobiasis, campylobacteriosis, cholera, E. coli infection, M. marinum infection, dysentery, legionellosis, leptospirosis, otitis externa, salmonellosis, typhoid fever, vibrio illness, severe acute respiratory syndrome, hepatitis (e.g., hepatitis A), poliomyelitis, polyomavirus infection, and Desmodesmus Infection. Examples of particles related to a water borne disease include Entamoeba histolytica, Cryptosporidium parvum, Cyclospora cayetanensis, Giardia lamblia, Microsporidia, Schistosoma, Dracunculus medinensis, Tapeworms of the genus Taenia, Fasciolopsis buski, Hymenolepis nana, Echinococcus granulosus, multiceps, Ascaris lumbricoides, Enterobius vermicularis, Clostridium botulinum, Campylobacter jejuni, Vibrio cholerae, Escherichia coli, Mycobacterium marinum, Shigella (e.g., Shigella dysenteriae), Salmonella, Legionella (e.g, Legionella pneumophila), Leptospira, Salmonella, Salmonella typhi, Vibrio vulnificus, Vibrio alginolyticus, Vibrio parahaemolyticus, Coronavirus, Hepatitis A virus, Poliovirus, Polyomavirus: JC virus, BK virus, and desmodesmus armatus.

In some cases, a sample can be from a chemical spill. In some cases, a sample can be from a mine, e.g., coal mine. In some cases, a sample can be an archeological sample. In some cases, a sample can be a forensic sample.

In some cases, a sample comprises an enzyme, e.g., a restriction enzyme, kinase (e.g., DNA kinase (e.g., T4 polynucleotide kinase), protein kinase, e.g., serine kinase, threonine kinase, tyrosine kinase), DNase, RNase, phosphatase, ligase (e.g., RNA ligase, DNA ligase), horseradish peroxidase (HRP), alkaline phosphatase (AP), glucose oxidase, polymerase (e.g., DNA polymerase (e.g., thermostable DNA polymerase, Taq polymerase) RNA polymerase), terminal deoxynucleotidyl transferase, reverse transcriptase (e.g., viral reverse-transcriptase, non-viral reverse transcriptase), telomerase, methylase, or topoisomerase. In some cases, methods and/or device used herein can be used to separate a label or enzyme from another component of a sample, e.g., a polynucleotide or cell.

A sample can comprise nucleic acid molecules, e.g., RNA (e.g., rRNA, tRNA, mRNA, miRNA, extracellular or circulating or cell-free RNA) or DNA (e.g., genomic DNA, cDNA, mitochondrial DNA, extracellular or circulating or cell-free DNA).

B. Number of Particles/Numbers of Different Types of Particles in a Sample

A sample can comprise one or more first particles. In some cases, a sample can comprise at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 first particles. In some cases, a sample can comprise at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 total particles. A sample can comprise one or more different types of particles. A sample can comprise at least 1, 2, 3, 4, 5, 6, 7, 8, 9, 10, 50, 100, 500, 1000, 10,000, 100,000, 1,000,000, 10,000,000, 100,000,000, 1,000,000,000, 10,000,000,000, 100,000,000,000, or 1,000,000,000,000 different types of particles.

The methods, systems, devices and kits can be used to separate particles whose concentration is less than 100000, 10000, 1000, 800, 600, 400, 200, 100, 90, 80, 70, 60, 50, 40, 30, 20, 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01 particle or particles per mL sample. In some cases, the methods, systems, devices and kits can be used to separate particles whose concentration is at least 10000, 1000, 800, 600, 400, 200, 100, 90, 80, 70, 60, 50, 40, 30, 20, 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01 particle or particles per mL sample. In some cases, the methods, systems, devices and kits can be used to separate particles whose concentration is at least 1000 particles per mL sample. In some cases, the methods, systems, devices and kits can be used to separate particles whose concentration is 0.1 particle per mL sample. For example, the particles are CTCs. In another case, the methods, systems, devices and kits can be used to separate particles whose concentration is less than 10 particles per mL sample. For example the particles are cells that are not CTCs.

C. Ratio of First and Second Particles in a Sample

A sample can comprise a first particle and a second particle. In some cases, the ratio of the abundance of the first particle to the second particle in the sample can be less than 100:1, 10:1, 1:1, 1:10, 1:100, 1:1000, 1:10,000, 1:100,000, 1:1,000,000, 1:10,000,000, 1:100,000,000, or 1:1,000,000,000. In some cases, the ratio of the abundance of the first particle to the second particle in the sample can be greater than 100:1, 10:1, 1:1, 1:10, 1:100, 1:1000, 1:10,000, 1:100,000, 1:1,000,000, 1:10,000,000, 1:100,000,000, or 1:1,000,000,000. In some cases, the ratio of the abundance of the first particle to the second particle in the sample can be about 100:1, 10:1, 1:1, 1:10, 1:100, 1:1000, 1:10,000, 1:100,000, or 1:1,000,000, 1:10,000,000, 1:100,000,000, 1:1,000,000,000, or any ratio in between.

In some cases, a sample can comprise a rare cell type. In some cases, the ratio of the abundance of the rare cell type to the abundance of cells of one or more other cell types in a sample can be about 1:100, 1:1000, 1:10,000, 1:100,000, 1:1,000,000, 1:10,000,000, 1:100,000,000, or 1:1,000,000,000. In some cases the ratio of abundance of cells of the rare cell type to the abundance of cells of one or more other cell types can be less than 1:100, 1:1000, 1:10,000, 1:100,000, 1:1,000,000, 1:10,000,000, 1:100,000,000, or 1:1,000,000,000.

D. Sample Dilution

In some cases, a sample can be diluted. In some cases, a sample, e.g., a blood sample, can be diluted before it can be applied to a device described herein. A sample can be diluted, e.g., in order to prevent clogging of a device described herein. In some cases, a sample can be diluted after being passed through a device described herein. A sample can be diluted, e.g., by adding water, buffer, and/or other fluid to the sample. In some cases, a sample can be diluted by adding an additive. In some cases, a sample can be diluted by a protein buffer diluent. For example, the protein buffer diluent can comprise at least 1% BSA in 1×PBS.

A sample can be diluted at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000, 4000, 5000, 6000, 7000, 8000, 9000, or 10,000-fold.

E. Additives

A sample can comprise one or more additives. As a function of the type of sample, the sample can be pre-treated with anticoagulants, nutrients, growth factors, enzymes, and/or fixatives to facilitate safe and effective processing through the system. Accordingly, as a function of downstream applications, the samples can be treated with sample preservatives. In some cases, use of cell growth compatible media to minimize potential sample preparation stress with fragile cells in culture can confer advantage in the isolation and preservation of viable circulating tumor cells. In some cases, system running media can include established culture media components including nutrients, specific additives, hormones, growth factors, enzymes. For problematic samples (e.g., lavages), pretreatment with specific enzymes can be performed.

The sample can comprise one or more other types of additives, e.g., sodium fluoride (NaF), Heparin, EDTA, or sodium citrate.

In some cases, the one or more additives can be an anticoagulant or antiplatelet agent, e.g., clopidogrel, prasugrel, ticagrelor, ticlopidine, argatroban, bivalirudin, dalteparin, enoxaparin, fondaparinux, heparin, heparin lock flush, lepirudin, anagrelide, apixaban, aspirin, aspirin/dipyridamole, cilostazol, dabigatran, dipyridamole, batroxobin, hementin, rivaroxaban, warfarin, or urokinase. In some cases, an anticoagulant can be an antithrombic, fibrinolytic, or thrombolytic.

In some cases, the one or more additives can be one or more antibiotics or antimycotics, e.g., actinoymycin D, ampicillin, antimycin, antipain, bacitracin, chloramphenicol, erythromycin, gentamicin, kanamycin, penicillin, rifamycin, or tetracycline.

The one or more additives can be one or more proteases, e.g., one or more serine proteases (e.g., trypsin or chymotrypsin), cysteine proteases, threonine proteases, aspartic proteases, glutamic proteases, glutamic proteases, or metalloproteases.

The one or more additives can be one or more collagenases, e.g., collagenase type 1, collagenase type 2, collagenase type 3, collagenase type 4, collagenase type 5. collagenase.

The one or more additives can be Kolliphor®, e.g., Kolliphor® P 188 (Poly(ethylene glycol)-block-poly(propylene lycol)-block-poly(ethylene glycol). In some cases, the one or more additives comprise Kolliphor® ELP, EL, RH 40, CS12, CS20, CS B, CS S, CS A, CS L, TPGS, PS 60, PS 80, HS15, P 407, P 237, P 338, or F127 (e.g., Pluronic F127, a triblock copolymer comprising a central hydrophobic block of polypropylene glycol flanked by two hydrophilic blocks of polyethylene glycol). The concentration of a Kolliphor can be about 0.5%, 1%, 1.5%, 2%, 3%, 4%, or 5%. For example, Kolliphor® can be Sigma K4894-500 g or Sigma P5556.

The sample can comprise one or more additives that are anticoagulants. In some cases, the one or more anticoagulants can be a chelating agent (e.g., EDTA). In some cases, the one or more anticoagulants can be one or more thrombin inhibitors (e.g., PPACK). The one or more chelating agents can be comprise one or more calcium-chelating agents. The one or more chelating agents can include acetylacetone, aerobactin, aminoethylethanolamine, aminopolycarboxylic acid, ATMP, BAPTA, $BDT_H2$, benzotriazole, Bipyridine, 2,2'-Bipyridine, 4,4'-Bipyridine, 1,2-Bis(dimethylarsino)benzene, 1,2-Bis(dimethylphosphino)ethane, 1,2-Bis(diphenylphosphino)ethane, Catechol, Chelex 100, Citric acid, Corrole, Crown ether, 18-Crown-6, Cryptand, 2.2.2-Cryptand, Cyclen, Deferasirox, Deferiprone, Deferoxamine, Dexrazoxane, Trans-1,2-Diaminocyclohexane, 1,2-Diaminopropane, Dibenzoylmethane, Diethylenetriamine, Diglyme, 2,3-Dihydroxybenzoic acid, Dimercaprol, 2,3-Dimercapto-1-propanesulfonic acid, Dimercaptosuccinic acid, Dimethylglyoxime, DIOP, Diphenylethylenediamine, DOTA, DOTA-TATE, DTPMP, EDDH, EDDS, EDTMP, EGTA, 1,2-Ethanedithiol, Ethylenediamine, Ethylenediaminetetraacetic acid (EDTA), Etidronic acid, Extended porphyrins, Ferrichrome, Fluo-4, Fura-2, Gluconic acid, Glyoxal-bis(mesitylimine), Hexafluoroacetylacetone, Homocitric acid, Iminodiacetic acid, Indo-1, Metal acetylacetonates, Metal dithiolene complex, Metallacrown, Nitrilotriacetic acid, Pendetide, Penicillamine, Pentetic acid, Phanephos, Phenanthroline, 0-Phenylenediamine, Phosphonate, Phytochelatin, Polyaspartic acid, Porphin, Porphyrin, 3-Pyridylnicotinamide, 4-Pyridylnicotinamide, Sodium diethyldithiocarbamate, Sodium polyaspartate, Terpyridine, Tetramethylethylenediamine, Tetraphenylporphyrin, 1,4,7-Triazacyclononane, Triethylenetetramine, Triphos, Trisodium citrate, or 1,4,7-Trithiacyclononane. In some cases, the sample, e.g., a blood sample, can be collected in a tube comprising K2EDTA or K3EDTA. In some cases, the sample comprises an agent that reduces the activity of calcium-dependent integrins. In some cases, the sample comprises an agent that reduces calcium dependent thrombin formation. In some cases, an agent that chelates calcium comprises acid citrate dextrose (ACD). The final concentration of ACD in a sample, e.g., a blood sample, can be 10%.

In some cases, the one or more chelating agents can comprise EDTA. In some cases, the one or more calcium chelating agents can comprise EDTA. In some cases, the final concentration of the one or more chelating agents in the sample can be at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mM. In some cases, the final concentration of EDTA in the sample can be at least 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, or 25 mM. In some cases, the concentration of EDTA can be about 2 mM to about 7 mM, or about 3 mM to about 6 mM.

The one or more thrombin inhibitors can be PPACK (D-Phe-Pro-Arg-CMK), benzamidine hydrochloride, p-APMSF, p-APMSF hydrochloride, TLCK hydrochloride, uPA inhibitor, PPACK dihydrochloride, PPACK dihydrochloride biotinylated, or heparin. In some cases, the one or more thrombin inhibitors can be a direct thrombin inhibitor. In some cases, a direct thrombin inhibitor can be a bivalent thrombin inhibitor. In some cases, a direct thrombin inhibitor can be a univalent thrombin inhibitor. In some cases, a direct thrombin inhibitor can be an allosteric inhibitor. A bivalent direct thrombin inhibitor can be hirudin, bivalirudin, lepirudin, or desirudin. A univalent direct thrombin inhibitor can be argatroban, melagatran, ximelagatran, or dabigatran. An allosteric direct thrombin inhibitor can be a DNA aptamer, benzofuran dimer, benzofuran trimer, or polymeric lignin. In some cases, a direct thrombin inhibitor can be PPACK (D-Phe-Pro-Arg-CMK).

In some cases, the final concentration of the one or more thrombin inhibitors, e.g., direct thrombin inhibitor in a sample can be at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, or 400 µM. In some cases, a final concentration a thrombin inhibitor in a sample can be about 30 to about 50 µM, or about 20 to about 60 µM.

In some cases, the final concentration of PPACK in a sample can be at least 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, or 400 µM. In some cases, a final concentration of PPACK in a sample can be about 30 to about 50 µM, or about 20 to about 60 µM.

The one or more additives can comprise one or more antifreezes. The one or more antifreezes can include glycerol, propylene glycol, ethylene glycol, methanol, dimethyl sulfoxide (DMSO), 2-Methyl-2,4-pentanediol (MPD), sucrose, and dimethylsulphoxide. In some cases, the sample can comprise one or more additives that are cryoprotectants. The one or more cryoprotectants can include DMSO, MPD, ethylene glycol, propylene glycol, glycerol, sucrose, or dimethylsulphoxide.

In some cases, the one or more additives can comprise one or more nucleosides and/or a derivative thereof. In some instances, nucleosides may generally be described as glycosylamines that can be e.g., nucleotides lacking a phosphate group. In some instances, a nucleoside can comprise a nucleobase or a nitrogenous base and a 5-carbon sugar (e.g, ribose or deoxyribose). The one or more nucleosides can include adenosine, cytidine, guanosine, inosine, 5-methyl uridine, thymidine, uridine, deoxyadenosine, deoxycytidine, deoxyguanosine, deoxyinosine, deoxythymidine, deoxyuridine, a derivative thereof, and a combination thereof. In some instances, the base in a nucleoside is bound to either ribose or deoxyribose via a beta-glycosidic linkage. In some embodiments, a nucleoside can reduce or prevent platelet activation in a biological sample. In some embodiments, a nucleoside can reduce or prevent shear-stress-induced platelet adhesion in a biological sample. For example, a biological sample can be contacted with a composition comprising a guanosine, thereby reducing the amount of shear-stress-induced platelet adhesion as the sample is flowed through a microfluidic channel. In another example, a biological sample can be contacted with a co-formulation of inosine, and cytidine, thereby reducing the amount of shear-stress-induced platelet aggregation as the sample is flowed through a DLD array.

In some cases, the one or more additives can comprise one or more thienopyridines and/or a derivative thereof. In some instances, a thienopyridine can generally be described as a class of selective, irreversible ADP receptor/P2Y12 inhibitors, e.g., that can be used for their anti-platelet activity. In some instances, a composition of the present disclosure can comprise any compound that directly or indirectly inhibits one or more ADP P2Y12 platelet receptors. Non-limiting examples of a thienopyridine include clopidogrel, prasugrel, ticlopidine, a derivative thereof, and a combination thereof. In some embodiments, a thienopyridine can reduce or prevent platelet activation in a biological sample. For example, a biological sample may be contacted with a composition comprising a clopiogrel, thereby reducing the amount of platelet aggregation and allowing the sample to flow freely through a microfluidic channel.

In some cases, the one or more additives can comprise one or more nonsteroidal anti-inflammatory drugs (NSAID). In some aspects, an NSAID can generally be described as a compound capable of inhibiting the activity of cyclooxygenase-1 (COX-1) and/or cyclooxygenase-2 (COX-2), thereby inhibiting the synthesis prostaglandins and thromboxanes. In some instances, the inhibition of COX-2 by an NSAID can result in anti-inflammatory effects. The one or more NSAIDs can include acetylsalicylic acid, celecoxib, choline, choline salicylate, diclofenac potassium, diclofenac sodium, diflunisal, etodolac, fenoprofen calcium, flurbiprofen, ibuprofen, indomethacin, ketoprofen, magnesium salicylate, meclofenamate sodium, mefenamic acid, meloxicam, misoprostol, nabumetone, naproxen, naproxen sodium, oxaprozin, piroxicam, rofecoxib, salsalate, sodium salicylate, sulindac, tolmetin sodium, valdecoxib, and a derivative thereof. In some embodiments, a composition of the present disclosure can comprise one or more NSAIDs. For example, a biological sample can be contacted with a composition comprising a flurbiprofen, thereby suppressing the production of prostaglandins and thromboxanes, and reducing platelet activation. In another example, a biological sample can be contacted with a co-formulation of acetylsalicylic acid, and sodium salicylate, thereby reducing the platelet aggregation.

In some cases, the one or more additives can comprise can comprise one or more dihydroxybenzoic acids (DHBA). In some instances, DHBAs can generally be described as phenolic acids. Non-limiting examples of DHBA include 2-gentisic acid, hypogallic acid, orsellinic acid, protocatechuic acid, Pyrocatechuic acid, α-Resorcylic acid, β-Resorcylic acid, γ-resorcylic acid, a derivative thereof. In some embodiments, a composition of the present disclosure can comprise one or more DHBAs. In some instances, a DHBA can be a compound that reduces or prevents platelet activation, aggregation, and/or adhesion. In some instances, a DHBA can be a compound that is an iron-chelating compound. In some embodiments, a DHBA can be a derivative of another class of compounds of the present disclosure. For example, pyrocatechuic acid can be a derivative or a metabolite of acetylsalicylic acid. In some embodiments, a DHBA can be a crystalline acid that is a carboxyl derivative of resorcinol and/or a dihydroxy derivative of benzoic acid. In some embodiments, a DHBA can be synthesized by carboxylation of hydroquinone. In some embodiments, a DHBA can induce apoptosis of cancer (e.g., leukemia) cells. In some instances, a DHBA can reduce or enhance tumour growth. In some instances, a DHBA can increase proliferation and inhibit apoptosis of stem cells. In some instances, a DHBA can induce an anti-genotoxic effect and/or tumoricidal activity.

In some cases, the one or more additives can comprise one or more antioxidants, e.g., glycine, n-acetyl-L-cysteine, glutamine, D-Mannitol, vitamin C (ascorbic acid), vitamin E (tocopherols and tocotrienols), green tea, ferulic acid, reduced glutathione, melatonin, resveratrol, vitamin A (palmitate), beta carotene, vitamin D-3 (cholecalciferol), selenium (1-seleno methionine), BHA, or BHT.

In some cases, the one or more additives can comprise one or more cell membrane stabilizers, e.g., potassium dichromate, cadmium chloride, or lithium chloride aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, *Ginkgo biloba* extract, diphenylhydantoin, perftoran, polyvinylpyrrolidone, phosphatidylserine, tegretol, PABA, disodium cromglycate, nedocromil sodium, phenyloin, zinc citrate, mexitil, dilantin, sodium hyaluronate, or polaxamer 188.

In some cases, the one or more additives can comprise one or more energy sources, e.g., glucose, lactose, fructose, or galactose.

In some case, the one or more additives can comprise one or more buffers, e.g., phosphate buffered saline (PBS), TAPS, Bicine, Tris, Tricine, HEPES, TES, MOPS, PIPES, Cacodylate, or MES.

In some cases, the one or more additives can comprise one or more antiplatelet drugs, e.g., theophylline or dipyridamole.

In some aspects, the one or more additives can be used for isolating, separating, and/or enriching particles from a blood sample using multiple particle separation devices. Upon collection, blood and its cellular components can continue to perform their biological function over a period of time. In some cases, continued performance of such biological functions (e.g., platelet activation, adhesion, and/or aggregation) can reduce the efficiency with which particles may be separated from a sample using a microfluidic device (e.g., a DLD array and/or magnetic separator). For example, upon activation, platelets may aggregate within a fluidic channel, thereby restricting the flow of a sample through the channel.

Platelets can be activated in a variety of ways. In one instance, obtaining a blood sample intravenously (e.g., blood drawing by needle) can break down several tissue layers, thereby releasing collagen and other extracellular proteins that can activate platelets and initiate the clotting response. In another instance, platelets can be activated by exposing them to abnormal shear-stress forces (e.g., a deviation from the fluid-flow properties of circulating blood). For example, in some instances, the fluid-flow properties of a microfluidic environment can induce platelet activation. These events can lead to the secretion of granules from platelets releasing thrombin and adenosine diphosphate (ADP), promote platelet adhesion to the surfaces of a microfluidic device, and can ultimately initiate the coagulation cascade, thereby blocking the microfluidic device. In yet another instance, aging platelets can also secrete granules, along with other cells releasing tissue factors, leading to the initiation of the alternative coagulation pathway. Platelets can also adhere to many different types of surfaces, including PMMA (e.g., independently of activation) due to shear stress alone leading to their local aggregation. This adhesion and aggregation can be driven by a multitude of adhesion proteins on the surface of the platelet, and soluble protein ligands in blood such as fibrinogen, VW factor or fibronectin.

The one or more additives can be added to a sample for inhibiting the adhesion, aggregation, and/or activation of platelets. In some cases, such additives can include one or more of the anticoagulant, antiplatelet agent, antibiotics or antimycotics, serine proteases, Kolliphor, chelating agent, thrombin inhibitors, antifreezes, nucleosides and/or a derivative thereof, thienopyridines and/or a derivative thereof, nonsteroidal anti-inflammatory drugs (NSAID), dihydroxybenzoic acids (DHBA), antioxidants, cell membrane stabilizers, energy sources, buffers, and antiplatelet drugs. In some cases, the additives can comprise nucleosides and/or a derivative thereof and a thienopyridines and/or a derivative thereof. In some cases, the additives can comprise nucleosides and/or a derivative thereof and an NSAID. In some cases, the additives can comprise nucleosides and/or a derivative thereof and a DHBA In some cases, the additives can comprise thienopyridines and/or a derivative thereof and an NSAID In some cases, the additives can comprise thienopyridines and/or a derivative thereof and a DHBA. In some cases, the additives can comprise an NSAID and a DHBA. In some cases, the additives can comprise nucleosides and/or a derivative thereof, thienopyridines and/or a derivative thereof, and an NSAID. In some cases, the additives can comprise nucleosides and/or a derivative thereof, thienopyridines and/or a derivative thereof, and a DHBA. In some cases, the additives can comprise thienopyridines and/or a derivative thereof, an NSAID, and a DHBA. In some cases, the additives can comprise nucleosides and/or a derivative thereof, an NSAID, and a DHBA. In some cases, the additives can comprise nucleosides and/or a derivative thereof, thienopyridines and/or a derivative thereof, an NSAID, and a DHBA.

The compositions disclosed herein can be a liquid formulation. In some cases, the liquid formulation can comprise at least about 0.01 mM, at least about 0.05 mM, at least about 0.1 mM, at least about 0.5 mM, at least about 1 mM, at least about 1.5 mM, at least about 2.0 mM, at least about 2.5 mM, at least about 3.0 mM, at least about 3.5 mM, at least about 4.0 mM, at least about 4.5 mM, at least about 5.0 mM, at least about 5.5 mM, at least about 6.0 mM, at least about 6.5 mM, at least about 7.0 mM, at least about 7.5 mM, at least about 8.0 mM, at least about 8.5 mM, at least about 9.0 mM, at least about 9.5 mM, at least about 10 mM, at least about 15 mM, at least about 20 mM, at least about 25 mM, at least about 50 mM, at least about 75 mM, at least about 100 mM, at least about 125 mM, at least about 150 mM, at least about 175 mM, at least about 200 mM, at least about 225 mM, at least about 250 mM, at least about 500 mM, at least about 750 mM, at least about 1000 mM, at least about 1500 mM, at least about 2000 mM, or at least about 2500 mM of a nucleoside. For example, a composition can comprise at least about 1 mM of thymidine. In another example, a composition can comprise at least about 100 mM of inosine.

The compositions disclosed herein may be a liquid formulation. In some cases, the liquid formulation can comprise at least about 0.01 mM, at least about 0.05 mM, at least about 0.1 mM, at least about 0.5 mM, at least about 1 mM, at least about 1.5 mM, at least about 2.0 mM, at least about 2.5 mM, at least about 3.0 mM, at least about 3.5 mM, at least about 4.0 mM, at least about 4.5 mM, at least about 5.0 mM, at least about 5.5 mM, at least about 6.0 mM, at least about 6.5 mM, at least about 7.0 mM, at least about 7.5 mM, at least about 8.0 mM, at least about 8.5 mM, at least about 9.0 mM, at least about 9.5 mM, at least about 10 mM, at least about 15 mM, at least about 20 mM, at least about 25 mM, at least about 50 mM, at least about 75 mM, at least about 100 mM, at least about 125 mM, at least about 150 mM, at least about 175 mM, at least about 200 mM, at least about 225 mM, at least about 250 mM, at least about 500 mM, at least about 750 mM, at least about 1000 mM, at least about 1500 mM, at least about 2000 mM, or at least about 2500 mM of a thienopyridine. For example, a composition can comprise at least about 0.1 mM of clopidogrel. In another example, a composition can comprise at least about 100 mM of prasugrel.

The compositions disclosed herein may be a liquid formulation. In some cases, the liquid formulation can comprise at least about 0.1 µM, 0.5 µM, 1 µM, 5 µM, 0.01 mM, at least about 0.05 mM, at least about 0.1 mM, at least about 0.5 mM, at least about 1 mM, at least about 1.5 mM, at least about 2.0 mM, at least about 2.5 mM, at least about 3.0 mM, at least about 3.5 mM, at least about 4.0 mM, at least about 4.5 mM, at least about 5.0 mM, at least about 5.5 mM, at least about 6.0 mM, at least about 6.5 mM, at least about 7.0 mM, at least about 7.5 mM, at least about 8.0 mM, at least about 8.5 mM, at least about 9.0 mM, at least about 9.5 mM, at least about 10 mM, at least about 15 mM, at least about 20 mM, at least about 25 mM, at least about 50 mM, at least about 75 mM, at least about 100 mM, at least about 125 mM, at least about 150 mM, at least about 175 mM, at least about 200 mM, at least about 225 mM, at least about 250 mM, at least about 500 mM, at least about 750 mM, at least about 1000 mM, at least about 1500 mM, at least about 2000 mM, or at least about 2500 mM of an NSAID. For example, a composition can comprise at least about 0.5 mM of magnesium salicylate. In another example, a composition can comprise at least about 0.5 µM of acetylsalicylic acid.

The compositions disclosed herein can be a liquid formulation. In some cases, the liquid formulation can comprise at least about 0.01 mM, at least about 0.05 mM, at least about 0.1 mM, at least about 0.5 mM, at least about 1 mM, at least about 1.5 mM, at least about 2.0 mM, at least about 2.5 mM, at least about 3.0 mM, at least about 3.5 mM, at least about 4.0 mM, at least about 4.5 mM, at least about 5.0 mM, at least about 5.5 mM, at least about 6.0 mM, at least about 6.5 mM, at least about 7.0 mM, at least about 7.5 mM, at least about 8.0 mM, at least about 8.5 mM, at least about 9.0 mM, at least about 9.5 mM, at least about 10 mM, at least about 15 mM, at least about 20 mM, at least about 25 mM, at least about 50 mM, at least about 75 mM, at least about 100 mM, at least about 125 mM, at least about 150 mM, at least about 175 mM, at least about 200 mM, at least about 225 mM, at least about 250 mM, at least about 500 mM, at least about 750 mM, at least about 1000 mM, at least about 1500 mM, at least about 2000 mM, or at least about 2500 mM of a DHBA. For example, a composition can comprise about 50 mM of gentisic acid. In another example, a composition can comprise at least about 1000 mM of Pyrocatechuic acid. Table 1 illustrates exemplary compositions of the present disclosure.

In some embodiments, the composition of the present disclosure can be a stock concentration requiring dilution with a biological sample to attain a final working concentration of a nucleoside, a thienopyridine, an NSAID, and/or a DHBA in the composition in the biological sample. In some instances a composition of the present disclosure can be diluted by about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, about 1:100, about 1:1,000, about 1:10,000, or about 1:>10,000. For example, a composition comprising 500 mM of clopidogrel may be diluted by about 1:1000 with a biological sample.

In some embodiments, the stock concentration can be diluted by an excipient. Some examples of suitable excipients include lactose, dextrose, sucrose, sorbitol, mannitol, ethanol, starches, gum acacia, calcium phosphate, phosphate buffered saline, alginates, tragacanth, gelatin, calcium silicate, microcrystalline cellulose, PEG, polyvinylpyrrolidone, cellulose, water, sterile saline, syrup, and methyl cellulose.

TABLE 1

Exemplary compositions of the present disclosure

1. Cytidine (10 mM), Ticlopidine (550 µM), Acetylsalicylic acid (20 µM)
2. Uridine (16 mM), Prasugrel (350 µM), 2-gentisic acid (25 µM)
3. Thymidine (20 mM), Misoprostol (10 mM), β-Resorcylic acid (12 µM)
4. Inosine (4 mM), Ticlopidine (200 µM), and Protocatechuic acid (50 µM)
5. Clopidogrel (920 µM), Flurbiprofen (15 mM), γ-resorcylic acid (40 µM)
6. Thymidine (9 mM), Magnesium salicylate (1 mM), Pyrocatechuic acid (100 µM)
7. Cytidine (10 mM), Prasugrel (1000 µM), Sodium salicylate (8 µM), γ-resorcylic acid (90 µM)
8. Deoxy guanosine (15 mM), Misoprostol (12 mM), 2-gentisic acid (95 µM)
9. Cytidine (15 mM), Clopidogrel (250 µM), β-Resorcylic acid (45 µM)
10. Adenosine (4 mM), Prasugrel (550 µM), 2-gentisic acid (50 µM)
11. Cytidine (10 mM), Ticlopidine (550 µM), Acetylsalicylic acid (20 µM), 2-gentisic acid (45 µM)
12. Uridine (16 mM), Prasugrel (350 µM), Naproxen (10 mM), 2-gentisic acid (25 µM)
13. Thymidine (20 mM), Clopidogrel (250 µM), Misoprostol (10 mM), β-Resorcylic acid (12 µM)
14. Inosine (4 mM), Ticlopidine (200 µM), Acetylsalicylic acid (0.5 µM), and Protocatechuic acid (50 µM)
15. Adenosine (12 mM), Clopidogrel (920 µM), Flurbiprofen (15 mM), γ-resorcylic acid (40 µM)
16. Thymidine (9 mM), Ticlopidine (450 µM), Magnesium salicylate (1 mM), Pyrocatechuic acid (100 µM)
17. Cytidine (10 mM), Prasugrel (1000 µM), Sodium salicylate (8 µM), γ-resorcylic acid (90 µM)
18. Deoxyguanosine (15 mM), Ticlopidine (125 µM), Misoprostol (12 mM), 2-gentisic acid (95 µM)
19. Cytidine (15 mM), Clopidogrel (250 µM), Acetylsalicylic acid (15 µM), β-Resorcylic acid (45 µM)
20. Adenosine (4 mM), Prasugrel (550 µM), Ketoprofen (15 mM), 2-gentisic acid (50 µM)
21. Thymidine (6 mM), Ticlopidine (500 µM), Flurbiprofen (14 mM), β-Resorcylic acid (90 µM)
22. Adenosine (4 mM), Ticlopidine (200 µM), Acetylsalicylic acid (0.5 µM), and Protocatechuic acid (50 µM)
23. Uridine (9 mM), Clopidogrel (250 µM), Sodium salicylate (1 mM), α-Resorcylic acid (20 µM)
24. Inosine (4 mM), Ticlopidine (100 µM), Acetylsalicylic acid (0.5 µM), and Protocatechuic acid (100 µM)

TABLE 1-continued

Exemplary compositions of the present disclosure

25. Thymidine (20 mM), Clopidogrel (200 μM), Ketoprofen (50 μM), γ-resorcylic acid (150 μM)
26. Adenosine (4 mM), Clopidogrel (100 μM), Misoprostol (16 mM), 2-gentisic acid (150 μM)
27. Adenosine (12 mM), Ticlopidine (175 μM), Ketoprofen (10 mM), α-Resorcylic acid (125 μM)
28. Cytidine (15 mM), Ticlopidine (150 μM), Flurbiprofen (8 mM), Pyrocatechuic acid (110 μM)
29. 5-methyl uridine (6 mM), Clopidogrel (125 μM), Indomethacin (5 mM), Pyrocatechuic acid (35 μM)
30. Uridine (8 mM), Prasugrel (150 μM), Flurbiprofen (50 mM), 2-gentisic acid (60 μM)

The methods and compositions disclosed herein inhibit trogocytosis, e.g., by using one or more of the additives described herein. The active process of trogocytosis, where upon a cell membrane following active interaction with immune killing cells, takes on a fused phenotype, reflecting the target and the killer cell. In some cases, methods of inhibiting trogocytosis in a sample can comprise contacting the sample with a one or more of anticoagulant, antiplatelet agent, antibiotics or antimycotics, serine proteases, Kolliphor, chelating agent, thrombin inhibitors, antifreezes, nucleosides and/or a derivative thereof, thienopyridines and/or a derivative thereof, NSAID, DHBA, antioxidants, cell membrane stabilizers, energy sources, buffers, and antiplatelet drugs. In some cases, the methods of inhibiting trogocytosis in a sample can comprise contacting the sample with one or more of nucleosides and/or a derivative thereof, thienopyridines and/or a derivative thereof, NSAID, DHBA. In some cases, the methods of inhibiting trogocytosis in a sample can comprise contacting the sample with a chelating agent, e.g., EDTA.

The methods and composition can distinguish typical cells and atypical cells. Atypical cells can be cells that carry one or more white blood cells due to trogocytosis. For example, the attack of an epithelial marker-containing cell by a CD45 positive killer cell can result in a CD45 positive cell that has some of the target cells epithelial markers remaining on the surface of the cell. In some cases, a CTC can carry a white blood cell marker, e.g., CD45, resulted from trogocytosis. In such cases, depletion of white cells based on white cell markers may also deplete atypical cells carrying such white cell markers. The methods and compositions herein can inhibit trogocytosis, thus reducing the number of atypical cells, e.g., CTCs carrying white blood cell markers.

F. Sample Volumes

The volume of sample that can be applied to a device and/or processed by a device can be at least 0.001, 0.005, 0.01, 0.02, 0.03, 0.04, 0.05, 0.06, 0.7, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 125, 150, 175, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or 3000 mL. The volume of sample that can be applied to a device and/or processed by a device can be less than 0.01 mL. In some cases, the sample volume applied to the systems and devices herein can be scalable.

G. Sample Temperature

The sample applied to the systems and devices herein can be at a temperature. In some cases, the sample can be at the temperature before entering the systems and devices. In some cases, the sample can be at the temperature after entering the systems and devices. For example, the sample can be heated or cooled to a certain temperature. In some cases, the sample temperature can be at least −20, −10, 0, 4, 10, 15, 20, 22, 23, 24, 25, 26, 30, 35, 37, 40, 45, 50, 55, 60, 65, 70, 75, 80, 85, 90, 95, or 100° C.

H. Concentration of Particles in a Sample

A concentration of particles in a sample can be at least 1, 5, 10, 50, 100, 500, 1000, $10^4$, $10^5$, $10^6$, $10^7$, $10^8$, $10^9$, $10^{10}$, or $10^{11}$ per mL of sample. In some cases, a sample may comprise no particle.

IV. Particles

Particles herein can include biological particles (e.g., cells, viruses, biomolecules) and non-biological particles, e.g., beads, or chemicals. For example, particles can include cells, components of cells (e.g., soluble components of cells), proteins, protein complexes, nucleic acids (including synthetic nucleic acids (PNA)) of all physical lengths.

A. Cells

A particle can be a cell. The particles can be prokaryotic cells (e.g. bacterial cells), or eukaryotic cells (e.g., animal cells, fungi cells, or plant cells). For example, the particles can be trichocytes, keratinocytes, gonadotropes, cardiomyocytes, CAR-T cells, corticotropes, thyrotropes, somatotropes, lactotrophs, chromaffin cells, parafollicular cells, glomus cells melanocytes, nevus cells, merkel cells, odontoblasts, cementoblasts corneal keratocytes, retina muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, ECL cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic α cells, pancreatic β cells, pancreatic δ cells, pancreatic F cells (e.g., PP cells), pancreatic ε cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, dendritic cells. In some cases, the cells can be a population of cells with less than 0.001% positive of normal leukocytes, e.g., antigen specific cells, genetically modified cells associated with cell therapy, circulating tumor cells, dendritic and antigen processing cells, mast cells, stem cells, cardiomyocytes, or adipocytes. In some cases, the systems and devices can be used for recovery of infectious agents (e.g., for identification, quantification and analysis).

A particle can be a stem cell. In some cases, the stem cells can be adult stem cells (somatic stem cells). In some cases, the adult stem cell can be hematopoietic stem cells (HSCs) hematopoietic progenitor cell (HPC), a mesenchymal stem cell, a neural stem cell, an epithelial stem cell, or a skin stem cell. In some cases, the stem cells can be embryonic stem (ES) cells, or induced stem cells (iSC), e.g., induced pluripotent stem cells (iPSCs).

In some cases, the particles can be dividing cells. In some cases, the particles can be cells at different stages in the cell cycle, G0 (Gap 0/Resting), G1 (Gap 1), S (Synthesis), M (Mitosis), or G2 (Gap 2). In some cases, the particles can be dead cells, and/or debris. In some cases, the particles can be plants, bacteria, viruses, prions or other microbes. In some cases, the particles can be cancer cells from tumors. In some cases, the particles can be infiltrating or stromal host cells from a tumor. For example, tumor-infiltrating lymphocytes can be white blood cells that have left the bloodstream and migrated to a tumor. Stromal cells can be connective tissue. Stromal cells can provide an extracellular matrix on which tumors can grow. In some cases, a cell is any cell of the innate or adaptive immune system. In some cases, a particle can be a cancer cell, a circulating tumor cell (CTC), an epithelial cell, a circulating endothelial cell (CEC), a circulating stem cell (CSC), or cancer stem cells. In some cases, a particle can be a bone marrow cell, progenitor cell foam cell, fetal cell, mesenchymal cell, circulating epithelial cell, circulating endometrial cell, trophoblast, immune system cell (host or graft), connective tissue cell, bacterium, fungus, virus, protozoan, algae, or plant cell.

A particle can be a CTC. Examples of CTCs include traditional CTCs, cytokeratin negative CTCs, apoptotic CTCs, small CTCs, and CTC clusters. Traditional CTCs can be confirmed cancer cells with an intact, viable nucleus. In some cases, the traditional CTCs can express cytokeratins (e.g., cytokeratin 19), which demonstrate epithelial origin. In some cases, the traditional CTCs can have an absence of CD45, indicating the cell is not of hematopoietic origin. In some cases, CTCs can be separated from other cells in a sample by labeling other cells and leaving CTCs unlabeled. The labeled other cells can be depleted from a sample using characteristics of their labels, e.g., fluorescence and/or magnetic susceptibility by one or more particle separators disclosed herein, e.g., a magnetic separator, FACS, etc. For example, white blood cells can be labeled using labels comprising anti-CD45 antibodies. In some cases, the traditional CTCs can be often larger cells with irregularity shape or subcellular morphology. Cytokeratin negative CTCs can be cancer stem cells or cells undergoing epithelial-mesenchymal transition (EMT). Apoptotic CTCs can be traditional CTCs that are undergoing apoptosis. Small CTCs can be cytokeratin positive and CD45 negative, but with sizes and shapes similar to white blood cells. CTC clusters can comprise two or more individual CTCs bound together.

The particles can be cells from any source. For example, the cells can be from blood, saliva, urine, stool, amniotic fluid, a tumor, or a biopsy. In some cases, the particles can be circulating cells. For example, the particles can be circulating cells from a pregnant subject (e.g., a pregnant woman).

In some cases, a particle can be a rare cell. Rare cells can be intact cells, or small clusters of cells cannot be reliably detected, or reliably characterized in biological specimens without some significant selection, or enrichment approach being applied. In some cases, rare cells can be less than 0.000001% of the total number of cells in a body fluid sample (<1000 cell of interest per 1 billion other cells). Examples of rare cells include circulating tumor cells (CTC) s, circulating endothelial cells (CECs), circulating multiple myeloma cells, circulating melanoma cells, white blood cells in emboli, cancer stem cells, activated or infected cells, such as activated or infected blood cells, circulating fetal cells (e.g., in maternal blood), natural antigen-specific T cells, acute myeloid leukemia stem cells, dendritic cells, genetically modified cells for therapeutic use, and cells infected by a virus. If sample is a water sample, a rare cell can be a pathogenic bacterium or cell infected with a virus.

In some cases, the methods, systems, devices and/or kits can be used to remove or isolated clumps of rare cells, e.g. rare cell clusters. The clumps of rare cells can include micrometastases (i.e., micromets). Micrometastases can be clumps of tumor cells. A micrometastase (i.e., a micromet) can comprise at least 1, 5, 10, 20, 30, 40, 50, 60, 70, 80, 90, 100, 200, 300, 400, 500, 600, 700, 800, 900, or 1000 cells. In some cases, the number of cells in a micrometastase (i.e., a micromet) can be about 1, 5, 10, 20, 30, 40, 50, 60, 70, 80, 90, 100, 200, 300, 400, 500, 600, 700, 800, 900, 1000, or any number in between. The size of a micrometastase can be less than 0.05, 0.1, 0.2, 0.3, 0.4, 0.5, 0.6, 0.7, 0.8, 0.9, or 1 mm. In some cases, the size of a micrometastase can be about 0.05, 0.1, 0.2, 0.3, 0.4, 0.5, 0.6, 0.7, 0.8, 0.9, 1 mm, or any number of mm in between. In some cases, the methods, systems, devices, and/or kits herein can be used to remove or isolate micrometastases as described in Nature Medicine, 20, 897-903 (2014), doi:10.1038/nm.3600, and NETS Module 9: Breast Malignancies, http://www.cdc.gov/cancer/nper/training/nets/module9/nets9_3.pdf, which are incorporated herein by reference in their entireties. Isolation of the micromets for downstream analysis can be clinically relevant. In some cases, the micromets can be captured by a filter disclosed herein. The micromets can be flushed out from the filter (either by a reverse flush or a separate flush inlet and/or outlet) for further analysis. In some cases, the DLD array can comprise a "large cluster" portion that deflects clusters of cells into a bypass channel. In some case, the large cluster bumping region can rely upon obstacles of non-circular geometry (e.g., triangular, oval, or rounded triangular). The obstacles of non-circular geometry can include obstacles with any cross-sectional shapes disclosed herein. Using pillars with a non-rounded geometry allows for establishing the same critical size of an array with larger gap sizes. Such an array can be used for bumping larger clusters. The array can have large gap sizes and low shear, and is gentle on the cells clusters. The array can allow the cells be deflected as a unit with minimal damage to the cluster. In some cases, this larger cluster portion of the array can be continuous with the downstream array. In some cases, the large cluster portion of the array can be separate from the downstream array. In some cases, the clusters can be deflected into the same product collection stream as the smaller rare cells. In some cases, the clusters can collected separately.

In some cases, the systems and devices can be used to enrich cardiomyocytes in enriched CTC population to assess cardiac toxicity profiles of patients undergoing chemotherapy (e.g., taxanes). In some cases, the systems and devices can be used to enrich CAR-T cells following CAR-T cell therapy (e.g., to ensure efficacy and function). In some cases, the systems and devices can be used to enrich stem cells for future gene modification steps.

In some cases, T-lymphocytes (e.g., CD4 cells) can be stimulated using beads (e.g., magnetic beads) coated with anti-CD3 and anti-CD28. The T-lymphocytes can be stimulated in a manner that partially mimics stimulation by antigen-presenting cells. The T-lymphocytes can be restimulated by adding fresh beads coated with anti-CD$^3$/anti-CD28. In some cases, T-lymphocytes bound to beads comprising anti-CD3 and anti-CD28 are purified using a DLD array, magnetic separator, and/or concentrator described herein. In some cases, soluble anti-CD3 is used to stimulate T-lymphocytes, e.g., CD8 cells.

A particle (e.g., cell) purified using a method provided herein can be introduced into a subject, e.g., a patient. The particle (e.g., cell) from a subject that is purified using a method provided herein can be re-introduced into the same subject. The particle, e.g., cell, that is re-introduced into the subject can be modified after being taken from the subject and before being reintroduced into the subject.

B. Blood Components

A particle can be a blood component. Blood components can include platelets, red blood cells (erythrocytes), white blood cells (e.g., granulocytes, neutrophil, basophil, eosinophil, agranulocyte, lymphocyte, monocyte, or macrophage). In some cases, the particles can be red blood cells. In some cases, the particles can be white blood cells.

In some cases, the particles can be leukocytes (white blood cells). A leukocyte can be a neutrophil, eosinophil, basophil, lymphocyte, or monocyte. A leukocyte can be a granulocyte or agranulocyte. In some cases, a granulocyte can be a neutrophil, basophil, or eosinophil. In some cases, an agranulocyte can be a lymphocyte, monocyte, or macrophage. A lymphocyte can be, e.g., a B-cell or a T-cell. A T-cell can be, e.g., a CD4+T helper cell (e.g, $T_H1$, $T_H2$, $T_H3$, $T_H17$, $T_H9$, or $T_{FH}$), a CD8+ cytotoxic T-cell, a γδ T cell, a regulatory (suppressor) T-cell, a Natural Killer T (NKT) cell, an or antigen-specific T-cell, e.g., memory T cell, e.g., central memory T-cells, $T_{EM}$ cells, or $T_{EMRA}$ cell. A B-cell can be a plasma B-cell, a memory B-cell, a B-1 cell, a B-2 cell, a marginal-zone B-cell, a follicular B-cell, or a regulatory B-cell. In some cases, the particles can be regulatory macrophages. In some cases, the particles can be plasmacytoid dendritic cells (pDCs). In some cases, the particles can be myeloid-derived suppressor cells (MDSCs). In some cases, the particles can be megakarocytes.

C. Other Particles

In some cases, a particle can be a cellular fragment. In some cases, a cellular fragment is a membrane, cellular organelle, nucleosome, exosome, or nucleus. In some cases, a cellular fragment is a mitochondria, rough endoplasmic reticulum, ribosome, smooth endoplasmic reticulum, chloroplast, golgi apparatus, golgi body, glycoprotein, glycolipid, cisternae, liposome, peroxisome, glyoxysome, centriole, cytoskeleton, lysosome, cilia, flagellum, contractile vacuole, vesicle, nuclear envelope, vacuole, cell membrane, microtubule, nucleolus, plasma membrane, endosome, or chromatin.

A cellular fragment can be a biomolecule, e.g., a nucleic acid, a polypeptide (e.g., a protein), a carbohydrate, a lipid, or any biomolecule known in the art.

In some cases, a cellular fragment is a protein. In some cases, a protein is an antibody, or antibody fragment. In some cases, a cellular fragment is a T-cell receptor. In some cases, a protein is an immunoglobulin. In some cases, a particle is a polypeptide.

In some cases, a particle can be a nucleic acid. A nucleic acid can be, e.g., DNA or RNA. DNA can be genomic DNA, mitochondrial DNA, and/or cell-free (e.g., extracellular or circulating) DNA. RNA can be, e.g., messenger RNA (mRNA), ribosomal RNA (rRNA), transfer RNA (tRNA), signal recognition particle RNA, small nuclear RNA, small nucleoar RNA, SmY RNA, small cajal body-specific RNA, telomerase RNA, spliced leader RNA, antisense RNA, CRISPR RNA, long noncoding RNA (long ncRNA), microRNA (miRNA), short interfering RNA (siRNA), short hairpin RNA (shRNA), trans-acting siRNA, repeat associated siRNA, and/or cell-free (e.g., extracellular or circulating) RNA. In some cases, a particle can be cell-free DNA. For example, a particle can be circulating tumor DNA. In another example, a particle can be circulating fetal DNA. In another example, a particle can be circulating microRNA.

In some cases, a polynucleotide can be a DNA analog or an RNA analog. For example, a polynucleotide can be an artificial nucleic acid, including a peptide nucleic acid (PNA), a morpholino, a locked nucleic acid, a glycol nucleic acid (GNA), a threose nucleic acid (TNA), or a bridged nucleic acid (BNA). A polynucleotide can be single-stranded or double-stranded. In some cases, the nucleic acid is intranuclear, intracellular, or extracellular.

One or more particles described herein can be in a sample. In some cases, one or more different types of particles described herein can be in a sample. In some cases, a sample comprise cells, subcellular particles, and biomolecules. For example, a sample can comprise one or more of white blood cells, red blood cells, platelets, exosomes, nucleosomes, micro-vesicles, nucleic acids, and proteins.

The particles herein can also include reagents. In some cases, the particles can be beads or tags for labeling other particles, e.g., cells. In some cases, particles can include unbound beads or tags for labeling other particles, e.g., cells. For example, the particle can be magnetic or fluorescent beads. In some cases, the particles can include assay indexing particles (e.g., assay indexing particles that are not viable cellular entities), spectrally indexed beads (e.g., from Luminex, BD-CBA), light scatter indexed particles, latex, hydrogels (e.g., from Firefly Bio), infectious agents, such as prions, virus, bacteria, parasites. In some cases, the particles can include pathogens and particle assay substrates.

D. Labels

The particles herein can comprise labels. The labels can allow the detection, separation, and analysis of a particular group of particles. A label can be any reagent capable of binding to a particle being internalized or otherwise absorbed, and being detected, e.g., through shape, morphology, color, fluorescence, luminescence, phosphorescence, absorbance, magnetic properties, or radioactive emission. In some cases, the labels can be spectral labels, e.g., fluorescent labels. A label can comprise a primary antibody binding to a molecule on the surface or inside a particle. In some cases, such primary antibody can comprise or be conjugated with a detectable group, e.g., a fluorophore, a radioactive isotope, a magnetic susceptibly molecule or bead. In some cases, a label comprising a primary antibody can further comprise a secondary antibody that binds to the primary antibody. The second antibody can comprise or be conjugated with a detectable group, e.g., a fluorophore, a radioactive isotope, a magnetic susceptibly molecule or bead. Specificity of defined cell populations can be achieved by the use of specific affinity labels tagged with characterize but discrete magnetic and/or spectral reporter properties. Examples of such labels include antibodies and fragments thereof, including engineered reporter constructs with engineered phage based affinity constructs, synthesized aptamers (e.g., the longer DeNano aptameric particles), haptens (e.g., both naturally occurring (Biotin) or those specifically designed to achieve a capture or identification function (e.g., His Tag, Flag Tag, or specific proteins in the case of patient specific cell therapies). Magnetically susceptible labels can include ferromagnetic, paramagnetic, and super-paramagnetic particles used at either micro or nano scale. Spectral reporters can include any colorimetric, or fluorescent reporting construct that can be created by fluorescent protein complexes, synthesized or naturally occurring organic chemicals, combinations thereof which have incorporate fluorescence resonance energy transfer properties, or exhibit higher quantum yield within in the presence of nucleic acid environments such as Propidium Iodide, YoYo, YoPro (Molecular probes catalog) and reporter constructs that are tuned for spectral performance (Brilliant Violet dye polymers, intercalating DNA dyes with FRET reporter molecules, hairpin designed FRET partners etc.). The labels can also include spectrally indexed beads (e.g., from Luminex, BD-CBA), light scatter indexed particles, latex, and hydrogels (e.g., from Firefly Bio). The labels can also include intercalators (e.g., DNA intercalator), such as berberine, ethidium bromide, proflavine, daunomycin, doxorubicin, and thalidomide.

Examples of the labels include various ligands, radionuclides (e.g., $^{32}P$, $^{35}S$, $^{3}H$, $^{14}C$, $^{125}I$, $^{131}I$ and the like), fluorescent dyes, chemiluminescent agents (e.g., acridinium esters, stabilized dioxetanes and the like), microparticles (e.g., quantum dots, nanocrystals, phosphors and the like), enzymes (e.g., enzymes capable of carrying out a detectable chemical reaction, such as horseradish peroxidase, beta-galactosidase, luciferase, and alkaline phosphatase, beta-glucuronidase, beta-D-glucosidase, urease, glucose oxidase plus peroxide and alkaline phosphatase), colorimetric labels (e.g., dyes, colloidal gold and the like), magnetically susceptible labels (e.g., Dynabeads™), Photochromic compounds (e.g., diarylethene), photoswitchable proteins (e.g., PADRON-C, rs-FastLIME-s and bs-DRONPA-s), biotin, dioxigenin or other haptens and proteins for which antisera or monoclonal antibodies are available, antibodies, antibody fragments, stains (e.g., ethidium bromide), nucleic acid adapters, radioactive molecules, oligonucleotides, probes (e.g., fluorescently-labeled probes), phages, sodium nitrite, and functionalized beads. In some cases, a functionalized bead can be a magnetic bead. In some cases, a functional bead can comprise detectable molecules, e.g., a fluorophore and/or a radioactive isotope. A label can comprise two or more characterizes. In some cases, a label can be both a fluorescent label and a magnetically susceptible label.

A label can be bound by a capture moiety. In some cases, binding with the capture moiety can allow the separation and/or detection of a particle comprising the label. A capture moiety can be bound to a label (e.g., a particle comprising the label) by any means known in the art, including chemical reaction, physical adsorption, entanglement, or electrostatic interaction. Examples of capture moieties include, without limitation, proteins (such as antibodies, avidin, and cell-surface receptors), charged or uncharged polymers (such as polypeptides, nucleic acids, and synthetic polymers), hydrophobic or hydrophilic polymers, small molecules (such as biotin, receptor ligands, and chelating agents), and ions. Such capture moieties can be used to specifically bind cells (e.g., bacterial, pathogenic, fetal cells, fetal blood cells, cancer cells, and blood cells), organelles (e.g., nuclei), viruses, peptides, protein, polymers, nucleic acids, supramolecular complexes, other biological molecules (e.g., organic or inorganic molecules), small molecules, ions, or combinations or fragments thereof.

In some cases, labels can comprise genetically engineered labels for identifying certain cell types that might not employ affinity tags but create enrichment of magnetic particles, e.g., intentional endocytosis of magnetic particles.

A particle can be labeled with one label. A particle can be labeled with two or more different labels. In some cases, a particle can be labeled with two or more labels of the same types. For example, a particle can be labeled with two or more fluorescent labels. In some cases, a particle can be labeled with two or more labels of different types (e.g., labels with different types of detectable groups). For example, a particle can be labeled with a fluorescent label and a magnetically susceptible label.

a. Beads

A label can comprise a solid support, e.g., a bead. A bead can be used to enrich particle comprising the label (e.g., by precipitation). A bead can also comprise a detectable property. For example, a bead can be magnetically susceptible. The beads can have various shapes and sizes. In some cases, the sizes of the beads can be from about 10 nm to about 200 μm in diameter or width and height in the case of nonspherical particles. For example, the beads can have a size of about 0.05 to about 50 μm, about 0.1 to about 20 μm, about 1 to about 20 μm, or about 3 to about 10 μm in diameter. The beads can have a different shape, such as a sphere, cube, rod or pyramid. The beads can be made of styrene monomers polymerized into hard rigid latex spheres, polystyrene or latex materials, brominated polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, POLYOX, EUDRAGIT, sugar spheres, hydrofuran, PLGA (poly(lactic coglycolic acid)) or combinations thereof. In some cases, the labels can comprise beads described in U.S. Pat. No. 7,507,588 and Canadian Patent No. CA 1248873, which are incorporated herein by reference in their entireties.

b. Magnetically Susceptible Labels

A particle can comprise one or more magnetic susceptible labels. Any particle that responds to a magnetic field may be employed in the devices and methods of the invention. Desirable particles are those that have surface chemistry that can be chemically or physically modified, e.g., by chemical reaction, physical adsorption, entanglement, or electrostatic interaction. In some cases, methods and compositions for separating particles using magnetically susceptible labels can include those described in U.S. Pat. No. 8,568,881, which is incorporated herein by reference in its entirety.

The magnetic susceptible labels can be magnetic beads, e.g., magnetically susceptible beads capable of being attracted to a magnet or magnetized subject. Materials for the magnetic beads include, but are not limited to, ferromagnetic, ferrimagnetic, or paramagnetic materials. Ferromagnetic materials can be strongly susceptible to magnetic fields and are capable of retaining magnetic properties when the field can be removed. Ferromagnetic materials include, but are not limited to, iron, cobalt, nickel, alloys thereof, and combinations thereof. Other ferromagnetic rare earth metals or alloys thereof can also be used to make the magnetic beads. In some cases, a magnetic bead can have a magnetite (e.g., $Fe_3O_4$) core and a coating comprising silicon dioxide ($SiO_2$). In some cases, a magnetically susceptible label can comprise ferrous oxide, $Fe_3O_4$, one or more coated particles suitable for particle separations, one or more MyOne Particles, or one or more MACS microbeads (e.g., 25 nm MACS microbeads). In some cases, the magnetically susceptible label can comprise ferrofluid. For example, a magnetically susceptible label can comprise a magnetic bead containing ferrofluid. In some cases, a magnetically susceptible label may not comprise any magnetic bead, but still comprise the material for making magnetic beads disclosed herein. In some cases, a magnetic bead can be coated with a binding agent, e.g., protein such as antibodies or antigens, or nucleic acids such as oligonucleotides or aptamers. In some cases, a magnetic bead can be a magnetic iron-dextran microsphere. In some cases, magnetic beads can be from a commercial source, e.g., Thermo Fischer Scientific (e.g., T1), eBioscience or Chemicell.

A particle can be treated by a reagent that alters the magnetic property of the particle. Example of such reagent include agents that oxidize or reduce transition metals, magnetic beads capable of binding to an particle, or reagents that are capable of chelating or otherwise binding iron, or other magnetic materials or particles. In some cases, the reagent for altering magnetic properties can be sodium nitrite. The reagent can act to alter the magnetic properties of an particle to enable or increase its attraction to a magnetic field, to enable or increase its repulsion to a magnetic field, or to eliminate a magnetic property such that the particle is unaffected by a magnetic field.

A magnetic bead can be in any size and/or shape. In some cases, a magnetic bead has a diameter of less than 500 nm, 400 nm, 300 nm, 200 nm, 100 nm, 90 nm, 80 nm, 70 nm, 60 nm, 50 nm, 40 nm, 30 nm, 20 nm, 10 nm, or 5 nm. In some cases, a magnetic bead can have a diameter of about 300 nm. In some cases, the magnetic beads can have a diameter that is between 10-1000 nm, 20-800 nm, 30-600 nm, 40-400 nm, or 50-200 nm. In some cases, a magnetic bead can have a diameter of more than 10 nm, 50 nm, 100 nm, 200 nm, 500 nm, 1000 nm, or 5000 nm. In some cases, the magnetic beads can be dry or in liquid form. Mixing of a fluid sample with a second liquid medium containing magnetic particles can occur by any means known in the art.

Some particles can comprise intrinsic magnetically susceptible labels. In some cases, the particles can be red blood cells, which can be responsive to a magnetic field. In some cases, a magnetic separator herein can be used to separate red blood cells from other non-magnetic susceptible particles in a sample.

The sample can be treated with a reagent that includes magnetically susceptible labels prior to application of a magnetic field. As described herein, the magnetically susceptible labels can be coated with appropriate capture moieties such as antibodies to which a particle can bind. Application of a magnetic field to the treated sample can selectively attract a particle bound to magnetic particles.

A sample can also be treated by a reagent that alters an intrinsic magnetic property of one or more particles in the sample. The altered particle can be rendered more or less magnetically susceptible or can be rendered magnetically unresponsive by the reagent as compared to the unaltered particle. In one example, a sample (e.g., a maternal blood sample that has, for example, been depleted of maternal red blood cells) containing fetal red blood cells (fRBCs) can be treated with sodium nitrite, thereby causing oxidation of fetal hemoglobin contained within the fRBCs. This oxidation can alter the magnetic responsiveness of the fetal hemoglobin relative to other components of the sample, e.g., maternal white blood cells, thereby allowing separation of the fRBCs. In addition, differential oxidation of fetal and maternal cells can be used to separate fetal versus maternal nucleated RBCs. Any cell containing magnetically responsive components such as iron found in hemoglobin (e.g., adult or fetal), myoglobin, or cytochromes (e.g., cytochrome C) may be modified to alter intrinsic magnetic responsiveness of a particle such as a cell, or a component thereof (e.g., an organelle). Furthermore, particles can be contacted with reagents that induce, prevent, increase, or decrease expression of proteins or other molecules that are magnetically responsive.

A magnetically susceptible label can be linked to a particle. In some cases, a magnetically susceptible label can be linked with one or more molecules binding to a marker of a particle. Such molecules can be a ligand of a cell surface receptor, an antibody, an antigen, or any molecule binding to a marker on a particle. For example, a magnetically susceptible label can be an immunomagnetically susceptible label, e.g., an immunomagnetic bead. An immunomagnetically susceptible label can comprise a magnetically susceptible label linked with an antibody or antigen binding to marker of a particle. In some cases, a magnetically susceptible label can comprise a molecule bind to a particle marker with a generic structure. For example, the magnetically susceptible label can comprise a molecule binding to a heavy chain or a light chain of an antibody. Such molecule can bind to antibody-producing cells, e.g., antibody-producing cells in myelomas. In some cases, the molecule can be Protein A or Protein G.

One particle can be labeled with multiple magnetically susceptible labels. The multiple magnetically susceptible labels have different sizes, shapes, and/or magnetic susceptibilities. For example the multiple magnetically susceptible labels can comprise magnetic beads of different sizes, shapes, and/or magnetic susceptibilities. In some cases, the multiple magnetically susceptible labels can bind to the particle through the same antibody (e.g., an antibody that binds to a marker (e.g., a surface molecule) on the particle). In some case, the multiple magnetically susceptible labels can bind to the particle through different antibodies (e.g., antibodies that bind to different markers (e.g., different surface molecules) on the particle.

c. Fluorescent Labels

A particle can comprise one or more fluorescent labels. The fluorescent labels can allow the detection and/or separation by a fluorescence based means, e.g., FACS. A fluorescent label can comprise one or more fluorophores. Examples of fluorophores include fluorescein, rhodamine, phycobiliproteins, cyanine, coumarin, pyrene, green fluorescent protein, BODIPY®, and their derivatives. Both naturally occurring and synthetic derivatives of fluorophores can be used. Examples of fluorescein derivatives include fluorescein isothiocyanate (FITC), Oregon Green, Tokyo Green, seminapthofluorescein (SNAFL), and carboxynaphthofluorescein. Examples of rhodamine derivatives include rhodamine B, rhodamine 6G, rhodamine 123, tetramethyl rhodamine derivatives TRITC and TAMRA, sulforhodamine 101 (and its sulfonyl chloride form Texas Red), and Rhodamine Red. Phycobiliproteins include phycoerythrin, phycocyanin, allophycocyanin, phycoerythrocyanin, and peridinin chlorophyll protein (PerCP). Types of phycoerythrins include R-phycoerythrin, B-phycoerythrin, and Y-phycoerythrin. Examples of cyanine dyes and their derivatives include Cy2 (cyanine), Cy3 (indocarbocyanine), Cy3.5, Cy5 (indodicarbocyanine), Cy5.5, Cy7, BCy7, and DBCy7. Examples of green fluorescent protein derivatives include enhanced green fluorescent protein (EGFP), blue fluorescent protein (BFP), enhanced blue fluorescent protein (EBFP), cyan fluorescent protein (CFP), yellow fluorescent protein (YFP), and enhanced yellow fluorescent protein (EYFP). BODIPY® dyes (Invitrogen) are named either for the common fluorophore for which they can substitute or for their absorption/emission wavelengths. BODIPY® dyes include BODIPY FL, BODIPY R6G, BODIPY TMR, BODIPY TR, BODIPY 581/591, BODIPY 630/650, and BODIPY 650/665. Fluorophores can also include Alexa Fluor® dyes (Invitrogen) are also suitable for use in accordance with inventive methods and compounds. Alexa Fluor® dyes are named for the emission wavelengths and include Alexa Fluor 350, Alex Fluor 405, Alexa Fluor 430, Alexa Fluor 488, Alex Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and Alexa Fluor 750. In some cases, the fluorescent label can be a fluorescent protein, e.g., green fluorescent protein (GFP), yellow fluorescent protein (YFP), or enhanced derivatives thereof (e.g., enhanced GFP and enhanced YFP). In some cases, the fluorescent label can be a molecule inside the particle. For example, when the particle is a cell, the fluorescent label can be a fluorescent protein expressed in a cell. In some cases, the fluorescent label can be a Förster resonance energy transfer (FRET) based reporter using a combination of protein and organic moieties. In some cases, the fluorescent label can be a silicon-based nanocrystal, such as a QDOT or eVolve particle.

d. Labels for Changing Particle Sizes

A particle comprising a label can have a size different from the same particle without the label. In some cases, such labels can be beads, e.g., immunoaffinity beads. In some cases, binding to a bead can increase the size of a particle. In some cases, such labels can be used to separate particles of similar size. For example, a first particle and a second particle may not be separated by a DLD array because both their sizes are below the critical size of the DLD array. In this case, the first particle can be labeled so the labeled first particle can have a size above the critical size of the DLD array, which can then separate the labeled first particle and the second particle. In the case of epithelial cells, e.g., CTCs, such label can increase their size and thus result in an even more efficient enrichment. In some cases, the size of smaller cells may be increased to the extent that they become the largest objects in solution or occupy a unique size range in comparison to the other components of the cellular sample, or so that they co-purify with other cells. The size of a labeled particle can be at least 10%, 100%, or 1,000% greater than the size of such a particle in the absence of label. The label can be beads made of polystyrene, magnetic material, or any other material that may be adhered to cells. In some cases, such beads can be neutrally buoyant so as not to disrupt the flow of labeled cells through the device of the invention.

Labels for changing the size of a particle can be a collapsible immuno-bubble. In some case, the collapsible immuno-bubble can be conjugated to a particle for changing the size of the particle. For example, conjugation of the immuno-bubble to the particle can increase the size (e.g., hydrodynamic size) of the particle. Enlarging the particle can allow a more specific fractionation of the enlarged particle by a DLD array. In some cases, the immuno-bubble can have pressure inside of the bubble. The pressure can be released for further processing. Releasing of the pressure can allow preventing or reducing the encumbrances on light scatter or other application inhibitory steps (e.g., relating to cell culture). In some cases, the collapsible labels can include those described in U.S. Pat. No. 8,513,032, which is incorporated herein by reference in its entirety. The strategy of changing the size of a particle can augment the ability for the systems and device to get more parameters in sorting scenarios which are applicable under DLD separation alone, DLD separation with immunomagnetic separation, or DLD separation with immunomagnetic separation and fluorescent separation. Such strategy can allow for achieving multiparameter complex sorts based on multiple phenotypic and physical criteria (e.g., criteria independent of FACS-like fluorescence approaches).

e. Multiple Labels on One Particle

A particle can comprise multiple labels. The multiple labels can allow the particle be detected and/or separated by multiple devices. In some cases, a particle can comprise multiple labels, each of which binds to a different marker on the particle. For example, a cell can have a first label binding to a first surface protein of the cell and a second label binding to a second surface protein of the cell. In some cases, a particle can comprise multiple labels, each of which binds to the same marker on the particle, but has different characteristics. In some cases, a particle can comprise multiple labels binding to different markers on the particle and having different characteristics. The different characteristics of the labels can be different types of detectable groups. The labels can comprise two or more of a fluorescent label, a magnetically susceptible label, a radioactive label and any labels disclosed herein. In some cases, the labels can comprise multiple magnetically susceptible labels of different sizes. For example, a particle can be labeled with two magnetic beads of different beads. In some cases, the two magnetic beads can bind the particle by conjugating with an antibody binding to marker of the particle. In some cases, the two magnetic beads can bind the particle by conjugating different antibodies binding to different markers of the particle.

The different characteristics of the labels can be different intensities of the detectable signals given by the labels. For example, the labels can be fluorescent labels with different fluorescent intensities. In another example, the labels can be magnetically susceptible labels with different magnetic susceptibilities. For example, one or more magnetically susceptible labels of different magnetic susceptibilities can be used in conjunction with one or more other labels. In some cases, a particle can comprise two or more of a fluorescent label, a magnetically susceptible label, a radioactive label and any labels disclosed herein, where all the labels bind to the same marker on the particle. In some cases, a particle can comprise one or more labels binding to one or more markers on the surface of the particle and one or more labels binding to one or more markers in the interior of the particle.

A particle with multiple labels can comprise at least 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000 or 50000 labels. A particle with multiple labels can comprise at least 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000 or 50000 different types of labels (e.g., labels with different types of detectable groups). In some cases, two or more of the labels bind to the same marker on the particle. In some cases, two or more of the labels bind to different markers on the particle.

In some cases, a particle can be labeled with a label that is magnetically susceptible and has one or more other detectable properties (e.g., fluorescence). In some cases, such label can comprise an antibody with a magnetic tag (e.g., a magnetic bead) and a fluorescent tag (e.g., a conjugated fluorophore). The label can be used to clean up and/or further isolate magnetic separations with fluorescent signal based approaches (e.g., FACS). This approach can allow for faster flow rates and confirmed clean up prior to any mechanical sorting mechanism. Particle sorting decisions after the magnetic separation can be made to create an appropriate extra mechanism (e.g., using fluorescence criteria such as negative selection, positive selection, or a combination thereof) to achieve better separation. In some cases, multiple antibodies with mono-specific but dual reporter/isolation labels can be used to address potential sources of downstream sort contaminants when trying to enrich particles (e.g., rare particles such as rare cells).

A particle can comprise multiple magnetically susceptible labels of different sizes. Such labels can allow better magnetic separation of the particle in a sample. In some cases, the multiple magnetically susceptible labels can bind to the same marker on the particle. In some cases, the multiple magnetically susceptible labels can bind to different markers on the particle. For example, a particle can comprise a biotin-SA particle and a direct magnetic particle, wherein the biotin-SA particle is bigger than the direct magnetic particle.

In some cases, a label can have a reporter tag and an isolation tag, along with a molecule to bind to a particle. For example, a label can be an antibody recognizing a marker on a particle (e.g., a cell) and have a magnetic tag for separation and a fluorescent tag to be detected by a particle sensor.

f. Markers

A particle can comprise one or more labels binding to one or more markers on the particle. In some cases, a type of particle can comprise labels selectively binding to particle-specific markers. For example, the labels can selectively bind to markers of a type of cells. In some cases, the label can bind to a marker of the surface of the particle (e.g. cell surface marker). In some cases, the label can bind to a marker in the interior of the particle (e.g., intracellular marker).

A label can bind to one or more makers of a type of cells. Such labels can be used in separation and/or detection of the type of cells. In some cases, the label can bind to a marker of leukocytes. In some cases, the cell surface marker on a leukocyte can be a cluster of differentiation (CD) protein. Examples of CD proteins include CD1a, 1b, 1c, 1d, 2, 3, 4, 5, 8, 10, 11a, 11b, 11c, 13, 14, 15, 16/32, 19, 20, 21/35 (CR2/CR1), 22, 23, 25, 26, 31, 33, 38, 39, 40, 44, 45, 45RB, 45RA, 45R/B220, 49b (pan-NK cells), 49d, 52, 53, 54, 57, 62L, 63, 64, 66b, 68, 69, 70, 73, 79a (Igα), 79b (Igβ), 80, 83, 85g/ILT7, 86, 88, 93, 94, 103, 105 (Endoglin), 107a, 107 (Mac3), 114, 115, 117, 119, 122, 123, 124, 127, 129, 134, 137(4-1BB), 138 (Syndecan-1), 158 (Kir), 161, 163, 183, 184 (CXCR4), 191, 193 (CCR3), 194 (CCR4), 195, 195 (CCR5), 197, 197 (CCR7), w198 (CCR8), 203c, 205/Dec-205, 207 (Langerin), 209DC-SIGN), 223, 244 (2B4), 252 (OX4OL), 267, 268 (BAFF-R), 273 (B7-DC, PD-L2), 278 (ICOS), 279/PD-1, 282 (TLR2), 289 (TLR9), 284 (TLR4), 294, 303, 304, 305, 314 (NKG2D), 319 (CRACC), 328 (Siglec-7), and 335 (NKp46). In some cases, the cell surface marker on a leukocyte can be a surface marker. Examples of leukocyte surface markers include surface IgM, IgD, DC Marker (33D1), F4/80, CMKLR-1, HLA-DR, Siglex H, MHC Class II, LAP (TGF-b), GITR, GARP, FR4, CTLA-4, TRANCE, TNF-β, TNF-α, Tim-3, LT-βR, IL-18R, CCR1, TGF-β, IL-1R, CCR6, CCR4, $CRT_H2$, IFN-γR, Tim-1, Vα24-Jα18 TCR (iNKT), Ly108, Ly49, CD56 (NCAM), TCR-α/β, TCR-γ/δ, CXCR1, CXCR2, GR-1, JAML, TLR2, CCR2, Ly-6C, Ly-6G, F4/80, VEGFR1, C3AR, FcεRIα, Galectin-9, MRP-14, Siglec-8, Siglec-10. TLR4, IgE, GITRL, HLA-DR, ILT-3, Mac-2 (Galectin-3). CMKLR-1, and DC Marker (33D1). In some cases, the cell surface marker on a leukocyte can be a intracellular marker. Examples of leukocyte intracellular markers include Pax-5, Helios, FoxP3, GM-CSF, IL-2, IFN-γ, T-bet, IL-21, IL-17A, IL-17F, IL-22, RORyt, RORα, STAT3, IL-10, IL-13, IL-5, IL-4, IL-6, GATA3, c-Maf, Granzyme B, Perforin, and Granulysin.

A label can bind to a marker of tumor cells, e.g., circulating tumor cells. Such labels can be used for the detection and/or separation of tumor cells from a sample. For example, such labels can be used for the detection and/or separation of circulating tumor cells in blood. Examples of tumor cells markers include EGFR, HER2, ERCC1, CXCR4, EpCAM, E-Cadherin, Mucin-1, cytokeratins (e.g., cytokeratin 8, cytokeratin 19), PDGF, ErbB2, L6, PSA, PSMA, RRM1, Androgen Receptor, Estrogen Receptor, Progesterone Receptor, IGF1, cMET, EML4, or Leukocyte Associated Receptor (LAR), CD105, CD106, CD144, CD 146 TEM1, TEM5, and TEM8. In some cases, tumor cell markers can include any proteins listed in FIG. 3 of U.S. Patent Application No. 20140234986, which is incorporated herein by reference in its entirety.

In some cases, the particles can be labeled downstream of any sample accessioning steps. For example, the particles in a sample can be labeled before the sample is passed into a system or device herein. In some cases, the particles in a sample can be labeled inside a system or device herein. For example, the particles in a sample can be passed into a system or device herein with a labeling reagent, which labels the particles when they are flowing in the system or device. In some cases, the labeling step can comprise cap piercing for addition or removal of fluids in a volumetric and temporally controlled manner. In some cases, the labeling can be performed by flow-through labeling, e.g., flowing the sample through a device (e.g., a DLD device) in the system. The flow-through labeling can allow lower the coefficient of variation (% CV). For example, the particles can be labeled with antibodies and magnetic beads, (e.g., antibody-linked magnetic beads). In some cases, the labeling can be performed in a single step, e.g., incubating the particles, antibodies, and magnetic beads in the same reaction. In some cases, the labeling can be performed in two or more steps. For example, the antibodies (e.g., mAbs) can be incubated with the magnetic beads first. Then the resulting antibody-linked magnetic beads can be incubated with particles. In some cases, the labeling reagent can be added to a sample in a timed manner, so that each particle in the sample can be exposed with substantially the same concentration of the labeling reagent in the device. For example, the labeling reagent can be added to the sample flow stream starting from or before the sample flow stream enters the device. The addition of the labeling reagent to the sample flow stream can last until the entire sample enters the device, or longer. The labeling step or steps can be upstream of particle separation (e.g., DLD separation or magnetic separation). In some cases, such labeling can create a homogeneously-labeled population of particles. For example, if it takes 40 minutes for the sample to enter the device, the labeling reagent can be added to the sample flow stream for 40 minutes, so that the degree of labeling can be substantially the same on all particles, regardless the particle enters the device first or last. In some cases, the flow-through labeling can be performed anywhere in the process, e.g., downstream or upstream of DLD separation. In some cases, the flow-through labeling can be performed in a DLD array. For example, the flow-through labeling can be performed in a "car wash" DLD device disclosed herein and as described in PCT Application No. WO 20140145152, which is incorporated herein by reference in its entirety.

The labeling can be performed with a labeling reagent. The labeling reagent can comprise specific reagents to allow for discrimination in applications downstream the separation steps. In some cases, the labeling reagent can comprise reporter tagged affinity reagents (including fluorescent, acoustic, radioactive or other discrete emitters etc., magnetic, colorimetric, and suspension array capture matrix), genetically modified and genetically non-modified molecule-based affinity tags (including antibodies, nucleic acids, His tags, FLAG tags (e.g., for labeling CAR-T cells)), nucleic acids, proteins, reagents with cell compartment-specific detection capability (including nucleic acid reporter molecules as labels for any derived signal, bDNA, hybridization-specific intercalating dyes, FISH, CISH Invader reporter constructs, reagents for homogenous DNA hybridization applications), and/or tagged particles or cell type specific encapsulation approaches that confer larger physical size attributes and behavior of labeled particle in DLD separation. The labeling reagent can also comprise liquids to enable efficient and clog free operation of the integrated system. In some cases, such reagents can comprise proteins including enzymes, detergents, salts, and/or pH and particle charge impacting components. The reagents can also comprise cell lysis buffers, and/or disinfection and system cleaning solutions for biosafety.

For labeling, a sample (e.g., body fluid) and the reagents can be mixed for labeling reaction. In some cases, the mixing can be performed in a container not included in the system or device herein. In some cases, the mixing can be performed in the system or device herein. In some cases, such mixing can facilitate complete labeling reaction.

The labeling step can be performed to make calibrated in-line dilutions of the input sample (e.g., body fluid) to achieve downstream DLD or analytical assay performance.

g. Particle Sizes

A particle can have a size at least 0.001, 0.01, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15, 5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 200, 300, 400, 500, 600, 700, 800, 900, 1000 μm, 2 mm, 5 mm, 10 mm, 50 mm, or 1 cm. In some cases, where a particle is polynucleotide, the polynucleotide comprises at least 1, 2, 5, 10, 20, 30, 40, 50, 60, 70, 80, 90, 100, 150, 200, 250, 300, 350, 400, 450, 500, 600, 700, 800, 900, 1000, 1500, 2000, 3000, 4000, 5000, 6000, 7000, 8000, 9000, 10,000, 20,000, 30,000, 40,000, 50,000, 60,000, 70,000, 80,000, 90,000, or 100,000 bases. In some cases, a polynucleotide is a whole chromosome. In some cases, a polynucleotide is a human chromosome 1, 2, 3, 4, 5, 6, 7, 8, 9, 10, 11, 12, 13, 14, 15, 16, 17, 18, 19, 20, 21, 22, X or Y.

h. Yield

Methods, devices, systems, and/or kits described herein can be used to give a yield of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of first particles, e.g., cells from a sample.

In some cases, methods, devices and systems described herein can be used to isolate leukocytes from blood. In some cases, at least 80%, 85%, 90%, 95%, 99%, or 100% of leukocytes can be recovered (or removed) from a whole blood sample without introducing bias among the leukocyte population. In some cases, at least 99.2% of leukocytes can be recovered (or removed). In some cases, from 98.6% to 99.8% of leukocytes can be recovered (or removed). In some cases, at least 90%, 95%, or 99% of the red blood cells in the blood can be removed. In some cases, at least 99.9% of the red blood cells can be removed. In some cases, at least 99.95% of the red blood cells can be removed. In some cases, at least 99.98% of the red blood cells can be removed.

i. Viability

The systems and devices herein can be configured to isolate living particles, e.g., cells or organisms. In some cases, when isolated by the systems and devices, the particles (e.g., cell or organisms) can remain alive. In some cases, methods, devices, systems, and/or kits described herein can be used to isolate particles (e.g., cells or organisms) that are about at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% viable. In some cases, about 100% of the isolated particle can be viable.

In some cases, a sample comprises leukocytes and erythrocytes. In some cases, the method, compositions, devices, systems, and/or kits described herein can be used to isolate leukocytes from a sample such that the leukocytes are greater than 90% pure (e.g., less than 10% erythrocytes), greater than 90% of the leukocytes in the sample are isolated (greater than 90% yield), and greater than 90% of the leukocytes in the sample are viable.

j. Purity

Methods, devices, systems, and/or kits described herein can be used isolate first particles, e.g., cells that are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% pure. In some cases, methods, devices, systems, and/or kits described herein can be used isolate first particles, e.g., cells that are at least 90% pure. In some cases, methods, devices, systems, and/or kits described herein can be used isolate first particles, e.g., cells that are at least 95% pure. In some cases, methods, devices, systems, and/or kits described herein can be used isolate first particles, e.g., cells that are at least 99% pure. In some cases, methods, devices, systems, and/or kits described herein can be used isolate first particles, e.g., cells that are at least 99.1, 99.5, 99.9, or 100% pure.

In some cases, a sample comprises leukocytes and erythrocytes. In some cases, the method, compositions, devices, systems, and/or kits described herein can be used to isolate leukocytes from a sample such that the leukocytes are greater than 90, 95, 99, or 100% pure. In some cases, the leukocytes can be at least 99.1, 99.5, 99.9, or 100% pure. In some cases, at least 90, 95, or 99 of the red blood cells in the blood can be removed. In some cases, at least 99.1, 99.5, or 99.9% of the red blood cells can be removed.

V. Kits

Provided herein are kits for separating particles in a sample. The kits can comprise any devices and systems disclosed herein. In some cases, the kits can comprise one or more reagents. For example, the kits can comprise one or more buffers (e.g., washing buffers), labeling reagents (e.g., cell surface labeling reagents and intracellular labeling reagents), fixation reagents, cell permeability reagents, or any combination thereof. The kits can further comprise instructions for using the devices, systems, buffers and reagents.

VI. Methods

Provided herein are methods for concentrating particles in a sample. The methods can comprise flowing a sample comprising particles through a microfluidic channel for concentrating particles disclosed herein. When flowing through the microfluidic channel, the particles can be deflected by one or more arrays of obstacles in a direction, so that the particles flow out of the microfluidic channel through a product outlet in a solution. The particles can be concentrated in the solution. In some cases, the particles can be larger than a critical size to be deflected by the one or more arrays of obstacles. In some cases, the methods further comprise evacuating the microfluidic channel, e.g., pushing a sample or solution out of the microfluidic channel. For example, the evacuating can be performed by flowing an air plug through the microfluidic channel.

In some cases, the methods further comprise flowing a buffer through the microfluidic channel, e.g., to fill one or more DLD arrays in the microfluidic channel with the buffer. In some cases, the full width of the DLD arrays can be filled with the buffer before a sample is flowed through the microfluidic channel. In some cases, the entire DLD arrays can be filled with the buffer before a sample is flowed through the microfluidic channel.

In some cases, when a sample flows through a microfluidic channel, there is no more than one flow stream flowing through the channel. In some cases, when the sample flows through the microfluidic channel, there are two or more flow streams (e.g., parallel flow streams) flowing through the channel. For example, the microfluidic channel can be a carwash device described herein.

When the particles flow out of the microfluidic channel (e.g., through a product outlet) in a solution, the particles in the solution can be concentrated by less than 1.5, 2, 2.5, 3, 4, 5, 6, 7, 8, 9, 10, 20, 30, 40, 50, 60, 70, 80, 90, or 100 fold compared to the concentration of the particles in the sample. In some cases, the particles in the solution can be concentrated by greater than or about, 1.5, 2, 2.5, 3, 4, 5, 6, 7, 8, 9, 10, 20, 30, 40, 50, 60, 70, 80, 90, 100, 200, 500, 1000, 2000, 3000, 4000, 5000, 6000, 7000, 8000, 9000, 10,000, or 15,000 fold compared to the concentration of the particles in the sample.

The ratio of the concentration of the particles in the solution flowing through the product outlet (e.g., the output concentration) to the concentration of the particles in the sample (e.g., the input concentration) can be referred to as a "concentration factor". Various parameters can affect the concentration factor. In some cases, the parameters include the relative throughput of the sample and the buffer, and percentage of the buffer running down a bypass channel. In some cases, the parameters include the ratio of volume flowing through the waste outlets to the volume flowing through the product outlets. For example, the ratio of the volume flowing through the waste outlets to the volume flowing through the product outlets can be at least, or about, 1:100, 1:90, 1:80, 1:70, 1:60, 1:50, 1:40, 1:30, 1:20, 1:10, 1:5, 1:2, 1:1, 2:1, 5:1, 10:1, 20:1, 30:1, 40:1, 50:1, 60:1, 70:1, 80:1, 90:1, or 100:1. In some cases, the parameters include the configuration of the DLD arrays (e.g., length, width, and tilt). For example, the longer and/or wider the DLD arrays are, the higher the concentration factor can be. In some cases, DLD arrays with lower tilt (e.g., larger gaps) can achieve higher concentration factor. In some cases, less resistive arrays (e.g., arrays comprising more flow through array than bypass channels) can achieve higher concentration factor.

Provided herein also include methods for separating particles. The methods can be performed using any devices, systems and kits disclosed herein. In some cases, provided herein is a method comprising passing a sample comprising particles through one or more of DLD arrays, magnetic separators, fluorescence-based separators, and other particle separators. The separated particles can be detected by a particle sensor. In some cases, the separated particles can be dispensed by a particle dispenser to a location, e.g., a slide or cell culture dish for further processing and/or analysis. In some cases, the separated particles can be analyzed using an analytical device. The combination of multiple particle separators, particle sensors, particle dispensers and/or analytical devices allow isolation, enriching, purification, analysis, and/or detection of particles from a sample in an integrated system, thus improving the efficiency and/or lowering the cost of the process.

Methods for separating particles in a sample can comprise passing the sample through one or more DLD arrays and another particle separator (e.g., a magnetic separator). The sample can be passed through the combination of DLD arrays and other particle separators in any order. In some cases, sample can be passed through one or more DLD arrays first. Then all or a subgroup of the particles in the sample passing through the DLD arrays can be passed to another particle separator (e.g., a magnetic separator) for further separation. In some cases, sample can be passed through one or more particle separators other than DLD arrays (e.g., a magnetic separator) first. Then all or a subgroup of the particles in the sample passing through the one or more particle separators (e.g., a magnetic separator) can be passed to one or more DLD arrays for further separation. In some cases, the samples from a DLD array or a magnetic separator can be passed to a flow cytometer (e.g., FACS or MACS) for further separation.

The methods can comprise labeling one or more particles a sample before passing the sample into a particle separator. The labeling can be performed using a reagent comprising any labels disclosed herein.

The method can comprise passing a sample through the devices and systems at a flow rate. In some cases, the flow rate can be constant. In some cases, the flow rate can be variable. In some cases, the flow rate can be adjustable, e.g. via a pressure source fluidically connected with the device and system. In some cases, the flow rate can be at least 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87. 88, 89, 90, 91, 92, 93, 94, 95, 96, 97, 98, 99, 100, 105, 110, 115, 120, 125, 130, 135, 140, 145, 150, 155, 160, 170, 175, 180, 185, 190, 200, 250, 300, 350, 400, 450, or 500 mL/min. In some cases, the flow rate can be at least 100, 110, 120, 130, 140, 150, 160, 170, 180, 190, 200, 210, 22, 230, 240, 250, 260, 270, 280, 290, 300, 400, 500, 600, 700, 800, 900, 1000, 2000, 4000, 6000, 8000, or 100000 µL/min, or any number in between. In some cases, the flow rate can be at least 240 µL/min. In some cases, separation and/or processing of particles by the methods, systems and devices herein can be high-throughput. In some cases, the high-throughput methods comprise flow rates of at least 1 mL/min, at least 5 mL/min, at least 10 mL/min or at least 20 mL/min. In some cases, devices described herein can process less than 1 ml, at least 10 mL, at least 100 mL, or at least 300 mL of sample.

The systems and devices herein can complete the isolation of particles in a sample within certain time. In some cases, particle isolation can be completed within 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes. In some cases, particle isolation can take more than 60 minutes. In some cases, completion of the particle isolation can include dispensing the isolated particles to a location, e.g., a slide or a cell culture dish. In some cases, a particle can be isolated and deposited to a location for further analysis within 30 minutes.

Methods for separating particles herein can comprise one or more of the following steps: providing a sample comprising first particles of at least a first critical size and second particles less than the first critical size; passing the sample through a first array of obstacles, wherein the first array of obstacles allows the first particles to a first direction and the second particles to a second direction different from the first direction, and wherein the first critical size is less than 3 µm, thereby separating the first particles and the second particles; passing third particles and fourth particles in a magnetic separator, wherein the magnetic separator is configured to separate particles with magnetically susceptible labels from particles without magnetically susceptible labels, wherein the magnetic separator is fluidically connected with the first array of obstacles, and wherein the third particles comprise magnetically susceptible labels, and the fourth particles do not comprise magnetically susceptible labels, thereby separating the third particles and the fourth particles, wherein the third particles and the fourth particles are subgroups of the first particles, wherein the third particles and the fourth particles are subgroups of the second particles, wherein the first particles and the second particles are subgroups of the third particles, or wherein the first particles and the second particles are subgroups of the fourth particles. The steps can be performed in any order. Each step can be performed one or more times.

Methods for separating particles herein can comprise one or more of the following steps: labeling one or more particles in a sample with labels, wherein each of the labeled particles is labelled with a first label and a second label, wherein the first label and the second label are different, and wherein the sample comprises first particles of at least a first critical size and second particles less than the first critical size; passing the sample through a first array of obstacles, wherein the first array of obstacles allows the first particles to a first direction and the second particles to a second direction different from the first direction, thereby separating the first particles and the second particles; and passing third particles and fourth particles in a magnetic separator, wherein the magnetic separator is configured to separate particles with magnetically susceptible labels from particles without magnetically susceptible labels, wherein the magnetic separator is fluidically connected with the first array of obstacles, and wherein the third particles comprise magnetically susceptible labels and the fourth particles do not comprise magnetically susceptible labels, thereby separating the third particles and the fourth particles, wherein the third particles and the fourth particles are subgroups of the first particles, wherein the third particles and the fourth particles are subgroups of the second particles, wherein the first particles and the second particles are subgroups of the third particles, or wherein the first particles and the second particles are subgroups of the fourth particles. The steps can be performed in any order. Each step can be performed one or more times.

Also provided herein are methods for dispensing particles using a particle dispenser disclosed herein. In some cases, the methods can be used to dispense particles separated from a sample by the devices and systems herein. In some cases, the methods can be used to dispense particles in a sample, and the dispensed particles can be further separated by the devices and systems herein. In some cases, the methods can be used to dispense a single particle. For example, the methods can be used to dispense a single cell on a slide or culture dish for further processing and/or analysis. The methods for dispensing particles can comprise one or more of the following steps: D Methods for separating particles herein can comprise one or more of the following steps: providing a sample comprising a particle of interest; passing the sample into a fluidic duct in a flow stream, wherein the fluidic duct comprises a sensing zone; detecting the passing of the sensing zone by the particle of interest using a sensor, wherein the sensor generates a signal when the particle of interest passes the sensing zone; moving a capture tube to a first position, wherein the capture tube is movable between the first position and a second position, wherein the capture tube is fluidically connected with the fluidic duct at the first position and not fluidically connected with the fluidic duct at the second position, wherein the moving is driven by a switch configured to drive the capture tube from the first position to the second position after receiving the signal, and wherein the capture tube remains at the first position unless driven by the switch, thereby catching the particle of interest from the fluidic duct into the catch tube; and flushing an air flow to the capture tube after the capture tube catches the particle of interest, wherein the air flow is flushed by a pressure source. The steps can be performed in any order. Each step can be performed one or more times.

Figure 4D:
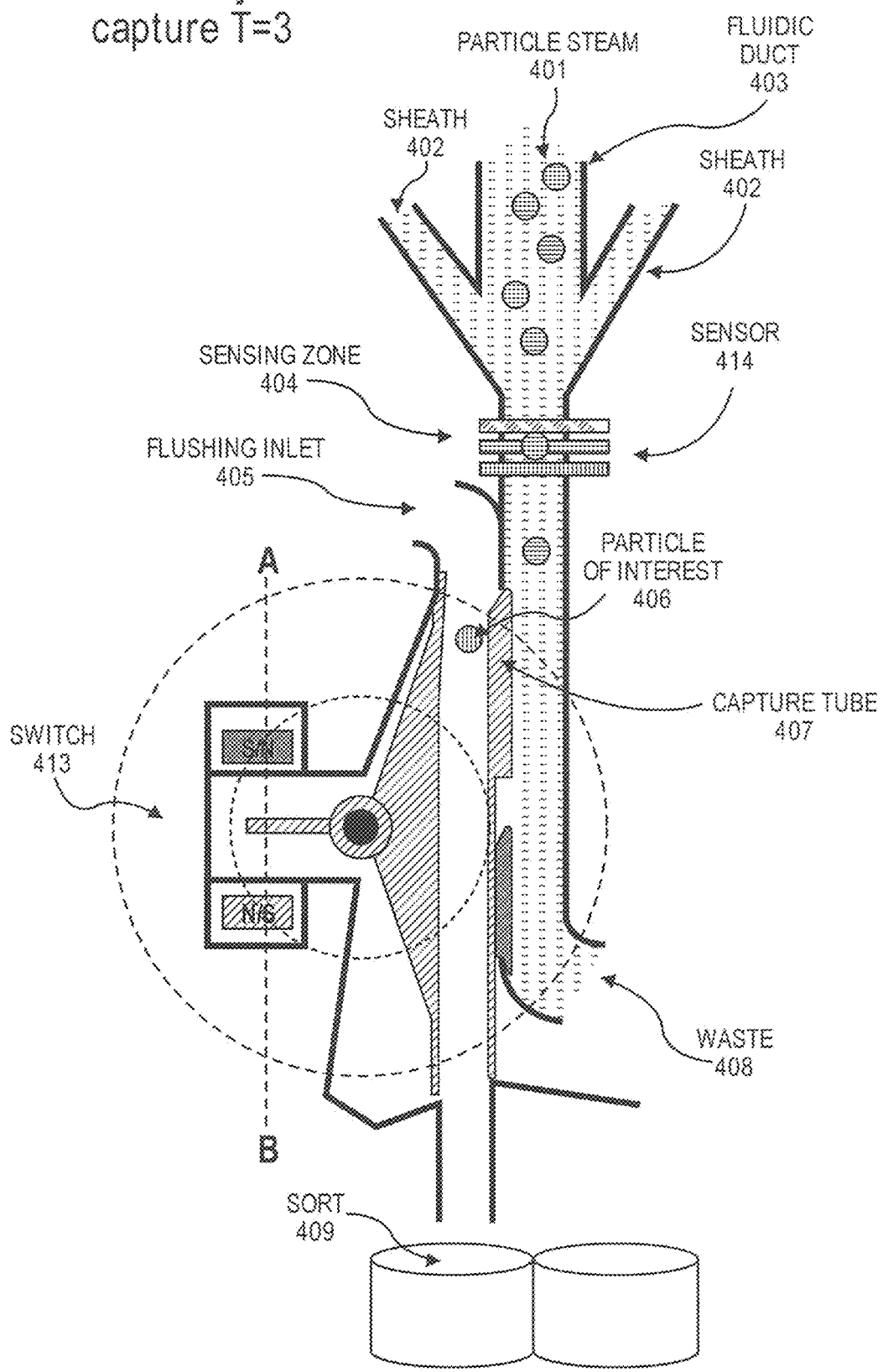
Figure 4E:
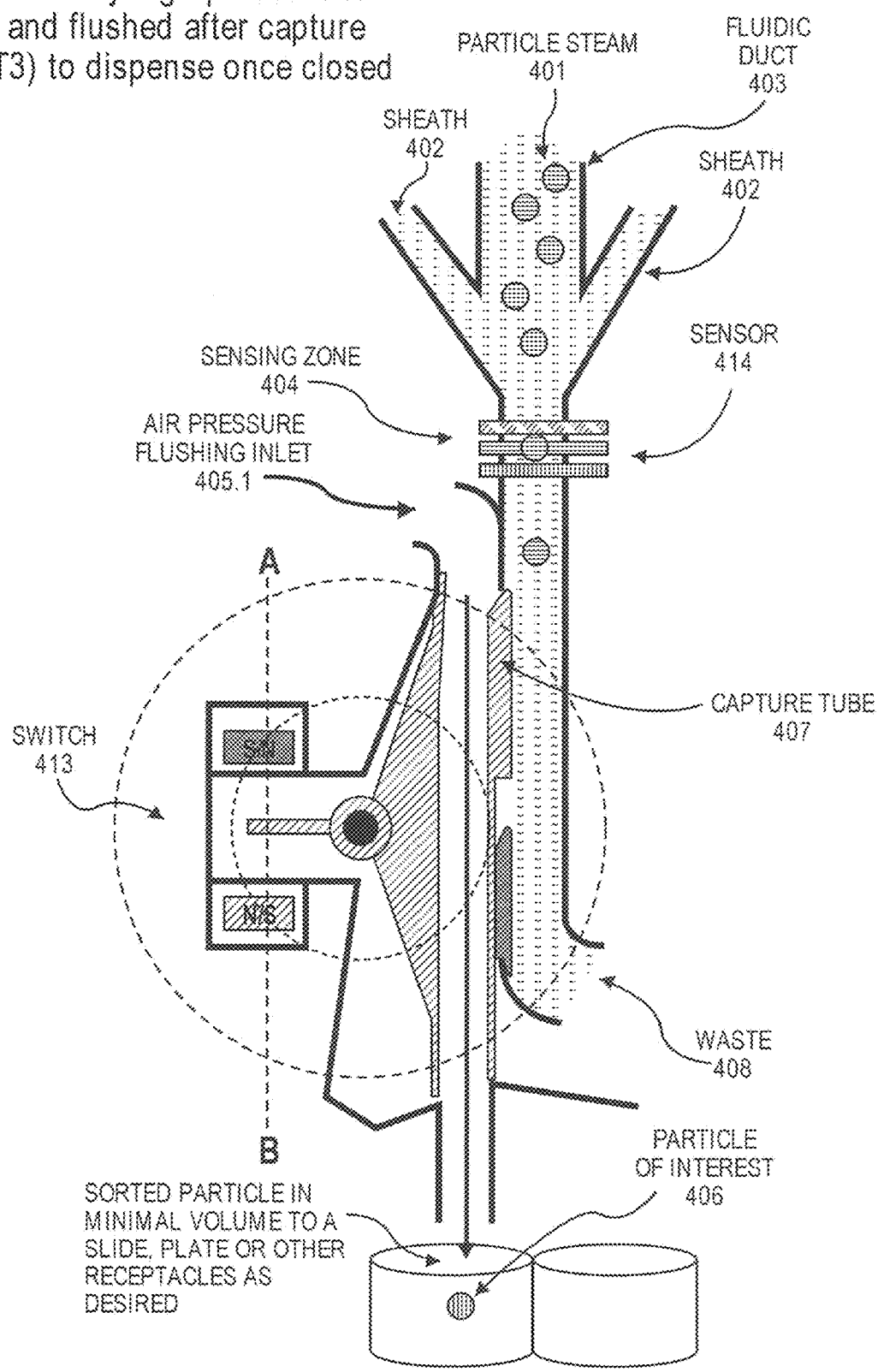

An exemplary method for dispensing particles is shown in FIGS. 4A-4F. A sample comprising a particle of interest (406) enters the particle dispenser's fluidic duct (403) with the particle stream (401). At T=0, the particle of interest (406) arrives at a sensing zone (404). A sensor (414) senses the particle of interest (406) and sends a signal to a switch (413), which drives a capture tube (407) to a position fluidically connected with the particle stream (401). The capture tube catches the particle of interest (406) (FIG. 4C), and then moves back to the original position (FIG. 4D). The particle of interest (406) is captured with a plug of fluid from the particle stream (401) (FIG. 4D). A flushing inlet (405) flushes an air flow to the capture tube (407), facilitating dispensing the particle of interest (406) to a location for further analysis.

Methods for separating particles in a sample can comprise passing the sample through one or more DLD arrays. The methods can comprise passing the sample through at least 1, 2, 3, 4, 5, 6, 7, 8, 9, 10, 11, 12, 13, 14, 15, 16, 17, 18, 19, 20 or more DLD arrays.

The method can comprise passing a sample into a system or device herein by any means. In some cases, the sample is passed into a system or device herein by a pressure source. For example, the pressure source can be coupled with a pipette or a tubing. In some cases, the sample can be passed into a system or device by venous pressure. For example, the system or device can be a part of a blood collector that connected with a vein of a blood donor. In some cases, the blood from the blood donor is flowed into a chamber of the system herein. The chamber can comprise a solution that can be mixed with the blood before the blood enters any separator herein. The solution can comprise any additive of a sample disclosed herein. In some cases, the approach can be used to perform leukodepletion to address immune cell-mediated transfusion reactions. The approach can be used to separate particles in blood before the particles have a chance to age and/or precipitate, which may release degranulation products and non-desired cells and subcellular components.

VII. Systems and Methods for Separating and Enriching Particles

Any two or more devices or elements of devices provided herein can be combined into a system for separating and enriching particles, e.g., from a sample such as blood.

For example, provided herein is a system for separating particles in a sample, comprising a DLD array and a magnetic separator. The DLD array can comprise an array of obstacles configured to allow first particles of at least a critical size to flow in a first direction to a first outlet and second particles of less than the critical size to flow in a second direction to a second outlet.

The DLD array can have any critical size disclosed through the application, such as less than 5 µm, 4 µm, 3 µm, 2 µm, 1.5 µm, 1 µm, 800 nm, 600 nm, 400 nm, 200 nm, 100 nm, or 50 nm.

The first particles, e.g., particles of at least the critical size of the DLD array, can comprise larger particles including red blood cells, white blood cells, other blood cells (including rare cells, e.g., circulating cells such as circulating tumor cells), or any combination thereof. The second particles, e.g., particles smaller than the critical size of the DLD array, can comprise exosomes, platelets, microvesicles, nucleosomes, cell-free DNA (e.g., circulating tumor DNA) or any subcellular particles disclosed herein.

The particles (the first particles and/or the second particles) can comprise particles with magnetically susceptible labels and particles without magnetically susceptible labels. The particles with magnetically susceptible labels and particles without magnetically susceptible labels can be further separated with a magnetic separator.

Exosomes can be from different types of cells, including, but not limited to tumor specific cells, T cells, B cells, stem cells, or other type of cells.

Particles can be labeled with magnetically susceptible labels via a reagent recognizing a marker on the particle. The reagent can be an antibody, a polypeptide, a polynucleotide, or any molecule that recognizes a marker on a particle. For example, platelets can be labeled via an antibody, e.g., an anti-CD41 antibody. White blood cells can be labeled with via an antibody, e.g., an anti-CD45

Exosomes from different types of cells can be selectively labeled with magnetically susceptible labels using antibodies recognizing a marker on the exosomes. For example, exosomes from tumor specific cells can be labeled with magnetically susceptible labels through an anti-CD44 antibody. Exosomes from T cells can be labeled with magnetically susceptible labels through an anti-CD3 antibody. Exosomes from B cells can be e labeled with magnetically susceptible labels through an anti-CD19 antibody. Exosomes from stem cells can be labeled with magnetically susceptible labels through an anti-CD34 antibody. Exosomes from multiple types of cells can be labeled magnetically susceptible labels with an anti-CD63 antibody.

The system can further comprise a concentrator described herein. Such system can be used to enrich rare particles from a sample. The system can comprise a first array of obstacles configured to allow first particles of at least a critical size to flow in a first direction to a first outlet and second particles of less than the critical size to flow in a second direction to a second outlet, wherein the critical size is less than 5 µm, and wherein the first particles comprise third particles with magnetically susceptible labels and fourth particles without magnetically susceptible labels; a magnetic separator fluidically connected to the first outlet, wherein the magnetic separator is configured to separate fourth particles from the third particles; and a concentrator fluidically connected to the magnetic separator, wherein the concentrator is a microfluidic channel comprising an inlet, a second array of obstacles, a product outlet, and a waste outlet, wherein the second array of obstacles is configured to deflect the fourth particles so that the fourth particles flow through the product outlet in a solution at a higher concentration compared to in the sample.

The system can further comprise one or more analyzer for characterizing the separated or enriched particles. The analyzer can be any device described herein. For example, when nucleic acids (e.g., cell-free DNA such as circulating tumor DNA) are isolated or enriched, the system can comprise a sequencer, e.g., a next-generation sequencer, for analyzing the nucleic acids. Other analyzer for characterizing nucleic acids can include PCR devices, qPCR devices, or any other molecular biology experiment devices. Analysis of subcellular particles such as platelets, exosomes and microvesicles can be performed as described in Best M G et al., Cancer Cell. 2015 Nov. 9; 28(5):666-76 and Lee Y et al., Hum Mol. Genet. 2012 Oct. 15; 21(R1):R125-34, which are incorporated by references herein in their entireties.

Disclosed herein are methods for separating particles from a sample using a system comprising a DLD array and a magnetic separator. The methods can comprise passing a sample through a DLD array, labeling one or more types of particles in the sample with magnetically susceptible labels and passing the particles through a magnetic separator, thereby separating particles with magnetically susceptible labels.

The labeling step can be performed before passing the sample to the DLD array. For particles smaller than the critical size of the DLD array, such labels can increase the size of the particles above the critical sizes. Alternatively, the labels may not increase the sizes of the particles above the critical sizes. Different labels can be used for different separation strategies.

Also disclosed herein are methods for enriching particles using a system comprising a DLD array, a magnetic separator, and a concentrator. The method can comprise a) mixing the sample with magnetically susceptible labels whereby first particles in the sample are labeled with the magnetically susceptible labels; b) passing the sample through a first array of obstacles, wherein the first array of obstacles is configured to allow second particles of at least a critical size to flow in a first direction to a first outlet and third particles of less than the critical size to flow in a second direction to a second outlet, wherein the critical size is less than 3 µm, and wherein the second particles comprise i) first particles labeled with magnetically susceptible labels from a), ii) fourth particles without magnetically susceptible labels; c) passing the second particles through a magnetic separator, thereby separating the first particles from the fourth particles; d) concentrating the fourth particles with a concentrator, wherein the concentrator is a microfluidic channel comprising an inlet, a second array of obstacles, a product outlet, and a waste outlet, wherein the second array of obstacles is configured to deflect the fourth particles so that the fourth particles flow through the product outlet in a solution at a higher concentration compared to in the sample.

VIII. Downstream Applications

The methods, systems, devices and kits herein can be used to isolate cells, e.g., rare cells. The isolated cells can be detected and/or analyzed by cell biology and molecular biology techniques, including immunoassays, immunostaining, mass spectrometry, fluorescence in situ hybridization, sequencing, polymerase chain reaction (PCR) (e.g., real-time PCR such as quantitative real-time PCR), expression (e.g., gene expression, mRNA expression, miRNA expression, or protein expression) assays (e.g., microarray assays), cell cultures, polynucleotides amplification (e.g., whole genome amplification). The downstream applications of the detection and analyses of the isolated cells, e.g., rare cells, can be used to determine cell phenotypes, mutations of genes, translocations and expression of genes, gene copy numbers, gene copy number variants, gene fusion, proliferation cycle of cells, and drug response of cells. The downstream applications can also include multiplexed gene expression screens, RNA and/or protein expression profiling, and cell culture for functional tests (e.g., drug sensitivity).

Cells isolated by the methods, systems, devices, and/or kits here can be used for in vitro or in vivo cell culture and/or expansion. The cultured and/or expanded cells can modified genetically or in other ways. The resulting cells can be used for gene therapy, enrichment for reinfusion, and/or stimulation. A subgroup of cells in the isolated cells can be further enriched based on one or more molecules (e.g., protein and/or nucleic acid s) specifically possessed by the subgroup cells. In some cases, such enrichment can be performed as preparatory for other types of analyses, such as probing or sequencing for specific strains, or any analysis using an alternate technology.

Downstream assays or tests can be performed on the particles (e.g., cells) isolated by the methods, systems, devices, and/or kits herein can also include counting the particles. The assays and tests can also include characterization and/or identification of the particles. The characterization and/or identification can be made based on intrinsic properties of the particles. Such intrinsic properties can be used as an identifier for a subgroup of the particles. Methods of characterization and/or identification can include use of spectrally indexed beads (e.g., from Luminex, BD-CBA), light scatter indexed particles, latex, or hydrogels (e.g., from Firefly Bio). The characterization and/or identification can be performed by detection and assessments of the particles using directly covalently and non-covalently bound components that interact with the particles with specific affinity. The particles characterized and/or identified can include cells, components of cells (e.g., soluble components of cells), proteins, protein complexes, nucleic acids (including synthetic nucleic acids (PNA)) of all physical lengths.

A. Tumor Diagnosis

The methods, systems, devices and/or kits herein can be used to perform liquid biopsies. For example, the methods, systems, devices and/or kits herein can be used to isolate, detect and/or analyze particles in a body fluid, thus generating a diagnosis. In some cases, the methods, systems, devices and/or kits herein can be used to evaluate cancer patients and those at risk for cancer. Either the presence or the absence of an indicator of cancer, e.g., a cancer cell such as a circulating tumor cell, or tumor DNA such as circulating tumor DNA, can be used to generate a diagnosis. In one example, the circulating tumor cells and/or circulating tumor DNA can be isolated, detected and/or analyzed in a blood sample (e.g., cancer liquid biopsy) using the methods systems, devices and/or kits herein. In one example, a blood sample can be drawn from the patient and introduced to a system herein with a DLD array with a critical size chosen appropriately to enrich circulating tumor cells, from other blood cells. Using an analytical device herein, the number of circulating tumor cells in the blood sample can be determined. In some cases, the cells can be labeled with an antibody that binds to EpCAM, and the antibody can have a covalently bound fluorescent label. A bulk measurement can then be made of the enriched sample produced by the device, and from this measurement, the number of circulating tumor cells present in the initial blood sample can be determined. Microscopic techniques can be used to visually quantify the cells in order to correlate the bulk measurement with the corresponding number of labeled cells in the blood sample.

By making a series of measurements, optionally made at regular intervals such as one day, two days, three days, one week, two weeks, one month, two months, three months, six months, or one year, one can track the level of circulating tumor cells present in a patient's bloodstream as a function of time. In the case of existing cancer patients, this approach can provide a useful indication of the progression of the disease and assists medical practitioners in making appropriate therapeutic choices based on the increase, decrease, or lack of change in circulating tumor cells, e.g., circulating tumor cells, in the patient's bloodstream. For those at risk of cancer, a sudden increase in the number of cells detected can provide an early warning that the patient has developed a tumor. This early diagnosis, coupled with subsequent therapeutic intervention, is likely to result in an improved patient outcome in comparison to an absence of diagnostic information.

Diagnostic methods include making bulk measurements of labeled circulating tumor cells, e.g., circulating tumor cells, isolated from blood, as well as techniques that destroy the integrity of the cells. For example, PCR can be performed on a sample in which the number of target cells isolated is very low; by using primers specific for particular cancer markers, information can be gained about the type of tumor from which the analyzed cells originated. Additionally, RNA analysis, proteome analysis, or metabolome analysis can be performed as a means of diagnosing the type or types of cancer present in the patient.

B. Nucleic Acids Analysis

Methods, systems, devices and/or kits herein can be used to separate nucleic acids and/or proteins from a sample (e.g., blood) for further analysis. The isolated nucleic acids and/or proteins can be analyzed using one or more of the following techniques: genetic testing using G-banded karotyping, fragile X testing, chromosomal microarray (CMA, also known as comparative genomic hybridization (CGH)) (e.g., to test for submicroscopic genomic deletions and/or duplications), array-based comparative genomic hybridization, detecting single nucleotide polymorphisms (SNPs) with arrays, subtelomeric fluorescence in situ hybridization (ST-FISH) (e.g., to detect submicroscopic copy-number variants (CNVs)), expression profiling, DNA microarray, high-density oligonucleotide microarray, whole-genome RNA expression array, peptide microarray, enzyme-linked immunosorbent assay (ELISA), genome sequencing, de novo sequencing, 454 sequencing (Roche), pyrosequencing, Helicos True Single Molecule Sequencing, SOLiD™ sequencing (Applied Biosystems, Life Technologies), SOLEXA sequencing (Illumina sequencing), nanosequencing, chemical-sensitive field effect transistor (chemFET) array sequencing (Ion Torrent), ion semiconductor sequencing (Ion Torrent), DNA nanoball sequencing, nanopore sequencing, Pacific Biosciences SMRT sequencing, Genia Technologies nanopore single-molecule DNA sequencing, Oxford Nanopore single-molecule DNA sequencing, polony sequencing, copy number variation (CNV) analysis sequencing, small nucleotide polymorphism (SNP) analysis, immunohistochemistry (IHC), immunoctyochemistry (ICC), mass spectrometry, tandem mass spectrometry, matrix-assisted laser desorption ionization time of flight mass spectrometry (MALDI-TOF MS), in-situ hybridization, fluorescent in-situ hybridization (FISH), chromogenic in-situ hybridization (CISH), silver in situ hybridization (SISH), polymerase chain reaction (PCR), digital PCR (dPCR), reverse transcription PCR, quantitative PCR (Q-PCR), single marker qPCR, real-time PCR, nCounter Analysis (Nanostring technology), Western blotting, Southern blotting, SDS-PAGE, gel electrophoresis, or Northern blotting. In some cases, analysis comprise exome sequencing.

The isolated nucleic acid (e.g., cell-free DNA such as circulating tumor DNA) can be sequenced. The sequencing can be performed using next generation sequencing techniques, including Helicos True Single Molecule Sequencing (tSMS) (see e.g., Harris T. D. et al. (2008) Science 320:106-109); 454 sequencing (comprising pyrosequencing)(Roche) (see e.g., Margulies, M. et al. 2005, Nature, 437, 376-380); SOLiD technology (Applied Biosystems); SOLEXA sequencing (comprising bridge amplification on a flow cell and use of reversibly dye terminators) (Illumina); single molecule, real-time (SMRT™) technology of Pacific Biosciences; or nanopore sequencing (Soni G V and Meller A. (2007) Clin Chem 53: 1996-2001; Oxford Nanopore, Genia Technologies, and Nabsys); semiconductor sequencing (Ion Torrent (Life Technologies); Personal Genome Machine); DNA nanoball sequencing (e.g., Complete Genomics); sequencing using technology from Dover Systems (Polonator). Methods next generation sequencing are described, e.g., in PCT Publication No. WO2012149472, which is herein incorporated by reference in its entirety.

Methods, systems, devices and/or kits herein can be used to construct a library, e.g., a next generation sequencing library. A liquid containing nucleic acid (e.g., cells, nuclei) can be flowed through a channel in a device comprising an array of obstacles. The array of obstacles can be configured to deflect particles of a critical size (critical size) into a flow path that is diagonal to the direction of bulk fluid flow. Smaller particles can be directed with the bulk fluid flow. Adapters can be added to nucleic acids before the nucleic acids are flowed through a device, while the nucleic acids are being flowed through a device, or after nucleic acids have flowed through a device. In some cases, adapters are compatible with sequencing using Iluminia sequencing or 454 sequencing. The adaptors can comprise sequences that are complementary to one or more sequencing primers. Nucleic acids larger and/or smaller than a critical size can be used for library formation, e.g., next generation sequencing library formation.

In some cases, nucleic acids are amplified before being flowed through a device comprising an array of obstacles. In some cases, nucleic acids are amplified after being flowed through a device comprising an array of obstacles. In some cases, particles of at least a critical size are amplified after being flowed through a device comprising an array of obstacles. In some cases, particles of less than a critical size are amplified after being flowed through a device comprising an array of obstacles. In some cases, adaptors comprise barcodes. Barcodes can be used to identify a sample, organism, or cell from which a nucleic acid is derived.

EXAMPLES

Figure 5:
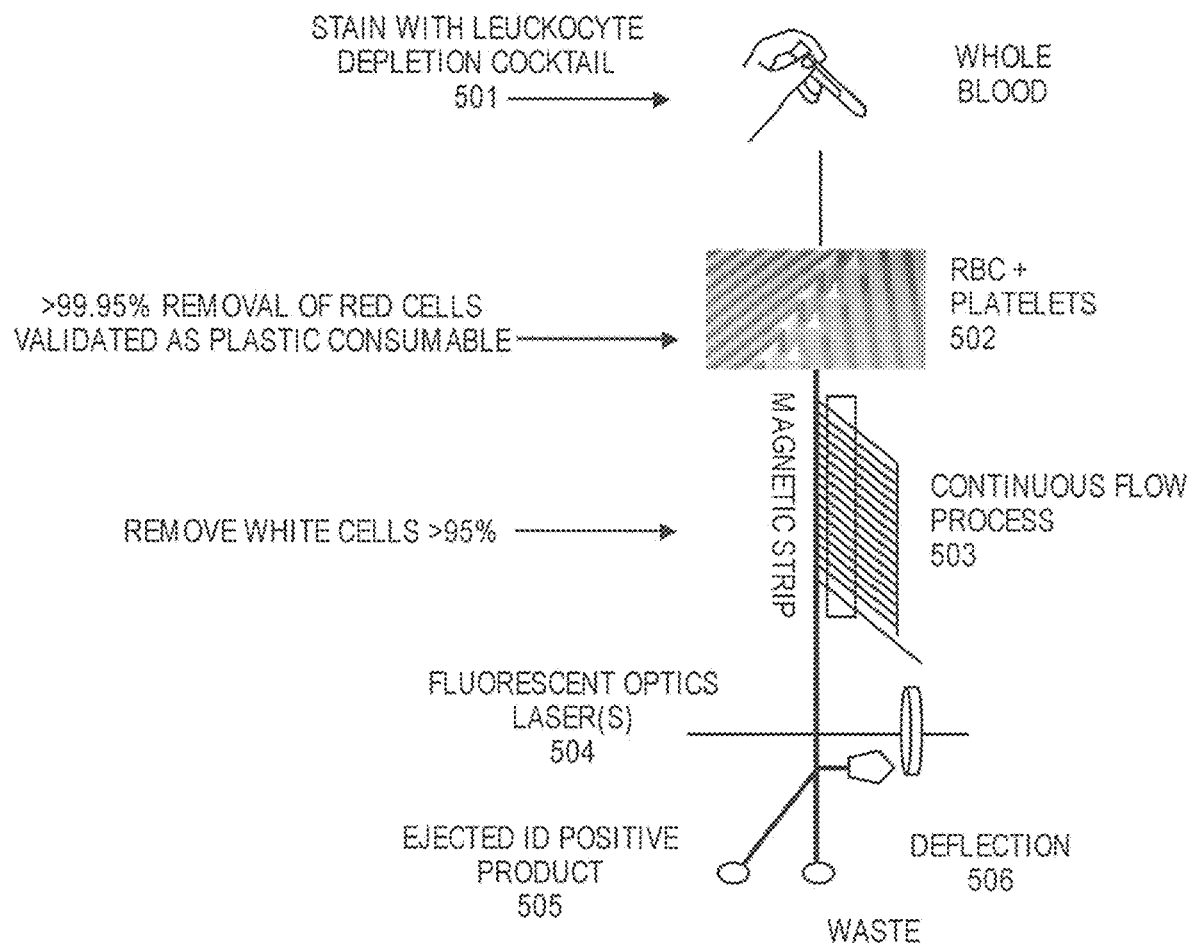
FIG. 5 is a flow chart demonstrating methods for separating circulating tumor cells from a whole blood sample as described in Example 1.

Example 1: Isolating CTCs from Whole Blood by Labeling the CTCs with a Fluorescent Label A whole blood sample is collected from a patient and mixed with a labeling solution (FIG. 5, 501). The labeling solution comprises magnetic beads-conjugated anti-CD45 antibodies, and FITC-conjugated anti-EpCAM antibodies. After mixing, the white blood cells in the sample are bound by the magnetic beads-conjugated anti-CD 45 antibodies. The circulating tumor cells in the sample are bound by the FITC-conjugated anti-EpCAM antibodies.

The labeled blood sample is loaded to a DLD array with critical size of no more than 5 µm, e.g., about 4 µm (FIG. 5, 502). The white blood cells and CTCs are separated from red blood cells and smaller particles (e.g., platelets) in the sample by the DLD array. The sample fraction comprising the white blood cells and CTCs is then passed to a magnetic separator (FIG. 5, 503), wherein the white blood cells are separated from the CTCs.

The resulting sample fraction comprising the CTCs is then passed to a FACS device, which detects and sorts the FITC-labeled circulating tumor cells (FIGS. 5, 504 and 505). The FACS device is coupled with a single cell dispenser, which dispenses the circulating tumor cells to a microscope slide. The number of the circulating tumor cells is then counted to generate a diagnosis of cancer for the patient.

Example 2: Isolating Circulating Tumor DNA from Whole Blood

A whole blood sample is collected from a patient and mixed with a labeling solution. The labeling solution comprises magnetic beads-conjugated anti-CD45 antibodies. The white blood cells in the sample are bound by the magnetic beads-conjugated anti-CD45 antibodies.

The labeled blood sample is loaded to a DLD array with a critical size of 20 µm to remove cell aggregates. The resulting sample is then passed to a DLD array with a critical size of no more than 5 µm, e.g., about 4 µm. Red blood cells and subcellular particles are separated from the white blood cells. The resulting sample is then passed through a magnetic separator, which deflects the red blood cells from other particles without magnetic susceptibilities. The resulting sample fraction comprising subcellular particles is then passed through a DLD array with a critical size of 50 nm, which separates cell-free DNA and nucleosomes from other particles. Circulating tumor DNA is then amplified from the sample fraction comprising cell-free DNA. The copy number of the circulating tumor DNA is analyzed to determine the circulating tumor DNA concentration in the patient's blood, which is used to generate a diagnosis of cancer for the patient.

Example 3: Isolating CTCs from Whole Blood by Labeling the CTCs with Two Fluorescent Labels A whole blood sample is collected from a patient. The sample is permeabilized and fixed, and mixed with a labeling solution. The labeling solution comprises magnetic beads-conjugated anti-CD45 antibodies, FITC-conjugated anti-EpCAM antibodies, and Cy5-conjugated anti-cytokeratin 19 antibodies.

After mixing, the white blood cells in the sample are bound by the magnetic beads-conjugated anti-CD 45 antibodies. The circulating tumor cells in the sample are bound by the FITC-conjugated anti-EpCAM antibodies and Cy5-conjugated anti-cytokeratin 19 antibodies.

The labeled blood sample is loaded to a DLD array with critical size of no more than 5 µm, e.g., about 4 µm. The white blood cells and CTCs are separated from red blood cells and smaller particles (e.g., platelets) in the sample by the DLD array. The sample fraction comprising the white blood cells and CTCs are then passed to a magnetic separator wherein the white blood cells are separated from the CTCs.

The resulting sample fraction comprising the CTCs is then passed to a FACS device, which detects and sorts the FITC-labeled cells. FITC-labeled cells are then passed into to single cell dispenser. The single cell dispenser comprises a sensor for detecting Cy5 labels. The FITC-labeled cells that are also labeled by Cy5 are detected by the sensor. The single cell dispenser can isolate the FITC- and Cy5-labeled cells in single cell on to a microscope slide. The isolated FITC- and Cy5-labeled cells can be purer CTC population compared with the CTC population isolated in Example 1. The number of the circulating tumor cells is then counted to generate a diagnosis of cancer for the patient.

Example 4: Separating CTCs from White Blood Cells by Removing White Blood Cells Labeled with a Magnetically Susceptible Labelmagnetically Susceptible Label and a Fluorescent Label A whole blood sample is collected from a patient. The sample is permeabilized and fixed, and mixed with a labeling solution. The labeling solution comprises magnetic beads-conjugated anti-CD45 antibodies, Cy5-conjugated anti-CD45 antibodies, and FITC-conjugated anti-EpCAM antibodies. After mixing, the white blood cells in the sample are bound by the magnetic beads-conjugated anti-CD 45 antibodies and Cy5-conjugated anti-CD45 antibodies. The circulating tumor cells in the sample are bound by the FITC-conjugated anti-EpCAM antibodies.

The labeled blood sample is loaded to a DLD array with critical size of no more than 5 µm, e.g., about 4 µm. The white blood cells and CTCs are separated from red blood cells and smaller particles (e.g., platelets) in the sample by the DLD array. The sample fraction comprising the white blood cells and CTCs are then passed to a magnetic separator wherein the white blood cells are separated from the CTCs.

The resulting sample fraction comprising the CTCs is then passed to a FACS device, which detects and sorts the Cy5-labeld cells and FITC-labeled cells. In this step, the white blood cells not removed by the magnetic separator are further separated from CTCs by the FACS. FITC-labeled cells are then passed into to single cell dispenser. The single cell dispenser then dispenses the circulating tumor cells to a microscope slide. The number of the circulating tumor cells is then counted to generate a diagnosis of cancer for the patient.

Example 5: Isolating Circulating Tumor Cells from Whole Blood by Labeling the CTCs with Collapsible Immuno-Bubble Labels A whole blood sample is collected from a patient and mixed with a labeling solution. The labeling solution comprises magnetic beads-conjugated anti-CD45 antibodies, and collapsible immuno-bubble with FITC-conjugated anti-EpCAM antibodies. After mixing, the white blood cells in the sample are bound by the magnetic beads-conjugated anti-CD 45 antibodies. The circulating tumor cells in the sample are bound by the collapsible immuno-bubble with FITC-conjugated anti-EpCAM antibodies. The immuno-bubble-labeled CTCs have sizes at least than 18 µm, which is larger than the size of white blood cells (12 µm to 15 µm).

The labeled blood sample is loaded to a DLD array with critical size of no more than 5 µm, e.g., about 4 µm. The white blood cells and CTCs are separated from red blood cells and smaller particles (e.g., platelets) in the sample by the DLD array. The sample fraction comprising the white blood cells and CTCs are then passed to a DLD array with 17 µm. The immuno-bubble-labeled CTCs and the white blood cells are separated by their sizes. The resulting sample fraction is then passed to a magnetic separator, which further separates the white blood cells from the CTCs.

The resulting sample fraction comprising the CTCs is then passed to a FACS device, which detects and sorts the FITC-labeled circulating tumor cells. The FACS device is coupled with a single cell dispenser, which dispenses the circulating tumor cells to a microscope slide. The number of the circulating tumor cells is then counted to generate a diagnosis of cancer for the patient.

Example 6: Isolating Circulating Tumor Cells from Whole Blood Collected from a Patient Driven by Venous Pressure An intravenous needle is inserted to a patient's vein, connecting the patient's vein with a microfluidic system comprising a DLD array and a magnetic separator. Driven by the venous pressure, the patient's blood is flowed into a chamber to mix with a labeling solution and then flowed into the microfluidic device by the patient's own vein pressure. The chamber is fluidically connected with the microfluidic device. The labeling solution comprises magnetic beads-conjugated anti-CD45 antibodies, and FITC-conjugated anti-EpCAM antibodies. After mixing, the white blood cells in the sample are bound by the magnetic beads-conjugated anti-CD 45 antibodies. The circulating tumor cells in the sample are bound by the FITC-conjugated anti-EpCAM antibodies.

The labeled blood sample is loaded to a DLD array with critical size of no more than 5 µm, e.g., about 4 µm. The white blood cells and CTCs are separated from red blood cells and smaller particles (e.g., platelets) in the sample by the DLD array. The sample fraction comprising the white blood cells and CTCs are then passed to a magnetic separator, wherein the white blood cells are separated from the CTCs.

The resulting sample fraction comprising the CTCs is then passed to a FACS device, which detects and sorts the FITC-labeled circulating tumor cells. The FACS device is coupled with a single cell dispenser, which dispenses the circulating tumor cells to a microscope slide. The number of the circulating tumor cells is then counted to generate a diagnosis of cancer for the patient.

Example 7: Isolating CTCs and Circulating Tumor DNA from Whole Blood Sample Taken Form a Patient A whole blood sample is collected from a patient and mixed with a labeling solution. The labeling solution comprises magnetic beads-conjugated anti-CD45 antibodies, and FITC-conjugated anti-EpCAM antibodies. After mixing, the white blood cells in the sample are bound by the magnetic beads-conjugated anti-CD 45 antibodies. The circulating tumor cells in the sample are bound by the FITC-conjugated anti-EpCAM antibodies.

The labeled blood sample is loaded to a DLD array with critical size of no more than 5 µm, e.g., about 4 µm. The white blood cells and CTCs are separated from red blood cells and smaller particles (e.g., DNA) in the sample by the DLD array. The sample fraction comprising the white blood cells and CTCs are then passed to a magnetic separator, wherein the white blood cells are separated from the CTCs. The sample fraction comprising the red blood cells and smaller particles are then passed through another magnetic separator, which deflects the red blood cells from other particles without magnetic susceptibilities. The resulting sample fraction comprising subcellular particles is then passed through a DLD array with a critical size of 50 nm, which separates cell-free DNA and nucleosomes from other particles.

The resulting sample fraction comprising the CTCs is then passed to a FACS device, which detects and sorts the FITC-labeled circulating tumor cells. The FACS device is coupled with a single cell dispenser, which dispenses the circulating tumor cells to a microscope slide. The number of the circulating tumor cells is then counted. The Circulating tumor DNA is amplified from the sample fraction comprising cell-free DNA. The copy number of the circulating tumor DNA is analyzed to determine the circulating tumor DNA concentration in the patient's blood. The number of circulating tumor cells and copy number of the circulating tumor DNA are then used to generate a diagnosis of cancer for the patient.

Example 8: Concentrating Cells by Passing a Sample Through a DLD Device

A DLD device as shown schematically in FIG. 7A was assembled in a manifold and connected to input and output ports by tubing. A buffer was flowed through the DLD device from the buffer inlet so that the entire device is filled with the buffer. The buffer input tubing was clamped.

200 uL of Sample 1 comprising $6\times10^3$ cells/mL was loaded into a sample syringe. Another 200 uL of Sample 1 was kept for further analysis. The 200 uL of Sample 1 was loaded to the DLD device by applying 10 psi pressure to the sample syringe. The 200 uL Sample 1 was fully flowed through the DLD device. Then an air plug was injected through the DLD device to evacuate the DLD device.

Product and waste were collected at the ports of the outlets. Volumes collected were measured. The input sample, product collected from the product outlet, and waste collected from the waste outlets were analyzed by flow cytometry to determine the total number of cells in each measured volume. Final cell concentration was determined as ratio of the output concentration to input concentration.

Sample 2 comprising $6\times10^2$ cells/mL was also processed and analyzed using the same DLD device in a separate run by the same method as used for processing and analyzing Sample 1. FIG. 7B shows the input and output concentrations of sample 1 and sample 2. FIG. 7C shows the concentration factors achieved by the DLD device for sample 1 and sample 2.

Example 9: Exemplary Magnetic Separator

Figure 8:
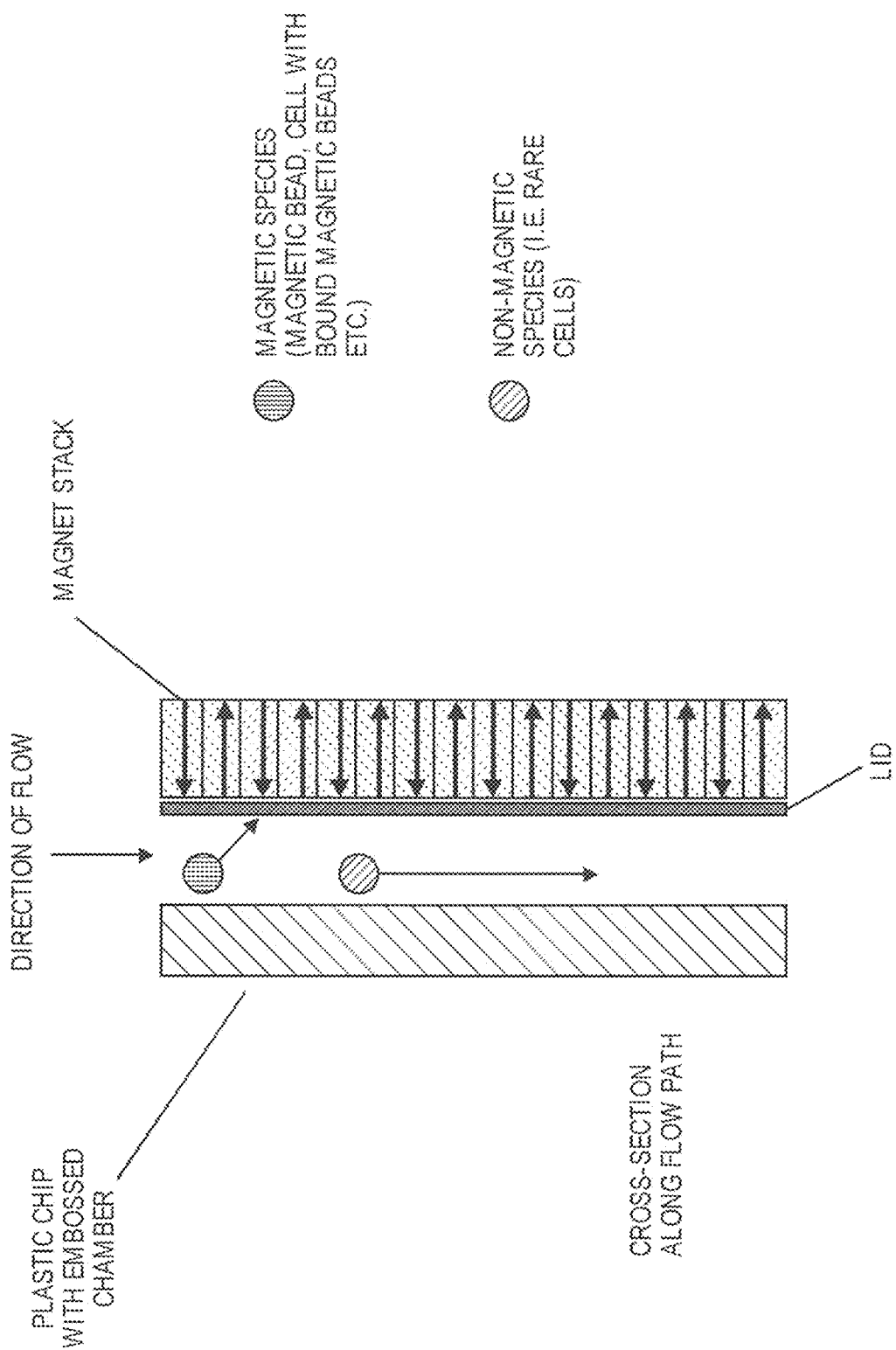
FIG. 8 is an exemplary magnetic separator described in Example 9.

This example shows an exemplary magnetic separator (FIG. 8). The exemplary magnetic separator includes a flow-through chamber that was at mm scale. The depth of the chamber ranges from 100 to 500 µm depending on the design. The magnetic separator has a stack of magnets that are arranged along the tape-side of the chamber. This design provides a minimum separation between the magnets and the chamber. The magnets are arranges with poles alternating: either towards or away from the chamber, and they are stacked side by side. The configuration of the magnets creates a very strong magnetic field gradient that pulls particles with magnetically susceptible labels towards the magnets. The magnetic field is optimized to be used for moving particles magnetically susceptible labels towards the tape edge, where they are then flushed out of a separate waste channel. The pulling force is strong enough such that the labeled particles are retained against the surface of the tape in an accumulation region. The magnetic separator thus has one input and one output, and particles without magnetically susceptible labels pass through the magnetic separator to a product collector.

Example 10: Isolating Cells and Subcellular Particles from Blood

Figure 9:
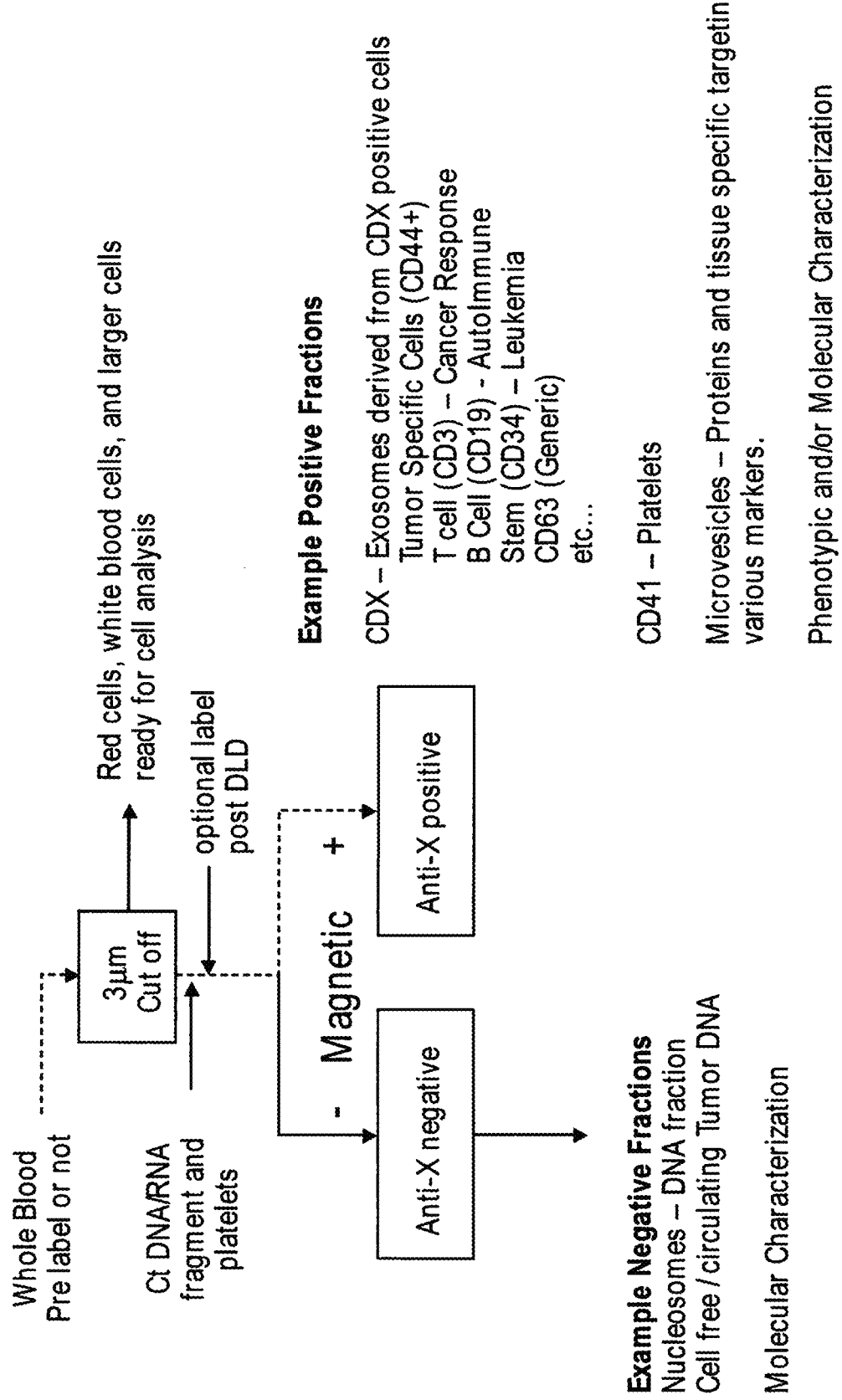
FIG. 9 shows an exemplary method for isolating cells and subcellular particles from a blood sample described in Example 10.

This example shows an exemplary method for isolating cells and subcellular particles from a blood sample (FIG. 9). Whole blood sample is mixed with labeling reagents, so that one or more types of subcellular particles in the blood are selectively labeled with magnetic beads conjugated with antibodies recognizing the subcellular particles. The antibodies include anti-CD44 antibody (for labeling exosomes from tumor specific cells), anti-CD3 antibody (for labeling exosomes from T cells), anti-CD19 antibody (for labeling exosomes from B cells), anti-CD34 antibody (for labeling exosomes from stem cells), anti-CD63 antibody (for labeling all exosomes), anti-CD41 antibody (for labeling platelets), and any combination thereof. Nucleosomes and cell-free DNA (e.g., circulating tumor DNA) are not labeled with magnetic beads. The labeling of the subcellular particles do not change the size of the particles to greater than 3 µm.

The labeled blood sample is then passed through an array of obstacles that has a critical size of 3 µm. The array of obstacles separates particles of at least 3 µm (e.g., blood cells including red blood cells, white blood cells, and other cells in blood) from particles less than 3 µm (e.g., platelets, exosomes, microvesicles, nucleosomes and cell-free DNA (e.g., circulating tumor DNA). The cells (e.g., of at least 3 µm) are used for cell analysis.

The particles less than 3 µm from the DLD array are then passed through a magnetic separator, which separate particles labeled with magnetic beads with particles without magnetic labels. The isolated nucleosomes and/or cell-free DNA (e.g., circulating tumor DNA) are subject molecular biology analysis. Alternatively, the labeling step is performed after passing the blood to the array of obstacles and before passing the samples to the magnetic chamber.

The isolated exosomes, platelets, and/or microvesicles are used for phenotypic and/or molecular analysis. Nucleic acids, such as DNA and/or RNA are isolated from the exosomes, platelets and/or microvesicles and the sequences of the DNA and/or RNA is determined by a next generation sequencing.

Example 11: Enriching Rare Cells from Blood

Figure 10A:
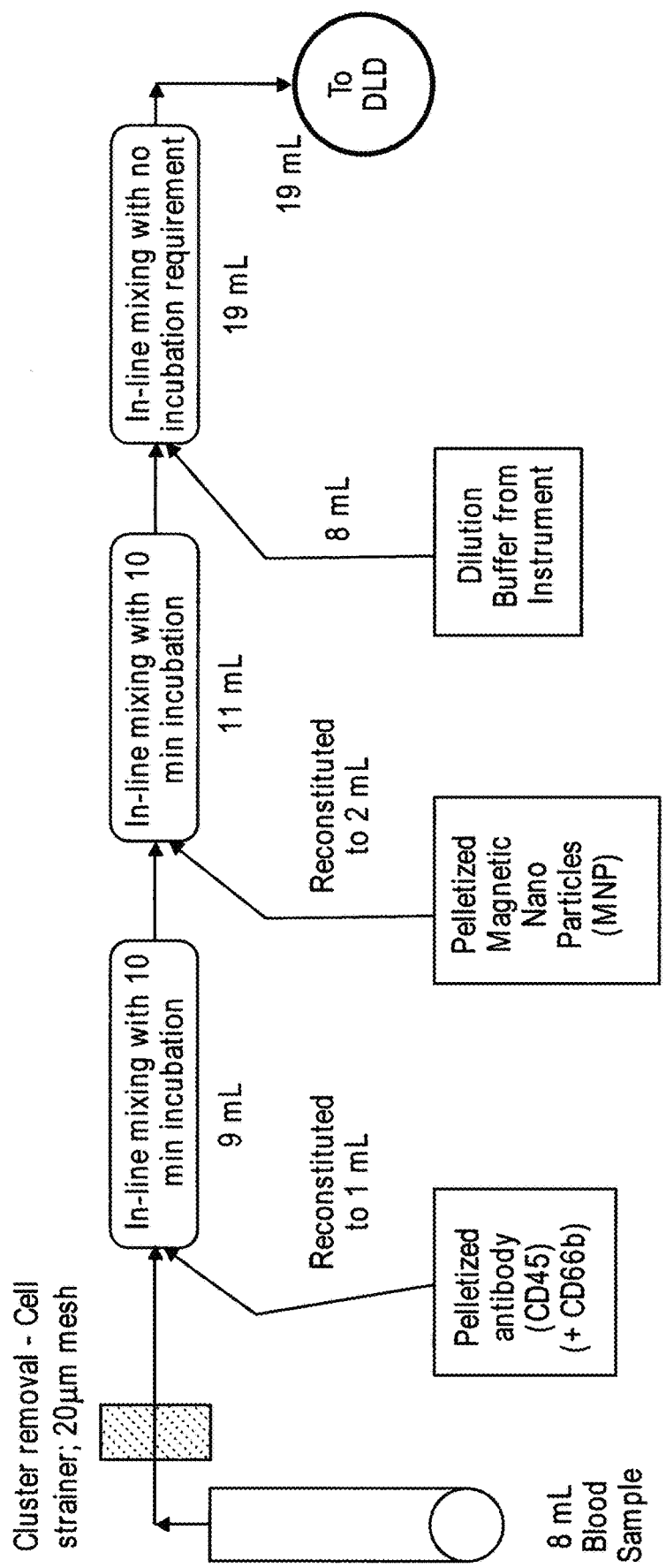
FIGS. 10A-10E shows an exemplary method for enriching rare cells from blood.

This example shows an exemplary method for enriching rare cells from blood. 8 mL blood sample is collected from a patient. The blood sample is passed through a 20 μm mesh so clusters and clumps are removed from the sample. The resulting sample is incubated with 1 mL reconstituted anti-CD45 antibody and/or anti-CD66b antibody for 10 minutes. The antibodies specifically bind to white blood cells in the blood. The sample is then mixed 2 mL reconstituted magnetic nanoparticles and incubated for 10 minutes. The resulting 11 mL sample is then mixed with 8 mL dilution buffer. The dilution buffer contains biotin to stop the reaction (FIG. 10A).

Figure 10B:
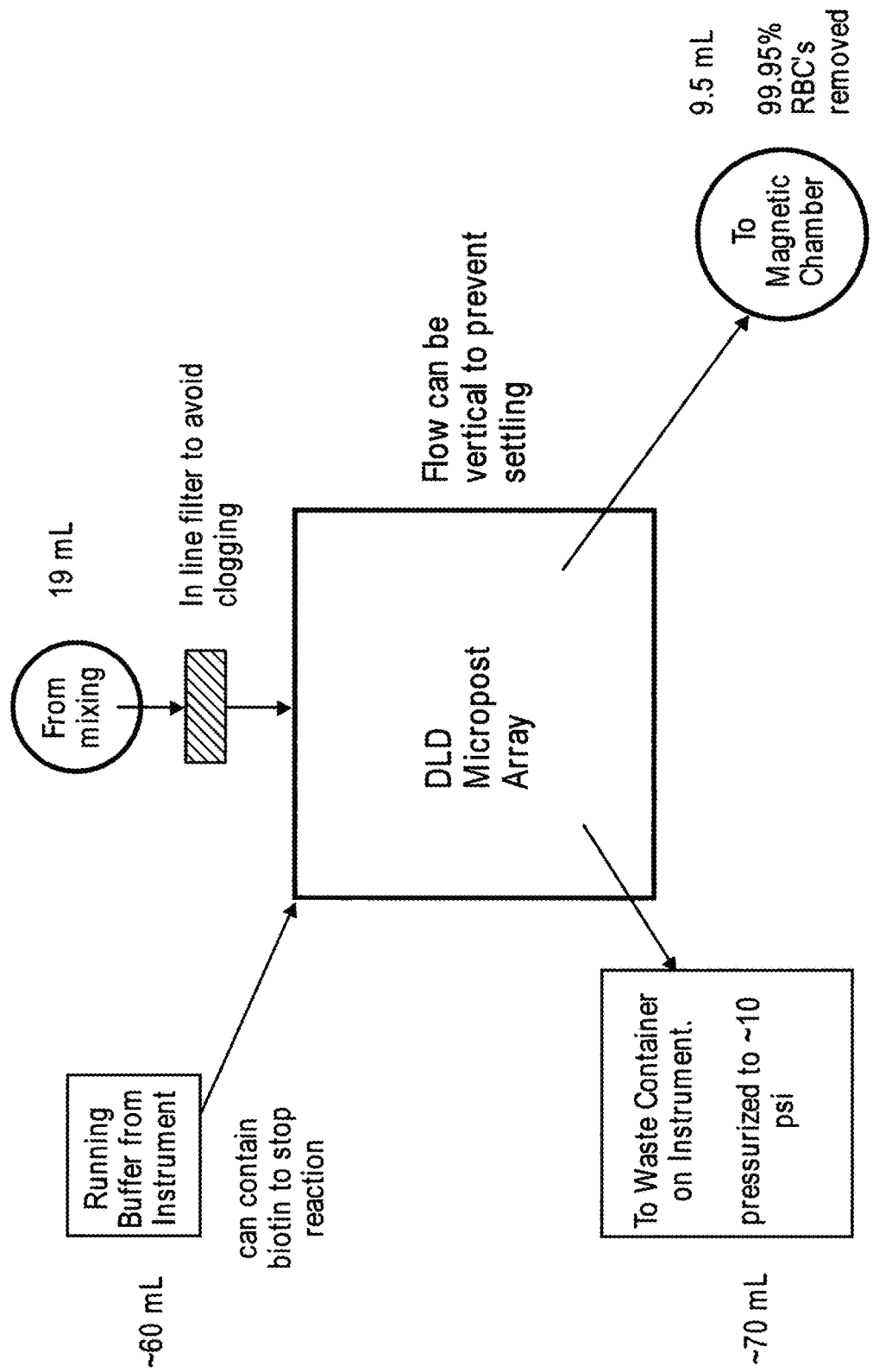

The resulting 19 mL sample is filtered to avoid clogging. The filtered sample and about 60 mL running buffer (containing biotin to stop reaction) are then loaded to a DLD array. The flow is set to vertical to prevent settling of particles. The DLD array has a critical size of 5 μm, so the white blood cells larger cells (e.g., rare cells) separated from smaller particles (e.g., red blood cells and subcellular particles). The smaller particles are deflected by the DLD array to a waste container. Pressure (e.g., about 10 psi) is needed to push the waste out of the array. The DLD array removes 99.5% red blood cells from the blood, and the white blood cells and rare cells are collected to a 9.5 mL solution, which is then passed through a magnetic chamber (FIG. 10B).

Figure 10C:
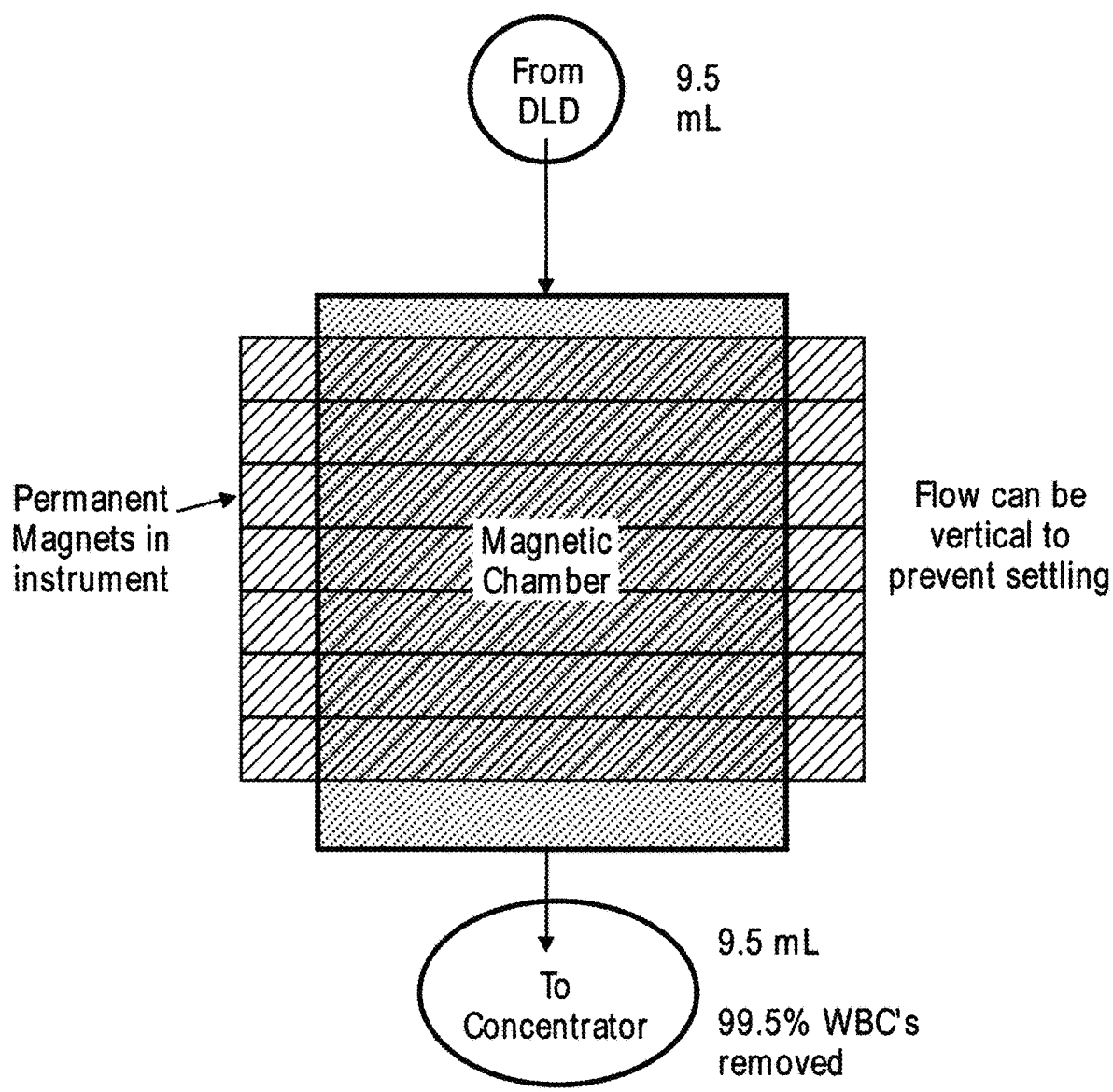

The magnetic chamber deflects white blood cells labeled with magnetic beads, thus separates the white blood cells from other cells (e.g., rare cells) that are not magnetic labeled. The magnetic chamber removes 99.5% white blood cells from the sample. The cells without magnetic labels are collected in a 9.5 mL solution, which only contains no more than 0.5% blood cells. When passing through the magnetic chamber, the flow is set to be vertical to prevent settling of the particles (FIG. 10C).

Figure 10D:
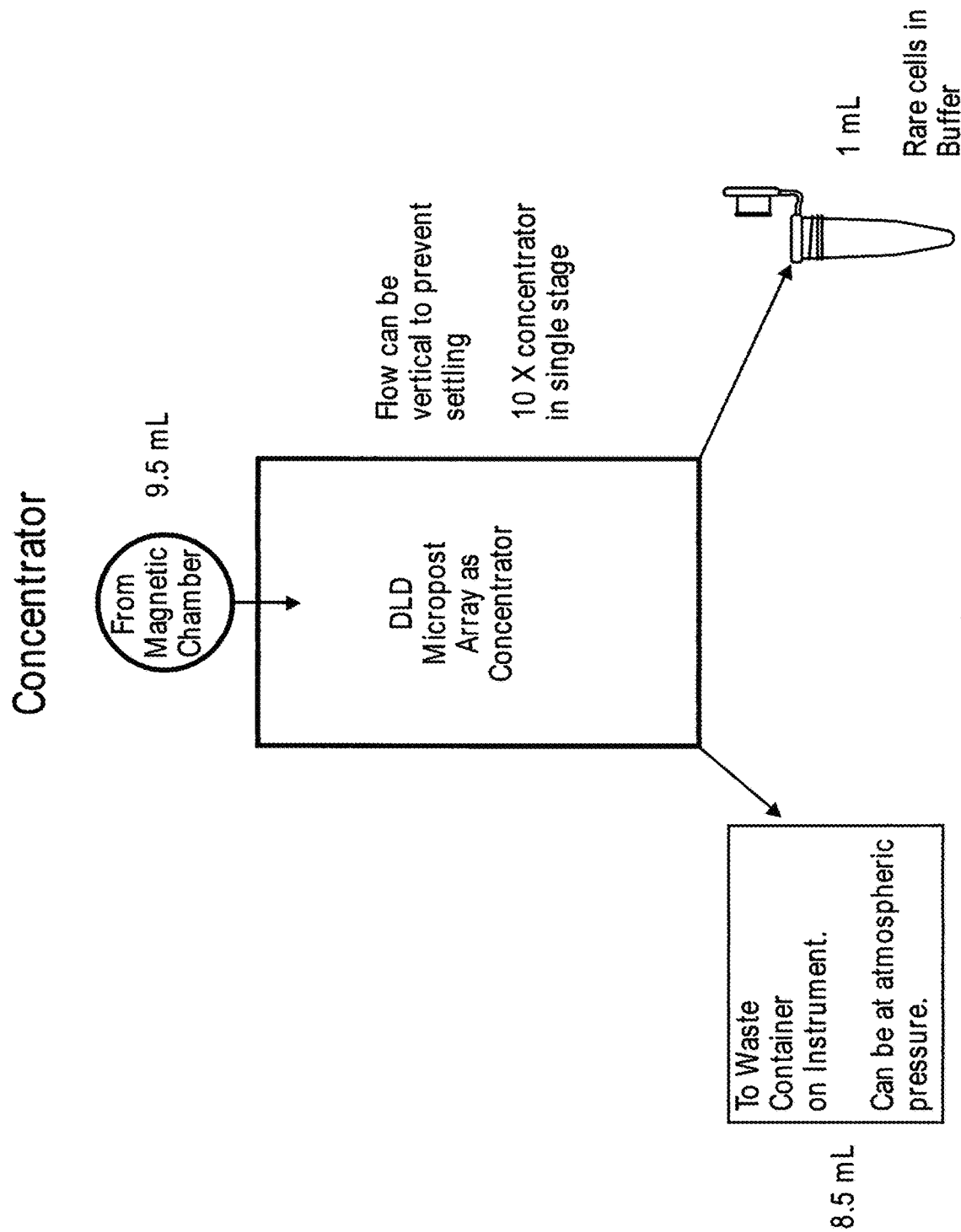
Figure 10E:
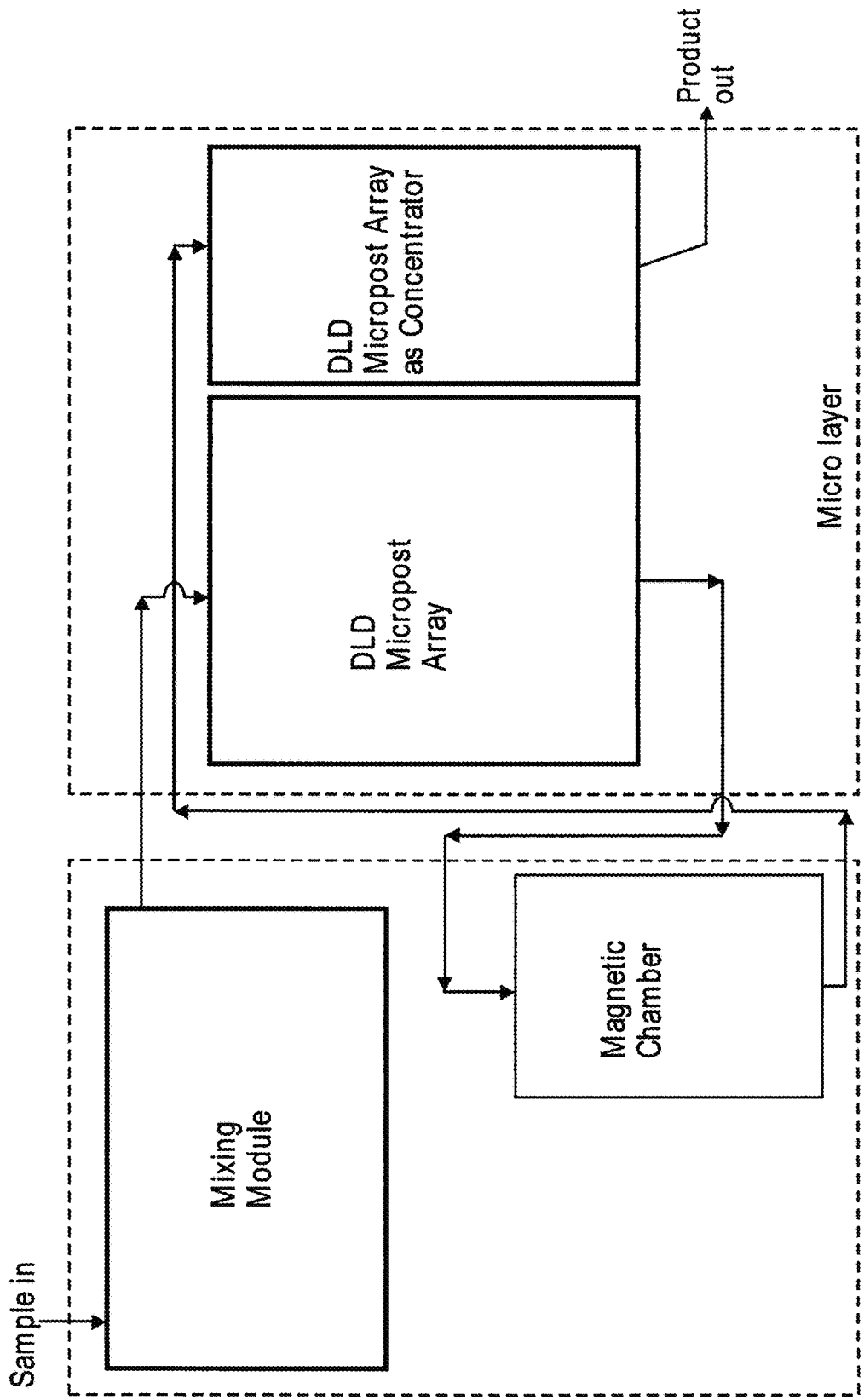

9.5 mL solution from the magnetic chamber is then passed through another DLD array which functions as a concentrator. The DLD array concentrates the rare cells by 10 times in a 1 mL solution (FIG. 10D). The physical layout of the system used in the example is shown in FIG. 10E.

DNA and RNA of the enriched rare cells are isolated for further analysis. Gene expression in the rare cells is analyzed by microarray. Sequences and quantities of DNA and RNA in the rare cells are analyzed by next-generation sequencing. The rare cells are also analyzed using cytometry, e.g., fluorescence-activated cell sorting.

Example 12

Microfluidic methods using deterministic lateral displacement (DLD) can provide an effective and gentle way of processing cells, an example, presented here, being the isolation of circulating tumor cells (CTC's) from 1 in a billion blood cells from Breast Cancer Patients.

Using DLD, a polymer based chip-to-chip approach to purify circulating tumor cells is developed. The first microchip contains an array of microposts arranged to specifically separate cells larger than ~6.0 μm. When connected to a second magnetic-separation chip, the system is capable of positive, or negative, approaches to affinity capturing specific cells following the initial size based discrimination. Under constant pressure, fluid flow through the DLD ensures removal of plasma and RBC's (and particles <6.0 μm) leaving particles >6.0 μm to process through a second chip that is designed to capture magnetized cells, such as WBC's, allowing purification of size discriminated, non-magnetic cells in a continuous process. This approach demonstrates ~4 log fold enrichment of CTC's.

Figure 11A:
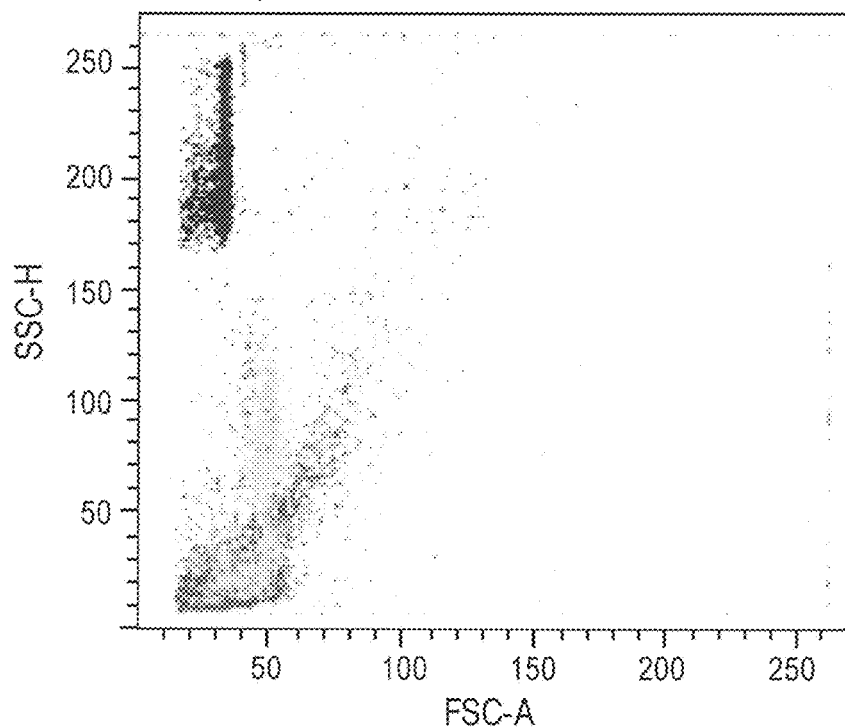
FIGS. 11A-11D illustrate a cell analysis.
Figure 11A:
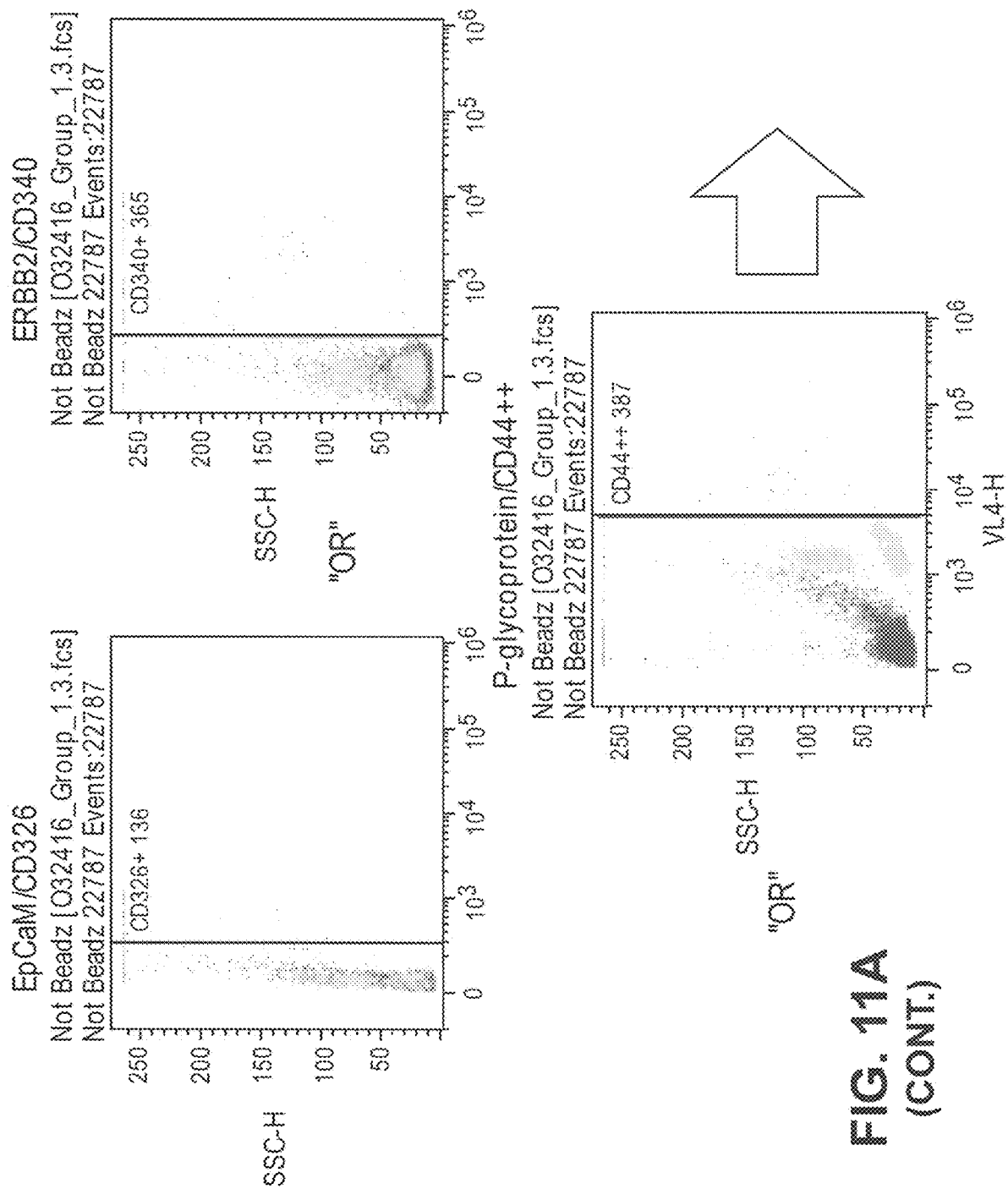
Figure 11A:
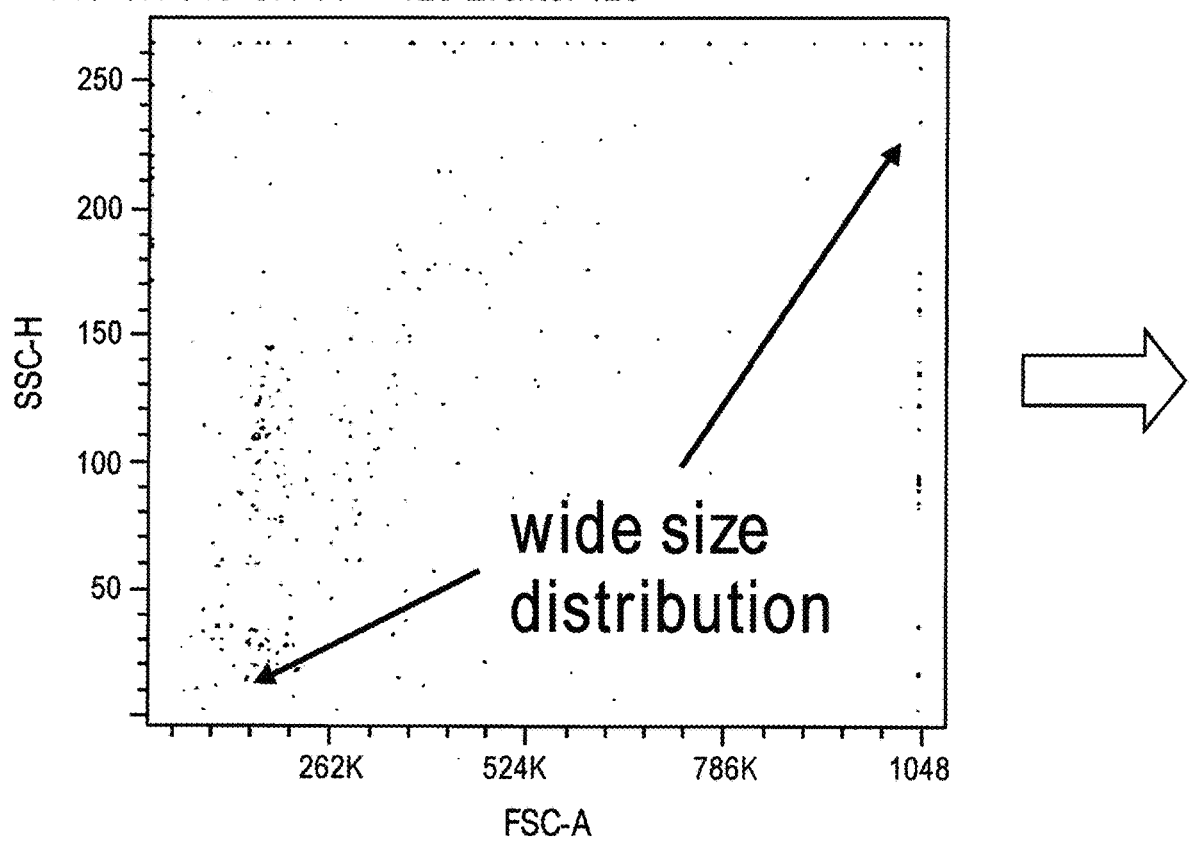
Figure 11B:
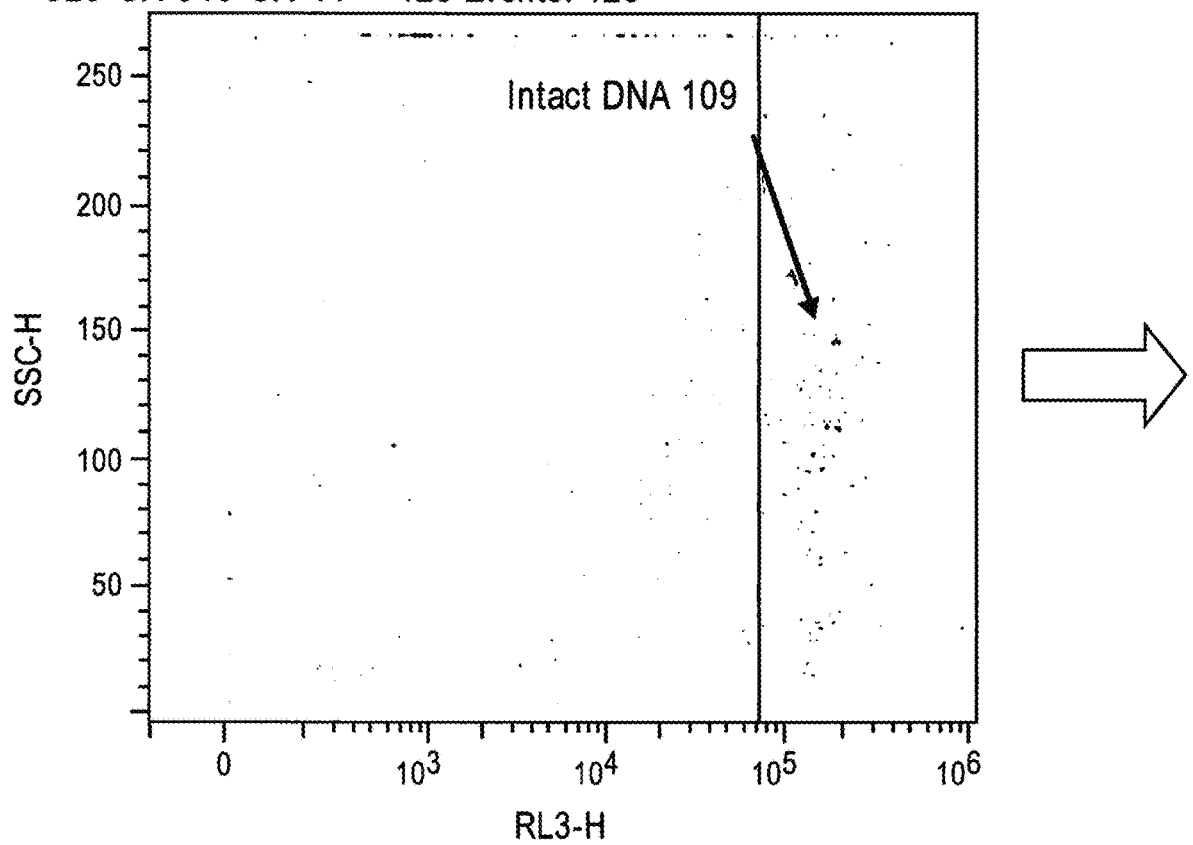
Figure 11B:
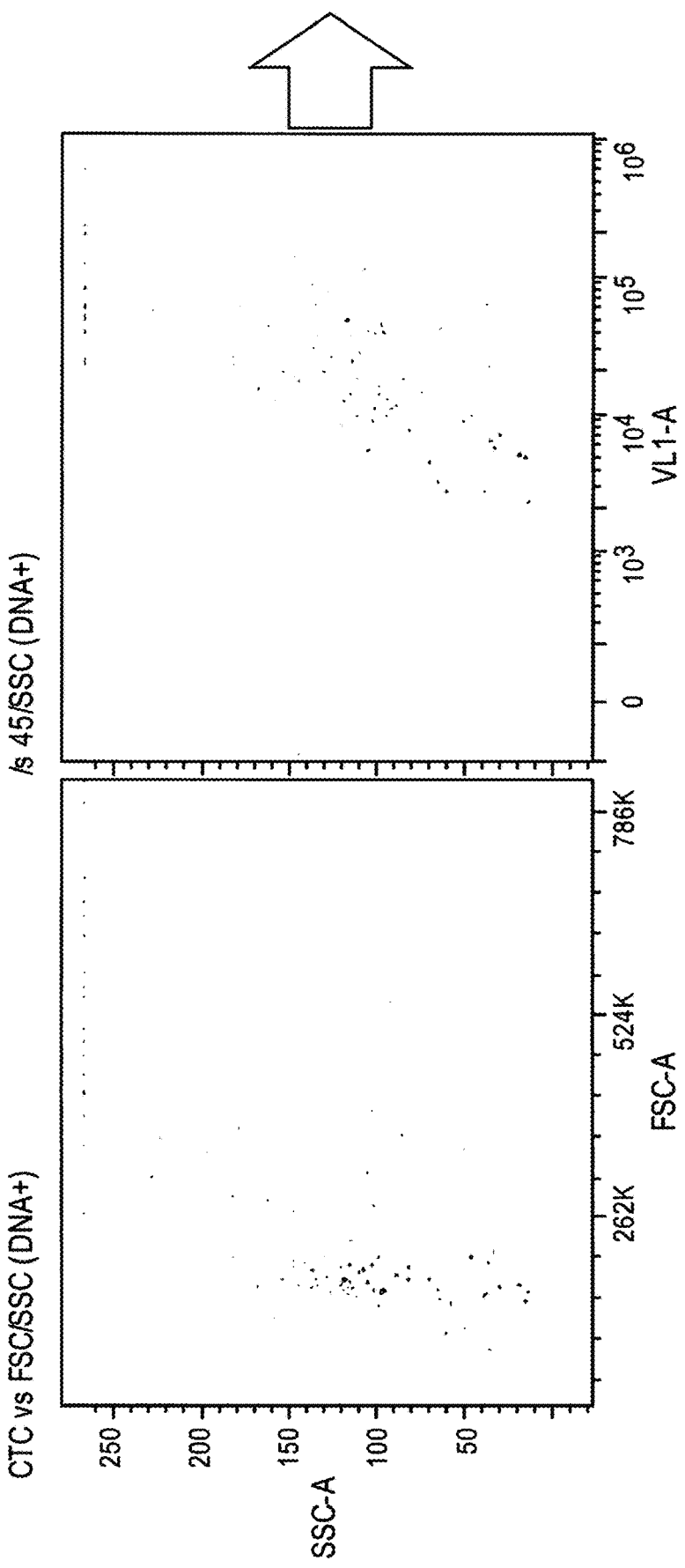
Figure 11B:
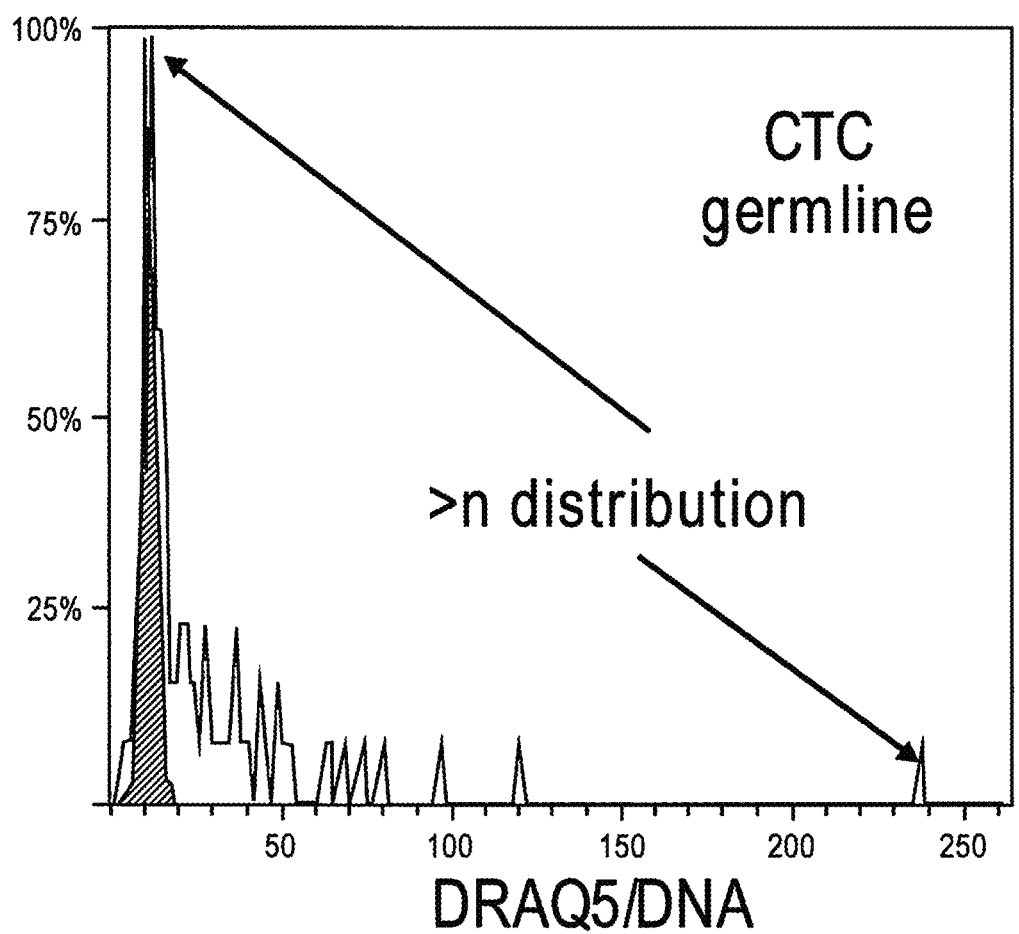
Figure 11C:
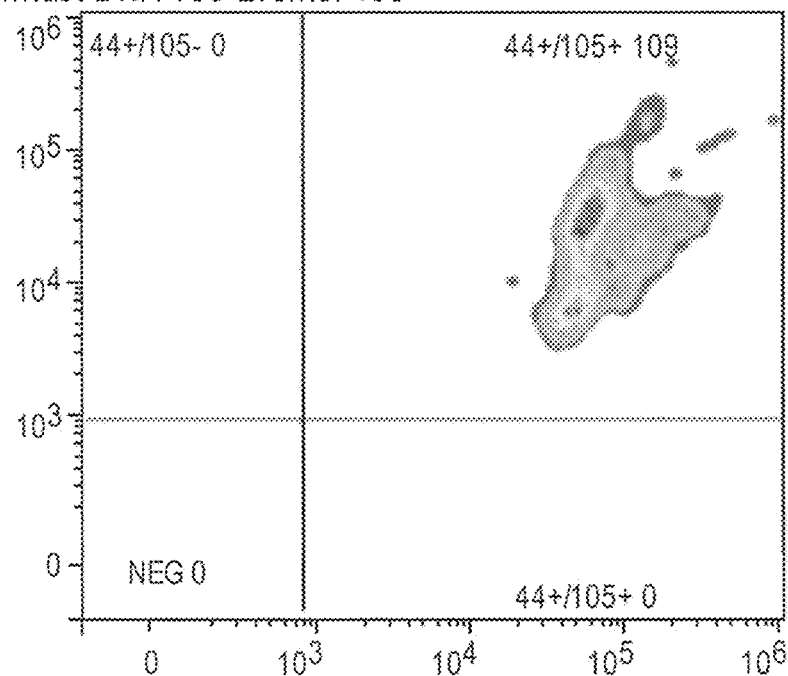
Figure 11C:
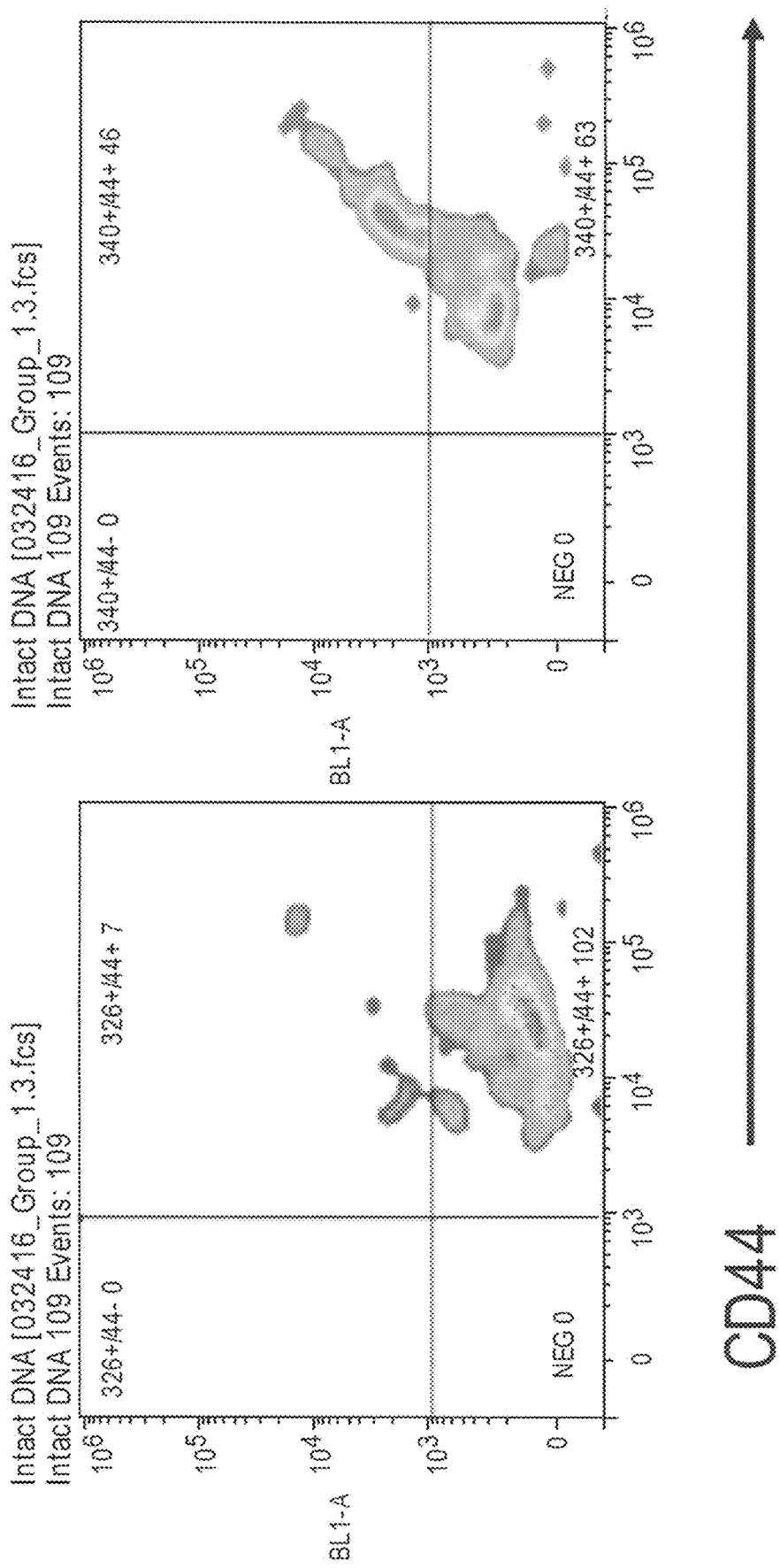
Figure 11C:
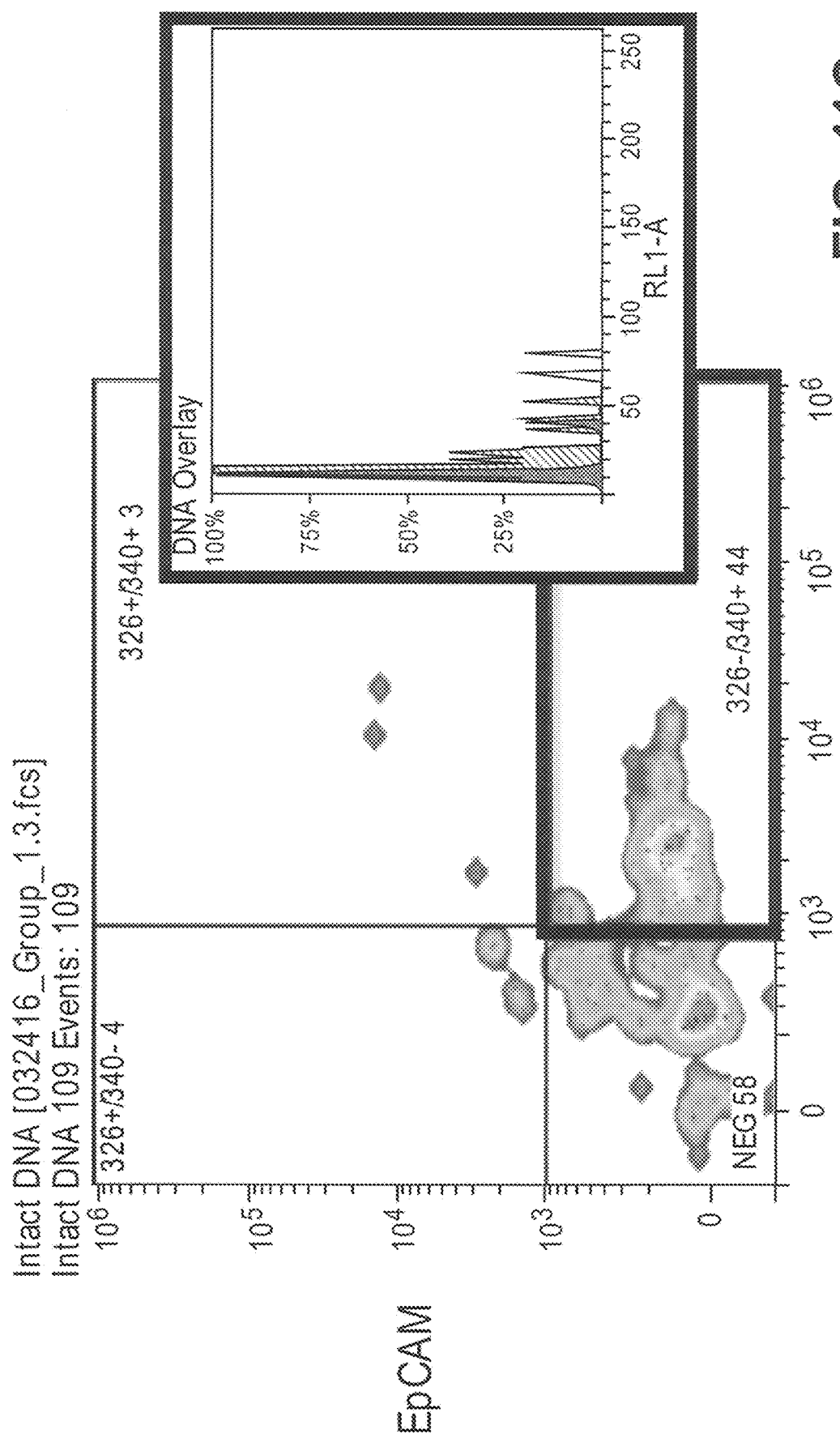

FIGS. 11A-11D illustrates a cell analysis. FIG. 11A DLD-Magnetic chip rare cell/CTC product was evaluated by flow cytometry using a modified Milan protocol to merge 3 "or" gates using P-Glycoprotein/CD44 bright, EpCAM/CD326 and ERBB2/CD340 to identify where potential Breast cancer CTC might reside. FIG. 11B: CTC (DNA+) Mapped to Scatter and CD45 (Size), Blue=CTC (CD326, or CD340, or CD44 bright positive) and evaluated for relative DNA Content. FIG. 11C: Analysis of breast tumor associated markers shows significant heterogeneity of clusters. This example affirms that antibody cocktail based enrichment approaches can miss CTC.

Figure 11D:
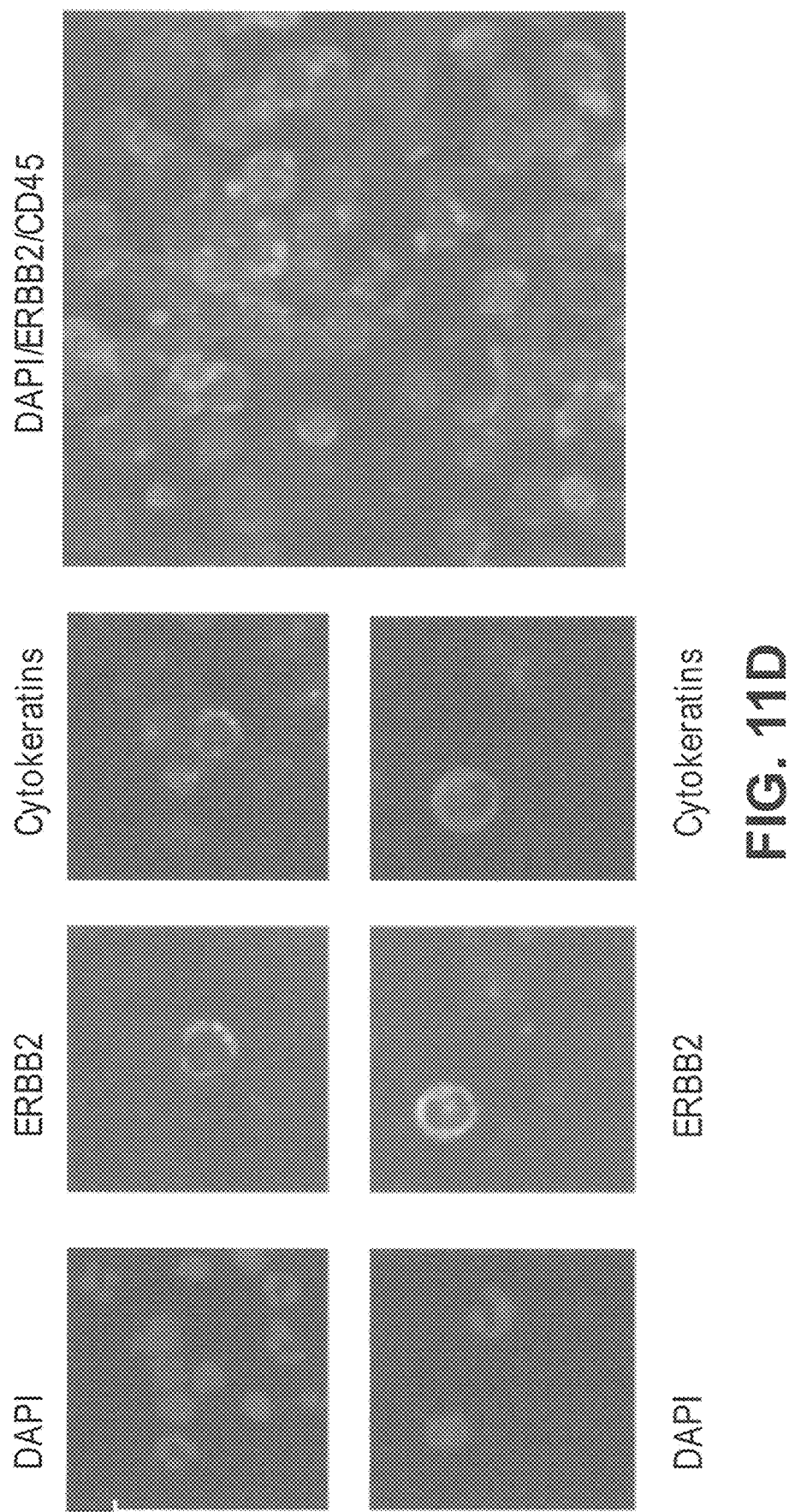

FIG. 11D. Isolated DLD-Magnetic cell product were attached to microscope slides by a cytospin and then fixed, blocked (5% goat serum 2h), and stained overnight with antibodies to pan Cytokeratins, EpCAM, ERBB2 and CD45. Secondary antibodies (Alexa 488/647) were used prior to mounting in anti-fading medium containing DAPI before analysis.

Analysis of DLD-Magnetic chip purified "CTC fraction" enables a closer look at the complexity and heterogeneity of this 1 in a $10^9$ cell population. Enriched CTC's can have a complex set of characteristics including largely differing cell size, wide expression levels of known markers of tumor cells, including CD44, CD105, CD326, and CD340 and their associations with white blood cells.

Example 13

Figure 12A:
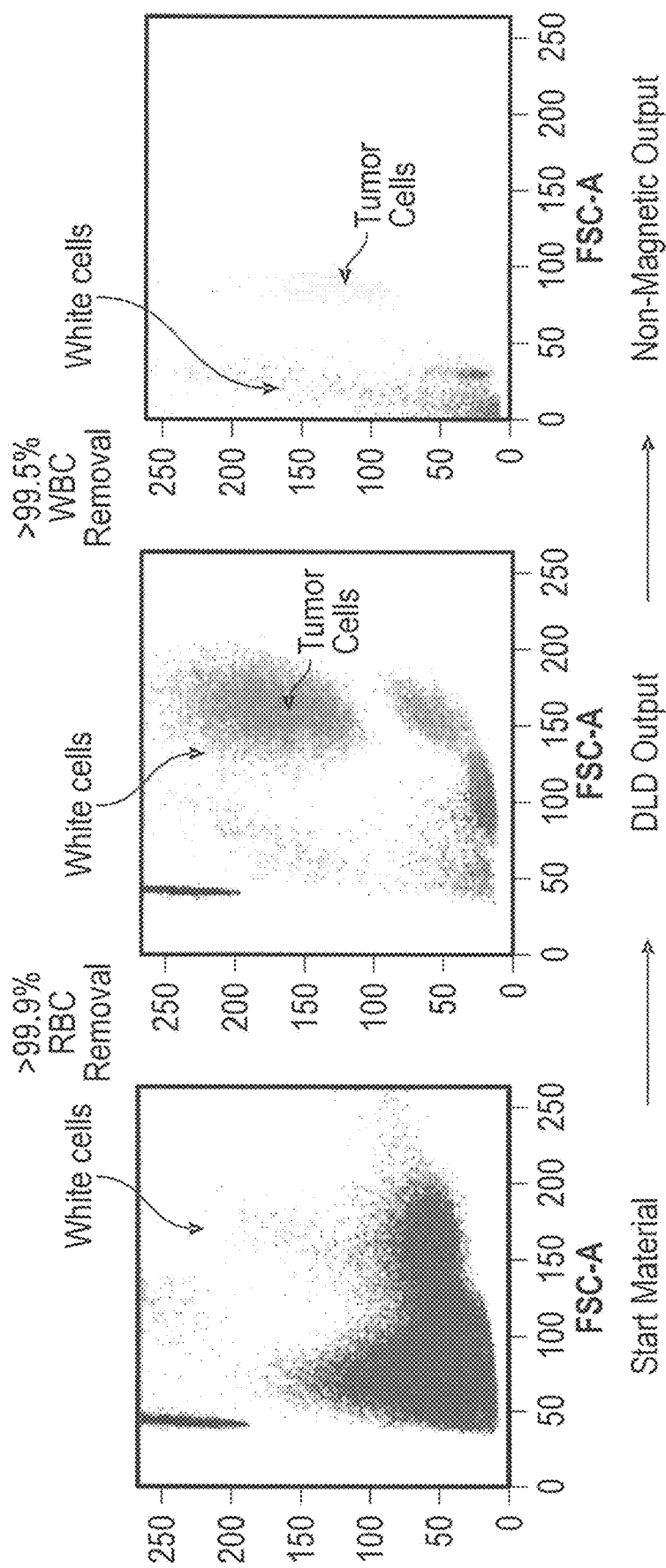
FIGS. 12A-12E illustrate cell isolation.
Figure 12B:
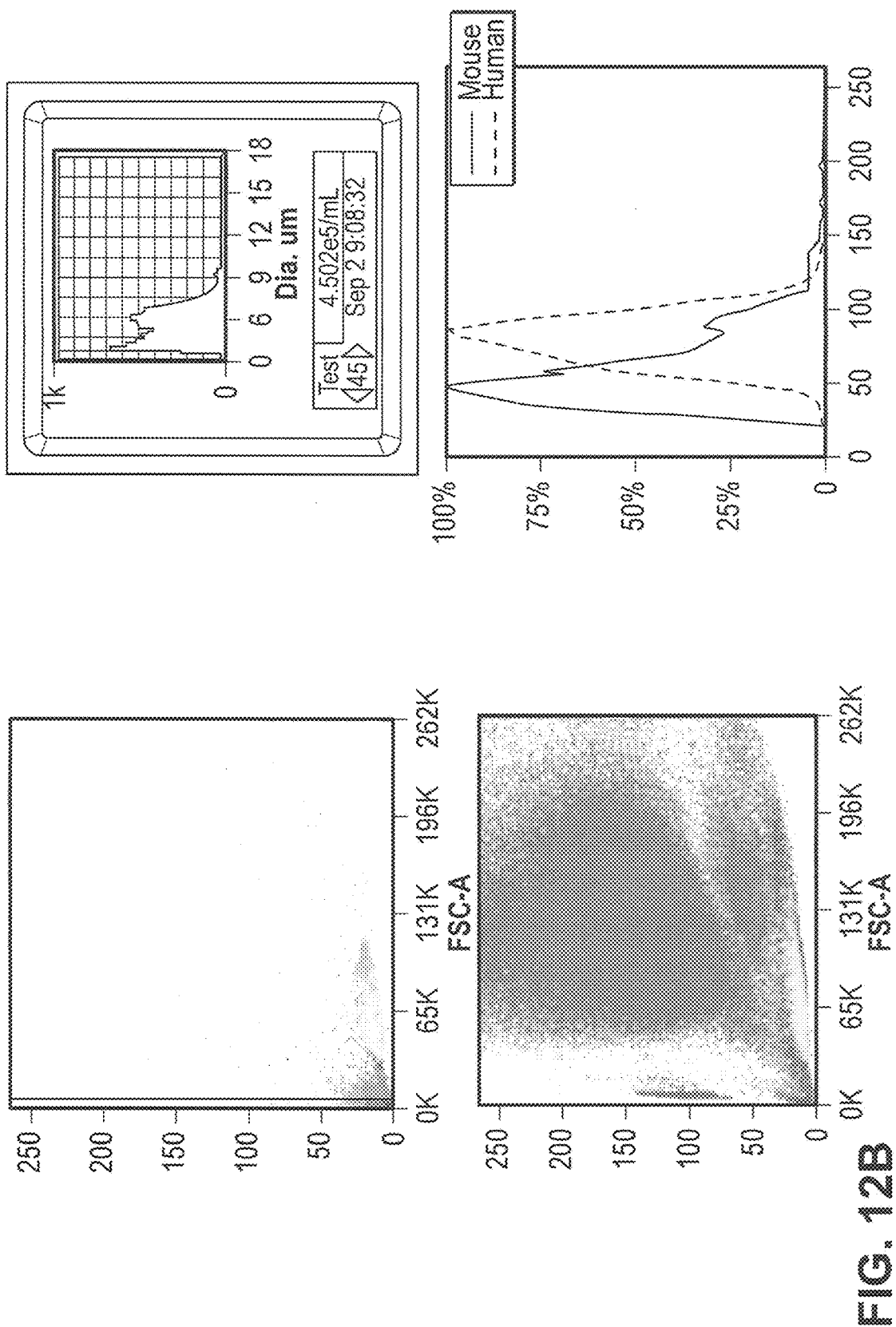
Figure 12C:
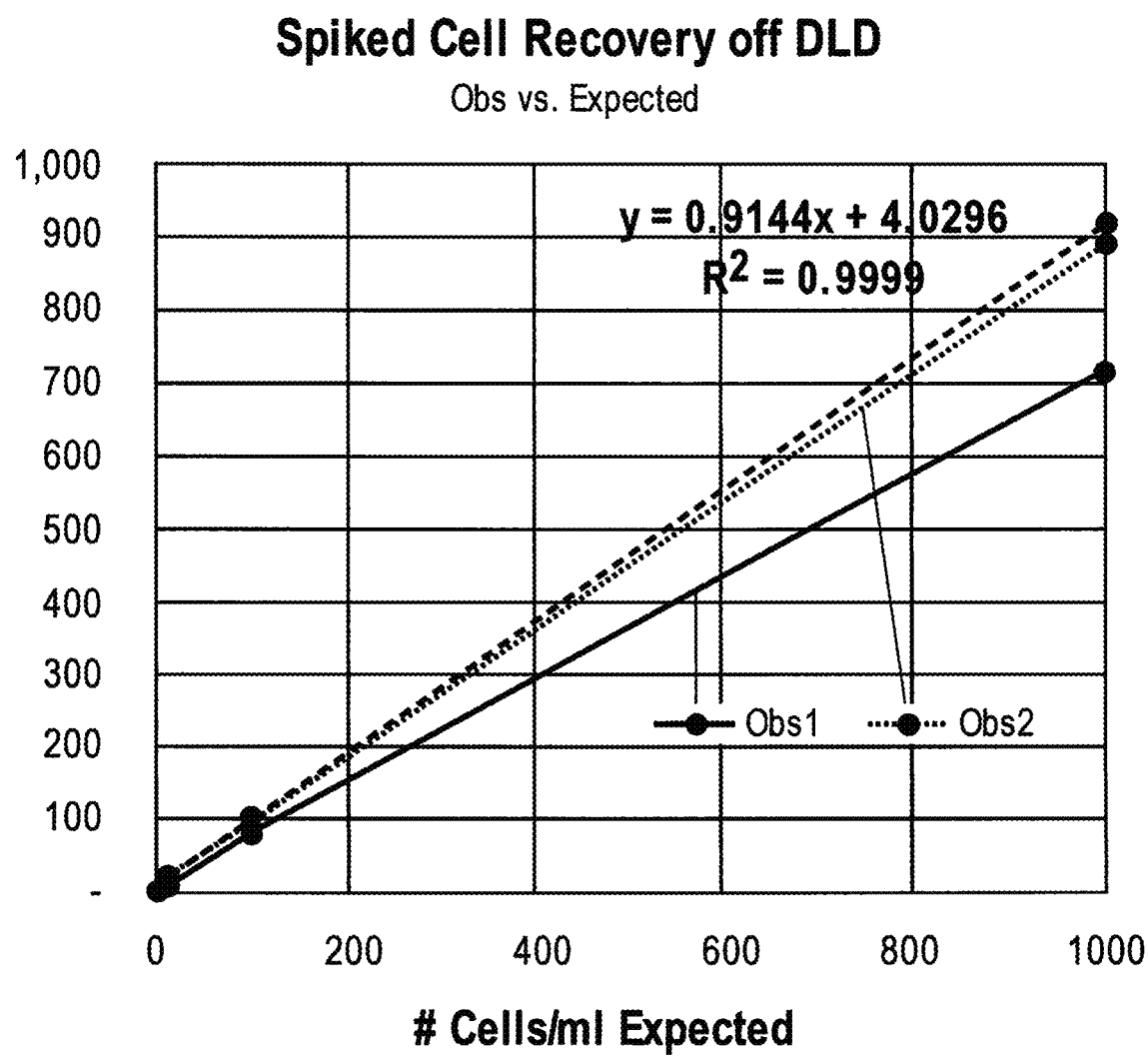
Figure 12D:
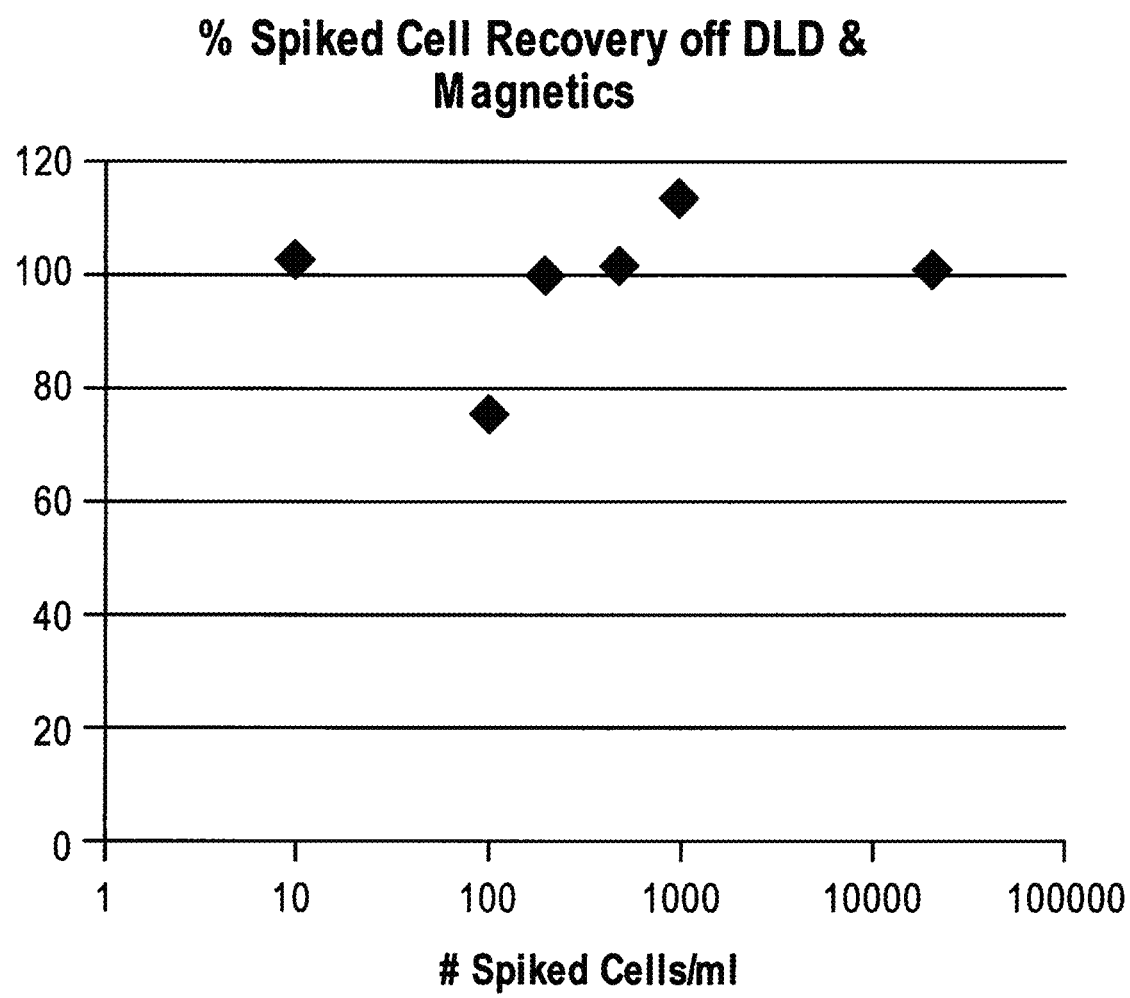
Figure 12E:
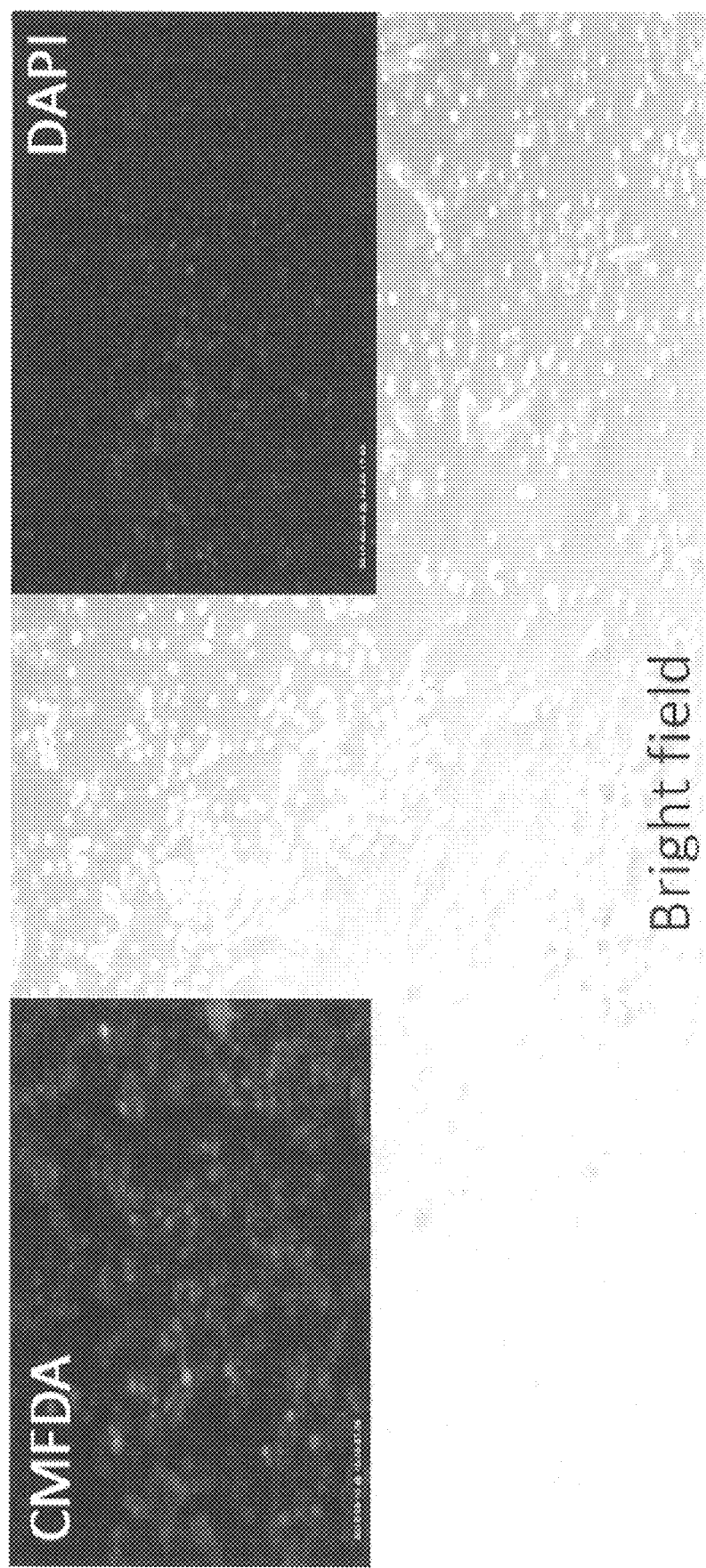

FIGS. 12A-12E illustrate cell isolation. Cells (i.e. MDA-MB-231, SK-BR-3, H1650) labeled with green CMFDA (ThermoFisher) were spiked into blood and incubated with CD45 (eBioscience) and anti-CD66b (Miltenyi) biotinylated antibodies for 10 min followed by 10 min incubation with streptavidin-MNP's (ThermoFisher). Blood is then diluted 1:1 in buffer and loaded onto the chips using a syringe. The system is pressurized at 10 psi, and run until completion. Product cells are collected and analyzed by molecular techniques, flow, imaging or cultured in 24-well plates (Corning). FIG. 12A. Flow cytometric analysis of the blood+cells before processing, after the DLD chip and after the magnetic chip. FIG. 12B. Mouse splenocytes labeled with CMFDA were spiked into normal human blood, processed in the DLD chip and analyzed by flow cytometry to verify the recovery of small cells well below the nominal threshold of most sieve based approaches. FIG. 12C. Linearity of recovery off the DLD was verified by spiking different numbers of CMFDA-labeled cells into whole blood and measured by flow cytometry. FIG. 12D. Average cell recovery of ~95% after the DLD and magnetic chips (n=15 experiments). FIG. 12E. The isolated green-fluorescent MDA-MB-231 cells were cultured for 24 h. The viability of the spiked and recovered cells was >90% (n=3 experiments).

Example 14

Figure 13:
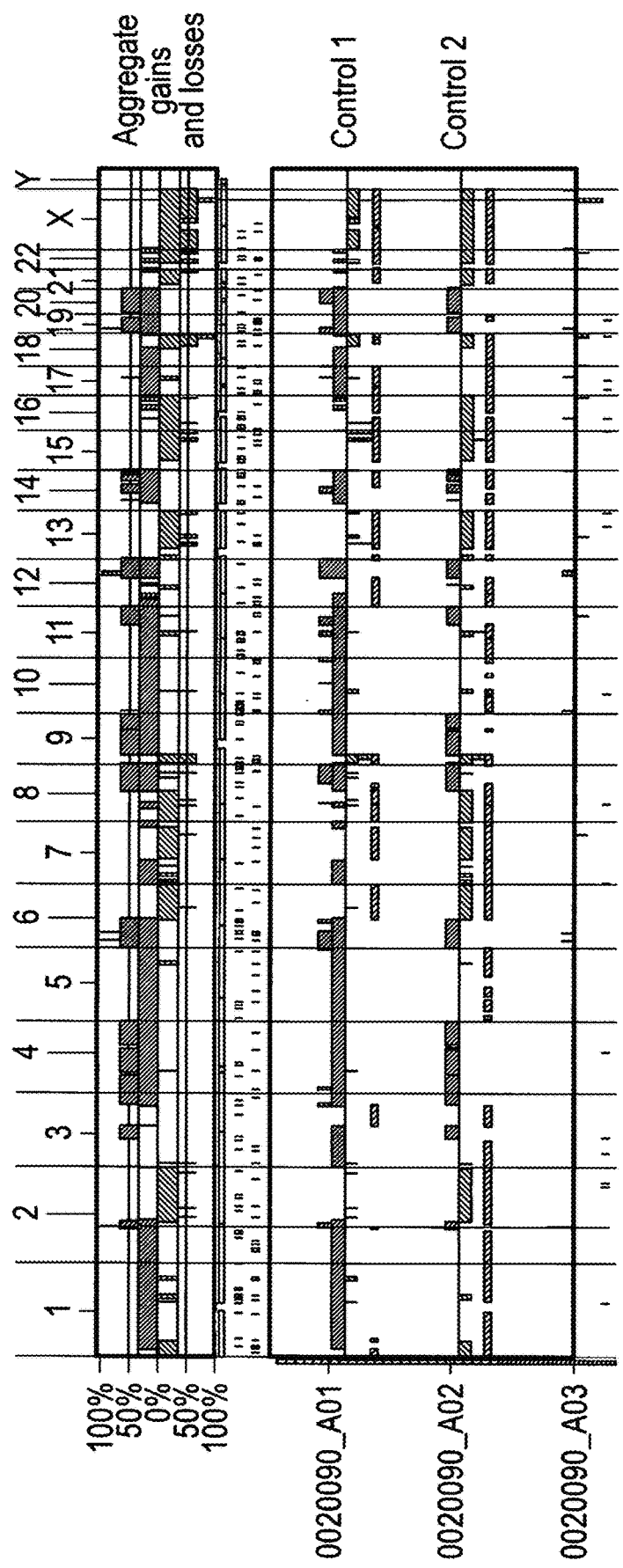
FIG. 13 illustrates molecular assessment of CTCs.

FIG. 13 illustrates molecular characterization of circulating tumor cells. DNA was extracted and purified from the CTC's fraction after the DLD-Magnetic chip separation. The purified DNA was ligated to MIP probes to fill possible gaps, amplified linearized and probed on the OncoScanArray (Affymetrix) containing approximately 900 genes across the human 23 chromosomes to determine copy number variation-indicative of changes in the somatic lineage. Gains (blue) loses (red) and loss of heterozygozity regions (orange).

Approaches provided herein can remove >99.95% of red blood cells and >99.5% of white blood cells. The effective size separation of devices can be greater than 6.0 µm, and therefore can be inclusive of small tumor initiating cells. DLD-Magnetic chip combination can enable recovery and detection of viable rare cells with approximately 4 logs of depletion demonstrated. The chip-to-chip approach can efficiently recover intact cells with a viability of >90% from whole blood, and can be suitable for cell culture and downstream applications. The isolated CTC's can include the characteristic phenotype typical of breast carcinomas ERBB2+/CD45-cells and EpCAM+/Cytokeratin+ as well as non prototypic phenotypes, which can demonstrate the high degree of heterogeneity that can be missed by using defined markers only for identification. Pooled genotypic signatures can confirm the presence of breast tumor cells.

Example 15: Post Geometry Design for High-Throughput Capture of Nucleated Cells from Blood with Reduced Erythrocyte Contamination Using DLD Arrays Overview of Goal When separating nucleated cells, such as cancer cells and leukocytes, from whole blood using deterministic lateral displacement (DLD) arrays, the yield of target cells, as determined by the critical size of the array, was increased. Also, the displacement of erythrocytes, which aligned with the flow in deep-channel DLD arrays such that their critical size was reduced to approximately 2.5 µm, into the product was reduced. As the flow rate, and correspondingly the Reynolds number (Re), increased, post shape was made to achieving these goals.

As the flow rate increased, the shear rate of the fluid in the gap between the posts increased, since the fluid velocity at the surface of the posts bounding the gap was constrained to zero. Shear caused compression of cells, as opposite sides of the cell experienced different fluid velocities. This shear-induced compression of cells reduced yield if the compression reduced the diameter of the cells below the critical size of the array. The shear rate of the fluid near the post, particularly within the first streamline adjacent to the bumping side of the post, was also dependent on post geometry. This was the streamline within which particles (cells) above the critical size of the array reside.

As the flow rate increased, inertial effects affected the behavior of both the fluid and the particles in the DLD array, even though the flow remained laminar. The effect of these inertial effects on the behavior of erythrocytes was critical in reducing erythrocyte displacement into the product at high flow rates. In this example, the Stokes number of erythrocytes did not exceed 0.3 in the experiments. Displacement of particles below the critical size of the array had also been observed at high flow rates, corresponding to Re as high as 30.

Experimental and Model-Based Prediction

Post shapes with vertices pointing into the gap in the bumping direction were identified as reducing shear-induced cell compression that results in reduced yield of target cells. The reduced shear force was because post shapes with vertices pointing into the gap had smaller high fluid shear regions on the side of the posts compared to post shapes that did not.

In the experiments of this example, post shapes that lacked symmetry about an axis parallel to the flow direction resulted in flow-velocity-dependent displacement of erythrocytes into the product comprising cells or cell aggregates larger than erythrocytes. For post shapes that lacked symmetry about an axis parallel to the flow direction, the displacement of erythrocyte into the product was also related to the angle-of-attack of the leading edge of the post into the gap in the bumping direction.

Diamond posts simultaneously achieved the goals of reducing shear-induced cell compression and reducing flow-velocity-dependent erythrocyte displacement into the product. 83% of leukocytes were captured from 3.7 mL of blood in 38 minutes, with less than 0.01% of erythrocytes displaced into the product. This was higher than previously reported leukocyte capture efficiency in a DLD array operated with an average shear rate above 10,000 $s^{-1}$ and represented a nearly 50-fold improvement in terms of blood volume processed, a 20-fold improvement in flow rate, and 100-fold improvement in erythrocyte contamination of the product over the previously reported largest scale separation of leukocytes from blood.

Quantitative and qualitative models were developed to predict shear-induced cell compression and flow-velocity-dependent erythrocyte displacement for different post shapes. Post shapes with a vertex facing into the gap in the bumping direction were predicted to reduce shear-induced cell compression. Quantitatively, such post shapes were predicted to reduce the shear from fluid bending around the post, strongly correlating with shear-induced cell deformation. Post shapes with symmetry about an axis parallel to the average flow direction were predicted to reduce flow-velocity-dependent erythrocyte contamination of the product. For post shapes that lacked symmetry about an axis parallel to the flow direction, the amount of flow-velocity-dependent erythrocyte displacement was related to the angle-of-attack of the leading edge of the post into the gap in the bumping direction. The mechanism driving flow-velocity-dependent displacement of erythrocytes for post shapes lacking symmetry about an axis parallel to the flow direction was similar to the mechanism upon which pinched-flow fractionation was based. Quantitatively, the amount of flow-velocity-dependent erythrocyte displacement was predicted by integrating the centripetal acceleration (acceleration perpendicular to the streamlines) weighted by the vertical velocity (parallel to the flow direction) across the width of the gap.

Post shapes in which a larger fraction of the flow occurred closer to the center of the gap were used to overcome the effect of steep tilt ageless (e.g., title >1/40). To this end, teardrop posts were used (FIGS. 14A and 14B). A larger fraction of the flow was closer to the center of the gap with teardrop posts compared with diamond posts because there was more surface area along the edge of the post at which the fluid velocity was constrained to zero for the teardrop posts compared to the diamond posts.

Figure 15:
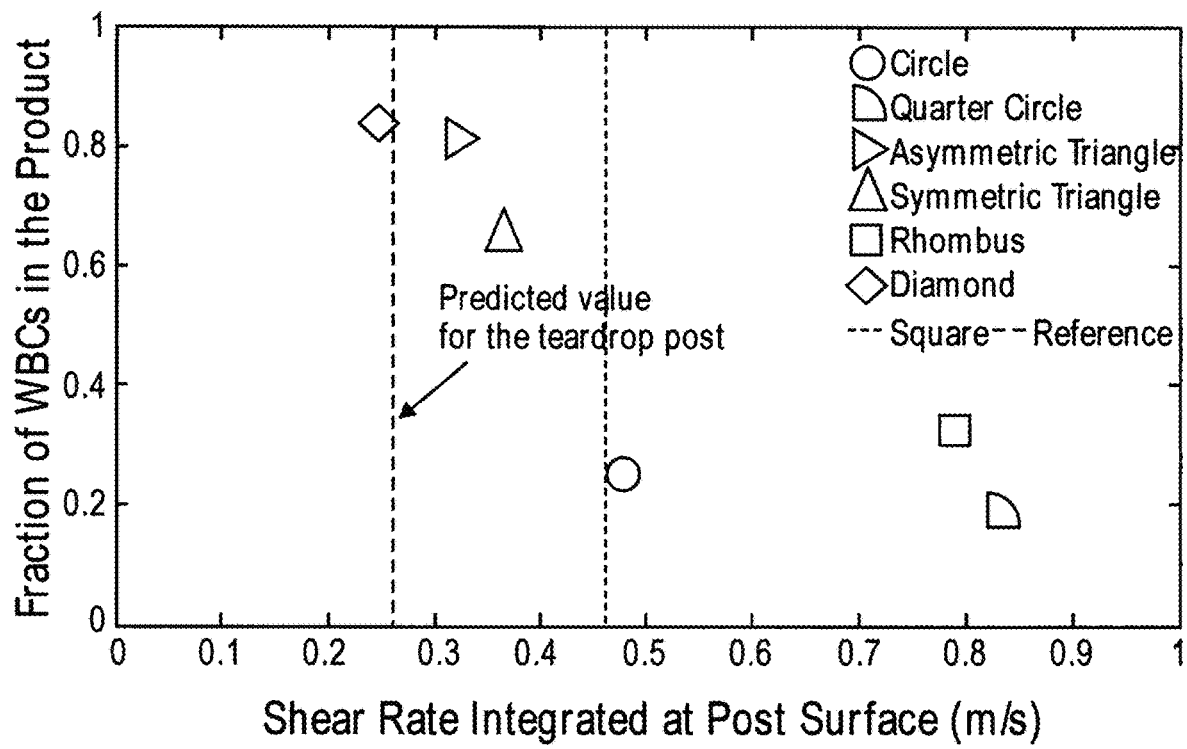
FIG. 15 shows experimentally observed fraction of leukocytes displaced into the product versus the shear rate from fluid bending around the post integrated at the surface of the post against which the cell was compressed for six different post shapes.
Figure 16:
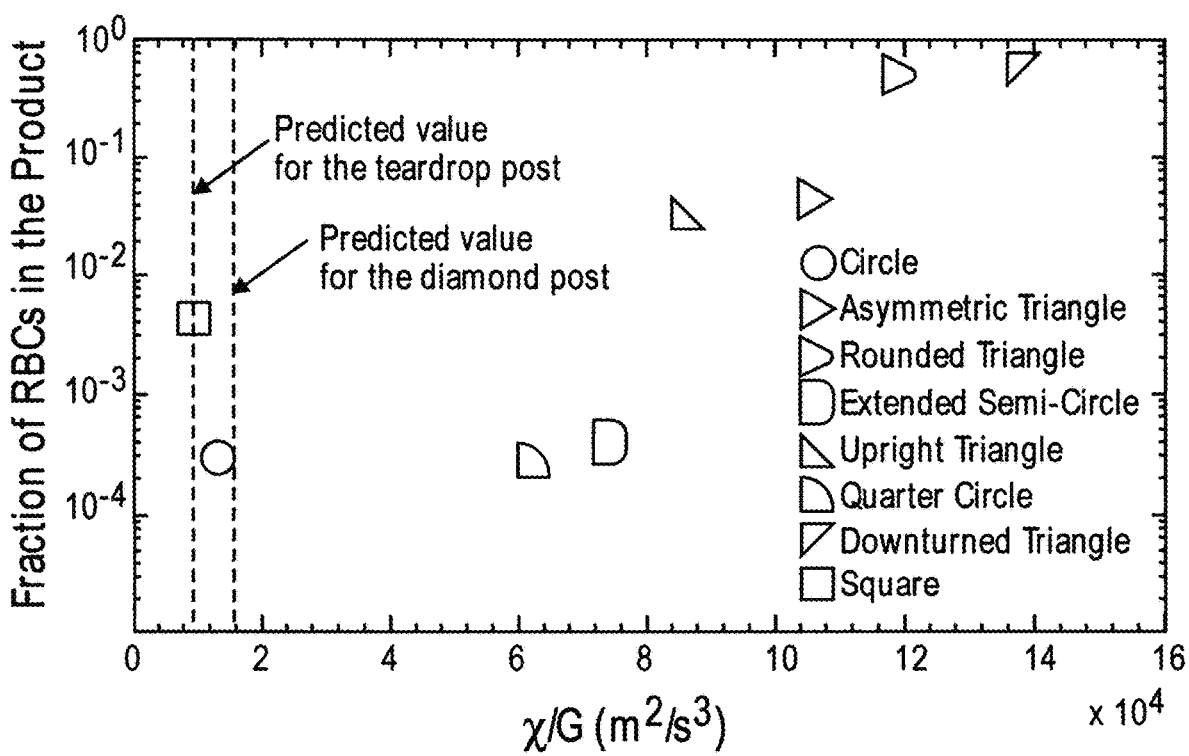
FIG. 16 shows experimentally observed fraction of erythrocytes displaced into the product versus the integral of the centripetal acceleration multiplied by the vertical velocity across the width of the gap for eight different post shapes.
Figure 17:
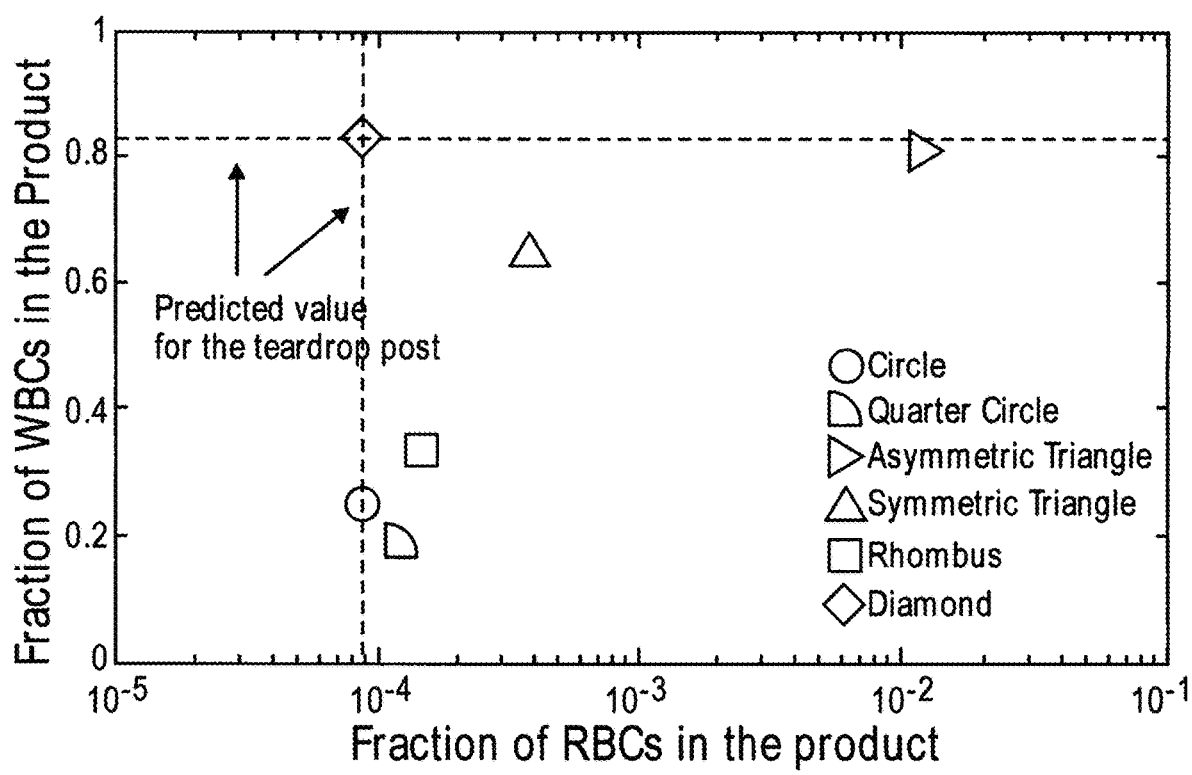
FIG. 17 shows experimentally observed fraction of leukocytes displaced into the product versus fraction of erythrocytes displaced into the product for six different post shapes.

Like diamond posts, teardrop posts also had a vertex pointing into the gap, which reduced shear-induced cell compression, as observed by a particle flowing from top to bottom as the posts were oriented in FIG. 14C. It was predicted that the extent of shear-induced cell compression was only 10% greater with tear drop posts compared with diamond posts (FIG. 15). Furthermore, both diamond posts and teardrop posts were symmetric about an axis parallel to the flow direction, which reduced flow-velocity-dependent erythrocyte displacement into the product. Due to more of the flow being closer to the center of the gap, tear drop posts was predicted to be more resistant to asymmetry created by the tilt of the array at steeper tilt angles. A parameter, X, was identified to predict the extent of flow-velocity-dependent displacement of erythrocytes into the product based on asymmetry in the fluid centripetal acceleration distribution in the gap. This parameter was about 30% lower for teardrop posts compared with diamond posts (FIG. 16), which indicated a greater resistance to asymmetry from the tilt of the array at steeper tilt angles. Using the quantitative models developed herein, the leukocyte yield, which was reduced by shear-induced cell compression, and the amount flow-velocity-dependent displacement of erythrocytes in to the product for teardrop posts were predicted (FIG. 17).

Conclusions

The optimal post shape for high-throughput capture of nucleated cells from blood had two characteristics: (1) high nucleated cell (leukocyte or cancer cell) collection efficiency and (2) low collection efficiency of undesired erythrocytes. The first characteristic involved low fluid shear at the post surface against which the cell was compressed and was achieved using post shapes that have a vertex pointing into the gap in the bumping direction. The second characteristic involved that the flow in the gap had a symmetric centripetal acceleration distribution and was satisfied using post shapes that are symmetric about an axis parallel to the average flow direction in arrays with shallow tilt angles (tilt <$\frac{1}{20}$).

Figure 20:
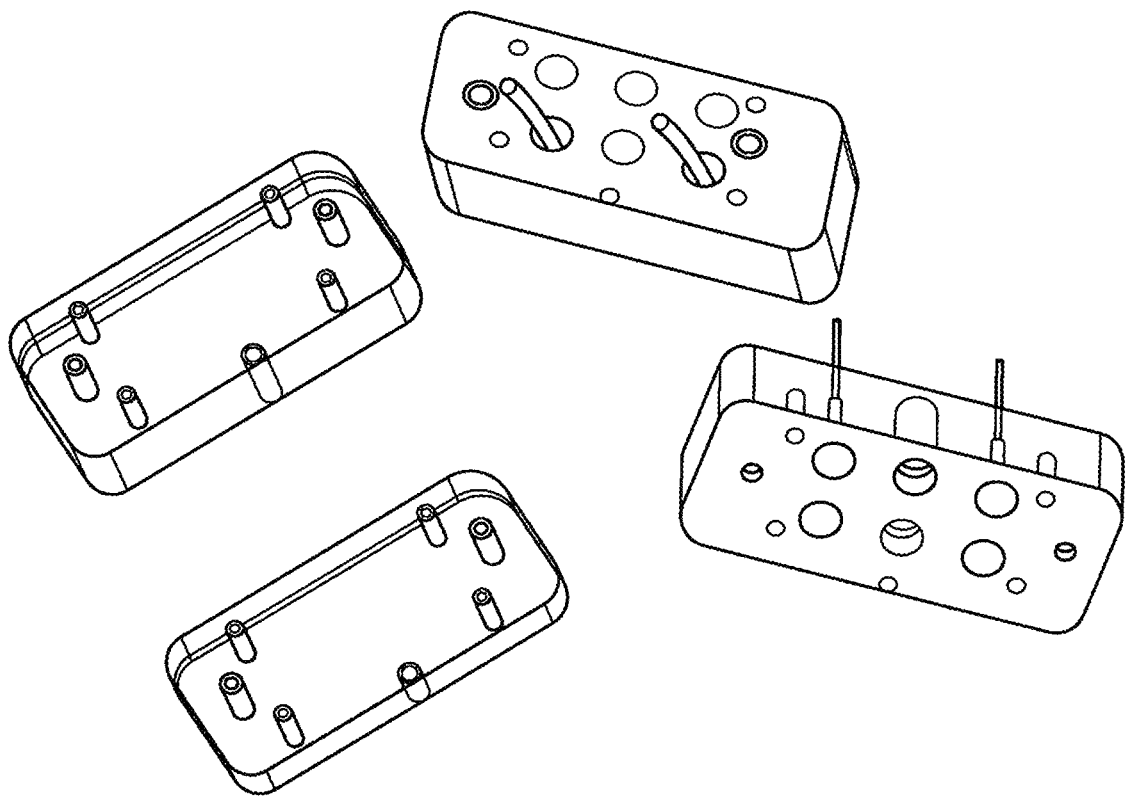
FIG. 20 illustrates manifold, tubing, and ferrules.
Figure 21:
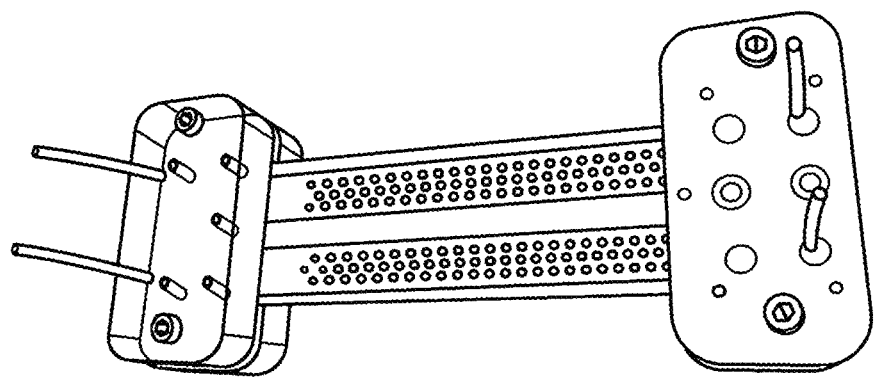
FIG. 21 illustrates a magnetic chamber chip with manifolds.

Example 16: DLD/Magnetic Setup with Magnets Holder for Trapping Magnetically Labeled Cells FIG. 20 illustrates manifold, tubing, and ferrules. FIG. 21 illustrates a magnetic chamber chip with manifolds. Slip the flangeless ferrules over 3 cm long of 0.03" tubing. Insert the tubing with the ferrule into the receiving port on the manifold. Position the magnetic chamber on the manifold to ensure that the inlet and outlet ports of the magnetic chip is aligned with the through holes on the chip. Make adjustments to the chip position as needed. Use an allen head screw driver to tighten until manifold is uniformly tightened (FIG. 21). Place manifold and chip in clamp on ring stand. Channels should be in vertical orientation, with inlet connections on top (FIG. 22).

Figure 22:
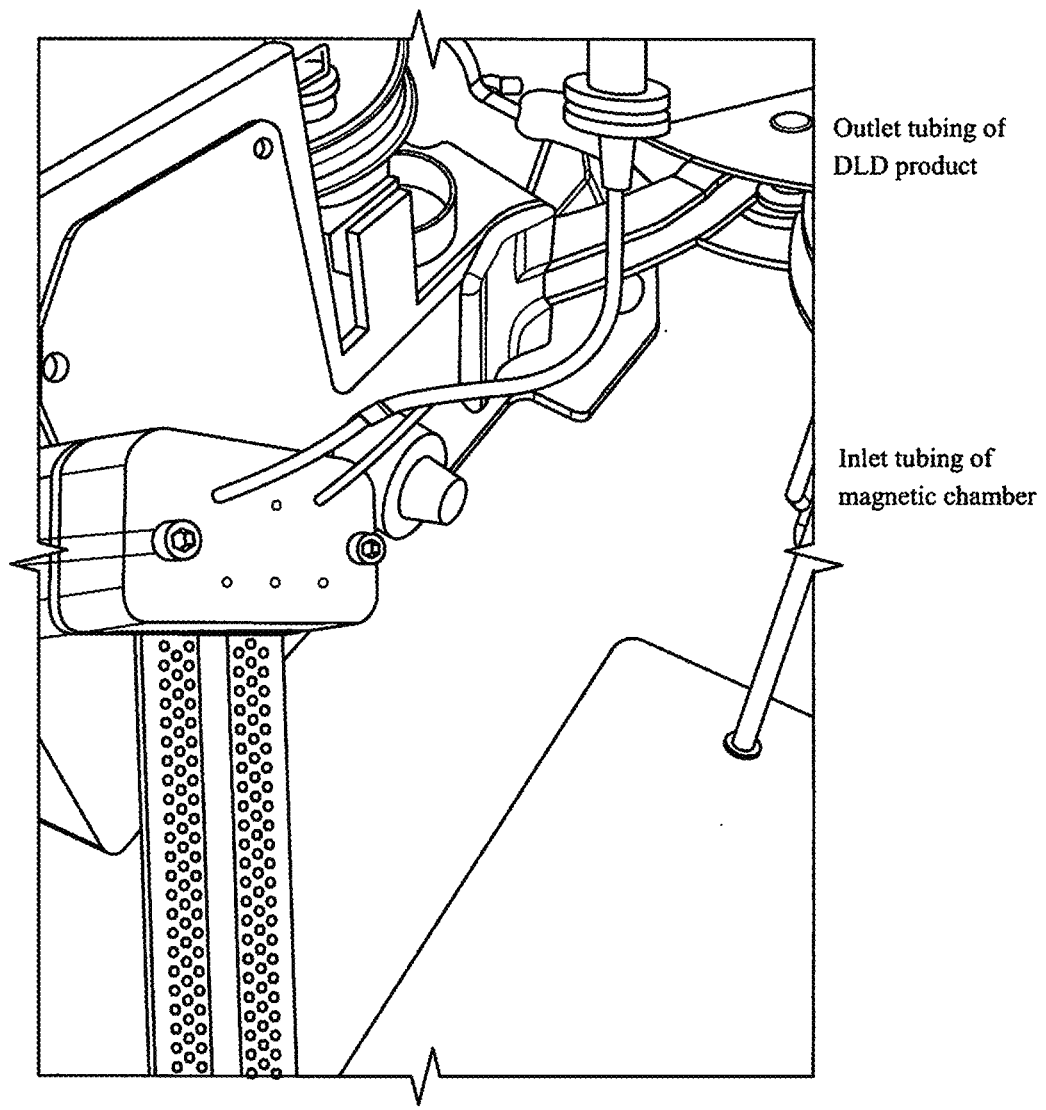
FIG. 22 illustrates a magnetic chamber connected in series to the DLD line.
Figure 23:
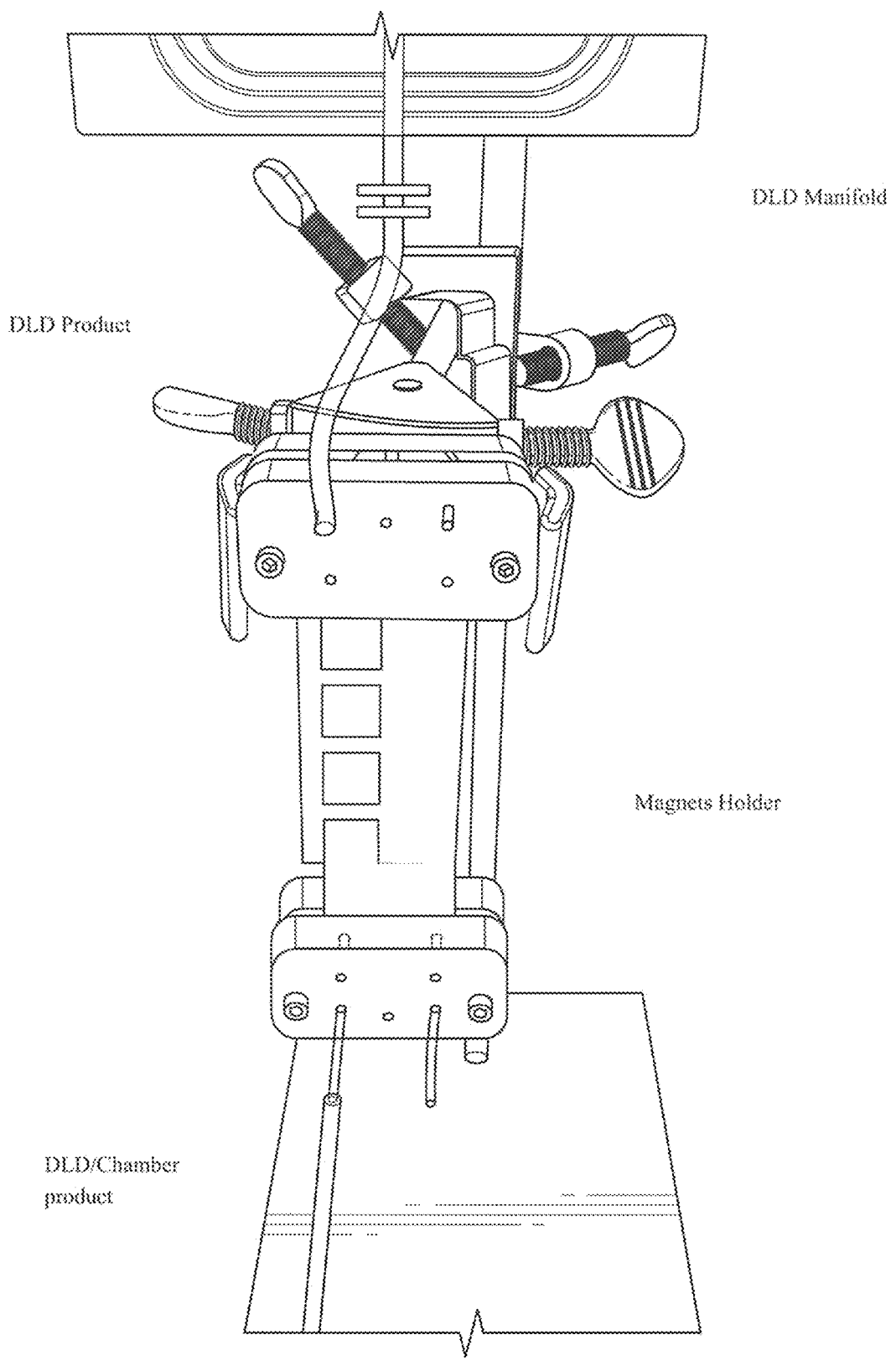
FIG. 23 illustrates DLD/Magnetic setup with magnets holder for trapping magnetically labeled cells.

FIG. 22 illustrates a magnetic chamber connected in series to the DLD line. FIG. 23 illustrates DLD/Magnetic setup with magnets holder for trapping magnetically labeled cells.

Priming Chip (Connecting to the DLD)

To prime the magnetic chip, connect the inlet tubing of the magnetic chamber to the DLD product line. Hold the chip vertically and allow the buffer to fill the chamber completely (and to prevent air bubble from forming in the chip). Assemble the magnets holder on the chip with the tape side facing the magnets.

Sample Run:

Remove 1% F127/PBS buffer from the blood syringe using a pipette. Load filtered diluted (1:1) blood (from blood prep above) into blood sample syringe, being careful that no air is trapped at bottom of syringe or at entry to tubing. Put the stopper on blood sample syringe and turn on pumps to 10 psi (buffer) and 8.7 psi (blood). Remove the clamp from the buffer syringe first, then remove clamp from blood sample inlet tubing and allow blood to enter the chip. As blood is visibly entering the chip replace RBC and WBC collection tubes to collect the samples with minimal dilution. Allow blood to run through the chip. When sample reaches the syringe neck and passes the luer connection, clamp the sample inlet tube and turn off the sample pump. Open the stopper on the sample syringe and add 1.0 mL of buffer into the sample syringe to do a buffer flush. Place the stopper back on the sample syringe, turn the pump on, and release the clamp. Allow the sample to flow into the inlet tubing until it almost reaches the metal sample inlet (DLD manifold), then clamp the sample inlet tube—RUN IS COMPLETE. Clamp the buffer inlet tube and turn off air pressure.

Clean Manifold:

Unscrew manifold from chip. Rinse manifold with H2O—forcing H2O through the outlets and inlets. Rinse with 10% Bleach solution—forcing it through the outlets and inlets. Rinse once again with DI $H_2O$ Allow to dry or use pressurized air to force any remaining fluid out of inlets/outlets.

Example 17: DLD Setup

Figure 24:
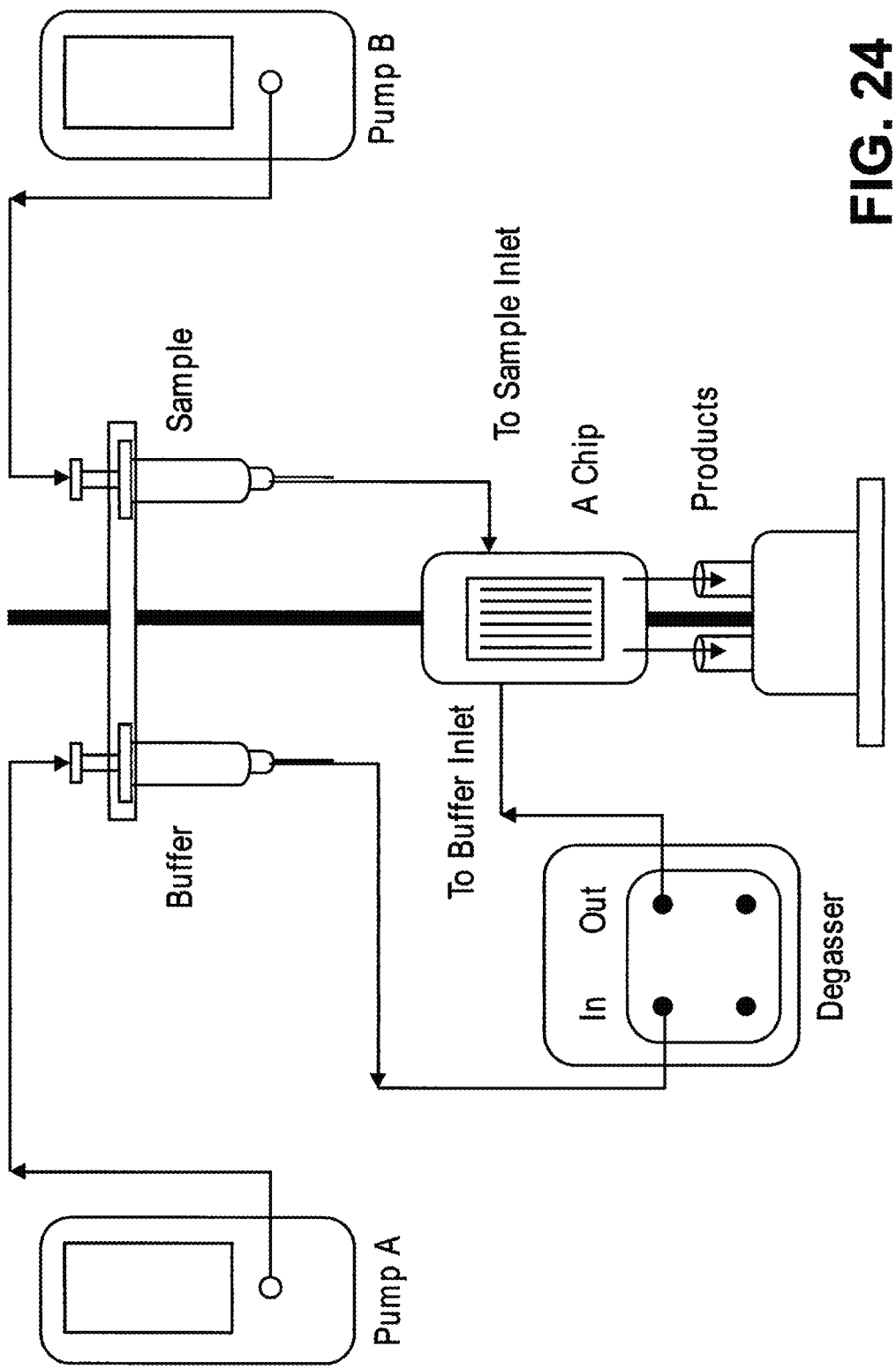
FIG. 24 illustrates a schematic of a DLD system setup.
Figure 25:
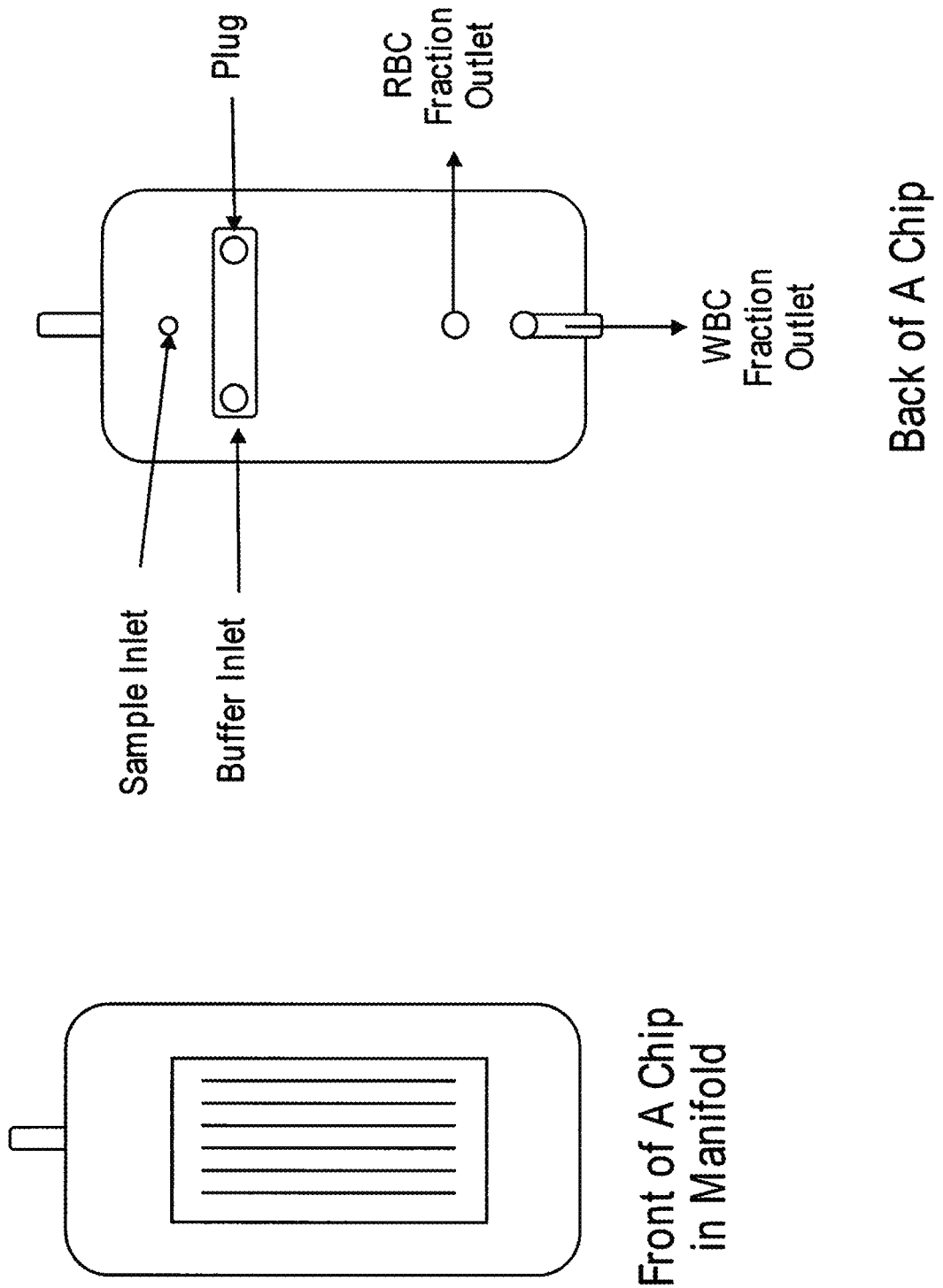
FIG. 25 illustrates a schematic of a chip in a manifold and tubing connections.

FIG. 24 illustrates a schematic of a DLD system setup. FIG. 25 illustrates a schematic of a chip in a manifold and tubing connections.

Priming Chip:

Clamp the buffer inlet tubing, to completely pinch it off. Add 20 mL of 1% KP/10 mM EDTA/PBS buffer to the buffer syringe. Place stopper into buffer syringe and set pump to 3 psi (blood syringe is not capped and is at atmospheric pressure). Turn on in-line degasser. Turn on pump A (Buffer pump) and release clamp; buffer will flow through the degasser, enter the chip and slowly advance through the arrays. Allow buffer to completely fill the buffer chamber, then close the buffer chamber outlet with a male luer 'plug' to start priming the chip. Inspect array and confirm it is filled all the way to exit channels, then increase pressure to ~10 psi to flush air/bubbles from tubing lines and fill dead spaces at outlet ports with buffer. Allow buffer to fill blood sample inlet tubing—as soon as buffer passes the luer connection and enters the syringe (fluid front is accessible at bottom of syringe), clamp blood sample inlet tubing and force all buffer to the RBC and WBC fraction outlet tubing. Add 5 mL of buffer to the blood syringe by loading the buffer directly where the luer connection is, being careful so no air is trapped at bottom of syringe or at entry to tubing. Place stopper on blood syringe and pressurize the buffer channel to 10 psi and the sample channel to 8.70 psi (turn on pressure and release both clamps). Run for ~5 minutes to prime the chip. Inspect inlet port in manifold and confirm that any bubbles trapped during priming have been dissolved. If bubbles remain, continue to flow buffer from both syringes for an additional ~5 min. Clamp both buffer and blood tubes and turn off pressure.

Blood Prep:

Mix blood well and dilute 1:1 with non-degassed 1% KP/10 mM EDTA/PBS buffer. Mix well and filter through 20 μm filter. Sample is ready to load.

Sample Run:

Remove 1% KP/10 mM EDTA/PBS buffer from the blood syringe using a pipette. Load filtered diluted (1:1) blood (from blood prep above) into blood sample syringe, being careful that no air is trapped at bottom of syringe or at entry to tubing. Put the stopper on blood sample syringe and turn on pumps to 10 psi (buffer) and 8.7 psi (blood). Remove the clamp from the buffer syringe first, then remove clamp from blood sample inlet tubing and allow blood to enter the chip As blood is visibly entering the chip replace RBC and WBC collection tubes to collect the samples with minimal dilution. Allow blood to run through the chip. When sample reaches the syringe neck and passes the luer connection, clamp the sample inlet tube and turn off the sample pump. Open the stopper on the sample syringe and add 1.0 mL of buffer into the sample syringe to do a buffer flush. Place the stopper back on the sample syringe, turn the pump on, and release the clamp. Allow the sample to flow into the inlet tubing until it almost reaches the metal sample inlet, then clamp the sample inlet tube—RUN IS COMPLETE. Clamp the buffer inlet tube and turn off air pressure.

Air Purge (Optional):

Allow sample to run through the chip and then air to follow the sample into the chip and force air into the RBC and WBC collection containers—RUN IS COMPLETE—Clamp buffer inlet tube and turn off air pressure.

Clean Manifold:

Unscrew manifold from chip. Rinse manifold and gasket in warm H2O—forcing H2O through the outlets and inlets. Rinse with DiH2O—forcing H2O through the outlets and inlets. Rinse with 70% Isopropanol—forcing it through the outlets and inlets. Allow to dry or used canned air to force any remaining fluid out of inlets/outlets.

Clean Degasser and Tubing

Connect a 30 mL syringe filled with ~30 mL $H_2O$ to the inlet tubing of the in-line degasser. Manually flush the entire volume through the degasser over ~30 s to 1 min. Disconnect the syringe and remove the plunger. Refill the syringe with ~20 mL 70% Isopropanol, and flush again. Purge the system with air using and empty syringe, confirming that no more liquid is expelled from the tubing.

Materials List:

Chip Assembly: 2 piece manifold for holding chip (with 6 screws); PDMS Gasket for front of chip (to protect lanes and arrays from manifold pressure); PMMA Chip with lid applied; Screw driver for manifold screws; 4 O-ring gaskets for sealing the manifold to chip. Syringe assembly: 2—syringe stoppers with O-ring gaskets (to apply pressure to syringes); 2-20 ml syringes; Luer lock for syringe tip (female luer 1/16" ID tubing, Cole Palmer, 45508-00); Luer lock for connecting air pressure to syringe hardware (male luer 1/16" ID tubing, Cole Palmer, 45518-22); Luer lock for connecting to pump air filter (female luer 1/16" ID tubing, Cole Palmer, 45508-00). Inlet tubing assembly for degasser: ~8 inches of tubing, finger-tight nut and ferrule. Outlet tubing assembly for degasser: ~finger-tight nut and ferrule, ~8 inches of larger ID tubing (1/8×0.062 PFA IDEX 1508), male and female luer connectors to join tubing, and ~3 inches of 0.03" ID tubing (Cole Palmer, 95802-01); Tubing for connecting blood syringe to chip (input tubing—0.03" ID); Tubing to direct RBC and WBC fractions to their collection tubes (output tubing—0.03" ID); Tubes to collect RBC and WBC fractions; Tubing clamps. Equipment: 2 pressure pumps that can deliver up to 10 psi; Degasi in-line degasser; Sterile filters for air from pumps; Degassing apparatus, stir plate, and stir bars for solutions. Other Lab Supplies: Blood filters (20 μm cutoff—Streriflip Vacuum Filtration System, Millipore, SCNY00020); P200 with tips (long neck for getting to the bottom of the syringes); Pipettes and pipettor; Nalgene vacuum filtration system (0.2 μm pore size, capacity 250 mL, Sigma Aldrich Z370606). Reagents: Phosphate Buffered Saline (PBS—Ca and Mg free); Bovine Serum Albumin (BSA); 1% Kolliphor Buffer; EDTA; 70% Isopropanol.

Example 18: Exemplary Protocol

Count WBC. Calculate amount of Mab to stain cells with Mab (Direct or Indirect). Incubate for 10 min with mixing. Add 125 MNP (magnetic nanoparticles) per 1 cell, incubate 10 Min with mixing, (OR if using direct—incubate additional 10'). Dilute Whole Blood 1:1 in running buffer (using F127 poloxamer). While incubating—connect DLD and magnetic separation chamber in series. Prime DLD-Chamber fluid path(s) and establish bubble free fluid path. Add 1:1 Diluted whole blood under pressure. Run at pressure of 10:9.8 PSI RB:Input ratio until all blood has entered system. Add additional buffer (~5× the dead volume of the internal fluidics of the entire fluid path) into sample inlet and run to completion. Collect Waste, Product into appropriate receptacles Example 19: Distinguishing Typical CTCs from Atypical CTCs Peripheral blood from a breast cancer patient was collected in Acid Citrate Dextrose anticoagulant (with inhibitor cocktail) to afford optimal processing via DLD. Following staining with CD45+CD66b biotin and streptavidin magnetic particles, the blood sample was processed via DLD and a magnetic chamber set up.

Resultant rare cell populations separated were further stained with CD45 (e450 conjugate) and cancer cell specific markers (EpCAM (CD326), Her2 (CD340) and CD44), and an associated leukocyte subset marker (CD56-NK cells, CD8+ T cells, or CD14 for Monocytes). A DNA dye (DRAQS) was also used to determine cell ploidy. Flow cytometry was performed and data were acquired using log fluorescence for all antibody markers. Light scatter and DNA ploidy analysis were visualized in linear measurements to assess scatter profile and aneuploidy status on a linear scale.

Two discrete populations of tumor cell marker-positive populations were observed. Both populations appeared to be physically large, but the compositions at a DNA content level were different. A classical "CTC" population that was CD45-negative, tumor marker-positive, and aneuploid by DNA content was observed. In addition, an "atypical" CTC population was also present. These "atypical" cells were the result of immune surveillance and clearance (trogocytosis) and created doublets (or larger) of white blood cells that took on the surface phenotype of cells that they killed, but did not demonstrate greater than scatter/DNA content ratios of diploid cell multiples, which was different from the classical CTC which clearly showed higher DNA/scatter ratios as expected in aneuploidy cells. Thus, without a DNA index confirming the ploidy status, it is possible to mis-identify CTC by flow cytometry.

Further, the unique combination of CD45 bright "tumor marker-positive" cells did not appear to be systematically discriminated using ploidy analysis because of their rare nature. Analysis using a model system confirmed that normal white cells did take on a mixed phenotype as a result of their killing the target cells, a process known as trogocytosis.

Separately, the results showed that following 4 hours of incubation (foreign cell (or cancer cell) into host) the trogocytosis process was observed in normal donors using spiked cells. Therefore, blood collection not factoring in the process of trogocytosis can be at risk for underestimating the number of CTC in a patient sample. CTC blood collection was in EDTA. Further, to process via DLD (EDTA's can aggregate cells and beads), adequate blood inhibition was present at the time of blood collection.

This experiment confirmed that the process of trogocytosis replicated the signature seen in patients in that sample collected into ACD and even fixation tubes with a slow acting fixate.

Figure 26A:
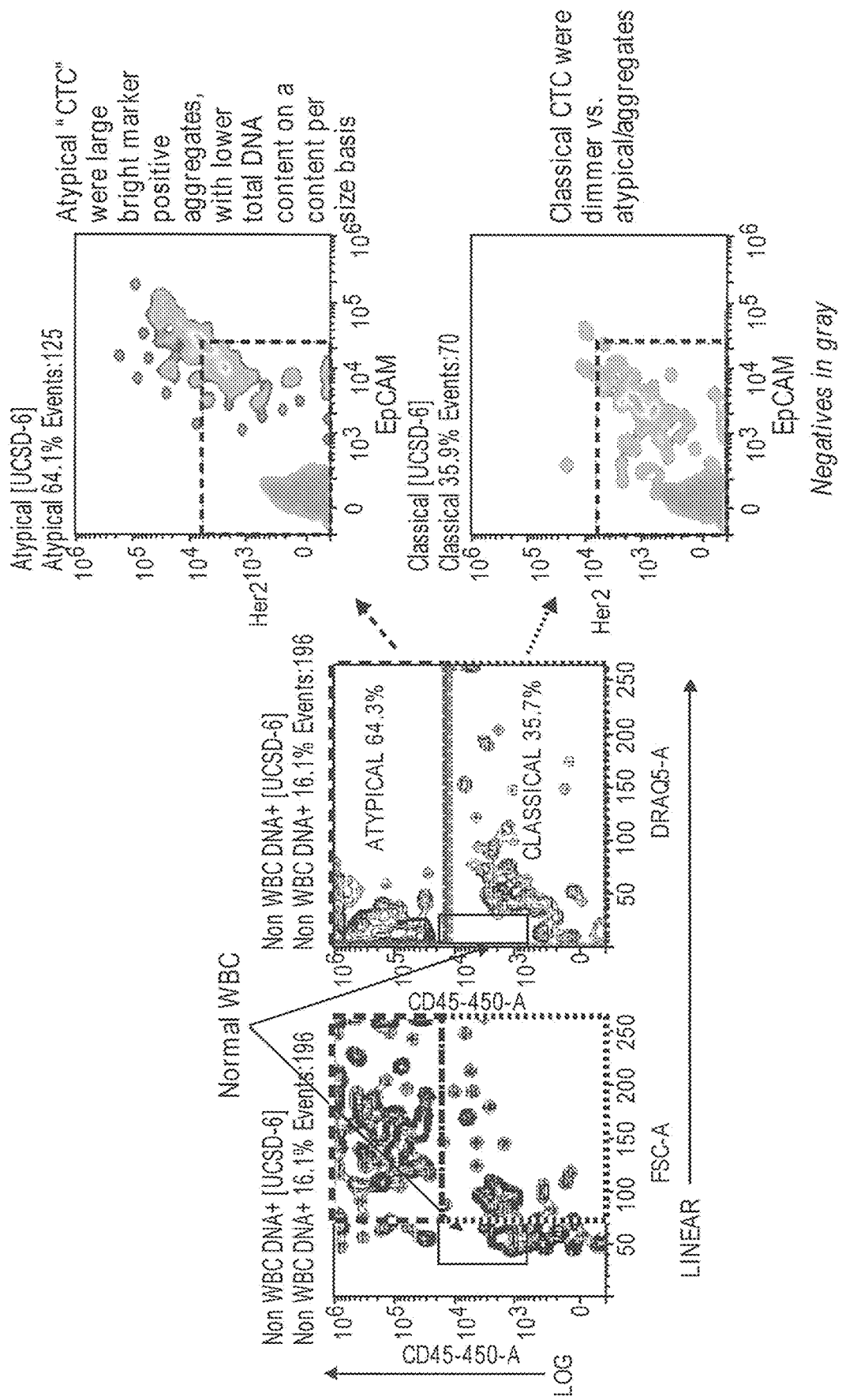
FIG. 26A shows observation of typical and atypical CTC populations. DNA Size/CD45 fluorescence signature on "atypical" CTC's was not well aligned with multimers, i.e., fractions of DNA vs. abundance of DNA content.
Figure 26B:
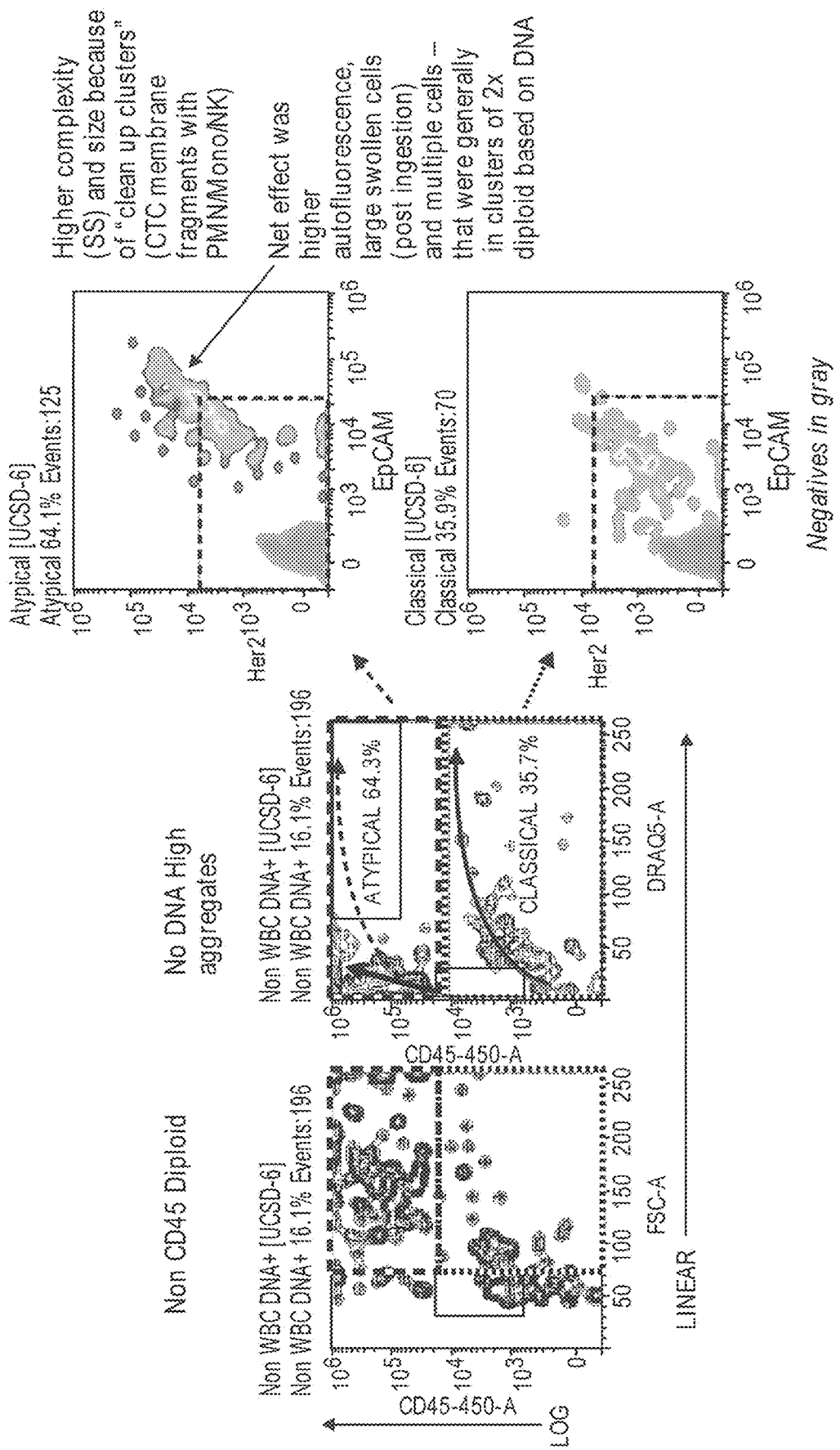
FIG. 26B shows the interpretation of the data. The degree varied by patient.

The results are shown in FIG. 26A and FIG. 26B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It can be intended that the following claims define the scope of the invention and that methods and structures within the scope of these claims and their equivalents be covered thereby.

What is claimed is:

1. A system for separating white blood cells or stem cells from platelets in a sample, the system comprising:
    a) a microfluidic channel comprising a first array of obstacles wherein said obstacles have a polygonal cross-section and are configured to separate cells by deterministic lateral displacement (DLD) based on their sizes, such that white blood cells or stem cells flow in a first direction and platelets flow in a second direction different from the first direction;
    b) a magnetic separator comprising one or more hard magnets, soft magnets, electromagnets, superconductor magnets, or combination thereof configured to separate particles or cells with magnetically susceptible labels from particles or cells without magnetically susceptible labels, wherein the first array of obstacles is fluidically connected with the magnetic separator;
    c) a particle sensor which is fluidically connected to the DLD array or magnetic separator and which, in response to particles or cells with magnetically susceptible labels arriving in a sensing zone, generates an actuation signal to create an actuation event;
    d) a particle dispenser fluidically connected to the DLD array or magnetic separator for dispensing particles to a particle collector, wherein the particle dispenser comprises:
        i) a fluidic duct configured to allow particles to flow into the fluid duct in a flow stream;
        ii) the particle sensor of paragraph c); and
        iii) a switch configured to receive the actuation signal.

2. The system of claim 1, wherein the particle sensor includes a computer module.

3. The system of claim 1, wherein the actuation signal is caused by magnetically labeled cells and due to a change in impedance, or due to light scatter, morphological, colorimetric, or fluorescent spectral signature or a combination thereof.

4. The system of claim 3, wherein the actuation signal is caused by magnetically labeled cells and due to a change in impedance.

5. The system of claim 1, wherein the particle sensor measures impedance.

6. The system of claim 1, wherein the first array of obstacles is upstream from the magnetic separator; and the system, further comprises:
    c) at least a second array of obstacles fluidically connected with the first array of obstacles and the magnetic separator wherein the second array has a critical size different from the critical size of the first array and is downstream from the magnetic separator.

7. The system of claim 1, wherein a vertex of each of two adjacent obstacles points toward each other in a direction substantially perpendicular to a flow direction of the sample through the array of obstacles.

8. The system of claim 7, wherein the DLD array comprises an array of obstacles that have a cross-sectional shape of a hexagon or are diamond-shaped.

9. The system of claim 1, wherein the DLD array comprises an array of obstacles with a critical diameter of from about 1 µm to about 5 µm.

10. The system of claim 1, wherein the particles or cells with magnetically susceptible labels are white blood cells or stem cells and the actuation signal is in response to the flow of these cells with magnetically susceptible labels into the sensing zone.

11. The system of claim 10, wherein the particle dispenser further comprises: d) a capture tube, wherein the capture tube is movable between a first position and a second position, wherein capture tube is not fluidically connected with the fluidic duct at the first position, and is fluidically connected with the fluidic duct at the second position, wherein the capture tube remains at the first position unless driven by the switch, wherein the switch drives the capture tube from the first position to the second position after receiving the actuation signal.

12. The system of claim 1, wherein the magnetic separator comprises one or more microfluidic channels, wherein at least one microfluidic channel in the magnetic separator is 200-1600 µm in width and wherein at least one microfluidic channel in the magnetic separator comprises one or more posts disposed along the center of the channel.

13. The system of claim 1, wherein, during operation, the system comprises a sample which has one or more additives that block the adhesion or activation of platelets.

* * * * *